United States Patent
Accetta et al.

(10) Patent No.: US 10,584,128 B2
(45) Date of Patent: Mar. 10, 2020

(54) BICYCLIC DIHYDROPYRIMIDINE-CARBOXAMIDE DERIVATIVES AS RHO-KINASE INHIBITORS

(71) Applicant: CHIESI FARMACEUTICI S.p.A., Parma (IT)

(72) Inventors: Alessandro Accetta, Parma (IT); Fabio Rancati, Parma (IT); Anna Maria Capelli, Parma (IT); David Edward Clark, Saffron Walden (GB); Patrizia Tisselli, Saffron Walden (GB); Christine Edwards, Saffron Walden (GB); Gurdip Bhalay, Saffron Walden (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 15/850,720

(22) Filed: Dec. 21, 2017

(65) Prior Publication Data
US 2018/0170939 A1  Jun. 21, 2018

(30) Foreign Application Priority Data
Dec. 21, 2016 (EP) .................................. 16205661

(51) Int. Cl.
| | | |
|---|---|---|
| *A61K 31/519* | (2006.01) | |
| *C07D 487/04* | (2006.01) | |
| *A61P 11/06* | (2006.01) | |
| *A61K 9/00* | (2006.01) | |
| *A61K 45/06* | (2006.01) | |
| *A61P 11/00* | (2006.01) | |
| *A61P 37/00* | (2006.01) | |

(52) U.S. Cl.
CPC .......... *C07D 487/04* (2013.01); *A61K 9/0073* (2013.01); *A61K 31/519* (2013.01); *A61K 45/06* (2013.01); *A61P 11/00* (2018.01); *A61P 11/06* (2018.01); *A61P 37/00* (2018.01)

(58) Field of Classification Search
CPC ........................... A61K 31/519; C07D 487/04
USPC ........................................ 514/259.3; 544/281
See application file for complete search history.

(56) References Cited

FOREIGN PATENT DOCUMENTS

| CN | 103 193 780 | | 7/2013 | |
|---|---|---|---|---|
| WO | WO2001040231 | * | 6/2001 | ........... C07D 487/04 |
| WO | 2014/144781 | | 9/2014 | |

OTHER PUBLICATIONS

European Search Report in Application No. 16205661.8 dated Feb. 13, 2017.
International Search Report in Application No. PCT/EP2017/084271 dated Feb. 22, 2018.
U.S. Appl. No. 15/883,729, filed Jan. 30, 2018, Alessandro Accetta, et al.

* cited by examiner

*Primary Examiner* — Jeffrey H Murray
(74) *Attorney, Agent, or Firm* — Oblon, McClelland, Maier & Neustadt, L.L.P.

(57) ABSTRACT

Bicyclic dihydropyrimidine-carboxamide compounds of formula I described herein inhibit Rho Kinase and may be useful in the treatment of many disorders associated with ROCK enzymes mechanisms, such as pulmonary diseases including asthma, chronic obstructive pulmonary disease (COPD), idiopathic pulmonary fibrosis (IPF), and pulmonary arterial hypertension (PAH).

14 Claims, No Drawings

BICYCLIC DIHYDROPYRIMIDINE-CARBOXAMIDE DERIVATIVES AS RHO-KINASE INHIBITORS

CROSS REFERENCES TO RELATED APPLICATIONS

This application claims priority to European Patent Application No. 16205661.8 filed on Dec. 21, 2016, which is incorporated herein by reference in its entirety.

BACKGROUND OF THE INVENTION

Field of the Invention

The present invention relates to compounds which inhibit Rho Kinase (hereinafter ROCK Inhibitors), in particular, compounds that are bicyclic dihydropyrimidine-carboxamide derivatives. The present invention also relates to methods of preparing such a compound, pharmaceutical compositions which contain such a compound, and therapeutic uses of such a compound.

Discussion of the Background

Rho-associated coiled-coil forming protein kinase (ROCK) belongs to the AGC (PKA/PKG/PKC) family of serine-threonine kinases. Two human isoforms of ROCK have been described, ROCK-I (also referred to as p160 ROCK or ROKβ) and ROCK-II (ROKα) are approximately 160 kDa proteins containing an N-terminal Ser/Thr kinase domain, followed by a coiled-coil structure, a pleckstrin homology domain, and a cysteine-rich region at the C-terminus (see Riento, K.; Ridley, A. J. Rocks: multifunctional kinases in cell behaviour. Nat. Rev. Mol. Cell Biol. 2003, 4, 446-456, which is incorporated herein by reference in its entirety).

Both ROCK-II and ROCK-I are expressed in many human and rodent tissues including the heart, pancreas, lung, liver, skeletal muscle, kidney and brain (Riento, K.; Ridley, A. J. Rocks: multifunctional kinases in cell behaviour. Nat. Rev. Mol. Cell Biol. 2003, 4, 446-456, which is incorporated herein by reference in its entirety). ROCK has been identified as an effector molecule of RhoA, and is involved in a variety of cell functions, including actin organization, cell adhesion, cell migration and cytokinesis (Riento, K.; Ridley, A. J. Rocks: multifunctional kinases in cell behaviour. Nat. Rev. Mol. Cell Biol. 2003, 4, 446-456; and Feng Y, LoGrasso P V, Defert O, Li R. Rho Kinase (ROCK) Inhibitors and Their Therapeutic Potential. J Med Chem. 2016; 59(6):2269-300, both of which are incorporated herein by reference in their entireties). It is also involved in regulating smooth muscle contraction, through the phosphorylation of effectors such as myosin light chain phosphatase (MLC). Indeed ROCK plays an important role in signal transduction initiated by several agents regulating smooth muscle cell contraction in blood vessels and/or airways, including serotonin, angiotensin II, endothelin I, platelet derived growth factor (PDGF) and urotensin II (Li Q, Xu Y, Li X, Guo Y, Liu G. Inhibition of Rho-kinase ameliorates myocardial remodeling and fibrosis in pressure overload and myocardial infarction: role of TGF-β1-TAK1. Toxicol Lett. 2012; 211(2):91-7; and Shi J, Wei L. Rho kinases in cardiovascular physiology and pathophysiology: the effect of fasudil. J Cardiovasc Pharmacol. 2013; 62(4): 341-54, both of which are incorporated herein by reference in their entireties,).

To date only two ROCK inhibitors have been approved for clinical use, in Japan and/or in China: Fasudil (Suzuki Y, Shibuya M, Satoh S, Sugiyama H, Seto M, Takakura K. Safety and efficacy of fasudil monotherapy and fasudil-ozagrel combination therapy in patients with subarachnoid hemorrhage: sub-analysis of the post-marketing surveillance study. Neurol Med Chir (Tokyo). 2008; 48(6):241-7, which is incorporated herein by reference in its entirety) was approved in 1995 for the treatment of cerebral vasospasm, and ripasudil (Tanihara H, Inoue T, Yamamoto T, Kuwayama Y, Abe H, Fukushima A, Suganami H, Araie M; K-115 Clinical Study Group. One-year clinical evaluation of 0.4% ripasudil (K-115) in patients with open-angle glaucoma and ocular hypertension. Acta Ophthalmol. 2016; 94(1):e26-34, which is incorporated herein by reference in its entirety) was approved in 2014 for the treatment of glaucoma.

ROCK mediate vasoconstriction and endothelial dysfunction, two key components of several cardiovascular diseases, including, hypertensive heart disease, coronary artery diseases, atherosclerosis, restenosis, Raynaud phenomenon, stroke and glaucoma (Hartmann S, Ridley A J, Lutz S. The Function of Rho-Associated Kinases ROCK1 and ROCK2 in the Pathogenesis of Cardiovascular Disease. Front Pharmacol. 2015 Nov. 20; 6:276, which is incorporated herein by reference in its entirety). In particular, pharmacological data from clinical trials show that ROCK inhibitors decrease intraocular pressure and demonstrate beneficial effects in glaucoma patients (Inoue T, Tanihara H. Rho-associated kinase inhibitors: a novel glaucoma therapy. Prog Retin Eye Res. 2013; 37:1-12, which is incorporated herein by reference in its entirety). In patients with pulmonary hypertension, ROCK activity is significantly higher in both lung tissues and circulating neutrophils as compared with controls (Duong-Quy S, Bei Y, Liu Z, Dinh-Xuan A T. Role of Rho-kinase and its inhibitors in pulmonary hypertension. Pharmacol Ther. 2013; 137(3):352-64, which is incorporated herein by reference in its entirety,). A significant correlation was established between neutrophil ROCK activity and the severity and duration of pulmonary hypertension (Duong-Quy S, Bei Y, Liu Z, Dinh-Xuan A T. Role of Rho-kinase and its inhibitors in pulmonary hypertension. Pharmacol Ther. 2013; 137(3):352-64, which is incorporated herein by reference in its entirety). ROCK can also contribute to the development of cardiac fibrosis, hypertrophy, and subsequent heart failure. Recent experimental studies using ROCK inhibitors, such as fasudil, have shown the benefits of ROCK inhibition in cardiac remodeling (Li Q, Xu Y, Li X, Guo Y, Liu G. Inhibition of Rho-kinase ameliorates myocardial remodeling and fibrosis in pressure overload and myocardial infarction: role of TGF-β1-TAK1. Toxicol Lett. 2012; 211(2):91-7, which is incorporated herein by reference in its entirety). Mice lacking each ROCK isoform also exhibit reduced myocardial fibrosis in a variety of pathological models of cardiac remodeling (Shimizu T1, Liao J K. Rho Kinases and Cardiac Remodeling. Circ J. 2016; 80(7):1491-8, which is incorporated herein by reference in its entirety).

ROCK is also a promising target for the treatment of cerebral vascular disorders. Indeed, preclinical studies indicate that Rho kinase inhibition may reduce the formation/growth/rupture of both intracranial aneurysms and cerebral cavernous malformations (Bond L M, Sellers J R, McKerracher L. Rho kinase as a target for cerebral vascular disorders. Future Med Chem. 2015; 7(8):1039-53, which is incorporated herein by reference in its entirety).

RhoA-ROCK signalling is important in maintaining a flaccid penile state, and pharmacological inhibition of ROCK signalling potentiates smooth-muscle relaxation in an NO-independent manner, suggesting that ROCK is a new therapeutic target for the treatment of erectile dysfunction (Sopko N A, Hannan J L, Bivalacqua T J. Understanding and targeting the Rho kinase pathway in erectile dysfunction. Nat Rev Urol. 2014; 11(11):622-8, which is incorporated herein by reference in its entirety,).

ROCK activity is an important signaling mechanism in leucocyte-platelet-endothelium interaction, leucocyte extravasation and oedema. Over-activation of Rho kinase in endothelial cells causes leakiness by disruption of cell-cell junctions favoring inflammatory cell recruitment. Taken together, these evidences point out a role of ROCK in pathological conditions associated with acute and chronic inflammation as well as autoimmune diseases. In particular, contribution of the ROCK pathway to autoimmunity and autoimmune disease is emerging (Zanin-Zhorov A, Flynn R, Waksal S D, Blazar B R. Isoform-specific targeting of ROCK proteins in immune cells. Small GTPases. 2016; 7(3):173-177, which is incorporated herein by reference in its entirety). This is supported by the demonstration of the role of ROCK signaling in T cell development and function, including adhesion, chemotactic responses, and antigen-dependent activation, as well as the beneficial effect of ROCK inhibition in experimental models of rheumatoid arthritis and lupus (LoGrasso, P.; Feng, Y. Rho kinase inhibitors and their application to inflammatory disorders. Curr. Top. Med. Chem. 2009; 9, 704-723; Yoshimi, E.; Kumakura, F.; Hatori, C.; Hamachi, E.; Iwashita, A.; Ishii, N.; Terasawa, T.; Shimizu, Y.; Takeshita, N. Antinociceptive effects of AS1892802, a novel rho kinase inhibitor, in rat models of inflammatory and noninflammatory arthritis. J. Pharmacol. Exp. Ther. 2010, 334, 955-963; and Stirzaker R A, Biswas P S, Gupta S, Song L, Bhagat G, Pernis A B. Administration of fasudil, a ROCK inhibitor, attenuates disease in lupus-prone NZB/W F1 female mice. Lupus. 2012 May; 21(6):656-61, all of which are incorporated herein by reference in their entireties). The inhibitory effect of Fasudil on T-cell migration might expand its clinical application as a new therapy for multiple sclerosis (Yu J Z, Ding J, Ma C G, Sun C H, Sun Y F, Lu C Z, Xiao B G. Therapeutic potential of experimental autoimmune encephalomyelitis by Fasudil, a Rho kinase inhibitor. J Neurosci Res. 2010; 88(8):1664-72, which is incorporated herein by reference in its entirety). Accumulating evidences also demonstrate that ROCK plays a key role in regulating three essential factors for pathogenesis of inflammatory bowel disease (IBD): disruptions of the intestinal barrier, exposure of the luminal content to mucosal immune cells and an abnormal immune response (Huang Y, Xiao S, and Jiang Q. Role of Rho kinase signal pathway in inflammatory bowel disease Int J Clin Exp Med. 2015; 8(3): 3089-3097, which is incorporated herein by reference in its entirety). The clinical use of ROCK inhibitors is under scrutiny also in psoriasis (Yiu Z Z, Warren R B. Novel Oral Therapies for Psoriasis and Psoriatic Arthritis. Am J Clin Dermatol. 2016; 17(3):191-200, which is incorporated herein by reference in its entirety).

There are several lines of evidence that ROCKs play a role in the pathology of diabetes. Indeed, ROCK1 KO mice exhibit insulin resistance and can have a significant increase in glucose-induced insulin secretion, leading to hyperinsulinemia (Lee D. H., Shi J., Jeoung N. H., Kim M. S., Zabolotny J. M., Lee S. W., et al. Targeted disruption of ROCK1 causes insulin resistance in vivo. J. Biol. Chem. 2009; 284, 11776-11780, which is incorporated herein by reference in its entirety). In addition, studies in models of type 1 and type 2 diabetes have indicated blood pressure-independent nephroprotective actions of ROCKi in diabetic kidney disease (Komers R. Rho kinase inhibition in diabetic kidney disease. Br J Clin Pharmacol. 2013; 76(4):551-9, which is incorporated herein by reference in its entirety).

There is now substantial evidence that ROCK is involved in many of the pathways that contribute to the pathologies associated with several acute and chronic pulmonary diseases, including asthma, COPD, bronchiectasis and ARDS/ALI. Given the biological effect of ROCK, selective inhibitors have the potential to treat a number of pathological mechanisms in respiratory diseases, such as smooth muscle hyper-reactivity, bronchoconstriction, airway inflammation and airway remodeling, neuromodulation and exacerbations due to respiratory tract viral infection (Fernandes L B, Henry P J, Goldie R G. Rho kinase as a therapeutic target in the treatment of asthma and chronic obstructive pulmonary disease. Ther Adv Respir Dis. 2007 October; 1(1):25-33, which is incorporated herein by reference in its entirety). Indeed the Rho kinase inhibitor Y-27632 causes bronchodilatation and reduces pulmonary eosinophilia trafficking and airways hyperresponsiveness (Gosens, R.; Schaafsma, D.; Nelemans, S. A.; Halayko, A. J. Rhokinase as a drug target for the treatment of airway hyperresponsiveness in asthma. Mini-Rev. Med. Chem. 2006, 6, 339-348, which is incorporated herein by reference in its entirety). Pulmonary ROCK activation has been demonstrated in humans with idiopathic pulmonary fibrosis (IPF) and in animal models of this disease. ROCK inhibitors can prevent fibrosis in these models, and more importantly, induce the regression of already established fibrosis, thus indicating ROCK inhibitors as potential powerful pharmacological agents to halt progression of pulmonary fibrosis (Jiang, C.; Huang, H.; Liu, J.; Wang, Y.; Lu, Z.; Xu, Z. Fasudil, a rho-kinase inhibitor, attenuates bleomycin-induced pulmonary fibrosis in mice. Int. J. Mol. Sci. 2012, 13, 8293-8307, which is incorporated herein by reference in its entirety).

Accumulating evidence supports the concept that ROCK plays important roles in tumor development and progression through regulating many key cellular functions associated with malignancy, including tumorigenicity, tumor growth, metastasis, angiogenesis, tumor cell apoptosis/survival and chemoresistance (Wei L, Surma M, Shi S, Lambert-Cheatham N, Shi J. Novel Insights into the Roles of Rho Kinase in Cancer. Arch Immunol Ther Exp (Warsz). 2016; 64(4):259-78, which is incorporated herein by reference in its entirety). Thus, indicating ROCK inhibitors also as potential powerful pharmacological agents in cancer.

The administration of an oral ROCK inhibitor effectively ameliorates clinical manifestations in experimental models of graft-vs.-host disease (GVHD) (see Biol Blood Marrow Transplant. 2014; 20(8):1104-11; and Blood. 2016; 127(17):2144-54, which are incorporated herein by reference in their entireties). Further findings highlight the Rho kinases as rational therapeutic targets to combat tau accumulation in Progressive Supranuclear Palsy (PSP) and Corticobasal Degeneration (CBD). (Gentry et al., J Neurosci. 2016; 36(4):1316-23, which is incorporated herein by reference in its entirety)

In various disorders of the central nervous system there is an abnormal activation of the Rho/ROCK pathway. ROCK is activated upon injury to the adult brain and spinal cord and inhibition of ROCKs results in accelerated regeneration and enhanced functional recovery after spinal-cord injury (Kubo T, Hata K, Yamaguchi A, Yamashita T. Rho-ROCK inhibitors as emerging strategies to promote nerve regeneration. Curr Pharm Des. 2007; 13(24):2493-9, which is incorporated herein by reference in its entirety). Inhibition of the Rho/ROCK pathway has also proved to be efficacious in animal models of stroke, inflammatory and demyelinating diseases, Alzheimer's disease and neuropathic pain (reviewed by Mueller, B. K.; Mack, H.; Teusch, N. Rho kinase, a promising drug target for neurological disorders. Nat. Rev. Drug Discovery 2005, 4, 387-398, which is incorporated herein by reference in its entirety).

Various compounds have been described in the literature as Rho Kinase Inhibitors. See e.g., WO 2004/039796; WO 2006/009889; WO 2010/032875; WO 2009/079008; WO 2014/118133, all of which are incorporated herein by reference in their entireties.

Heterocyclic dihydropyrimidines are disclosed in WO 2001/040231, which is incorporated herein by reference in its entirety, as potassium channel inhibitors. Dihydrotetrazolopyrimidine derivatives are disclosed in US 2016/113931, which is incorporated herein by reference in its entirety, for treating and/or preventing neurogenerative disease.

There remains, however, a potential for developing novel and pharmacologically improved ROCK inhibitors in many therapeutic areas such as: cardiovascular and respiratory diseases, erectile dysfunction, fibrotic diseases, insulin resistance, kidney failure, central nervous system disorders, auto-immune diseases and oncology.

In view of the number of pathological responses which are mediated by ROCK enzymes, there is a continuing need for inhibitors of such enzymes which can be useful in the treatment of many disorders.

SUMMARY OF THE INVENTION

Accordingly, it is one object of the present invention to provide novel compounds which inhibit Rho Kinase (hereinafter ROCK Inhibitors).

It is another object of the present invention to provide ROCK Inhibitors that are bicyclic dihydropyrimidine-carboxamide derivatives.

It is another object of the present invention to provide novel methods of preparing such a compound.

It is another object of the present invention to provide novel pharmaceutical compositions which contain such a compound.

It is another object of the present invention to provide novel therapeutic uses of such a compound.

These and other objects, which will become apparent during the following detailed description, have been achieved by the inventors' discovery that compounds of formula (I) described below are ROCK Inhibitors.

Thus, the present invention provides compounds of formula (I):

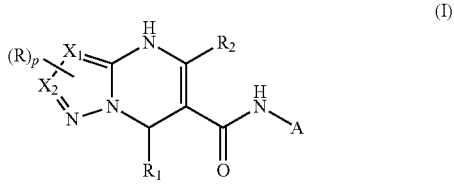

(I)

wherein $X_1$, $X_2$, $R_1$, $R_2$, A, p are as described below in the Detailed Description of the Preferred Embodiments.

The present invention also provided the use of such a compound as a ROCK inhibitor.

The present invention also provides processes for the preparation of such a compound.

The present invention also provides pharmaceutical compositions which contain such a compound, either alone or in combination with one or more active ingredient, in admixture with one or more pharmaceutically acceptable carrier.

In one aspect, the present invention provides the use of a compound of the invention for the manufacture of a medicament.

In a further aspect, the present invention provides the use of a compound of the invention for the preparation of a medicament for the treatment of any disease characterized by ROCK enzyme aberrant activity and/or wherein an inhibition of activity is desirable and in particular through the selective inhibition of the ROCK enzyme isoforms over other Kinases.

Moreover, the present invention provides a method for prevention and/or treatment of any disease wherein a ROCK enzyme inhibition is desirable, by administering to a patient in need of such treatment a therapeutically effective amount of a compound of the invention.

In particular the compounds of the invention alone or combined with other active ingredients may be administered for the prevention and/or treatment of a pulmonary disease including asthma, chronic obstructive pulmonary disease (COPD), idiopathic pulmonary fibrosis (IPF) and pulmonary hypertension (PH), and specifically pulmonary arterial hypertension (PAH).

More particularly, the compounds of the present invention are inhibitors of the activity or function of the ROCK-I and/or ROCK-II isoforms of the Rho-associated coiled-coil forming protein kinase (ROCK).

Therefore, the compounds of the present invention may be useful in the treatment of many disorders associated with ROCK enzymes mechanisms, such as pulmonary diseases including asthma, chronic obstructive pulmonary disease (COPD), idiopathic pulmonary fibrosis (IPF) and pulmonary arterial hypertension (PAH).

The present invention relates to novel compounds which are inhibitors of ROCK-I and ROCK-II isoforms of the Rho-associated coiled-coil forming protein kinase (ROCK) that have therapeutically desirable characteristics, particularly promising for some pulmonary diseases including asthma, chronic obstructive pulmonary disease (COPD), idiopathic pulmonary fibrosis (IPF) and pulmonary hypertension (PH), and specifically pulmonary arterial hypertension (PAH).

DETAILED DESCRIPTION OF THE PREFERRED EMBODIMENTS

The invention is directed to a class of compounds acting as inhibitors of the Rho Kinase (ROCK). Said class of compounds inhibits the activity or function of the ROCK enzyme and more specifically, they are inhibitors of ROCK-I and ROCK-II isoforms of the Rho-associated coiled-coil forming protein kinase (ROCK). The present invention relates to compounds of formula (I):

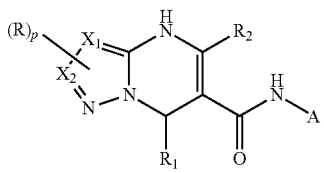
(I)

wherein
$X_1$ and $X_2$ are in each occurrence independently a carbon atom or a nitrogen atom;
each R, when present, is selected, in each occurrence independently, from the group consisting of
—H
—CN,
halogen,
—$NR_5R_6$,
($C_1$-$C_6$) alkyl,
($C_1$-$C_6$) haloalkyl,
($C_1$-$C_6$) hydroxyalkyl,
($C_1$-$C_6$) aminoalkyl,
($C_3$-$C_{10}$) cycloalkyl,
($C_2$-$C_6$) alkenyl,
($C_5$-$C_7$) cycloalkenyl,
($C_2$-$C_6$) alkynyl,
($C_2$-$C_6$) hydroxyalkynyl,
hydroxycarbonyl,
—$OR_7$,
($C_1$-$C_6$) alkylthio,
($C_1$-$C_6$) alkoxy-($C_1$-$C_6$) alkyl,
($C_1$-$C_6$) alkoxycarbonyl,
($C_1$-$C_6$) aminoalkylcarbonyl,
carbamoyl,
($C_3$-$C_6$) cycloalkyl-($C_1$-$C_6$) alkyl,
($C_3$-$C_6$) heterocycloalkyl-($C_1$-$C_6$) alkyl,
aryl,
heteroaryl, and
($C_3$-$C_6$) heterocycloalkyl;
wherein any of said ($C_3$-$C_6$) cycloalkyl, aryl, heteroaryl, and ($C_3$-$C_6$) heterocycloalkyl is in its turn optionally and independently substituted with one or more groups selected from
halogen,
—OH,
($C_1$-$C_6$) alkyl,
($C_1$-$C_6$) haloalkyl,
($C_1$-$C_6$) hydroxyalkyl,
($C_1$-$C_6$) aminoalkyl,
($C_3$-$C_{10}$) cycloalkyl,
($C_2$-$C_6$) alkenyl,
($C_5$-$C_7$) cycloalkenyl,
($C_2$-$C_6$) alkynyl,
($C_2$-$C_6$) hydroxyalkynyl,
($C_1$-$C_6$) alkoxyl, and
($C_1$-$C_6$) aminoalkylcarbonyl;
$R_5$ and $R_6$ are in each occurrence independently selected from the group
H,
($C_1$-$C_6$) alkyl,
($C_1$-$C_6$) haloalkyl,
($C_1$-$C_6$) hydroxyalkyl,
($C_1$-$C_6$) aminoalkyl,
($C_1$-$C_6$) aminoalkylcarbonyl
carbamoyl-($C_1$-$C_6$) alkyl
($C_1$-$C_6$) alkoxyl,
($C_1$-$C_6$) alkoxy-($C_1$-$C_6$) alkyl,
($C_3$-$C_6$) heterocycloalkyl-($C_1$-$C_6$) alkyl,
($C_3$-$C_6$) heterocycloalkyloxyl alkanoyl,
aryl,
heteroaryl, and
($C_3$-$C_6$) heterocycloalkyl;
wherein any of said aryl, heteroaryl and ($C_3$-$C_6$) heterocycloalkyl in its turn is optionally and independently substituted with one or more groups selected from
halogen,
—OH, and
($C_1$-$C_6$) alkyl; or
$R_5$ and $R_6$ taken together with the nitrogen atom they are linked to form a 4 to 6 membered heterocyclic radical, wherein at least one further ring carbon atom in the said heterocyclic radical may be replaced by at least one heteroatom selected from N, S, or O; said heterocyclic radical can be further optionally substituted by a group selected from
H,
—CN,
halogen,
oxo,
—$NR_5R_6$
($C_1$-$C_6$) alkyl,
($C_1$-$C_6$) haloalkyl,
($C_1$-$C_6$) hydroxyalkyl,
($C_1$-$C_6$) aminoalkyl,
($C_1$-$C_6$) alkoxyl,
($C_1$-$C_6$) alkoxy-($C_1$-$C_6$) alkyl, and
alkanoyl;
$R_7$ is in each occurrence independently selected from the group
H,
($C_1$-$C_6$) alkyl,
($C_1$-$C_6$) haloalkyl,
($C_1$-$C_6$) hydroxyalkyl,
($C_1$-$C_6$) aminoalkyl,
($C_1$-$C_6$) alkoxy-($C_1$-$C_6$) alkyl,
($C_3$-$C_6$) heterocycloalkyl-($C_1$-$C_6$) alkyl,
aryl,
heteroaryl, and
($C_3$-$C_6$) heterocycloalkyl;
wherein any of said aryl, heteroaryl and ($C_3$-$C_6$) heterocycloalkyl in its turn is optionally and independently substituted with one or more groups selected from
halogen,
—OH, and
($C_1$-$C_6$) alkyl;
p is zero or 1 or 2;
$R_1$ is selected from the group consisting of
($C_1$-$C_6$) alkyl,
($C_1$-$C_6$) haloalkyl,
($C_1$-$C_6$) hydroxyalkyl,
($C_1$-$C_6$) aminoalkyl,
($C_3$-$C_{10}$) cycloalkyl,
($C_2$-$C_6$) alkenyl,
($C_5$-$C_7$) cycloalkenyl,
($C_2$-$C_6$) alkynyl,
($C_2$-$C_6$) hydroxyalkynyl,
($C_3$-$C_6$) cycloalkyl-($C_1$-$C_6$) alkyl,
($C_3$-$C_6$) heterocycloalkyl-($C_1$-$C_6$) alkyl,
aryl ($C_1$-$C_6$) alkyl,
aryl,
heteroaryl, and
($C_3$-$C_6$) heterocycloalkyl;

each of which cycloalkyl, cycloalkenyl, aryl, heteroaryl and ($C_3$-$C_6$) heterocycloalkyl being in its turn optionally and independently substituted with one or more groups selected from
nitro,
halogen,
—$NR_5R_6$,
—CN,
—OH,
—$S(O)_2$—($C_1$-$C_6$) alkyl,
($C_1$-$C_6$) alkyl,
($C_1$-$C_6$) haloalkyl,
($C_1$-$C_6$) alkoxyl,
($C_1$-$C_6$) haloalkoxyl,
($C_1$-$C_6$) aminoalkoxyl,
($C_1$-$C_6$) hydroxyalkoxyl,
($C_3$-$C_6$) heterocycloalkyloxyl,
($C_3$-$C_6$) heterocycloalkyl ($C_1$-$C_6$) alkoxyl,
carbamoyl,
alkanoyl,
aryloxyl,
aryl ($C_1$-$C_6$) alkoxyl,
aryloxy-($C_1$-$C_6$) alkyl,
($C_1$-$C_6$) alkoxycarbonyl,
($C_1$-$C_6$) alkoxy-($C_1$-$C_6$) alkyl,
($C_1$-$C_6$) alkoxycarbonyl-amino-,
($C_1$-$C_6$) haloalkyl,
($C_1$-$C_6$) hydroxyalkyl,
($C_2$-$C_6$) alkenyl,
($C_2$-$C_6$) alkynyl,
($C_2$-$C_6$) hydroxyalkynyl,
aryl,
heteroaryl, and
($C_3$-$C_6$) heterocycloalkyl;
$R_2$ is selected from
($C_1$-$C_6$) alkyl,
($C_1$-$C_6$) haloalkyl,
($C_1$-$C_6$) hydroxyalkyl,
($C_1$-$C_6$) aminoalkyl,
($C_3$-$C_{10}$) cycloalkyl,
($C_1$-$C_6$) alkoxyl, and
($C_1$-$C_6$)alkoxy-($C_1$-$C_6$) alkyl;
A is a bicyclic heteroaryl optionally substituted by one or more groups selected from
halogen,
—OH,
($C_1$-$C_6$) alkyl,
($C_1$-$C_6$) alkoxyl,
($C_2$-$C_6$) alkenyl,
($C_2$-$C_6$) alkynyl,
aryl,
heteroaryl, and
($C_3$-$C_6$) heterocycloalkyl;
each of which aryl, heteroaryl and ($C_3$-$C_6$) heterocycloalkyl being in its turn further optionally substituted. and pharmaceutically acceptable salts and solvates thereof.

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic basic addition salts of acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, methane sulfonic acid, camphor sulfonic acid, acetic acid, oxalic acid, maleic acid, fumaric acid, succinic acid and citric acid.

The term "halogen atoms" or "halogen" as used herein includes fluorine, chlorine, bromine, and iodine, preferably chlorine or fluorine, alternatively named bromo, iodo, chloro, fluoro as substituent groups.

The term "($C_1$-$C_6$) alkyl" refers to straight-chained or branched alkyl groups wherein the number of constituent carbon atoms is in the range 1 to 6. Particular alkyl groups are methyl, ethyl, n-propyl, isopropyl and t-butyl.

The expressions "($C_1$-$C_6$) haloalkyl" refer to the above defined "($C_1$-$C_6$)alkyl" groups wherein one or more hydrogen atoms are replaced by one or more halogen atoms, which can be the same or different from each other.

Examples of said ($C_1$-$C_6$) haloalkyl groups may thus include halogenated, poly-halogenated and fully halogenated alkyl groups wherein all of the hydrogen atoms are replaced by halogen atoms, e.g. trifluoromethyl or difluoro methyl groups. By way of analogy, the terms "($C_1$-$C_6$) hydroxyalkyl" or "($C_1$-$C_6$) aminoalkyl" refer to the above defined "($C_1$-$C_6$) alkyl" groups wherein one or more hydrogen atoms are replaced by one or more hydroxy (OH) or amino group respectively. Non-limiting examples being respectively hydroxymethyl and aminomethyl, dimethylaminomethyl, dimethylaminoethyl and the like.

In the present description, unless otherwise provided, the definition of aminoalkyl encompasses alkyl groups (i.e. "($C_1$-$C_6$) alkyl" groups) substituted by one or more amino group ($NR_5R_6$). Thus, an example of aminoalkyl is a mono-aminoalkyl group such as $R_5R_6N$—($C_1$-$C_6$) alkyl.

With reference to the substituent $R_5$ and $R_6$ as above defined and below, it is here further explained that when $R_5$ and $R_6$ are taken together with the nitrogen atom they are linked to form a 4 to 6 membered heterocyclic radical, at least one further ring carbon atom in the said heterocyclic radical is optionally replaced by at least one heteroatom (e.g. N, NH, S, or O) and/or may bear -oxo (=O) substituent groups. It is understood that the said heterocyclic radical might be further optionally substituted on any available points in the ring, namely on a carbon atom, or on any heteroatom available for substitution. Substitution on a carbon atom includes spiro disubstitution as well as substitution on two adjacent carbon atoms, in both cases thus form an additional 5 to 6 membered heterocyclic ring. Thus, Examples of said heterocycle radicals are 1-pyrrolidinyl, 1-piperidinyl, 1-piperazinyl, 4-morpholinyl, piperazin-4yl-2-one, 4-methylpiperazine-1-yl, 4-methylpiperazine-1-yl-2-one, 7-methyl-2,7-diazaspiro[3.5]nonan-2-yl, 2-methyl-2,9-diazaspiro[5.5]undecan-9-yl, 9-methyl-3,9-diazaspiro[5.5]undecan-3-yl, and (3aR,6aS)-5-methyl-octahydropyrrolo[3,4-c]pyrrol-2-yl, 8-methyl-2,8-diazaspiro[4.5]decane-2-yl, 5-methyloctahydropyrrolo[3,4-c]pyrrol-2-yl, 1,1-dioxidothiomorpholin-4-yl. The term "($C_3$-$C_{10}$) cycloalkyl" refers to saturated cyclic hydrocarbon groups containing from 3 to 10 ring carbon atoms. Non-limiting examples include cyclopropyl, cyclobutyl, cyclopentyl, cyclohexyl and cycloheptyl, and polycyclic ring systems such as adamantan-yl.

The term "($C_2$-$C_6$) alkenyl" refers to straight or branched carbon chains with one or more double bonds, conjugated or not conjugated, in cis or trans configuration, wherein the number atoms is in the range 2 to 6.

By way of analogy, the terms "($C_5$-$C_7$) cycloalkenyl" refers to cyclic hydrocarbon groups containing from 5 to 7 ring carbon atoms and one or two double bonds. The term "($C_2$-$C_6$) alkynyl" refers to straight or branched carbon chains with one or more triple bonds wherein the number atoms is in the range 2 to 6.

The term "($C_2$-$C_6$) hydroxyalkynyl" refers to the above defined "($C_1$-$C_6$) alkynyl" groups wherein one or more hydrogen atoms are replaced by one or more hydroxy (OH) group.

The term "($C_2$-$C_6$) aminoalkynyl" refers to the above defined "($C_1$-$C_6$) alkynyl" groups wherein one or more hydrogen atoms are replaced by one or more (—$NR_5R_6$) groups.

The expression "aryl" refers to mono, bi- or tri-cyclic carbon ring systems which have 6 to 20, preferably from 6 to 15 ring atoms, wherein at least one ring is aromatic. The expression "heteroaryl" refers to mono-, bi- or tri-cyclic ring systems with 5 to 20, preferably from 5 to 15 ring atoms, in which at least one ring is aromatic and in which at least one ring atom is a heteroatom (e.g. N, NH, S, or O).

Examples of suitable aryl or heteroaryl monocyclic ring systems include, for instance, phenyl, thienyl, pyrrolyl, pyrazolyl, imidazolyl, isoxazolyl, oxazolyl, isothiazolyl, thiazolyl, pyridinyl, pyrimidinyl, pyrazinyl, triazinyl, furanyl radicals and the like.

Examples of suitable aryl or heteroaryl bicyclic ring systems include naphthalenyl, biphenylenyl, purinyl, pteridinyl, pyrazolopyrimidinyl, benzotriazolyl, benzoimidazole-yl, quinolinyl, isoquinolinyl, indolyl, isoindolyl, benzothiophene-yl, benzodioxinyl, dihydrobenzodioxinyl, indenyl, dihydro-indenyl, dihydrobenzo[1,4]dioxinyl, benzothiazole-2-yl, dihydrobenzodioxepinyl, benzooxazinyl, 1H-indazol-5-yl, 6-fluoro-1H-indazole-5-yl, isoquinoline-6-yl, thieno[2,3-c]pyridine-2-yl, thieno[3,2-c]pyridine-2-yl, [1,2,4]triazolo[4,3-a]pyridine-7-yl, 1,6-naphthyridin-2-yl radicals and the like.

Examples of suitable aryl or heteroaryl tricyclic ring systems include fluorenyl radicals as well as benzocondensed derivatives of the aforementioned heteroaryl bicyclic ring systems.

In an analogous manner, the expressions "arylene" and "heteroarylene" refer to divalent groups, such a phenylene, biphenylene and thienylene. Such groups are also commonly named as "arenediyl" or "heteroarenediyl" groups. For example o-phenylene is also named benzene-1,2-diyl. Thienyl-ene is alternatively named thiophenediyl.

The derived expression "($C_3$-$C_6$) heterocycloalkyl" refers to saturated or partially unsaturated monocyclic ($C_3$-$C_6$) cycloalkyl groups in which at least one ring carbon atom is replaced by at least one heteroatom (e.g. N, S, or O) or may bear an -oxo (=O) substituent group. The said heterocycloalkyl (i.e. heterocyclic radical or group) might be further optionally substituted on the available points in the ring, namely on a carbon atom, or on an heteroatom or heterogroup available for substitution. Substitution on a carbon atom includes spiro disubstitution as well as substitution on two adjacent carbon atoms, in both cases thus form additional condensed 5 to 6 membered heterocyclic ring. Non-limiting examples of ($C_3$-$C_6$) heterocycloalkyl are represented by: pyrrolidinyl, imidazolidinyl, thiazolidinyl, piperazinyl, piperidinyl, morpholinyl, thiomorpholinyl, dihydro- or tetrahydro-pyridinyl, tetrahydropyranyl, pyranyl, 2H- or 4H-pyranyl, dihydro- or tetrahydrofuranyl, dihydroisoxazolyl, pyrrolidin-2-one-yl radicals and the like.

Specific examples of said heterocycle radicals are 1-pyrrolidinyl, 1-methyl-2-pyrrolidinyl, 1-piperidinyl, 1-piperazinyl, 4-morpholinyl, piperazin-4yl-2-one, 4-methylpiperazine-1-yl, 1-methylpiperidin-4yl, 4-metylpiperazine-1-yl-2-one, 7-methyl-2,7-diazaspiro[3.5]nonan-2-yl, 2-methyl-2,9-diazaspiro[5.5]undecan-9-yl, 9-methyl-3,9-diazaspiro[5.5] undecan-3-yl, and (3aR,6aS)-5-methyl-octahydropyrrolo[3,4-c]pyrrol-2-yl. The term "aryl ($C_1$-$C_6$) alkyl" refers to an aryl ring linked to a straight-chained or branched alkyl groups wherein the number of constituent carbon atoms is in the range from 1 to 6, e.g. phenylmethyl (i.e. benzyl), phenylethyl or phenylpropyl.

The term "alkanoyl", refers to HC(O)— or to alkylcarbonyl groups (e.g. ($C_1$-$C_6$)alkylC(O)— wherein the group "alkyl" has the meaning above defined. Non-limiting examples include formyl, acetyl, propanoyl, butanoyl.

The term "carbamoyl" refers to amino carbonyl derived groups —C(O)$NR_5R_6$, wherein $R_5$ and $R_6$ are as defined above in the definition of aminoalkyl groups and including substituted (preferred aminoalkyl substituted) and spiro substituted derivatives. Non-limiting examples of such carbamoyl groups being aminocarbonyl, N,N dimethyl-aminocarbonyl, (3,3-difluorocyclobutyl)-aminocarbonyl, piperazine-1-carbonyl, morpholine-N-carbonyl, morpholine-N-carbonyl and N-(2-(dimethylamino)ethyl)aminocarbonyl, N-(2-(dimethylamino)ethyl)-N-methylaminocarbonyl, N-(3-(dimethylamino)propyl)-N-methylaminocarbonyl, 4-methylpiperazine-1-carbonyl, 4-(dimethylamino)piperidin-1-carbonyl, N-(2-(4-methylpiperazin-1-yl)ethyl)aminocarbonyl, (2 morpholino-ethyl) aminocarbonyl, N-methyl-N-(2 morpholino-ethyl) aminocarbonyl, N-(2-(piperidin-1-yl)ethyl) aminocarbonyl, N-methyl-N-(2-(piperidin-1-yl) ethyl)aminocarbonyl, N-(1-methylpiperidin-4-yl-methyl) aminocarbonyl, N-methyl-N-(1-methylpiperidin-4-yl)aminocarbonyl, N-methyl-N-(1-methylpiperidin-4-yl)aminocarbonyl, 5-methyloctahydropyrrolo[3,4-c]pyrrole-2 carbonyl, N-cyclopropyl-aminocarbonyl, 2-(piperidin-1-yl)ethyl aminocarbonyl.

The term "hydroxycarbonyl" refers to a terminal group HOC(O)—.

The term "($C_1$-$C_6$) alkoxy" or "($C_1$-$C_6$) alkoxyl" refers to a straight or branched hydrocarbon of the indicated number of carbons, attached through an oxygen bridge.

Likewise, the term "($C_1$-$C_6$) alkylthio" refers to a straight or branched hydrocarbon of the indicated number of carbons, attached through an sulfur (—S—) bridge. The derived expression "($C_1$-$C_6$) haloalkoxy" or "($C_1$-$C_6$) haloalkoxyl" refers to the above defined haloalkyl, attached through an oxygen bridge. Non-limiting example being trifluoromethoxy.

By analogy, derived expressions "($C_3$-$C_6$) heterocycloalkyloxyl" and "($C_3$-$C_6$) heterocycloalkyl ($C_1$-$C_6$) alkoxyl" refer to heterocycloalkyl groups attached through an oxygen bridge and chained heterocycloalkyl-alkoxyl groups respectively. Non-limiting examples of such ($C_3$-$C_6$) heterocycloalkyloxyl and ($C_3$-$C_6$) heterocycloalkyl ($C_1$-$C_6$) alkoxyl groups are respectively (piperidin-4-yl)oxy, 1-methylpiperidin-4-yl)oxy, 2-(piperidin-4-yl)ethoxyl, 2-(1-methylpiperidin-4-yl)ethoxy, and 2-(4-morpholino)ethoxy.

The derived expressions "Aryloxyl" and "Aryl ($C_1$-$C_6$) alkoxyl" refer to Aryl groups attached through an oxygen bridge and chained Aryl-alkoxyl groups. Non-limiting examples of such are phenyloxy and benzyloxy respectively.

Likewise, the derived expression "($C_3$-$C_6$) heterocycloalkyl-($C_1$-$C_6$) alkyl" and "(C3-C6) cycloalkyl-($C_1$-$C_6$) alkyl" refer to the above defined heterocycloalkyl and cycloalkyl groups attached to the rest of the molecule via an alkyl group of the indicated number of carbons. Non-limiting examples being piperidin-4-yl-methyl, cyclohexylethyl.

The derived expression "$(C_1-C_6)$ alkoxy-$(C_1-C_6)$ alkyl" refers to the above defined alkoxy group attached to the rest of the molecule via an alkyl group of the indicated number of carbons. Non-limiting examples being respectively methoxymethyl.

The derived expression "$(C_1-C_6)$ alkoxycarbonyl" refers to the above defined alkoxy group attached to the rest of the molecule via a carbonyl group. Non-limiting examples being ethoxycarbonyl.

Further derived expression like "$(C_1-C_6)$ alkoxycarbonylamino" refers to the above defined alkoxy group attached to the rest of the molecule via a carbonyl group followed by an amino group (—$NR_5$—). Non limiting example being tert-butoxy-carbonyl-amino.

Thus, "$(C_1-C_6)$ alkoxycarbonyl $(C_3-C_6)$ heterocycloalkyl $(C_1-C_6)$ alkyl" refers to alkoxy carbonyl heterocycloalkyl substituents enchained in the order and attached to the rest of the molecule via an alkyl group of the indicated number of carbons. Non limiting example being (tell-butyl piperidine-1-carboxylate)-4-yl-methyl.

And, "$(C_3-C_6)$ heterocycloalkyloxyl alkanoyl" refers to $(C_3-C_6)$ heterocycloalkyloxyl and alkanoyl substituents as above defined enchained in the order and attached to the rest of the molecule through the carbonyl group. Non limiting example being ((piperidin-4-yl)oxy)acetyl.

The derived expression "$(C_1-C_6)$ aminoalkoxyl" refers to $(C_1-C_6)$ aminoalkyl groups as above defined attached through an oxygen bridge, non-limiting example is (2-(dimethylamino)ethoxy.

And the expression "$(C_1-C_6)$ hydroxyalkoxyl" refers to hydroxyalkyl groups as above defined attached to the rest of the molecule through an oxygen bridge. Non-limiting example being hydroxyethoxy.

The derived expression "$(C_1-C_6)$ aminoalkylcarbonyl" refers to the above defined "$(C_1-C_6)$ aminoalkyl" group, as above defined, attached to the rest of the molecule through a carbonyl group.

Non-limiting examples being 2-(piperidin-1-yl)ethylcarbonyl, 2-(pyrrolidin-1-yl)acetyl. The derived expression "$(C_1-C_6)$ aminoalkylcarbamoyl" refers to a "carbamoyl" group, as above defined, substituted with a $(C_1-C_6)$ aminoalkyl group (i.e. —$C(O)NR_5R_6$ wherein e.g. $R_6$ is an $(C_1-C_6)$ aminoalkyl).

Non limiting examples being 2(dimethylamino) ethyl carbamoyl.

Likewise the derived expression "carbamoyl-$(C_1-C_6)$ alkyl" refers to a "carbamoyl" group, as above defined, linked to the rest of the molecule through an Alkyl bridge of the indicated number of carbons (i.e. a group —$(C_1-C_6)$ alkyl-$C(O)NR_5R_6$). Non-limiting examples being 3-oxo-3-(pyrrolidin-1-yl)propyl.

The term "aryl alkanoyl" refers to an arylC(O) or arylalkylcarbonyl group (e.g. Aryl($C_1-C_6$)alkylC(O)—) wherein aryl and alkyl have the meaning above defined. Non-limiting examples are represented by benzoyl, phenylacetyl, phenylpropanoyl or phenylbutanoyl radicals.

The expression "saturated, partially unsaturated or aromatic, five or six membered cycloalkane-diyl, arylene-diyl or heterocycle-diyl" refers to suitable vicinal disubstituted cycloalkane or heterocycle residue with five or six elements including 1,2-, 1,3- or 1,4-benzene-diyl; 2,3-, 3,4-, 4,5- or 5,6-pyridine-diyl; 3,4-, 4,5- or 5,6-pyridazine-diyl; 4,5- or 5,6-pyrimidine-diyl; 2,3-pyrazinediyl; 2,3-, 3,4- or 4,5-thiophene-diyl/furane-diyl/pyrrole-diyl; 4,5-imidazole-diyl/oxazole-diyl/thiazolediyl; 3,4- or 4,5-pyrazole-diyl/isoxazolediyl/isothiazole-diyl their saturated or partially unsaturated analogues and the like. Non-vicinal disubstituted residues (diradical) are included too, such as 1,3- or 1,4-benzene-diyl.

As used herein, the expression "ring system" refers to mono- or bicyclic or polycyclic ring systems which may be saturated, partially unsaturated or unsaturated, such as aryl, $(C_3-C_{10})$ cycloalkyl, $(C_3-C_6)$ heterocycloalkyl or heteroaryl.

As used herein the terms "group", "radical" or "fragment" or "substituent" are synonymous and are intended to indicate functional groups or fragments of molecules attachable to a bond or other fragments or molecules. A dash ("-") that is not between two letters or symbols is meant to represent the point of attachment for a substituent. When graphically represented the point of attachment in a cyclic functional group is indicated with a dot ("•") localized in one of the available ring atom where the functional group is attachable to a bond or other fragment of molecules.

As used herein an oxo moiety is represented by (O) as an alternative to the other common representation, e.g. (=O). Thus, in terms of general formula, the carbonyl group is herein preferably represented as —C(O)— as an alternative to the other common representations such as —CO—, —(CO)— or —C(=O)—. In general the parenthetical group is a lateral group, not included into the chain, and parentheses are used, when deemed useful, to help clarify linear chemical formulas; e.g. the sulfonyl group —$SO_2$— might be also represented as —$S(O)_2$— to distinguish e.g. with respect to the sulfinic group —S(O)O—.

Whenever basic amino or quaternary ammonium groups are present in the compounds of formula I, physiological acceptable anions, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate may be present. Likewise, in the presence of acidic groups such as COOH groups, corresponding physiological cation salts may be present as well, for instance including alkaline or alkaline earth metal ions.

It will be apparent to those skilled in the art that compounds of formula (I) when contain one or more stereogenic center, may exist as optical stereoisomers.

Where the compounds according to the invention have at least one stereogenic center, they may accordingly exist as enantiomers. Where the compounds according to the invention possess two or more stereogenic centers, they may additionally exist as diastereoisomers. It is to be understood that all such single enantiomers, diastereoisomers and mixtures thereof in any proportion are encompassed within the scope of the present invention. The absolute configuration (R) or (S) for carbon bearing a stereogenic center is assigned on the basis of Cahn-Ingold-Prelog nomenclature rules based on groups' priorities.

Atropisomers are resulting from hindered rotation about single bonds where the steric strain barrier to rotation is high enough to allow for the isolation of the conformers (see Bringmann G et al., *Angew. Chemie Int. Ed.*, 44 (34), 5384-5427, 2005. doi:10.1002/anie.200462661, which is incorporated herein by reference in its entirety).

Oki defined atropisomers as conformers that interconvert with a half-life of more than 1000 seconds at a given temperature (Oki M, Topics in Stereochemistry 14, 1-82, 1983, which is incorporated herein by reference in its entirety).

Atropisomers differ from other chiral compounds in that in many cases they can be equilibrated thermally whereas in the other forms of chirality isomerization is usually only possible chemically.

Separation of atropisomers is possible by chiral resolution methods such as selective crystallization. In an atropo-enantioselective or atroposelective synthesis one atropisomer is formed at the expense of the other. Atroposelective synthesis may be carried out by use of chiral auxiliaries like a Corey Bakshi Shibata (CBS) catalyst, an asymmetric catalyst derived from proline, or by approaches based on thermodynamic equilibration when an isomerization reaction favors one atropisomer over the other.

Racemic forms of compounds of formula (I) as well as the individual atropisomers (substantially free of its corresponding enantiomer) and stereoisomer-enriched atropisomers mixtures are included in the scope of the present invention.

Thus, the invention further concerns the corresponding deuterated derivatives of compounds of formula (I) that are included in the scope of the present invention. It is to be understood that all preferred groups or embodiments described above and herebelow for compounds of formula I may be combined among each other and apply as well mutatis mutandis.

In a first preferred embodiment, the present invention is directed to compounds of formula (I) as above defined wherein each of $X_1$ and $X_2$ is a carbon atom; represented by the formula Ia:

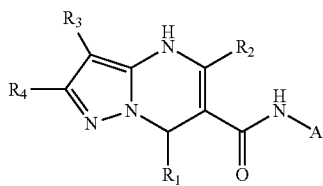

Ia wherein $R_3$ and $R_4$ are in each occurrence independently selected from the group consisting of
—H
—CN,
halogen,
—$NR_5R_6$,
($C_1$-$C_6$) alkyl,
($C_1$-$C_6$) haloalkyl,
($C_1$-$C_6$) hydroxyalkyl,
($C_1$-$C_6$) aminoalkyl,
($C_3$-$C_{10}$) cycloalkyl,
($C_2$-$C_6$) alkenyl,
($C_5$-$C_7$) cycloalkenyl,
($C_2$-$C_6$) alkynyl,
($C_2$-$C_6$) hydroxyalkynyl,
hydroxycarbonyl,
—$OR_7$
($C_1$-$C_6$) alkylthio,
($C_1$-$C_6$) alkoxy-($C_1$-$C_6$) alkyl,
($C_1$-$C_6$) alkoxycarbonyl,
($C_1$-$C_6$) aminoalkylcarbonyl,
carbamoyl,
aryl,
heteroaryl, and
($C_3$-$C_6$) heterocycloalkyl;
wherein any of said aryl, heteroaryl and ($C_3$-$C_6$) heterocycloalkyl is in its turn optionally and independently substituted with one or more groups selected from
halogen,
—OH,
($C_1$-$C_6$) alkyl,
($C_1$-$C_6$) haloalkyl,
($C_1$-$C_6$) hydroxyalkyl,
($C_1$-$C_6$) aminoalkyl,
($C_3$-$C_{10}$) cycloalkyl,
($C_2$-$C_6$) alkenyl,
($C_5$-$C_7$) cycloalkenyl,
($C_2$-$C_6$) alkynyl,
($C_2$-$C_6$) hydroxyalkynyl,
($C_1$-$C_6$) alkoxyl
($C_1$-$C_6$) aminoalkylcarbonyl;
all the other variables being as defined above;
and pharmaceutically acceptable salts thereof.

Particularly preferred in this first group of compounds of formula Ia are those wherein A is isoquinoline-6yl, 4-methylisoquinolin-6-yl, or 1H-indazole-5yl
each of $X_1$ and $X_2$ is a carbon atom;
$R_3$ is in each occurrence independently H or selected from the group consisting of
—CN,
halogen which is bromo, chloro, fluoro or iodo,
($C_1$-$C_6$) alkoxycarbonyl which is ethoxycarbonyl,
carbamoyl which is aminocarbonyl, N-(2-(dimethylamino)ethyl)aminocarbonyl or 4-methylpiperazine-1-carbonyl; and
$R_4$ is in each occurrence independently selected from the group consisting of
H;
—CN;
halogen which is bromo, chloro, fluoro or iodo;
—$NR_5R_6$ which is amino, 4-methylpiperazin-1-yl, 3-(piperidin-1-yl)propanamido, 2-(pyrrolidin-1-yl)acetamido, or ((1-methylpiperidin-4-yl)oxy)acetamido;
($C_1$-$C_6$) alkyl which is methyl, ethyl, propyl or isopropyl;
($C_1$-$C_6$) haloalkyl which is trifluoromethyl;
($C_1$-$C_6$) hydroxyalkyl which is hydroxymethyl;
($C_1$-$C_6$) alkylthio which is methylthio;
($C_1$-$C_6$) aminoalkyl which is aminomethyl, dimethylaminomethyl, 2-(N,N-dimethylamino)ethyl, N-methyl-N-(2 methoxyethyl)-2-aminoethyl, 2-(N-methyl-N-((1-methylpiperidin-4-yl)methyl)amino) ethyl, 3-methoxyazetidinyl-ethyl, 3-(N,N-dimethyl amino methyl)azetidinyl-ethyl, 3-(methoxymethyl)azetidinyl-ethyl, N-pyrrolidinyl-ethyl, N-piperidinyl-ethyl, 4-methoxypiperidinyl-ethyl, 4-(pyrrolidin-1-yl)piperidinyl-ethyl, 4-methylpiperazin-N-yl-ethyl, (1-acetylpiperazin-4-yl)-ethyl, morpholin-N-yl-ethyl, (thiomorpholine 1,1-dioxide)4yl-ethyl, (8-methyl-2,8-diazaspiro[4.5]decan-2-yl)ethyl, (3-(piperidin-1-yl)propanamido)methyl;
hydroxycarbonyl;
($C_1$-$C_6$) alkoxy-($C_1$-$C_6$) alkyl which is methoxymethyl;
($C_1$-$C_6$) alkoxycarbonyl which is ethoxycarbonyl;
carbamoyl which is aminocarbonyl, N,N dimethylaminocarbonyl, (3,3-difluorocyclobutyl)-aminocarbonyl, 3-oxo-3-(pyrrolidin-1-yl)propyl-aminocarbonyl, piperazine-1-carbonyl, morpholine-N-carbonyl, morpholine-N-carbonyl and N-(2-(dimethylamino)ethyl)aminocarbonyl, N-(2-(dimethylamino)ethyl)-N-methylaminocarbonyl, N-(3-(dimethylamino)propyl)-N-methylaminocarbonyl, 4-methylpiperazine-1-carbonyl, 4-(dimethylamino)piperidin-1-carbonyl, N-(2-(4-methylpiperazin-1-yl)ethyl)aminocarbonyl, (2-morpholino-ethyl) aminocarbonyl, N-methyl-N-(2-morpholino-ethyl)aminocarbonyl, N-(2-(piperidin-1-yl)ethyl)aminocarbonyl, N-methyl-N-(2-(piperidin-1-yl)ethyl)aminocarbonyl, N-(1-methylpiperidin-4-yl-methyl)aminocarbonyl, N-methyl-N-(1-methylpiperidin-4-yl)aminocarbonyl, N-methyl-N-(1-methylpiperidin-4-yl)aminocarbonyl, 5-methyloctahydropyrrolo[3,4-c]pyrrole-2 carbonyl, N-cyclopropyl-aminocarbonyl, 2-(piperidin-1-yl)ethyl aminocarbonyl; aryl which is p-methoxy-phenyl, m-methoxy-phenyl, o-methoxy-phenyl;
($C_3$-$C_6$) heterocycloalkyl which is oxetan-3-yl, (2-(piperidin-1-yl)ethylcarbonyl)piperidin-4-yl;
$R_1$ is selected from the group consisting of
($C_1$-$C_6$) alkyl, which is isopentanyl,
($C_3$-$C_{10}$) cycloalkyl which is cyclohexanyl, 4-(trifluoromethyl)cyclohexyl, adamantan-yl,
aryl ($C_1$-$C_6$) alkyl which is phenylethyl,
aryl which is p-methylphenyl, 4-(tert-butyl)phenyl, 4-(hydroxy)phenyl, p-fluorophenyl, p-chlorophenyl, p-bromophenyl, 4-chloro-2-fluoro-phenyl, 4-chloro-3-fluoro-phenyl, 3-fluoro-4-hydroxyphenyl, 4-(trifluoromethyl)phenyl, 3-fluoro-4-(trifluoromethyl)phenyl, 2,3-difluoro-4-(trifluoromethyl)phenyl, 4-chloro-3-(trifluoromethyl)phenyl 3-methoxy-phenyl, 2,3-dihydro-1H-inden-2yl, 3-phenoxyphenyl, 2,3-difluoro-4-methylphenyl, 3-fluoro-4-methylphenyl, 4-(difluoromethyl)-3-fluorophenyl;
heteroaryl which is piperidinyl, 2,3-dihydrobenzo[b][1,4]dioxine-2-yl, benzo[d]thiazol-2yl, 2-chloro-5-pyridinyl, 1H-indole-6yl, 2-phenylthiazol-5yl, 2-phenyloxazole-5yl, benzo[b]thiophene-6yl, 1-methyl-1H-benzo[d]imidazole-6-yl;
($C_3$-$C_6$) heterocycloalkyl which is 1-methylpiperidin-4-yl, morpholin-N-yl;
$R_2$ is selected from ($C_1$-$C_6$) alkyl which is methyl, ($C_3$-$C_{10}$) cycloalkyl which is cyclopropyl, ($C_1$-$C_6$) alkoxy-($C_1$-$C_6$) alkyl which is methoxymethyl;
and pharmaceutically acceptable salts and solvates thereof.

In a second preferred embodiment, the present invention is directed to compounds of formula (I) as above defined wherein p is 0 and each of $X_1$ and $X_2$ is nitrogen, represented by the formula Ib:

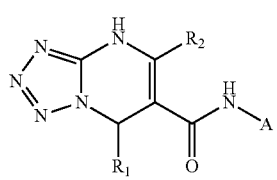

Ib all the other variables $R_1$, $R_2$, A being as defined above
and pharmaceutically acceptable salts and solvates thereof.

Particularly preferred in this second embodiment according to the invention are compounds according to formula Ib wherein
A is 1H-indazole-5yl;
each of $X_1$ and $X_2$ is a nitrogen atom;
$R_1$ is aryl which is p-fluorophenyl, p-chlorophenyl, 4-(trifluoromethyl)phenyl, 3-fluoro-4-(trifluoromethyl)phenyl;

$R_2$ is ($C_1$-$C_6$) alkyl which is methyl;
and pharmaceutically acceptable salts and solvates thereof.

Particularly preferred are compounds according to formula I wherein A is a bicyclic heteroaryl selected from 1H-indazol-5-yl, 6-fluoro-1H-indazole-5-yl, isoquinoline-6-yl, thieno[2,3-c]pyridine-2-yl, thieno[3,2-c]pyridine-2-yl, [1,2,4]triazolo[4,3-a]pyridine-7-yl, 1,6-naphthyridin-2-yl; all the other variable being as defined above, and pharmaceutically acceptable salts and solvates thereof.

An even still more preferred embodiment of the invention are the compounds of formula Ia wherein $R_3$ is H; $R_4$ is ($C_1$-$C_6$) aminoalkyl; $R_1$ is aryl substituted with one or more group selected from halogen and ($C_1$-$C_6$) haloalkyl; A is isoquinoline-6yl, $R_2$ is ($C_1$-$C_6$) alkyl which is methyl.

In a third preferred embodiment, the present invention is directed to compounds of formula (I) as above defined wherein $X_1$ is a nitrogen atom and $X_2$ is a carbon atom, represented by the formula Ic:

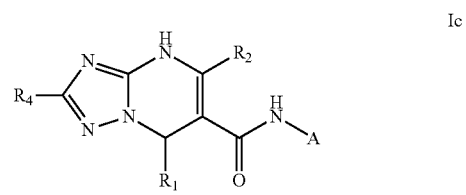

Ic all the other variables $R_1$, $R_2$, A being as defined above;
and pharmaceutically acceptable salts and solvates thereof.

The present invention also provides a pharmaceutical composition comprising a compound of formula I, Ia, or Ib or a pharmaceutically acceptable salt thereof in admixture with one or more pharmaceutically acceptable carrier or excipient, either alone or in combination with one or more active ingredient.

In one aspect the present invention provides a compound according to the invention for use as a medicament.

In a further aspect the present invention provides the use of a compound of the invention, or a pharmaceutically acceptable salt thereof, in the manufacture of a medicament for the treatment of disorders associated with ROCK enzymes mechanisms, particularly for the treatment of disorders such as pulmonary diseases.

In particular, the present invention provides compounds according to the invention for use in the prevention and/or treatment of pulmonary disease selected from the group consisting of asthma, chronic obstructive pulmonary disease COPD, idiopathic pulmonary fibrosis (IPF), pulmonary hypertension (PH) and specifically Pulmonary Arterial Hypertension (PAH).

Moreover the present invention provides a method for the prevention and/or treatment of disorders associated with ROCK enzymes mechanisms, said method comprising administering to a patient in need of such treatment a therapeutically effective amount of a compound of the invention.

In particular the invention provides methods for the prevention and/or treatment wherein the disorder is asthma, chronic obstructive pulmonary disease COPD idiopathic pulmonary fibrosis (IPF), Pulmonary hypertension (PH) and specifically Pulmonary Arterial Hypertension (PAH).

According to specific embodiments, the present invention provides the compounds listed in the table below and pharmaceutical acceptable salts thereof.

| Example | Comments | Name |
|---|---|---|
| 1 | | ethyl 6-(isoquinolin-6-ylcarbamoyl)-5-methyl-7-(4-(trifluoromethyl)phenyl)-4,7-dihydropyrazolo[1,5-a]pyrimidine-2-carboxylate |
| 2 | | ethyl 6-((1H-indazol-5-yl)carbamoyl)-5-methyl-7-(4-(trifluoromethyl)phenyl)-4,7-dihydropyrazolo[1,5-a]pyrimidine-2-carboxylate |
| 3 | | ethyl 6-((1H-indazol-5-yl)carbamoyl)-5-methyl-7-(p-tolyl)-4,7-dihydropyrazolo[1,5-a]pyrimidine-2-carboxylate |
| 4 | | ethyl 6-((1H-indazol-5-yl)carbamoyl)-7-(4-fluorophenyl)-5-methyl-4,7-dihydropyrazolo[1,5-a]pyrimidine-2-carboxylate |
| 5 | | ethyl 6-((1H-indazol-5-yl)carbamoyl)-7-(6-chloropyridin-3-yl)-5-methyl-4,7-dihydropyrazolo[1,5-a]pyrimidine-2-carboxylate |
| 6 | | ethyl 6-((1H-indazol-5-yl)carbamoyl)-7-(3-methoxyphenyl)-5-methyl-4,7-dihydropyrazolo[1,5-a]pyrimidine-2-carboxylate |
| 7 | | ethyl 6-((1H-indazol-5-yl)carbamoyl)-7-(4-chloro-2-fluorophenyl)-5-methyl-4,7-dihydropyrazolo[1,5-a]pyrimidine-2-carboxylate |
| 8 | | ethyl 7-(benzo[d]thiazol-2-yl)-6-(isoquinolin-6-ylcarbamoyl)-5-methyl-4,7-dihydropyrazolo[1,5-a]pyrimidine-2-carboxylate |
| 9 | | ethyl 7-(4-hydroxyphenyl)-6-(isoquinolin-6-ylcarbamoyl)-5-methyl-4,7-dihydropyrazolo[1,5-a]pyrimidine-2-carboxylate |
| 10 | | ethyl 7-(3-fluoro-4-hydroxyphenyl)-6-(isoquinolin-6-ylcarbamoyl)-5-methyl-4,7-dihydropyrazolo[1,5-a]pyrimidine-2-carboxylate |
| 11 | | ethyl 6-((1H-indazol-5-yl)carbamoyl)-5-methyl-7-(tetrahydro-2H-pyran-4-yl)-4,7-dihydropyrazolo[1,5-a]pyrimidine-2-carboxylate |
| 12 | | ethyl 6-((1H-indazol-5-yl)carbamoyl)-5-methyl-7-(1-methylpiperidin-4-yl)-4,7-dihydropyrazolo[1,5-a]pyrimidine-2-carboxylate |
| 13 | | ethyl 6-((1H-indazol-5-yl)carbamoyl)-7-isobutyl-5-methyl-4,7-dihydropyrazolo[1,5-a]pyrimidine-2-carboxylate |
| 14 | | ethyl 6-((1H-indazol-5-yl)carbamoyl)-7-cyclohexyl-5-methyl-4,7-dihydropyrazolo[1,5-a]pyrimidine-2-carboxylate |
| 15 | | ethyl 6-([1,2,4]triazolo[4,3-a]pyridin-7-ylcarbamoyl)-7-(3-fluoro-4-(trifluoromethyl)phenyl)-5-methyl-4,7-dihydropyrazolo[1,5-a]pyrimidine-2-carboxylate |
| 16 | | ethyl 6-((1H-indazol-5-yl)carbamoyl)-3-cyano-5-methyl-7-(4-(trifluoromethyl)phenyl)-4,7-dihydropyrazolo[1,5-a]pyrimidine-2-carboxylate |
| 17 | | ethyl 6-((1H-indazol-5-yl)carbamoyl)-7-(4-fluorophenyl)-5-methyl-4,7-dihydropyrazolo[1,5-a]pyrimidine-3-carboxylate |
| 18 | | 3-cyano-7-(4-fluorophenyl)-N-(1H-indazol-5-yl)-5-methyl-4,7-dihydropyrazolo[1,5-a]pyrimidine-6-carboxamide |
| 19 | | 7-(4-fluorophenyl)-N6-(1H-indazol-5-yl)-5-methyl-4,7-dihydropyrazolo[1,5-a]pyrimidine-3,6-dicarboxamide |
| 20 | | 7-(4-fluorophenyl)-N-(1H-indazol-5-yl)-2-(4-methoxyphenyl)-5-methyl-4,7-dihydropyrazolo[1,5-a]pyrimidine-6-carboxamide |
| 21 | | 7-(4-fluorophenyl)-N-(1H-indazol-5-yl)-2-(2-methoxyphenyl)-5-methyl-4,7-dihydropyrazolo[1,5-a]pyrimidine-6-carboxamide |
| 22 | | 3-bromo-7-(4-fluorophenyl)-N-(1H-indazol-5-yl)-5-methyl-4,7-dihydropyrazolo[1,5-a]pyrimidine-6-carboxamide |
| 23 | | 7-(4-fluorophenyl)-N-(1H-indazol-5-yl)-5-methyl-4,7-dihydrotetrazolo[1,5-a]pyrimidine-6-carboxamide |
| 24 | | 7-(4-chlorophenyl)-N-(1H-indazol-5-yl)-5-methyl-4,7-dihydrotetrazolo[1,5-a]pyrimidine-6-carboxamide |
| 25 | | 7-(3-fluoro-4-(trifluoromethyl)phenyl)-N-(1H-indazol-5-yl)-5-methyl-4,7-dihydrotetrazolo[1,5-a]pyrimidine-6-carboxamide |
| 26 | | 7-(2-fluoro-4-(trifluoromethyl)phenyl)-N-(1H-indazol-5-yl)-5-methyl-4,7-dihydrotetrazolo[1,5-a]pyrimidine-6-carboxamide |
| 27 | | N-(1H-indazol-5-yl)-5-methyl-7-(4-(trifluoromethyl)phenyl)-4,7-dihydrotetrazolo[1,5-a]pyrimidine-6-carboxamide |
| 28 | | 7-(4-fluorophenyl)-N-(1H-indazol-5-yl)-2,5-dimethyl-4,7-dihydropyrazolo[1,5-a]pyrimidine-6-carboxamide |

-continued

| Example | Comments | Name |
|---|---|---|
| 29 | | 2-(tert-butyl)-7-(4-fluorophenyl)-N-(1H-indazol-5-yl)-5-methyl-4,7-dihydropyrazolo[1,5-a]pyrimidine-6-carboxamide |
| 30 | | 2-bromo-7-(4-fluorophenyl)-N-(1H-indazol-5-yl)-5-methyl-4,7-dihydropyrazolo[1,5-a]pyrimidine-6-carboxamide |
| 31 | | 2-cyano-7-(4-fluorophenyl)-N-(1H-indazol-5-yl)-5-methyl-4,7-dihydropyrazolo[1,5-a]pyrimidine-6-carboxamide |
| 32 | | 7-(6-chloropyridin-3-yl)-N-(1H-indazol-5-yl)-5-methyl-2-(trifluoromethyl)-4,7-dihydropyrazolo[1,5-a]pyrimidine-6-carboxamide |
| 33 | | N-(1H-indazol-5-yl)-5-methyl-7-(1-methylpiperidin-4-yl)-2-(trifluoromethyl)-4,7-dihydropyrazolo[1,5-a]pyrimidine-6-carboxamide |
| 34 | | 2-cyano-N-(1H-indazol-5-yl)-5-methyl-7-(4-(trifluoromethyl)phenyl)-4,7-dihydropyrazolo[1,5-a]pyrimidine-6-carboxamide |
| 35 | | N-(1H-indazol-5-yl)-2-(methoxymethyl)-5-methyl-7-(4-(trifluoromethyl)phenyl)-4,7-dihydropyrazolo[1,5-a]pyrimidine-6-carboxamide |
| 36 | | 7-(3-fluoro-4-(trifluoromethyl)phenyl)-N-(isoquinolin-6-yl)-2-(methoxymethyl)-5-methyl-4,7-dihydropyrazolo[1,5-a]pyrimidine-6-carboxamide |
| 37 | | 2-(2-(dimethylamino)ethyl)-7-(3-fluoro-4-(trifluoromethyl)phenyl)-N-(isoquinolin-6-yl)-5-methyl-4,7-dihydropyrazolo[1,5-a]pyrimidine-6-carboxamide |
| 38 | | 7-(1H-indol-6-yl)-N-(isoquinolin-6-yl)-2-(methoxymethyl)-5-methyl-4,7-dihydropyrazolo[1,5-a]pyrimidine-6-carboxamide |
| 39 | | 7-(6-chloropyridin-3-yl)-N-(6-fluoro-1H-indazol-5-yl)-5-methyl-2-(trifluoromethyl)-4,7-dihydropyrazolo[1,5-a]pyrimidine-6-carboxamide |
| 40 | | N-(6-fluoro-1H-indazol-5-yl)-7-(3-fluoro-4-(trifluoromethyl)phenyl)-5-methyl-4,7-dihydrotetrazolo[1,5-a]pyrimidine-6-carboxamide |
| 41 | | ethyl 7-(3-fluoro-4-(trifluoromethyl)phenyl)-5-methyl-6-(thieno[3,2-c]pyridin-2-ylcarbamoyl)-4,7-dihydropyrazolo[1,5-a]pyrimidine-2-carboxylate |
| 42 | | ethyl 7-(3-fluoro-4-(trifluoromethyl)phenyl)-5-methyl-6-(thieno[2,3-c]pyridin-2-ylcarbamoyl)-4,7-dihydropyrazolo[1,5-a]pyrimidine-2-carboxylate |
| 43 | | 2-(hydroxymethyl)-N-(isoquinolin-6-yl)-5-methyl-7-(4-(trifluoromethyl)phenyl)-4,7-dihydropyrazolo[1,5-a]pyrimidine-6-carboxamide |
| 44 | | 2-(hydroxymethyl)-N-(isoquinolin-6-yl)-5-methyl-7-(1-methyl-1H-indol-4-yl)-4,7-dihydropyrazolo[1,5-a]pyrimidine-6-carboxamide |
| 45 | | 2-(hydroxymethyl)-N-(isoquinolin-6-yl)-5-methyl-7-(1-methyl-1H-benzo[d]imidazol-6-yl)-4,7-dihydropyrazolo[1,5-a]pyrimidine-6-carboxamide |
| 46 | | 7-(benzo[b]thiophen-6-yl)-2-(hydroxymethyl)-N-(isoquinolin-6-yl)-5-methyl-4,7-dihydropyrazolo[1,5-a]pyrimidine-6-carboxamide |
| 47 | | 7-(4-chloro-3-(trifluoromethyl)phenyl)-2-(hydroxymethyl)-N-(isoquinolin-6-yl)-5-methyl-4,7-dihydropyrazolo[1,5-a]pyrimidine-6-carboxamide |
| 48 | | 7-((3r,5r,7r)-adamantan-1-yl)-2-(hydroxymethyl)-N-(isoquinolin-6-yl)-5-methyl-4,7-dihydropyrazolo[1,5-a]pyrimidine-6-carboxamide |
| 49 | | 2-(hydroxymethyl)-N-(isoquinolin-6-yl)-5-methyl-7-(2-phenyloxazol-5-yl)-4,7-dihydropyrazolo[1,5-a]pyrimidine-6-carboxamide |
| 50 | | 2-(hydroxymethyl)-N-(isoquinolin-6-yl)-5-methyl-7-(3-phenoxyphenyl)-4,7-dihydropyrazolo[1,5-a]pyrimidine-6-carboxamide |
| 51 | | 2-(hydroxymethyl)-N-(isoquinolin-6-yl)-5-methyl-7-(3-(trifluoromethyl)phenyl)-4,7-dihydropyrazolo[1,5-a]pyrimidine-6-carboxamide |
| 52 | | 2-(hydroxymethyl)-N-(isoquinolin-6-yl)-5-methyl-7-(2-phenylthiazol-5-yl)-4,7-dihydropyrazolo[1,5-a]pyrimidine-6-carboxamide |
| 53 | | 2-(hydroxymethyl)-N-(isoquinolin-6-yl)-5-methyl-7-phenethyl-4,7-dihydropyrazolo[1,5-a]pyrimidine-6-carboxamide |

| Example | Comments | Name |
|---|---|---|
| 54 | | 7-(4-(tert-butyl)phenyl)-2-(hydroxymethyl)-N-(isoquinolin-6-yl)-5-methyl-4,7-dihydropyrazolo[1,5-a]pyrimidine-6-carboxamide |
| 55 | | 7-(4-bromo-3-fluorophenyl)-2-(hydroxymethyl)-N-(isoquinolin-6-yl)-5-methyl-4,7-dihydropyrazolo[1,5-a]pyrimidine-6-carboxamide |
| 56 | | 7-(2,3-difluoro-4-(trifluoromethyl)phenyl)-2-(hydroxymethyl)-N-(isoquinolin-6-yl)-5-methyl-4,7-dihydropyrazolo[1,5-a]pyrimidine-6-carboxamide |
| 57 | | 7-(4-chloro-3-fluorophenyl)-2-(hydroxymethyl)-N-(isoquinolin-6-yl)-5-methyl-4,7-dihydropyrazolo[1,5-a]pyrimidine-6-carboxamide |
| 58 | | 7-(3-fluoro-4-methylphenyl)-2-(hydroxymethyl)-N-(isoquinolin-6-yl)-5-methyl-4,7-dihydropyrazolo[1,5-a]pyrimidine-6-carboxamide |
| 59 | | 7-(2-fluoro-4-methylphenyl)-2-(hydroxymethyl)-N-(isoquinolin-6-yl)-5-methyl-4,7-dihydropyrazolo[1,5-a]pyrimidine-6-carboxamide |
| 60 | | 7-(2,3-dihydro-1H-inden-2-yl)-2-(hydroxymethyl)-N-(isoquinolin-6-yl)-5-methyl-4,7-dihydropyrazolo[1,5-a]pyrimidine-6-carboxamide |
| 61 | | 7-(4-bromophenyl)-2-(hydroxymethyl)-N-(isoquinolin-6-yl)-5-methyl-4,7-dihydropyrazolo[1,5-a]pyrimidine-6-carboxamide |
| 62 | | 7-(4-chlorophenyl)-2-(hydroxymethyl)-N-(isoquinolin-6-yl)-5-methyl-4,7-dihydropyrazolo[1,5-a]pyrimidine-6-carboxamide |
| 63 | | 2-(hydroxymethyl)-7-(1H-indol-6-yl)-N-(isoquinolin-6-yl)-5-methyl-4,7-dihydropyrazolo[1,5-a]pyrimidine-6-carboxamide |
| 64 | | 7-(4-chloro-2-fluorophenyl)-2-(hydroxymethyl)-N-(isoquinolin-6-yl)-5-methyl-4,7-dihydropyrazolo[1,5-a]pyrimidine-6-carboxamide |
| 65 | | 7-(3-fluoro-4-(trifluoromethyl)phenyl)-2-(hydroxymethyl)-N-(isoquinolin-6-yl)-5-methyl-4,7-dihydropyrazolo[1,5-a]pyrimidine-6-carboxamide |
| 66 | | 2-(hydroxymethyl)-N-(isoquinolin-6-yl)-5-methyl-7-(p-tolyl)-4,7-dihydropyrazolo[1,5-a]pyrimidine-6-carboxamide |
| 67 | | 2-(hydroxymethyl)-N-(1H-indazol-5-yl)-5-methyl-7-(p-tolyl)-4,7-dihydropyrazolo[1,5-a]pyrimidine-6-carboxamide |
| 68 | | 7-(4-chloro-2-fluorophenyl)-2-(hydroxymethyl)-N-(1H-indazol-5-yl)-5-methyl-4,7-dihydropyrazolo[1,5-a]pyrimidine-6-carboxamide |
| 69 | | 2-(hydroxymethyl)-N-(1H-indazol-5-yl)-5-methyl-7-(4-(trifluoromethyl)phenyl)-4,7-dihydropyrazolo[1,5-a]pyrimidine-6-carboxamide |
| 70 | | 7-(6-chloropyridin-3-yl)-2-(hydroxymethyl)-N-(1H-indazol-5-yl)-5-methyl-4,7-dihydropyrazolo[1,5-a]pyrimidine-6-carboxamide |
| 71 | | 7-(4-fluorophenyl)-2-(hydroxymethyl)-N-(1H-indazol-5-yl)-5-methyl-4,7-dihydropyrazolo[1,5-a]pyrimidine-6-carboxamide |
| 72A | first stereoisomer | 7-(2,3-dihydrobenzo[b][1,4]dioxin-2-yl)-2-(hydroxymethyl)-N-(isoquinolin-6-yl)-5-methyl-4,7-dihydropyrazolo[1,5-a]pyrimidine-6-carboxamide |
| 72B | second stereoisomer | 7-(2,3-dihydrobenzo[b][1,4]dioxin-2-yl)-2-(hydroxymethyl)-N-(isoquinolin-6-yl)-5-methyl-4,7-dihydropyrazolo[1,5-a]pyrimidine-6-carboxamide |
| 72C | third stereoisomer | 7-(2,3-dihydrobenzo[b][1,4]dioxin-2-yl)-2-(hydroxymethyl)-N-(isoquinolin-6-yl)-5-methyl-4,7-dihydropyrazolo[1,5-a]pyrimidine-6-carboxamide |
| 72D | fourth stereoisomer | 7-(2,3-dihydrobenzo[b][1,4]dioxin-2-yl)-2-(hydroxymethyl)-N-(isoquinolin-6-yl)-5-methyl-4,7-dihydropyrazolo[1,5-a]pyrimidine-6-carboxamide |
| 73 | | 6-((1H-indazol-5-yl)carbamoyl)-5-methyl-7-(4-(trifluoromethyl)phenyl)-4,7-dihydropyrazolo[1,5-a]pyrimidine-2-carboxylic acid |
| 74 | | 6-((1H-indazol-5-yl)carbamoyl)-5-methyl-7-(p-tolyl)-4,7-dihydropyrazolo[1,5-a]pyrimidine-2-carboxylic acid |
| 75 | | 6-((1H-indazol-5-yl)carbamoyl)-7-(4-fluorophenyl)-5-methyl-4,7-dihydropyrazolo[1,5-a]pyrimidine-2-carboxylic acid |
| 76 | | N-(1H-indazol-5-yl)-5-methyl-2-(4-methylpiperazine-1-carbonyl)-7-(4-(trifluoromethyl)phenyl)-4,7-dihydropyrazolo[1,5-a]pyrimidine-6-carboxamide |

| Example | Comments | Name |
|---|---|---|
| 77 | | 7-(3-fluoro-4-(trifluoromethyl)phenyl)-N6-(isoquinolin-6-yl)-5-methyl-N2-(2-(piperidin-1-yl)ethyl)-4,7-dihydropyrazolo[1,5-a]pyrimidine-2,6-dicarboxamide |
| 78 | | 7-(3-fluoro-4-(trifluoromethyl)phenyl)-N6-(isoquinolin-6-yl)-N2,5-dimethyl-N2-(2-(piperidin-1-yl)ethyl)-4,7-dihydropyrazolo[1,5-a]pyrimidine-2,6-dicarboxamide |
| 79 | | N2-(2-(dimethylamino)ethyl)-7-(3-fluoro-4-(trifluoromethyl)phenyl)-N6-(isoquinolin-6-yl)-5-methyl-4,7-dihydropyrazolo[1,5-a]pyrimidine-2,6-dicarboxamide |
| 80 | | N2-(2-(dimethylamino)ethyl)-7-(3-fluoro-4-(trifluoromethyl)phenyl)-N6-(isoquinolin-6-yl)-N2,5-dimethyl-4,7-dihydropyrazolo[1,5-a]pyrimidine-2,6-dicarboxamide |
| 81 | | 7-(3-fluoro-4-(trifluoromethyl)phenyl)-N6-(isoquinolin-6-yl)-5-methyl-N2-(2-(4-methylpiperazin-1-yl)ethyl)-4,7-dihydropyrazolo[1,5-a]pyrimidine-2,6-dicarboxamide |
| 82 | | 7-(3-fluoro-4-(trifluoromethyl)phenyl)-N6-(isoquinolin-6-yl)-5-methyl-N2-(2-morpholinoethyl)-4,7-dihydropyrazolo[1,5-a]pyrimidine-2,6-dicarboxamide |
| 83 | | 7-(3-fluoro-4-(trifluoromethyl)phenyl)-N6-(isoquinolin-6-yl)-N2,5-dimethyl-N2-(2-morpholinoethyl)-4,7-dihydropyrazolo[1,5-a]pyrimidine-2,6-dicarboxamide |
| 84 | | 7-(3-fluoro-4-(trifluoromethyl)phenyl)-N6-(isoquinolin-6-yl)-5-methyl-N2-((1-methylpiperidin-4-yl)methyl)-4,7-dihydropyrazolo[1,5-a]pyrimidine-2,6-dicarboxamide |
| 85 | | 7-(3-fluoro-4-(trifluoromethyl)phenyl)-N6-(isoquinolin-6-yl)-N2,5-dimethyl-N2-((1-methylpiperidin-4-yl)methyl)-4,7-dihydropyrazolo[1,5-a]pyrimidine-2,6-dicarboxamide |
| 86 | | 7-(3-fluoro-4-(trifluoromethyl)phenyl)-N-(isoquinolin-6-yl)-5-methyl-2-(5-methyloctahydropyrrolo[3,4-c]pyrrole-2-carbonyl)-4,7-dihydropyrazolo[1,5-a]pyrimidine-6-carboxamide |
| 87 | | 2-(4-(dimethylamino)piperidine-1-carbonyl)-7-(3-fluoro-4-(trifluoromethyl)phenyl)-N-(isoquinolin-6-yl)-5-methyl-4,7-dihydropyrazolo[1,5-a]pyrimidine-6-carboxamide |
| 88 | | 7-(3-fluoro-4-(trifluoromethyl)phenyl)-N6-(isoquinolin-6-yl)-N2,5-dimethyl-N2-(1-methylpiperidin-4-yl)-4,7-dihydropyrazolo[1,5-a]pyrimidine-2,6-dicarboxamide |
| 89 | | N2-(3-(dimethylamino)propyl)-7-(3-fluoro-4-(trifluoromethyl)phenyl)-N6-(isoquinolin-6-yl)-N2,5-dimethyl-4,7-dihydropyrazolo[1,5-a]pyrimidine-2,6-dicarboxamide |
| 90 | | 7-(4-fluorophenyl)-N-(1H-indazol-5-yl)-5-methyl-2-(morpholine-4-carbonyl)-4,7-dihydropyrazolo[1,5-a]pyrimidine-6-carboxamide |
| 91 | | 7-(4-fluorophenyl)-N-(1H-indazol-5-yl)-5-methyl-3-(4-methylpiperazine-1-carbonyl)-4,7-dihydropyrazolo[1,5-a]pyrimidine-6-carboxamide |
| 92 | | N3-(2-(dimethylamino)ethyl)-7-(4-fluorophenyl)-N6-(1H-indazol-5-yl)-5-methyl-4,7-dihydropyrazolo[1,5-a]pyrimidine-3,6-dicarboxamide |
| 93 | | 7-(4-fluorophenyl)-N-(1H-indazol-5-yl)-5-methyl-2-(piperazine-1-carbonyl)-4,7-dihydropyrazolo[1,5-a]pyrimidine-6-carboxamide |
| 94 | | 2-((dimethylamino)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide |
| 95 | | 7-(3-fluoro-4-(trifluoromethyl)phenyl)-N-(isoquinolin-6-yl)-5-methyl-2-(morpholinomethyl)-4,7-dihydropyrazolo[1,5-a]pyrimidine-6-carboxamide |
| 96 | | 7-(3-fluoro-4-(trifluoromethyl)phenyl)-N-(isoquinolin-6-yl)-5-methyl-2-((4-methylpiperazin-1-yl)methyl)-4,7-dihydropyrazolo[1,5-a]pyrimidine-6-carboxamide |
| 97 | | 7-(3-fluoro-4-(trifluoromethyl)phenyl)-N-(isoquinolin-6-yl)-5-methyl-2-(piperidin-1-ylmethyl)-4,7-dihydropyrazolo[1,5-a]pyrimidine-6-carboxamide |
| 98 | | 7-(3-fluoro-4-(trifluoromethyl)phenyl)-N-(isoquinolin-6-yl)-2-(((2-methoxyethyl)(methyl)amino)methyl)-5-methyl-4,7-dihydropyrazolo[1,5-a]pyrimidine-6-carboxamide |
| 99 | | 7-(3-fluoro-4-(trifluoromethyl)phenyl)-N-(isoquinolin-6-yl)-2-((4-methoxypiperidin-1-yl)methyl)-5-methyl-4,7-dihydropyrazolo[1,5-a]pyrimidine-6-carboxamide |
| 100 | | 7-(3-fluoro-4-(trifluoromethyl)phenyl)-N-(isoquinolin-6-yl)-2-((3-methoxyazetidin-1-yl)methyl)-5-methyl-4,7-dihydropyrazolo[1,5-a]pyrimidine-6-carboxamide |

-continued

| Example | Comments | Name |
|---|---|---|
| 101 | | 7-(3-fluoro-4-(trifluoromethyl)phenyl)-N-(isoquinolin-6-yl)-2-((3-(methoxymethyl)azetidin-1-yl)methyl)-5-methyl-4,7-dihydropyrazolo[1,5-a]pyrimidine-6-carboxamide |
| 102 | | 7-(3-fluoro-4-(trifluoromethyl)phenyl)-N-(isoquinolin-6-yl)-5-methyl-2-(pyrrolidin-1-ylmethyl)-4,7-dihydropyrazolo[1,5-a]pyrimidine-6-carboxamide |
| 103 | | 7-(3-fluoro-4-(trifluoromethyl)phenyl)-N-(isoquinolin-6-yl)-5-methyl-2-((8-methyl-2,8-diazaspiro[4.5]decan-2-yl)methyl)-4,7-dihydropyrazolo[1,5-a]pyrimidine-6-carboxamide |
| 104 | | 7-(3-fluoro-4-(trifluoromethyl)phenyl)-N-(isoquinolin-6-yl)-5-methyl-2-((methyl((1-methylpiperidin-4-yl)methyl)amino)methyl)-4,7-dihydropyrazolo[1,5-a]pyrimidine-6-carboxamide |
| 105 | | 7-(3-fluoro-4-(trifluoromethyl)phenyl)-N-(isoquinolin-6-yl)-5-methyl-2-((4-(pyrrolidin-1-yl)piperidin-1-yl)methyl)-4,7-dihydropyrazolo[1,5-a]pyrimidine-6-carboxamide |
| 106 | | 2-((3-((dimethylamino)methyl)azetidin-1-yl)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide |
| 107 | | N-(1H-indazol-5-yl)-5-methyl-2-(morpholinomethyl)-7-(4-(trifluoromethyl)phenyl)-4,7-dihydropyrazolo[1,5-a]pyrimidine-6-carboxamide |
| 108 | | 2-((1,1-dioxidothiomorpholino)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide |
| 109 | | 2-((4-acetylpiperazin-1-yl)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide |
| 110 | | 2-((dimethylamino)methyl)-7-(3-fluoro-4-methylphenyl)-N-(isoquinolin-6-yl)-5-methyl-4,7-dihydropyrazolo[1,5-a]pyrimidine-6-carboxamide |
| 111 | | 2-(aminomethyl)-N-(1H-indazol-5-yl)-5-methyl-7-(4-(trifluoromethyl)phenyl)-4,7-dihydropyrazolo[1,5-a]pyrimidine-6-carboxamide |
| 112 | | 2-(aminomethyl)-7-(3-fluoro-4-(trifluoromethyl)phenyl)-N-(isoquinolin-6-yl)-5-methyl-4,7-dihydropyrazolo[1,5-a]pyrimidine-6-carboxamide |
| 4A | first eluting enantiomer | ethyl 6-((1H-indazol-5-yl)carbamoyl)-7-(4-fluorophenyl)-5-methyl-4,7-dihydropyrazolo[1,5-a]pyrimidine-2-carboxylate |
| 4B | second eluting enantiomer | ethyl 6-((1H-indazol-5-yl)carbamoyl)-7-(4-fluorophenyl)-5-methyl-4,7-dihydropyrazolo[1,5-a]pyrimidine-2-carboxylate |
| 7A | first eluting enantiomer | ethyl 6-((1H-indazol-5-yl)carbamoyl)-7-(4-chloro-2-fluorophenyl)-5-methyl-4,7-dihydropyrazolo[1,5-a]pyrimidine-2-carboxylate |
| 7B | second eluting enantiomer | ethyl 6-((1H-indazol-5-yl)carbamoyl)-7-(4-chloro-2-fluorophenyl)-5-methyl-4,7-dihydropyrazolo[1,5-a]pyrimidine-2-carboxylate |
| 23A | first eluting enantiomer | 7-(4-fluorophenyl)-N-(1H-indazol-5-yl)-5-methyl-4,7-dihydrotetrazolo[1,5-a]pyrimidine-6-carboxamide |
| 23B | second eluting enantiomer | 7-(4-fluorophenyl)-N-(1H-indazol-5-yl)-5-methyl-4,7-dihydrotetrazolo[1,5-a]pyrimidine-6-carboxamide |
| 24A | first eluting enantiomer | 7-(4-chlorophenyl)-N-(1H-indazol-5-yl)-5-methyl-4,7-dihydrotetrazolo[1,5-a]pyrimidine-6-carboxamide |
| 24B | second eluting enantiomer | 7-(4-chlorophenyl)-N-(1H-indazol-5-yl)-5-methyl-4,7-dihydrotetrazolo[1,5-a]pyrimidine-6-carboxamide |
| 25A | first eluting enantiomer | 7-(3-fluoro-4-(trifluoromethyl)phenyl)-N-(1H-indazol-5-yl)-5-methyl-4,7-dihydrotetrazolo[1,5-a]pyrimidine-6-carboxamide |
| 25B | second eluting enantiomer | 7-(3-fluoro-4-(trifluoromethyl)phenyl)-N-(1H-indazol-5-yl)-5-methyl-4,7-dihydrotetrazolo[1,5-a]pyrimidine-6-carboxamide |
| 26A | first eluting enantiomer | 7-(2-fluoro-4-(trifluoromethyl)phenyl)-N-(1H-indazol-5-yl)-5-methyl-4,7-dihydrotetrazolo[1,5-a]pyrimidine-6-carboxamide |
| 26B | second eluting enantiomer | 7-(2-fluoro-4-(trifluoromethyl)phenyl)-N-(1H-indazol-5-yl)-5-methyl-4,7-dihydrotetrazolo[1,5-a]pyrimidine-6-carboxamide |
| 27A | first eluting enantiomer | N-(1H-indazol-5-yl)-5-methyl-7-(4-(trifluoromethyl)phenyl)-4,7-dihydrotetrazolo[1,5-a]pyrimidine-6-carboxamide |

-continued

| Example | Comments | Name |
|---|---|---|
| 27B | second eluting enantiomer | N-(1H-indazol-5-yl)-5-methyl-7-(4-(trifluoromethyl)phenyl)-4,7-dihydrotetrazolo[1,5-a]pyrimidine-6-carboxamide |
| 32A | first eluting enantiomer | 7-(6-chloropyridin-3-yl)-N-(1H-indazol-5-yl)-5-methyl-2-(trifluoromethyl)-4,7-dihydropyrazolo[1,5-a]pyrimidine-6-carboxamide |
| 32B | second eluting enantiomer | 7-(6-chloropyridin-3-yl)-N-(1H-indazol-5-yl)-5-methyl-2-(trifluoromethyl)-4,7-dihydropyrazolo[1,5-a]pyrimidine-6-carboxamide |
| 40A | first eluting enantiomer | N-(6-fluoro-1H-indazol-5-yl)-7-(3-fluoro-4-(trifluoromethyl)phenyl)-5-methyl-4,7-dihydrotetrazolo[1,5-a]pyrimidine-6-carboxamide |
| 40B | second eluting enantiomer | N-(6-fluoro-1H-indazol-5-yl)-7-(3-fluoro-4-(trifluoromethyl)phenyl)-5-methyl-4,7-dihydrotetrazolo[1,5-a]pyrimidine-6-carboxamide |
| 43A | first eluting enantiomer | 2-(hydroxymethyl)-N-(isoquinolin-6-yl)-5-methyl-7-(4-(trifluoromethyl)phenyl)-4,7-dihydropyrazolo[1,5-a]pyrimidine-6-carboxamide |
| 43B | second eluting enantiomer | 2-(hydroxymethyl)-N-(isoquinolin-6-yl)-5-methyl-7-(4-(trifluoromethyl)phenyl)-4,7-dihydropyrazolo[1,5-a]pyrimidine-6-carboxamide |
| 60A | first eluting enantiomer | 7-(2,3-dihydro-1H-inden-2-yl)-2-(hydroxymethyl)-N-(isoquinolin-6-yl)-5-methyl-4,7-dihydropyrazolo[1,5-a]pyrimidine-6-carboxamide |
| 60B | second eluting enantiomer | 7-(2,3-dihydro-1H-inden-2-yl)-2-(hydroxymethyl)-N-(isoquinolin-6-yl)-5-methyl-4,7-dihydropyrazolo[1,5-a]pyrimidine-6-carboxamide |
| 61A | first eluting enantiomer | 7-(4-bromophenyl)-2-(hydroxymethyl)-N-(isoquinolin-6-yl)-5-methyl-4,7-dihydropyrazolo[1,5-a]pyrimidine-6-carboxamide |
| 61B | second eluting enantiomer | 7-(4-bromophenyl)-2-(hydroxymethyl)-N-(isoquinolin-6-yl)-5-methyl-4,7-dihydropyrazolo[1,5-a]pyrimidine-6-carboxamide |
| 62A | first eluting enantiomer | 7-(4-chlorophenyl)-2-(hydroxymethyl)-N-(isoquinolin-6-yl)-5-methyl-4,7-dihydropyrazolo[1,5-a]pyrimidine-6-carboxamide |
| 62B | second eluting enantiomer | 7-(4-chlorophenyl)-2-(hydroxymethyl)-N-(isoquinolin-6-yl)-5-methyl-4,7-dihydropyrazolo[1,5-a]pyrimidine-6-carboxamide |
| 65A | first eluting enantiomer | 7-(3-fluoro-4-(trifluoromethyl)phenyl)-2-(hydroxymethyl)-N-(isoquinolin-6-yl)-5-methyl-4,7-dihydropyrazolo[1,5-a]pyrimidine-6-carboxamide |
| 65B | second eluting enantiomer | 7-(3-fluoro-4-(trifluoromethyl)phenyl)-2-(hydroxymethyl)-N-(isoquinolin-6-yl)-5-methyl-4,7-dihydropyrazolo[1,5-a]pyrimidine-6-carboxamide |
| 69A | first eluting enantiomer | 2-(hydroxymethyl)-N-(1H-indazol-5-yl)-5-methyl-7-(4-(trifluoromethyl)phenyl)-4,7-dihydropyrazolo[1,5-a]pyrimidine-6-carboxamide |
| 69B | second eluting enantiomer | 2-(hydroxymethyl)-N-(1H-indazol-5-yl)-5-methyl-7-(4-(trifluoromethyl)phenyl)-4,7-dihydropyrazolo[1,5-a]pyrimidine-6-carboxamide |
| 71A | first eluting enantiomer | 7-(4-fluorophenyl)-2-(hydroxymethyl)-N-(1H-indazol-5-yl)-5-methyl-4,7-dihydropyrazolo[1,5-a]pyrimidine-6-carboxamide |
| 71B | second eluting enantiomer | 7-(4-fluorophenyl)-2-(hydroxymethyl)-N-(1H-indazol-5-yl)-5-methyl-4,7-dihydropyrazolo[1,5-a]pyrimidine-6-carboxamide |
| 78A | first eluting enantiomer | 7-(3-fluoro-4-(trifluoromethyl)phenyl)-N6-(isoquinolin-6-yl)-N2,5-dimethyl-N2-(2-(piperidin-1-yl)ethyl)-4,7-dihydropyrazolo[1,5-a]pyrimidine-2,6-dicarboxamide |
| 78B | second eluting enantiomer | 7-(3-fluoro-4-(trifluoromethyl)phenyl)-N6-(isoquinolin-6-yl)-N2,5-dimethyl-N2-(2-(piperidin-1-yl)ethyl)-4,7-dihydropyrazolo[1,5-a]pyrimidine-2,6-dicarboxamide |
| 94A | first eluting enantiomer | 2-((dimethylamino)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide |
| 94B | second eluting enantiomer | 2-((dimethylamino)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide |
| 96A | first eluting enantiomer | 7-(3-fluoro-4-(trifluoromethyl)phenyl)-N-(isoquinolin-6-yl)-5-methyl-2-((4-methylpiperazin-1-yl)methyl)-4,7-dihydropyrazolo[1,5-a]pyrimidine-6-carboxamide |
| 96B | second eluting enantiomer | 7-(3-fluoro-4-(trifluoromethyl)phenyl)-N-(isoquinolin-6-yl)-5-methyl-2-((4-methylpiperazin-1-yl)methyl)-4,7-dihydropyrazolo[1,5-a]pyrimidine-6-carboxamide |

| Example | Comments | Name |
| --- | --- | --- |
| 97A | first eluting enantiomer | 7-(3-fluoro-4-(trifluoromethyl)phenyl)-N-(isoquinolin-6-yl)-5-methyl-2-(piperidin-1-ylmethyl)-4,7-dihydropyrazolo[1,5-a]pyrimidine-6-carboxamide |
| 97B | second eluting enantiomer | 7-(3-fluoro-4-(trifluoromethyl)phenyl)-N-(isoquinolin-6-yl)-5-methyl-2-(piperidin-1-ylmethyl)-4,7-dihydropyrazolo[1,5-a]pyrimidine-6-carboxamide |
| 104A | first eluting enantiomer | 7-(3-fluoro-4-(trifluoromethyl)phenyl)-N-(isoquinolin-6-yl)-5-methyl-2-((methyl((1-methylpiperidin-4-yl)methyl)amino)methyl)-4,7-dihydropyrazolo[1,5-a]pyrimidine-6-carboxamide |
| 104B | second eluting enantiomer | 7-(3-fluoro-4-(trifluoromethyl)phenyl)-N-(isoquinolin-6-yl)-5-methyl-2-((methyl((1-methylpiperidin-4-yl)methyl)amino)methyl)-4,7-dihydropyrazolo[1,5-a]pyrimidine-6-carboxamide |
| 110A | first eluting enantiomer | 2-((dimethylamino)methyl)-7-(3-fluoro-4-methylphenyl)-N-(isoquinolin-6-yl)-5-methyl-4,7-dihydropyrazolo[1,5-a]pyrimidine-6-carboxamide |
| 110B | second eluting enantiomer | 2-((dimethylamino)methyl)-7-(3-fluoro-4-methylphenyl)-N-(isoquinolin-6-yl)-5-methyl-4,7-dihydropyrazolo[1,5-a]pyrimidine-6-carboxamide |
| 113 | | ethyl 6-((1,6-naphthyridin-2-yl)carbamoyl)-7-(3-fluoro-4-(trifluoromethyl)phenyl)-5-methyl-4,7-dihydropyrazolo[1,5-a]pyrimidine-2-carboxylate |
| 114 | | ethyl 7-(3-fluoro-4-(trifluoromethyl)phenyl)-5-methyl-6-((4-methylisoquinolin-6-yl)carbamoyl)-4,7-dihydropyrazolo[1,5-a]pyrimidine-2-carboxylate |
| 115 | | ethyl 7-(4-(difluoromethyl)-3-fluorophenyl)-6-(isoquinolin-6-ylcarbamoyl)-5-methyl-4,7-dihydropyrazolo[1,5-a]pyrimidine-2-carboxylate |
| 116 | | 7-(3-fluoro-4-(trifluoromethyl)phenyl)-N-(isoquinolin-6-yl)-5-methyl-2-(oxetan-3-yl)-4,7-dihydropyrazolo[1,5-a]pyrimidine-6-carboxamide |
| 117 | | 7-(3-fluoro-4-(trifluoromethyl)phenyl)-N-(isoquinolin-6-yl)-5-methyl-2-(methylthio)-4,7-dihydropyrazolo[1,5-a]pyrimidine-6-carboxamide |
| 118 | | 5-cyclopropyl-7-(3-fluoro-4-(trifluoromethyl)phenyl)-2-(hydroxymethyl)-N-(isoquinolin-6-yl)-4,7-dihydropyrazolo[1,5-a]pyrimidine-6-carboxamide |
| 119 | | 7-(3-fluoro-4-(trifluoromethyl)phenyl)-2-(hydroxymethyl)-N-(isoquinolin-6-yl)-5-(methoxymethyl)-4,7-dihydropyrazolo[1,5-a]pyrimidine-6-carboxamide |
| 120 | | 2-((dimethylamino)methyl)-N-(isoquinolin-6-yl)-5-methyl-7-(4-(trifluoromethyl)cyclohexyl)-4,7-dihydropyrazolo[1,5-a]pyrimidine-6-carboxamide |
| 121 | | 7-(2,3-difluoro-4-methylphenyl)-2-((dimethylamino)methyl)-N-(isoquinolin-6-yl)-5-methyl-4,7-dihydropyrazolo[1,5-a]pyrimidine-6-carboxamide |
| 122 | | 7-(2,3-difluoro-4-(trifluoromethyl)phenyl)-2-((dimethylamino)methyl)-N-(isoquinolin-6-yl)-5-methyl-4,7-dihydropyrazolo[1,5-a]pyrimidine-6-carboxamide |
| 123 | | 2-((dimethylamino)methyl)-7-(3-fluoro-4-(trifluoromethyl)phenyl)-5-methyl-N-(1,6-naphthyridin-2-yl)-4,7-dihydropyrazolo[1,5-a]pyrimidine-6-carboxamide |
| 124 | | 7-(2,3-dihydro-1H-inden-2-yl)-2-((dimethylamino)methyl)-N-(isoquinolin-6-yl)-5-methyl-4,7-dihydropyrazolo[1,5-a]pyrimidine-6-carboxamide |
| 125 | | N2-cyclopropyl-7-(3-fluoro-4-(trifluoromethyl)phenyl)-N6-(isoquinolin-6-yl)-5-methyl-4,7-dihydropyrazolo[1,5-a]pyrimidine-2,6-dicarboxamide |
| 126 | | 7-(3-fluoro-4-(trifluoromethyl)phenyl)-N6-(isoquinolin-6-yl)-N2,N2,5-trimethyl-4,7-dihydropyrazolo[1,5-a]pyrimidine-2,6-dicarboxamide |
| 127 | | 7-(3-fluoro-4-(trifluoromethyl)phenyl)-N6-(isoquinolin-6-yl)-5-methyl-N2-(3-oxo-3-(pyrrolidin-1-yl)propyl)-4,7-dihydropyrazolo[1,5-a]pyrimidine-2,6-dicarboxamide |
| 128 | | N2-(3,3-difluorocyclobutyl)-7-(3-fluoro-4-(trifluoromethyl)phenyl)-N6-(isoquinolin-6-yl)-5-methyl-4,7-dihydropyrazolo[1,5-a]pyrimidine-2,6-dicarboxamide |
| 129 | | 7-(3-fluoro-4-(trifluoromethyl)phenyl)-N6-(isoquinolin-6-yl)-5-methyl-N2-(2-(piperidin-1-yl)ethyl)-4,7-dihydro-[1,2,4]triazolo[1,5-a]pyrimidine-2,6-dicarboxamide |
| 130 | | 2-amino-7-(3-fluoro-4-(trifluoromethyl)phenyl)-N-(isoquinolin-6-yl)-5-methyl-4,7-dihydropyrazolo[1,5-a]pyrimidine-6-carboxamide |

-continued

| Example | Comments | Name |
|---|---|---|
| 131 | | 7-(3-fluoro-4-(trifluoromethyl)phenyl)-N-(isoquinolin-6-yl)-5-methyl-2-(3-(piperidin-1-yl)propanamido)-4,7-dihydropyrazolo[1,5-a]pyrimidine-6-carboxamide |
| 132 | | 7-(3-fluoro-4-(trifluoromethyl)phenyl)-N-(isoquinolin-6-yl)-5-methyl-2-(2-(pyrrolidin-1-yl)acetamido)-4,7-dihydropyrazolo[1,5-a]pyrimidine-6-carboxamide |
| 133 | | 7-(3-fluoro-4-(trifluoromethyl)phenyl)-N-(isoquinolin-6-yl)-5-methyl-2-(2-((1-methylpiperidin-4-yl)oxy)acetamido)-4,7-dihydropyrazolo[1,5-a]pyrimidine-6-carboxamide |
| 134 | | 7-(3-fluoro-4-methylphenyl)-N-(isoquinolin-6-yl)-5-methyl-2-(2-(pyrrolidin-1-yl)acetamido)-4,7-dihydropyrazolo[1,5-a]pyrimidine-6-carboxamide |
| 135 | | 7-(3-fluoro-4-(trifluoromethyl)phenyl)-N-(isoquinolin-6-yl)-5-methyl-2-(1-(3-(piperidin-1-yl)propanoyl)piperidin-4-yl)-4,7-dihydropyrazolo[1,5-a]pyrimidine-6-carboxamide |
| 136 | | 7-(3-fluoro-4-(trifluoromethyl)phenyl)-N-(isoquinolin-6-yl)-5-methyl-2-(4-methylpiperazin-1-yl)-4,7-dihydropyrazolo[1,5-a]pyrimidine-6-carboxamide |
| 122a | first eluting enantiomer | 7-(2,3-difluoro-4-(trifluoromethyl)phenyl)-2-((dimethylamino)methyl)-N-(isoquinolin-6-yl)-5-methyl-4,7-dihydropyrazolo[1,5-a]pyrimidine-6-carboxamide |
| 122b | second eluting enantiomer | 7-(2,3-difluoro-4-(trifluoromethyl)phenyl)-2-((dimethylamino)methyl)-N-(isoquinolin-6-yl)-5-methyl-4,7-dihydropyrazolo[1,5-a]pyrimidine-6-carboxamide |
| 121b | second eluting enantiomer | 7-(2,3-difluoro-4-methylphenyl)-2-((dimethylamino)methyl)-N-(isoquinolin-6-yl)-5-methyl-4,7-dihydropyrazolo[1,5-a]pyrimidine-6-carboxamide |
| 124a | first eluting enantiomer | 7-(2,3-dihydro-1H-inden-2-yl)-2-((dimethylamino)methyl)-N-(isoquinolin-6-yl)-5-methyl-4,7-dihydropyrazolo[1,5-a]pyrimidine-6-carboxamide |
| 124b | second eluting enantiomer | 7-(2,3-dihydro-1H-inden-2-yl)-2-((dimethylamino)methyl)-N-(isoquinolin-6-yl)-5-methyl-4,7-dihydropyrazolo[1,5-a]pyrimidine-6-carboxamide |
| 129a | first eluting enantiomer | 7-(3-fluoro-4-(trifluoromethyl)phenyl)-N6-(isoquinolin-6-yl)-5-methyl-N2-(2-(piperidin-1-yl)ethyl)-4,7-dihydro-[1,2,4]triazolo[1,5-a]pyrimidine-2,6-dicarboxamide |
| 129b | second eluting enantiomer | 7-(3-fluoro-4-(trifluoromethyl)phenyl)-N6-(isoquinolin-6-yl)-5-methyl-N2-(2-(piperidin-1-yl)ethyl)-4,7-dihydro-[1,2,4]triazolo[1,5-a]pyrimidine-2,6-dicarboxamide |

The compounds of formula (I, Ia, Ib and Ic) according to the present invention:

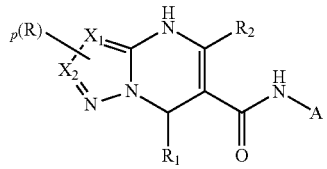

I

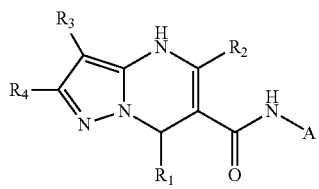

Ia

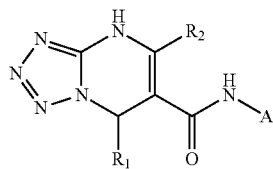

Ib

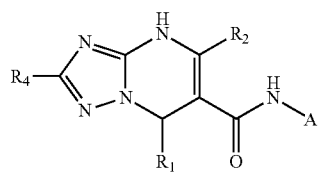

Ic including all the compounds here above listed, can be prepared from readily available starting materials using the following general methods and procedures or by using slightly modified processes readily available to those of ordinary skill in the art. Although a particular embodiment of the present invention may be shown or described herein, those skilled in the art will recognize that all embodiments or aspects of the present invention can be prepared using the methods described herein or by using other known methods, reagents and starting materials. When typical or preferred process conditions (i.e., reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by those skilled in the art by routine optimization procedures.

Thus, processes of preparation described below and reported in the following Schemes should not be viewed as limiting the scope of the synthetic methods available for the preparation of the compounds of the invention.

In some cases a step is needed in order to mask or protect sensitive or reactive moieties, generally known protective groups have been employed, in accordance to general principles of chemistry (T. W. Greene, P. G. M. Wuts, Protective groups in organic synthesis, 4$^{th}$ Edition, Wiley, 2007, which is incorporated herein by reference).

The compounds of formula (I, Ia, Ib and Ic), including all the compounds here above listed, can be generally prepared according to the procedures shown in the schemes below. Where a specific detail or step differs from the general Schemes it has been detailed in the specific examples and/or in additional schemes.

loxycarbonyl) or ethyl carbamate that will be removed in the most appropriate stage of the synthesis in accordance to general principles of chemistry (T. W. Greene, P. G. M. Wuts, Protective groups in organic synthesis, 4$^{th}$ Edition, Wiley, 2007, which is incorporated herein by reference in its entirety).

The reaction condition that may be applied to prepare compounds of formula I consists of heating the appropriate three components (IV, V and VI) in a polar suitable solvent such as DMF, THF, EtOH or MeCN in the presence, or not, of a base (such as NaHCO$_3$, pyridine or piperidine) or acid catalyst (such as H$_2$SO$_4$, TsOH or Yb(OTf)$_3$). The reaction is normally carried out at a temperature higher than RT and may take times ranging from hours to days. Beta-ketoamides

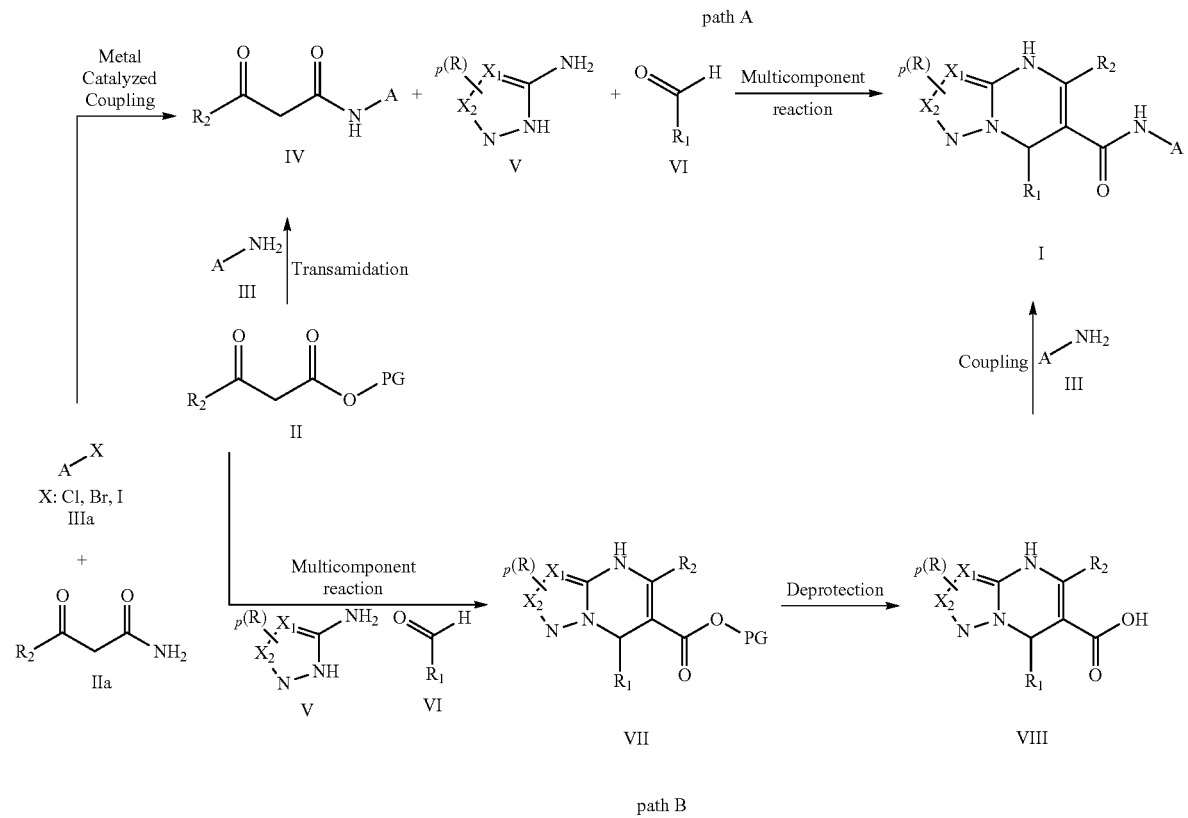

Compounds of formula I may be prepared according to Scheme 1 (path A) by means of multicomponent assembly of an amino five membered heterocycle of formula V, an aldehyde of formula VI and a beta-ketoamide of formula IV via Biginelli's reaction. Biginelli reaction may be accomplished by a variety of reaction conditions as described in *Strategic applications of named reaction in organic syntheses* (by L. Kurti, B. Czako; Strategic applications of Named reactions in Organic Syntheses, Elsevier academic Press, 2005, which is incorporated herein by reference in its entirety) and readily adapted and optimized by those skilled in the art. In some cases, wherein (R)$_p$ contains a primary or secondary amino group, it is evident to those skilled in the art that such an amino moiety may require one or more protective groups in order to mask amino group reactivity. A suitable protective group for the amino moiety can be a carbamate such as Boc (tert-butoxycarbonyl), Cbz (benzy- IV may be prepared by a transamidation reaction, by reacting a suitable beta-ketoester II, for example a tert-butyl ester, methyl ester or ethyl ester derivative, with the proper amino heterocycle III in a polar organic solvent such as MeCN, or DMF at high temperature (100-120° C. or higher). In another approach intermediate IV may be prepared by an appropriate heterocyclic halide IIIa and a beta-ketoamide IIa by metal catalized coupling such as a Buchwald heterocoupling. For example a heterocyclic bromide IIIa may be reacted with beta-ketoamide IIa in the presence of a suitable palladium catalytic system such as Pd$_2$(dba)$_3$/Xantphos by heating around 100° C. in a polar organic solvent such as dioxane or DMF for few hours. The scheme 1 (path A) provides at least one non limiting synthetic route for the preparation of examples 1 to 40, examples 113 to 117 and example 130, 136. Compounds of formula I may be optionally prepared (according to Scheme path B) by amide coupling of intermediate VIII and intermediate III in the presence of a suitable coupling agent such as HATU, COMU or EDC and a base such as DIPEA, TEA or DMAP in a suitable organic solvent such as DMF, THF or DCM. Generally the reaction is carried out for a few hours up to overnight, and at about room temperature. Intermediate VIII may be obtained by deprotection of a corresponding protected carboxylic acid VII and it is dependent upon the type of ester used as PG. For example when PG is t-butyl, deprotection may be performed in an apolar organic solvents such as DCM or Et$_2$O in the presence of TMSOTf/DIPEA or TFA. Intermediate VII may be prepared via Biginelli's reaction by assembly of a suitable protected beta-keto ester II, an amino five membered heterocycle V and an aldehyde VI, and it may be prepared by using the same reaction conditions as already described above for the preparation of compounds of formula I. The scheme 1 (path B) provides at least one non limiting synthetic route for the preparation of examples 41 and 42.

Compound of formula I that contains a primary or secondary amino group in (R)$_p$ may be further converted respectively into compound of invention containing the corresponding primary or secondary amide. Amide coupling may be performed by a variety of reaction conditions, for example the primary or secondary amine and the carboxylic acid may be reacted in the presence of a suitable coupling agent such as HATU, HBTU or COMU in the presence of an organic base such as DIPEA or TEA in a polar organic solvent such as DMF or Dioxane at room temperature or higher to give the desired amide product. Said transformation described provides at least one non limiting synthetic route for the preparation of examples 131 to 135 and examples 137A/137B and 138A/138B.

According to Scheme 2, compounds of formula Ia', wherein $R_3$ or $R_4$ is an amide ($R_3$ or $R_4$=—C(O)NR$_5$R$_6$), may be prepared by amide coupling of Ia", wherein $R_3$ or $R_4$ is a carboxylic acid ($R_3$ or $R_4$=—COOH) with amines of formula IX in the presence of a suitable coupling agent such as HATU, COMU or EDC and a base (DIPEA, TEA or DMAP) in a suitable organic media such as DMF, NMP, DCM or THF. Compounds of formula Ia", wherein $R_3$ or $R_4$ is a carboxylic acid ($R_3$ or $R_4$=—COOH) may be prepared by deprotection of the corresponding ester Ia''' ($R_3$ or $R_4$=—C(O)OPG), under conditions which are dependent upon the type of PG chosen and readily applicable by those skilled in the art. Alternatively, compounds Ia' ($R_3$ or $R_4$=—C(O)NR$_5$R$_6$) may be prepared from Ia''' ($R_3$ or $R_4$=—C(O)OPG) by a transamidation reaction using an amine of formula IX. For example, when PG is Et or Me, this transformation may be accomplished by reaction of ester Ia''' and amine IX in the presence of a suitable Lewis's acid such as AlMe$_3$ or DABAL in a suitable aprotic organic solvent such as toluene or 1,2-dichloroethane at room temperature or higher.

In another embodiment of the present invention, compounds of formula IP, wherein $R_3$ or $R_4$ is an hydroxymethylene residue ($R_3$ or $R_4$=—CH$_2$OH) may be prepared by reduction of corresponding precursor Ia''', wherein $R_3$ or $R_4$ is an ester ($R_3$ or $R_4$=—C(O)OPG). When PG is methyl or ethyl this transformation may be accomplished by reaction of the ester with a reducing agent such as LAH or DIBAL-H in a suitable aprotic organic solvent such as THF or Et$_2$O, at temperatures generally lower than RT.

Compounds of formula Ia$^v$ wherein $R_3$ or $R_4$ is a methylene amine ($R_3$ or $R_4$=—CH$_2$NR$_5$R$_6$) may be prepared from aldehyde intermediate X and amine IX under reductive amination conditions. For example, reductive amination can be performed in a solvent such as DCM, MeOH or THF using a reducing agent such as NaBH(OAc)$_3$, NaBH$_3$CN or NaBH$_4$. It could be useful to react X and IX before adding the reducing agent. The reaction proceeds smoothly at room temperature over a couple of hours. Intermediate X may be prepared by selective oxidation of the corresponding alcohol IP ($R_3$ or $R_4$=—CH$_2$OH) using an oxidant such as Dess-Martin periodinane, IBX or MnO$_2$ in a suitable organic solvent such as DCM or THF.

Scheme 2

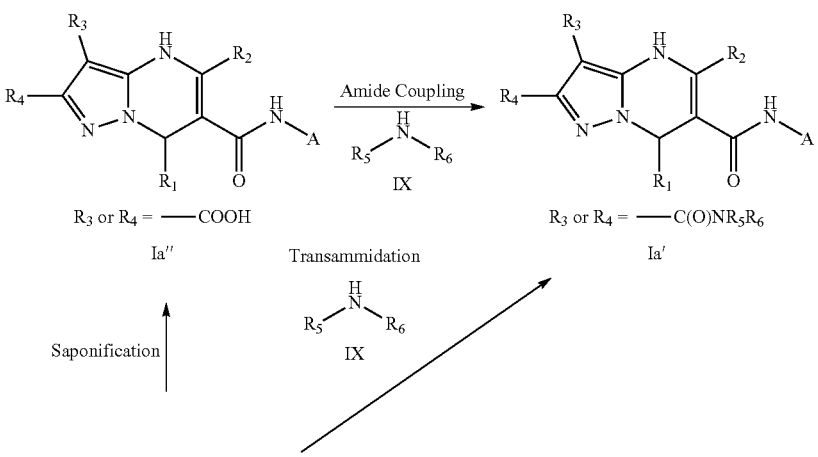

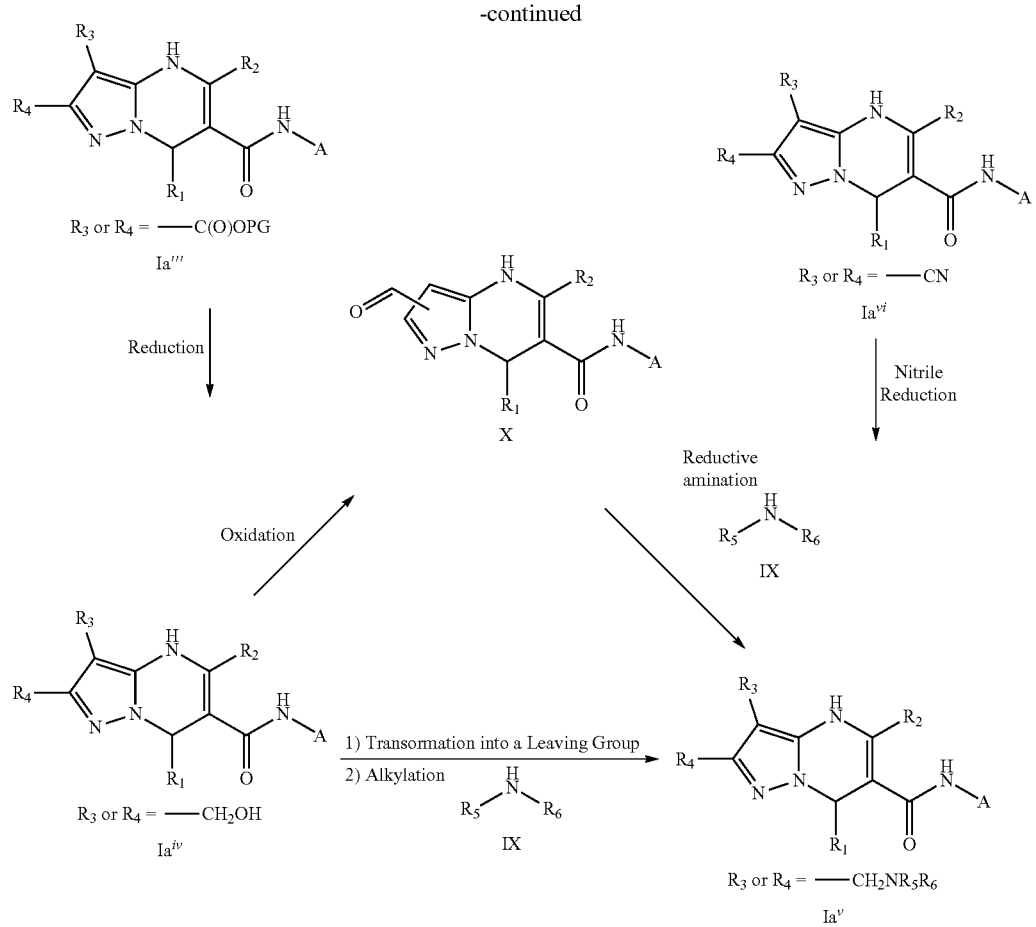

Compounds of formula Ia$^v$, wherein R$_3$ or R$_4$ is a methylene amine (R$_3$ or R$_4$=—CH$_2$NR$_5$R$_6$) may be optionally prepared from the corresponding alcohol IP (R$_3$ or R$_4$=—CH$_2$OH) by first converting the alcoholic moiety into a leaving group LG such as methanesulfonate, tosylate or halogen, and then displacement of LG with amine IX. For example, when methanesulphonate is used as LG, reaction of Ia$^{iv}$ (R$_3$ or R$_4$=—CH$_2$OH) with Ms-Cl may be carried out in an organic solvent such as DMF, THF or MeCN, in the presence of an organic base such as DIPEA or TEA, generally at a temperature lower than RT. An alcohol activated as methanesulphonate or halogen may also be used for alkylation of amine IX in polar organic solvent such as THF, DMF or MeCN at room or lower temperature. Scheme 2 provides at least one non-limiting synthetic route for the preparation of examples 43 to 110, and examples 118 to 128.

Scheme 2 may also apply to the synthesis of compound of formula Ic, as in the case of example 129.

Compounds of formula Ia$^v$, wherein R$_3$ or R$_4$ is a methylene primary amine (R$_3$ or R$_4$=—CH$_2$NH$_2$) may be optionally prepared by reduction of the corresponding nitrile (R$_3$ or R$_4$=—CN). Reduction may be performed with in situ prepared nickel boride or by catalytic hydrogenation. The corresponding nitriles of formula Ia$^{vi}$ (wherein R$_3$ or R$_4$=—CN) may be prepared in the same way as already described above in Scheme 1 (path A) for the preparation of compounds of formula I. Example 111 and 112 may be prepared by CN reduction according to method described.

Compounds of formula I contain at least one stereogenic center, as marked as asterisk * in the picture below.

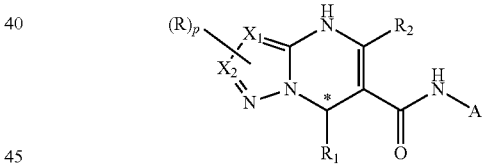

Enantiomerically pure compounds can be prepared from the corresponding parent racemates by means of chiral chromatography. Whenever, in one or more of the substituents of formula I, there is one or more additional stereogenic center, the structure is then characterized by different stereoisomers. Stereochemically pure compounds from a diastereoisomeric mixture may be prepared by chiral separation or stepwise by chromatographic separation of single diastereoisomers followed by further chiral separation into pure enantiomers.

In a more convenient approach, the synthesis of each single stereoisomer can be accomplished using, in the reactions described above, enantiomerically pure intermediates.

Compounds of the invention Ia, Ib, and Ic, may be theoretically present as a mixture of isomers resulting from NH tautomerisation within the 5,6-bicyclic ring system, wherein the NH may reside either in the six-membered ring or the five-membered ring as depicted below.

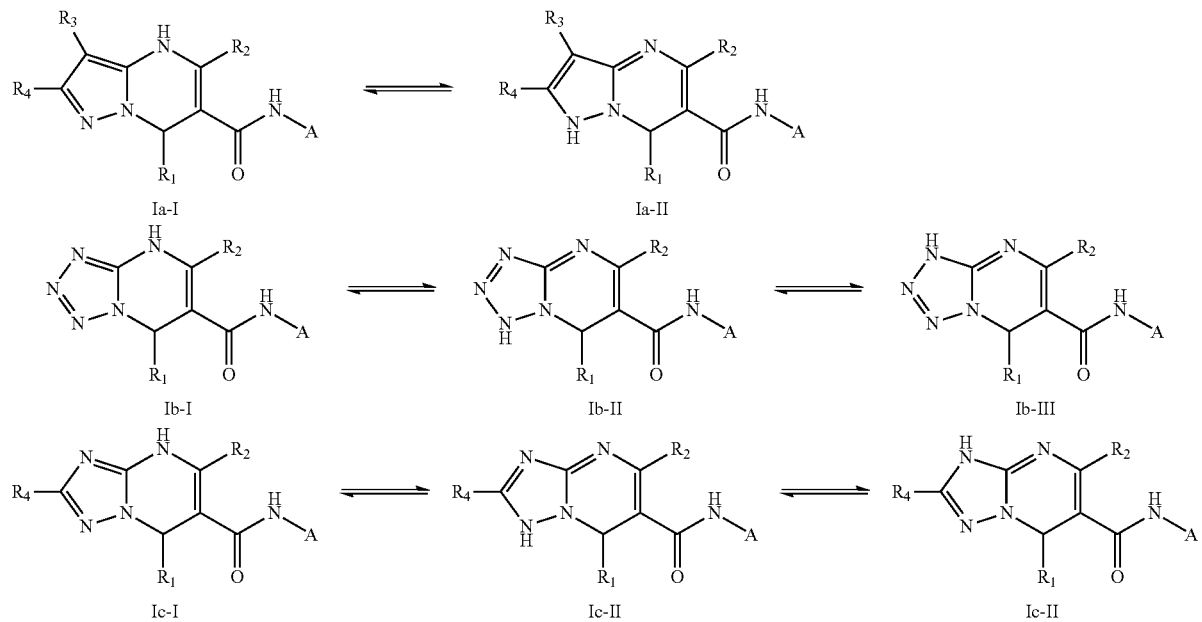

Indeed in some cases, even when not analytically detectable, tautomers are present and deemed to all effects compounds of the invention.

The compounds of the invention are inhibitors of kinase activity, in particular Rho-kinase activity. Generally speaking, compounds which are Rock inhibitors may be useful in the treatment of many disorders associated with Rock enzymes mechanisms.

In one embodiment, the disorders that can be treated by the compounds of the present invention include glaucoma, inflammatory bowel disease (IBD) and pulmonary diseases selected from asthma, chronic obstructive pulmonary disease (COPD), interstitial lung disease such as idiopathic pulmonary fibrosis (IPF) and pulmonary arterial hypertension (PAH).

In another embodiment, the disorder that can be treated by the compound of the present invention is selected from the group consisting of asthma, chronic obstructive pulmonary disease (COPD) and interstitial lung disease such as idiopathic pulmonary fibrosis (IPF) and pulmonary arterial hypertension (PAH).

In a further embodiment, the disorder is selected from idiopathic pulmonary fibrosis (IPF) and pulmonary arterial hypertension (PAH).

The methods of treatment of the invention comprise administering a safe and effective amount of a compound of formula (I) or a pharmaceutically acceptable salt thereof to a patient in need thereof. As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects, and it can nevertheless be routinely determined by the skilled artisan. The compounds of formula (I) or pharmaceutically acceptable salts thereof may be administered once or according to a dosing regimen wherein a number of doses are administered at varying intervals of time for a given period of time. Typical daily dosages may vary depending upon the particular route of administration chosen.

The invention also provides pharmaceutical compositions of compounds of formula (I) in admixture with one or more pharmaceutically acceptable carrier or excipient, for example those described in Remington's Pharmaceutical Sciences Handbook, XVII Ed., Mack Pub., N.Y., U.S.A.

Administration of the compounds of the present invention and their pharmaceutical compositions may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention can be administered as the sole active agent or in combination (i.e. as co-therapeutic agents administered in fixed dose combination or in combined therapy of separately formulated active ingredients) with other pharmaceutical active ingredients selected from organic nitrates and NO donors; inhaled NO; stimulator of soluble guanylate cyclase (sGC); prostaciclin analogue PGI2 and agonist of prostacyclin receptors; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors; human neutrophilic elastase inhibitors; compounds inhibiting the signal transduction cascade, such as tyrosine kinase and/or serine/threonine kinase inhibitors; antithrombotic agents, for example platelet aggregation inhibitors, anticoagulants or profibrinolytic substances; active substances for lowering blood pressure, for example calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists; neutral endopeptidase inhibitor; osmotic agents; ENaC blockers; anti-inflammatory including corticosteroids and antagonists of chemokine receptors; bronchodilatory for example beta2agonist and muscarinic antagonist; antihistamine drug; anti-tussive drug; antibiotic such as macrolide and DNase drug substance and selective cleavage agents such as recombinant human deoxyribonuclease I (rhDNase); agents that inhibit ALK5 and/or ALK4 phosphorylation of Smad2 and Smad3; tryptophan hydroylase 1 (TPH1) inhibitors and multi-kinase inhibitors.

In a preferred embodiment, the compounds of the invention are dosed in combination with phosphodiesterase V such as sildenafil, vardenafil and tadalafil; organic nitrates and NO donors (for example sodium nitroprusside, nitroglycerin, isosorbide mononitrate, isosorbide dinitrate, molsidomine or SIN-1, and inhalational NO); synthetic prostaciclin analogue PGI2 such as iloprost, treprostinil, epoprostenol and beraprost; agonist of prostacyclin receptors such as selexipag and compounds of WO 2012/007539, which is incorporated herein by reference in its entirety; stimulator of soluble guanylate cyclase (sGC) like riociguat and tyrosine kinase like imatinib, sorafenib and nilotinib and endothelin antagonist (for example macitentan, bosentan, sitaxentan and ambrisentan).

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) can be administered for example, at a dosage comprised between 0.001 and 1000 mg/day, preferably between 0.1 and 500 mg/day.

When the compounds of formula (I) are administered by inhalation route, they are preferably given at a dosage comprised between 0.001 and 500 mg/day, preferably between 0.1 and 100 mg/day.

A pharmaceutical composition comprising a compound of the present invention suitable to be administered by inhalation, can be in a form such as inhalable powders, propellant-containing metering aerosols or propellant-free inhalable formulations.

The invention is also directed to a device comprising the pharmaceutical composition comprising a compound according to the present invention, which may be a single- or multi-dose dry powder inhaler, a metered dose inhaler and a soft mist nebulizer.

Other features of the invention will become apparent in the course of the following descriptions of exemplary embodiments which are given for illustration of the invention and are not intended to be limiting thereof.

EXAMPLES

Preparation of Intermediates and Examples

General Experimental Details

Purification by chromatography refers to purification using the CombiFlash® Companion purification system or the Biotage SP1 purification system. Where products were purified using an Isolute® SPE Si II cartridge, 'Isolute SPE Si cartridge' refers to a pre-packed polypropylene column containing unbonded activated silica with irregular particles with average size of 50 μm and nominal 60 Å porosity. Fractions containing the required product (identified by TLC and/or LCMS analysis) were pooled and concentrated in vacuo. Where an SCX-2 cartridge was used, 'SCX-2 cartridge' refers to an Isolute® pre-packed polypropylene column containing a non-end-capped propylsulphonic acid functionalised silica strong cation exchange sorbent. Where HPLC was used for purification (Purification by MDAP) fractions containing the required product (identified by TLC and/or LCMS analysis) were pooled and the solvent removed using a Biotage EV10 Evaporator. Alternatively the pooled product fraction was lyophilized.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz or on a Bruker Fourier 300 spectrometer with a 5 mm dual probe operating at 300 MHz. Shifts are given in ppm relative to tetramethylsilane.

Chemical Names for examples and intermediates were generated with Structure To Name Enterprise 12.0 CambridgeSoft (Perkin Elmer).

Solutions of common inorganic salts used in workups are aqueous solutions. Brine refers to a saturated aqueous solution of NaCl. Unless otherwise specified.

LC-MS Method 1

Waters Micromass ZQ2000 mass spectrometer with a C18-reverse-phase column (100×2.1 mm Acquity BEH with 1.7 μm particle size) maintained at 40° C., elution with A: water+0.1% formic acid; B: MeCN+0.1% formic acid.

Gradient:

| Gradient - Time | flow (mL/min) | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA

MS ionization method—Electrospray (positive/negative ion).

LC-MS Method 2

Quattro Micro Mass Spectrometer with a C18-reverse-phase column (100×2.1 mm Acquity BEH with 1.7 μm particle size) maintained at 40° C., elution with A: water+0.1% formic acid; B: MeCN+0.1% formic acid.

Gradient:

| Gradient - Time | flow (mL/min) | % A | % B |
| --- | --- | --- | --- |
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA

MS ionization method—Electrospray (positive/negative ion).

LC-MS Method 3

Quattro Micro Mass Spectrometer with a C18-reverse-phase column (50×2.1 mm Acquity BEH with 1.7 μm particle size) maintained at 50° C., elution with A: water+0.1% formic acid; B: MeCN+0.1% formic acid.

Gradient:

| Gradient - Time | flow (mL/min) | % A | % B |
| --- | --- | --- | --- |
| 0.00 | 1 | 97 | 03 |
| 0.10 | 1 | 97 | 03 |
| 1.50 | 1 | 01 | 99 |
| 1.90 | 1 | 01 | 99 |
| 2.00 | 1 | 97 | 03 |

Detection—MS, UV PDA

MS ionization method—Electrospray (positive/negative ion).

LC-MS Method 4

Waters ZQ quadrupole mass spectrometer with a C18-reverse-phase column (30×4.6 mm Phenomenex Luna with 3 μm particle size) maintained at 50° C., elution with A: water+0.1% formic acid; B: MeCN+0.1% formic acid.

Gradient:

| Gradient - Time | flow (mL/min) | % A | % B |
| --- | --- | --- | --- |
| 0.00 | 2 | 95 | 05 |
| 0.30 | 2 | 95 | 05 |
| 4.30 | 2 | 05 | 95 |
| 5.30 | 2 | 05 | 95 |
| 5.80 | 2 | 95 | 05 |
| 6.00 | 2 | 95 | 05 |

Detection—MS, UV PDA

MS ionization method—Electrospray (positive/negative ion).

LC-MS Method 5

Waters ZMD mass spectrometer with a C18-reverse-phase column (30×4.6 mm Phenomenex Luna with 3 μm particle size) maintained at 50° C., elution with A: water+0.1% formic acid; B: MeCN+0.1% formic acid.

Gradient:

| Gradient - Time | flow (mL/min) | % A | % B |
| --- | --- | --- | --- |
| 0.00 | 2 | 95 | 05 |
| 0.50 | 2 | 95 | 05 |
| 4.50 | 2 | 05 | 95 |
| 5.50 | 2 | 05 | 95 |
| 6.00 | 2 | 95 | 05 |

Detection—MS, UV PDA

MS ionization method—Electrospray (positive/negative ion).

LC-MS Method 6

QDa Mass Spectrometer with a C18-reverse-phase column (50×2.1 mm Acquity CSH with 1.7 μm particle size) maintained at 40° C., elution with A: water+0.1% formic acid; B: MeCN+0.1% formic acid.

Gradient:

| Gradient - Time | flow (mL/min) | % A | % B |
| --- | --- | --- | --- |
| 0.00 | 1 | 97 | 3 |
| 1.50 | 1 | 1 | 99 |
| 1.90 | 1 | 1 | 99 |
| 2.00 | 1 | 97 | 3 |
| 2.50 | 1 | 97 | 3 |

Detection-MS, UV PDA

MS ionization method-Electrospray (positive/negative ion)

LC-MS Method 7

QDa Mass Spectrometer with a C18-reverse-phase column (50×2.1 mm Acquity CSH with 1.7 μm particle size) maintained at 40° C., elution with A: 95/5 water/acetonitrile+0.05% formic acid; B: 95/5 acetonitrile/water+0.05% formic acid.

Gradient:

| Gradient - Time | flow (mL/min) | % A | % B |
|---|---|---|---|
| 0.00 | 1 | 99 | 1 |
| 1.50 | 1 | 1 | 99 |
| 1.90 | 1 | 1 | 99 |
| 2.00 | 1 | 99 | 1 |

Detection-MS, UV PDA
MS ionization method-Electrospray (positive/negative ion)
MDAP Method (Acidic)

The following mass directed auto purification (MDAP) conditions were used unless otherwise stated:
Agilent Technologies 1260 Infinity purification system with an XSELECT CSH Prep C18 column (19×250 mm, 5 μm OBD) maintained at RT
Mobile Phase A: 0.1% aqueous formic acid
Mobile Phase B: 0.1% formic acid in acetonitrile
Flow Rate: 20 ml/min
Gradient Program: 10%-95%, 22 min, centred around a specific focused gradient
Sample: Injection of a 20-60 mg/ml solution in DMSO (+ optional formic acid and water)
MDAP Method (Basic)

The following mass directed auto purification (MDAP) conditions were used unless otherwise stated:
Agilent Technologies 1260 Infinity purification system with an XSELECT CSH Prep C18 column (19×250 mm, 5 μm OBD) maintained at RT
Mobile Phase A: 0.1% aqueous ammonia
Mobile Phase B: 0.1% ammonia in acetonitrile
Flow Rate: 20 ml/min
Gradient Program: 10%-95%, 22 min, centred around a specific focused gradient
Sample: Injection of a 20-60 mg/ml solution in DMSO (+ optional formic acid and water)

SFC Methods

Supercritical Fluid Chromatography (SFC) was carried out using either a Waters Thar Prep100 preparative SFC system (P200 CO2 pump, 2545 modifier pump, 2998 UV/VIS detector, 2767 liquid handler with Stacked Injection Module) or a Waters Thar Investigator semi preparative system (Waters Fluid Delivery Module, 2998 UV/VIS detector, Waters Fraction Collection Module). The column and isocratic method used is indicated for each compound and the single enantiomers were analyzed using the methods given. Some of the compounds may have gone through a second purification process in order to achieve the required % ee purity (>90% ee).

The stereoisomers were separated by SFC using the conditions specified in the description. The separated stereoisomers were named first and second and further isomers referring to the order of collection of the peaks as obtained following the procedure.

e.g.

Compound of example 4, obtained as a mixture of two enantiomers, was separated by SFC in two chromatographic peaks and named:

| 4A | first eluting enantiomer of | ethyl 6-((1H-indazol-5-yl)carbamoyl)-7-(4-fluorophenyl)-5-methyl-4,7-dihydropyrazolo[1,5-a]pyrimidine-2-carboxylate | Example 4A Rt = 2.4 min (1st eluting enantiomer) |
| 4B | second eluting enantiomer of | ethyl 6-((1H-indazol-5-yl)carbamoyl)-7-(4-fluorophenyl)-5-methyl-4,7-dihydropyrazolo[1,5-a]pyrimidine-2-carboxylate | Example 4B Rt = 3.7 min (2nd eluting enantiomer) |

Compound of example 72 was obtained as a mixture of four stereoisomers, separated by SFC into four single stereoisomer peaks and named:

| 72A | first stereoisomer | 7-(2,3-dihydrobenzo[b][1,4]dioxin-2-yl)-2-(hydroxymethyl)-N-(isoquinolin-6-yl)-5-methyl-4,7-dihydropyrazolo[1,5-a]pyrimidine-6-carboxamide | Example 72A Rt = 4.3 min (2nd eluting peak in the first separation step) First collected peak |
| 72B | second stereoisomer | 7-(2,3-dihydrobenzo[b][1,4]dioxin-2-yl)-2-(hydroxymethyl)-N-(isoquinolin-6-yl)-5-methyl-4,7-dihydropyrazolo[1,5-a]pyrimidine-6-carboxamide | Example 72B Rt = 5.3 min (3rd eluting in the first separation step) Second collected peak |
| 72C | third stereoisomer | -(2,3-dihydrobenzo[b][1,4]dioxin-2-yl)-2-(hydroxymethyl)-N-(isoquinolin-6-yl)-5-methyl-4,7-dihydropyrazolo[1,5-a]pyrimidine-6-carboxamide | Example 72C Rt = 2.2 min (1st eluting in second separation step) Third collected peak |

| | | | |
|---|---|---|---|
| 72D | fourth stereoisomer | 7-(2,3-dihydrobenzo[b][1,4]dioxin-2-yl)-2-(hydroxymethyl)-N-(isoquinolin-6-yl)-5-methyl-4,7-dihydropyrazolo[1,5-a]pyrimidine-6-carboxamide | Example 72D<br>Rt = 3.9 min<br>(2nd eluting in the second separation step)<br>Fourth collected peak |

Likewise compound of example 104

| | | | |
|---|---|---|---|
| 104A | first eluting enantiomer | 7-(3-fluoro-4-(trifluoromethyl)phenyl)-N-(isoquinolin-6-yl)-5-methyl-2-((methyl((1-methylpiperidin-4-yl)methyl)amino)methyl)-4,7-dihydropyrazolo[1,5-a]pyrimidine-6-carboxamide | Example 104A<br>Rt = 3.6 min<br>(1st eluting in the first separation step)<br>First collected peak |
| 104B | second eluting enantiomer | 7-(3-fluoro-4-(trifluoromethyl)phenyl)-N-(isoquinolin-6-yl)-5-methyl-2-((methyl((1-methylpiperidin-4-yl)methyl)amino)methyl)-4,7-dihydropyrazolo[1,5-a]pyrimidine-6-carboxamide | Example 104B<br>Rt = 4.5 mins,<br>(2st eluting in the first separation step, further purification required)<br>Rt = 3.3 min<br>(after separation and purification step)<br>Second collected peak |

Abbreviations used in the experimental section:
Ac acetyl
ATP adenosine 5'-triphosphate
Boc benzyloxycarbonyl
BSA bovine Serum Albumin
COMU 1-cyano-2-ethoxy-2-oxoethylidenaminooxy)dimethylamino-morpholino-carbenium hexafluorophosphate
DABAL bis(trimethylaluminum)-1,4-diazabicyclo[2.2.2]-octane
DIBAL-H diisobutylaluminum hydride
DCM dichloromethane
DEA diethylamine
DIPEA di-isopropylethylamine
DMF N,N-dimethylformamide
DMAP dimethylaminopyridine
DMSO dimethylsulphoxide
EDC N-(3-dimethylaminopropyl)-N'-ethylcarbodiimide
EtOH ethanol
Et$_2$O diethyl ether
h hour(s)
HATU (1-[bis(dimethylamino)methylene]-1H-1,2,3-triazolo[4,5-b]pyridinium 3-oxid hexafluorophosphate)
HPLC high performance liquid chromatography
IBX 2-iodoxybenzoic acid
LAH lithium aluminium hydride
LC-MS liquid chromatography-mass spectrometry
MD mass-directed
MeCN acetonitrile
MeOH methanol
Min minutes
NMP N-methylpyrrolidone
Rt retention time
RT room temperature
SFC supercritical fluid chromatography
SM starting material
TEA triethylamine
TFA trifluoroacetic acid
THF tetrahydrofuran
Tf triflate
TRIS 2-amino-2-(hydroxymethyl)-1,3-propanediol
Ts tosyl In the procedures that follow, some of the starting materials are identified through an "Intermediate" or "Example" number or step indications. This is provided merely for assistance to the reading.

Many of the compounds described in the following examples have been prepared from stereochemically pure starting materials, for example 95% ee.

Where the preparation of starting materials is not described, these are commercially available, known in the literature, or readily obtainable by those skilled in the art using standard procedures.

The stereochemistry of the compounds in the Examples, where indicated, has been assigned on the assumption that absolute configuration at resolved stereogenic centers of starting materials is maintained throughout any subsequent reaction conditions. When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Preparation of Intermediates 1A to 1H

Intermediate 1A

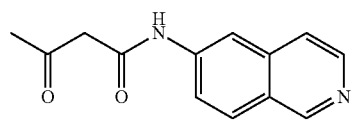 [SMILES: CC(=O)CC(=O)Nc1ccc2cnccc2c1]

N-(Isoquinolin-6-yl)-3-oxobutanamide (Intermediate 1A)

tert-Butyl acetoacetate (1.82 ml, 11 mmol) and isoquinoline-6-amine (1.44 g, 10 mmol) in MeCN (10 ml) were sealed in a reaction tube and heated to 120° C. for 2 h. The reaction mixture was evaporated then triturated with a mixture of MeCN and diethyl ether to give an off-white solid (1.50 g). Although this material contained approximately 10% SM, it was used in the next step without further purification.

LCMS (Method 3): Rt=0.46 min, m/z 229 [M+H]$^+$

Intermediates 1B, 1C and 1D were prepared using a similar procedure of that Intermediate 1A, by varying the amine, according to table reported below.

3-Cyclopropyl-N-(isoquinolin-6-yl)-3-oxopropanamide (Intermediate 1E)

6-Aminoisoquinoline (1.0 g, 6.94 mmol) was heated in methyl 3-cyclopropyl-3-oxopropanoate (5 mL) at 100° C. overnight. The reaction mixture was cooled to RT then applied to a pad of silica and washed with DCM then eluted using 5% methanol in DCM. This fraction was evaporated and the resultant crude product was chromatographed on a

| Intermediate | Structure/Chemical Name | Amine | LC-MS |
|---|---|---|---|
| 1B | 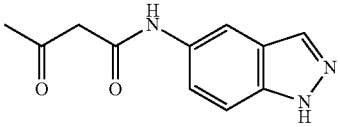 [SMILES: CC(=O)CC(=O)Nc1ccc2[nH]ncc2c1]<br>N-(1H-Indazol-5-yl)-3-oxobutanamide | 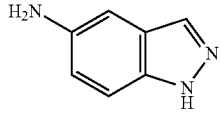<br>1H-Indazol-5-amine | Rt = 2.03 min, m/z 218.1 [M + H]+ (Method 5) |
| 1C | 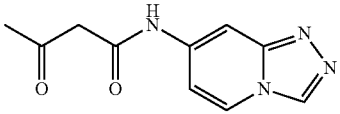 [SMILES: CC(=O)CC(=O)Nc1ccn2cnnc2c1]<br>N-([1,2,4]Triazolo[4,3-a]pyridin-7-yl)-3-oxobutanamide | 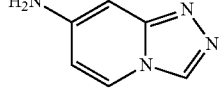<br>[1,2,4]Triazolo[4,3-a]pyridin-7-amine | Rt = 0.37 min, m/z 219.2 [M + H]+ (Method 5) |
| 1D | 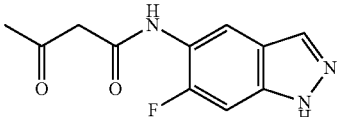<br>N-(6-Fluoro-1H-indazol-5-yl)-3-oxobutanamide | 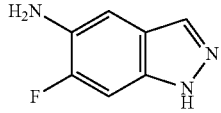<br>6-Fluoro-1H-indazol-5-amine | Rt = 1.90 min, m/z [M − H]− 234.3 (Method 5) |

Intermediate 1E

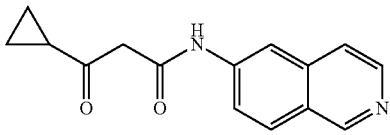 [SMILES: O=C(CC(=O)C1CC1)Nc1ccc2cnccc2c1]

100 g Si cartridge eluting with 0-5% methanol in DCM. The product was obtained as a brown oil (880 mg).

LCMS (Method 6): Rt=0.67 min, m/z 255.1 [M+H]$^+$

Intermediate 1F and 1G

The following intermediates 1F and 1G were prepared in a similar manner from the starting materials shown.

| Int. | Structure | Starting materials | LC-MS |
|---|---|---|---|
| 1F | 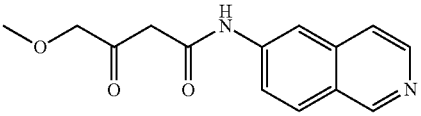 [SMILES: COCC(=O)CC(=O)Nc1ccc2cnccc2c1] | Methyl 4-methoxy-3-oxobutanoate and 6-aminoiso-quinoline | Rt = 0.58 min, m/z 259.1 [M + H]+ (Method 6) |
| 1G | 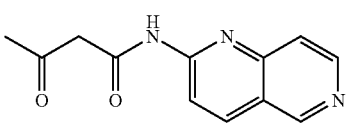 [SMILES: CC(=O)CC(=O)Nc1ccc2cnccc2n1] | Methyl 3-oxobutanoate and 1,6-naphthyridin-2-amine | Rt = 0.37 min, m/z 230.1 [M + H]+ (Method 6) |

Intermediate 1H

Step A

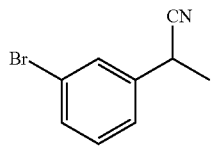

2-(3-Bromophenyl)propanenitrile (Intermediate 1H-a)

A suspension of potassium tert-butoxide (5.64 g, 50.26 mmol) in t-butanol (25 mL) was added to a solution of 3'-bromoacetophenone (3.16 mL, 25.13 mmol) and p-toluenesulfonylmethyl isocyanide (5.89 g, 30.16 mmol) in dry DME (75 mL) in an ice-bath under argon, keeping the internal temperature below 10° C. After 1 h, the ice bath was removed and the mixture was stirred at RT overnight. Water (60 mL) was added and the reaction mixture was extracted twice with iso-hexane. The organic phase was dried over sodium sulfate, filtered and evaporated. The resultant crude product was chromatographed on a 220 g Si cartridge eluting with 0-10% ethyl acetate in iso-hexane. The product was obtained as almost colorless liquid (2.1 g).

LCMS (Method 6): Rt=1.36 min, no mass ion observed $^1$H NMR (400 MHz, CDCl$_3$) 7.52-7.50 (m, 1H), 7.49-7.45 (m, 1H), 7.31-7.28 (m, 1H), 7.27-2.56 (m, 1H), 3.88 (q, J=7.4 Hz, 1H), 1.65 (d, J=1.64 Hz, 3H).

Step B

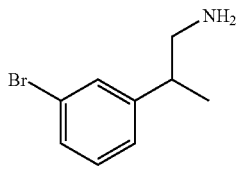

2-(3-Bromophenyl)propan-1-amine (Intermediate 1H-b)

Borane dimethyl sulfide complex (2M in THF, 7.29 mL, 14.57 mmol) was added to a solution of intermediate 1H-a (1.02 mL, 4.86 mmol) in dry THF (10 mL) at RT under argon, then heated at reflux for 5 h. The reaction was left to stand at RT overnight then quenched by dropwise addition of 6 M HCl (4 mL) and the mixture heated at reflux for 2 h. The reaction mixture was basified with 6 N NaOH then extracted three times with DCM. The organic phase was dried (Na$_2$SO$_4$), filtered and evaporated. The product was obtained as straw coloured liquid (981 mg).

LCMS (Method 6): Rt=0.76 min, m/z 214.1/216.1 [M+H]$^+$

Step C

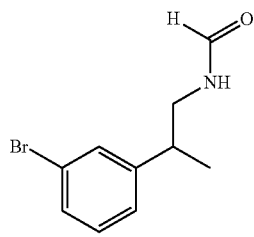

N-(2-(3-Bromophenyl)propyl)formamide (Intermediate 1H-c)

A solution of intermediate 1H-b (980 mg, 4.579 mmol) in ethyl formate (1.8 mL) was heated at reflux for 64 h then cooled to RT and evaporated. The crude product was obtained as a brown oil (934 mg).

LCMS (Method 6): 1.20 mins, m/z 242.1/244.1 [M+H]$^+$

Step D

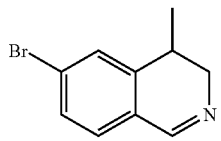

6-Bromo-4-methyl-3,4-dihydroisoquinoline (Intermediate 1H-d)

Polyphosphoric acid (13.8 g) was added to intermediate 1H-c (930 mg, 3.84 mmol) and the mixture was heated to 160° C. Phosphorus pentoxide (1.24 g, 8.77 mmol) was then added and heating continued overnight. The reaction mixture was cooled then treated carefully with ice and the dense black gum present was dissolved gradually on basification with 6 N sodium hydroxide solution and DCM. The aqueous phase was extracted twice with DCM then the organics were dried (Na$_2$SO$_4$), filtered and evaporated. The crude product was chromatographed on a 25 g Si cartridge eluting with 10-25% ethyl acetate in iso-hexane. The first eluting peak was a brown oil consistent with the desired product (254 mg).

LCMS (Method 6): 0.58 mins, m/z 224.0/226.0 [M+H]$^+$ $^1$H NMR (237297) (400 MHz, CDCl$_3$) δ 8.31 (t, J=2.2 Hz, 1H), 7.45 (dd, J=8.0, 2.0 Hz, 1H), 7.39 (br s, 1H), 7.15 (d, J=8.0 Hz, 1H), 3.87-3.78 (m Hz, 1H), 3.56-3.47 (m, 1H), 2.94-2.83 (m, 1H), 1.25 (d, J=7.0 Hz, 3H).

Step E

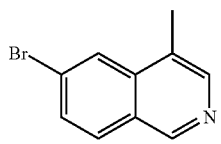

6-Bromo-4-methylisoquinoline (Intermediate 1H-e)

Manganese dioxide (8.15 g, 93.7 mmol) was added to a solution of intermediate 1H-d (1.40 g, 6.25 mmol) in 1,4-dioxane (85 mL) the mixture was heated at reflux overnight. The reaction mixture was cooled then filtered through Celite®, washing with DCM. The filtrate was evaporated to give the crude product as an orange liquid with some solid material present (850 mg), which was used directly in the next reaction.

LCMS (Method 6): 0.86 mins, m/z 222.0/224.0 [M+H]⁺
Step F

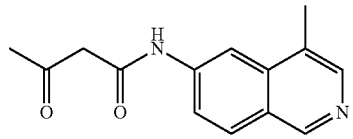 [SMILES: CC(=O)CC(=O)Nc1ccc2cncc(C)c2c1]

N-(4-Methylisoquinolin-6-yl)-3-oxobutanamide
(Intermediate 1H)

Intermediate 1H-e (560 mg, 2.25 mmol), acetoacetamide (255 mg, 2.25 mmol), Xantphos (146 mg, 0.25 mmol), cesium carbonate (1.64 g, 5.04 mmol) and Pd$_2$(dba)$_3$ (231 mg, 0.25 mmol) in 1,4-dioxane (10 mL) were degassed then heated in the microwave at 100° C. for 2 h. The reaction mixture was filtered through Celite®, washing with methanol then evaporated. The residue was partitioned between water and DCM and the phases separated. The organics were chromatographed on an 80 g Si cartridge eluting with 0-10% 2M methanolic ammonia in DCM. Intermediate 1H was obtained as an orange solid (195 mg), which was used without further purification.

LCMS (Method 6): 0.69 mins, m/z 243.1 [M+H]⁺

Example 1

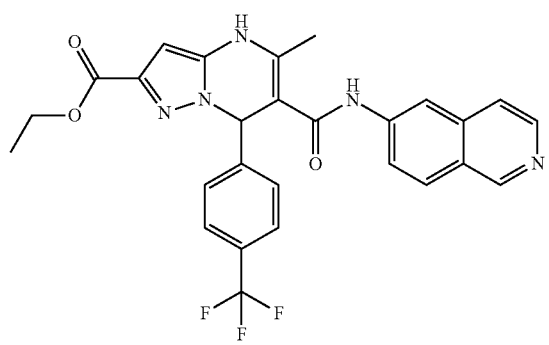 [SMILES: CCOC(=O)c1cc2n(n1)C(c1ccc(C(F)(F)F)cc1)C(C(=O)Nc1ccc3cnccc3c1)=C(C)N2]

ethyl 6-(isoquinolin-6-ylcarbamoyl)-5-methyl-7-(4-(trifluoromethyl)phenyl)-4,7-dihydropyrazolo[1,5-a]pyrimidine-2-carboxylate (Example 1)

A mixture of Intermediate 1A (398 mg, 1.74 mmol), ethyl 5-amino-1H-pyrazole-3-carboxylate (295 mg, 1.9 mmol) and 4-(trifluoromethyl)benzaldehyde (330 mg, 1.9 mmol) in DMF (3 mL) was heated at 120° C. for 3 h. The reaction mixture was allowed to cool to RT and LiCl (4% aq, 10 mL) was added followed by DCM (10 mL). The organic phase, which contained a suspension of solid material, was separated and then filtered. The solution was dried (Na$_2$SO$_4$) and evaporated to give the desired product as an off-white solid (330 mg). A portion of the crude product (100 mg) was purified by MDAP (acidic) to afford pure Example 1 as a white solid (62 mg).

LCMS (Method 1): Rt=3.47 min, m/z 522.2 [M+H]+

¹H NMR (400 MHz, d6-DMSO) δ 10.12 (s, 1H), 9.96 (s, 1H), 9.14 (s, 1H), 8.39 (d, J=5.8 Hz, 1H), 8.28 (d, J=1.8 Hz, 1H), 8.02 (d, J=8.9 Hz, 1H), 7.72-7.67 (m, 4H), 7.39 (d, J=8.1 Hz, 2H), 6.74 (s, 1H), 6.06 (s, 1H), 4.27-4.16 (m, 2H), 2.27 (s, 3H), 1.25 (t, J=7.1 Hz, 3H).

Examples 2 to 40 and Examples 113 to 117

The following examples were prepared by analogous procedures to that used in Example 1 by varying Intermediate 1A, 4-(trifluoromethyl)benzaldehyde and ethyl 5-amino-1H-pyrazole-3-carboxylate respectively with Intermediate 1A, 1B, 1C, 1D, 1E, 1F, 1G or 1H, aldehyde and amino heterocycle given in the table below.

| Ex. | Structure | Intermediate 1X/aldehyde/amino heterocycle | 1H NMR | LC-MS |
| --- | --- | --- | --- | --- |
| 2 | ethyl 6-((1H-indazol-5-yl)carbamoyl)-5-methyl-7-(4-(trifluoromethyl)phenyl)-4,7-dihydropyrazolo[1,5-a]pyrimidine-2-carboxylate | Intermediate 1B/4-(trifluoromethyl)benz-aldehyde/ethyl 5-amino-1H-pyrazole-3-carboxylate | ¹H NMR (400 MHz, d6-DMSO) δ 12.95 (s, 1H), 9.78 (s, 1H), 9.73 (s, 1H), 8.01-7.97 (m, 2H), 7.69 (d, J = 8.2 Hz, 2H), 7.46-7.36 (m, 4H), 6.69 (s, 1H), 6.03 (s, 1H), 4.27-4.16 (m, 2H), 2.23 (s, 3H), 1.24 (t, J = 7.1 Hz, 3H). | Rt = 3.89 min, m/z 511.2 [M + H]+ (Method 2) |

| Ex. | Structure | Intermediate 1X/aldehyde/amino heterocycle | 1H NMR | LC-MS |
|---|---|---|---|---|
| 3 | ethyl 6-((1H-indazol-5-yl)carbamoyl)-5-methyl-7-(p-tolyl)-4,7-dihydropyrazolo[1,5-a]pyrimidine-2-carboxylate | Intermediate 1B/4-methylbenz-aldehyde/ethyl 5-amino-1H-pyrazole-3-carboxylate | $^1$H NMR (400 MHz, d6-DMSO) δ 12.93 (s, 1H), 9.65 (s, 1H), 9.59 (s, 1H), 8.02-7.97 (m, 2H), 7.45-7.37 (m, 2H), 7.08 (s, 4H), 6.56 (s, 1H), 45.98 (s, 1H), 4.26-4.15 (m, 2H), 2.22 (s, 6H), 1.24 (dd, J = 7.1, 7.1 Hz, 3H). | Rt = 3.73 min, m/z 457.2 [M + H]+ (Method 1) |
| 4 | ethyl 6-((1H-indazol-5-yl)carbamoyl)-7-(4-fluorophenyl)-5-methyl-4,7-dihydropyrazolo[1,5-a]pyrimidine-2-carboxylate | Intermediate 1B/4-fluorobenz-aldehyde/ethyl 5-amino-1H-pyrazole-3-carboxylate | $^1$H NMR (400 MHz, d6-DMSO) δ 12.93 (s, 1H), 9.68-9.65 (m, 2H), 7.99-7.97 (m, 2H), 7.46-7.34 (m, 2H), 7.27-7.22 (m, 2H), 7.16-7.10 (m, 2H), 6.60 (s, 1H), 5.99 (s, 1H), 4.27-4.16 (m, 2H), 2.22 (s, 3H), 1.25 (t, J = 7.0 Hz, 3H). | Rt = 3.56 min, m/z 461.3 [M + H]+ (Method 1) |
| 5 | ethyl 6-((1H-indazol-5-yl)carbamoyl)-7-(6-chloropyridin-3-yl)-5-methyl-4,7-dihydropyrazolo[1,5-a]pyrimidine-2-carboxylate | Intermediate 1B/6-chloronicotin-aldehyde/ethyl 5-amino-1H-pyrazole-3-carboxylate | $^1$H NMR (400 MHz, d6-DMSO) δ 12.95 (s, 1H), 9.82 (s, 1H), 9.72 (s, 1H), 8.32 (d, J = 2.3 Hz, 1H), 7.99-7.97 (m, 2H), 7.67-7.64 (m, 1H), 7.51-7.43 (m, 2H), 7.38-7.34 (m, 1H), 6.62 (s, 1H), 6.02 (s, 1H), 4.27-4.16 (m, 2H), 2.24 (s, 3H), 1.25 (t, J = 7.1 Hz, 3H). | Rt = 3.30 min, m/z 478.1 [M + H]+ (Method 2) |
| 6 | ethyl 6-((1H-indazol-5-yl)carbamoyl)-7-(3-methoxyphenyl)-5-methyl-4,7-dihydropyrazolo[1,5-a]pyrimidine-2-carboxylate | Intermediate 1B/3-methoxybenz-aldehyde/ethyl 5-amino-1H-pyrazole-3-carboxylate | $^1$H NMR (400 MHz, d6-DMSO) δ 12.94 (s, 1H), 9.68 (s, 1H), 9.64 (s, 1H), 8.03-7.98 (m, 2H), 7.46-7.38 (m, 2H), 7.21 (t, J = 7.9 Hz, 1H), 6.83-6.80 (m, 1H), 6.74-6.67 (m, 2H), 6.58 (s, 1H), 6.00 (s, 1H), 4.28-4.15 (m, 2H), 3.65 (s, 3H), 2.22 (s, 3H), 1.25 (t, J = 7.1 Hz, 3H). | Rt = 3.48 min, m/z 473.2 [M + H]+ (Method 2) |

-continued

| Ex. | Structure | Intermediate 1X/aldehyde/ amino heterocycle | 1H NMR | LC-MS |
|---|---|---|---|---|
| 7 | ethyl 6-((1H-indazol-5-yl)carbamoyl)-7-(4-chloro-2-fluorophenyl)-5-methyl-4,7-dihydropyrazolo[1,5-a]pyrimidine-2-carboxylate | Intermediate 1B/4-chloro-2-fluorobenz-aldehyde/ethyl 5-amino-1H-pyrazole-3-carboxylate | $^1$H NMR (400 MHz, d6-DMSO) δ 12.94 (s, 1H), 9.76-9.74 (m, 2H), 7.99-7.97 (m, 2H), 7.46-7.33 (m, 3H), 7.26-7.23 (m, 2H), 6.79 (s, 1H), 5.98 (s, 1H), 4.27-4.15 (m, 2H), 2.20 (s, 3H), 1.25 (t, J = 7.1 Hz, 3H). | Rt = 3.80 min, m/z 495.1 [M + H]+ (Method 2) |
| 8 | ethyl 7-(benzo[d]thiazol-2-yl)-6-(isoquinolin-6-ylcarbamoyl)-5-methyl-4,7-dihydropyrazolo[1,5-a]pyrimidine-2-carboxylate | Intermediate 1A/ benzothiazole-2-carbaldehyde/ ethyl 5-amino-1H-pyrazole-3-carboxylate | $^1$H NMR (400 MHz, d6-DMSO) δ 10.27-10.24 (m, 2H), 9.15 (s, 1H), 8.39 (d, J = 5.7 Hz, 1H), 8.32 (d, J = 1.6 Hz, 1H), 8.04 (d, J = 8.7 Hz, 2H), 7.94 (d, J = 7.9 Hz, 1H), 7.76-7.68 (m, 2H), 7.51-7.39 (m, 2H), 7.14 (s, 1H), 6.13 (s, 1H), 4.29-4.18 (m, 2H), 2.32 (s, 3H), 1.26 (t, J = 7.1 Hz, 3H). | Rt = 3.20 min, m/z 511.2 [M + H]+ (Method 1) |
| 9 | ethyl 7-(4-hydroxyphenyl)-6-(isoquinolin-6-ylcarbamoyl)-5-methyl-4,7-dihydropyrazolo[1,5-a]pyrimidine-2-carboxylate | Intermediate 1A/ 4-hydroxybenz-aldehyde/ ethyl 5-amino-1H-pyrazole-3-carboxylate | $^1$H NMR (400 MHz, d6-DMSO) δ 10.00 (s, 1H), 9.73 (s, 1H), 9.41 (s, 1H), 9.13 (s, 1H), 8.38 (d, J = 5.7 Hz, 1H), 8.28 (d, J = 1.7 Hz, 1H), 8.01 (d, J = 9.0 Hz, 1H), 7.72-7.66 (m, 2H), 7.05-7.02 (m, 2H), 6.67-6.63 (m, 2H), 6.57 (s, 1H), 5.99 (s, 1H), 4.27-4.16 (m, 2H), 2.25 (s, 3H), 1.25 (t, J = 7.1 Hz, 3H). | Rt = 2.55 min, m/z 470.2 [M + H]+ (Method 1) |
| 10 | ethyl 7-(3-fluoro-4-hydroxyphenyl)-6-(isoquinolin-6-ylcarbamoyl)-5-methyl-4,7-dihydropyrazolo[1,5-a]pyrimidine-2-carboxylate | Intermediate 1A/ 3-fluoro-4-hydroxybenz-aldehyde/ethyl 5-amino-1H-pyrazole-3-carboxylate | $^1$H NMR (400 MHz, d6-DMSO) δ 10.03 (s, 1H), 9.90 (s, 1H), 9.80 (s, 1H), 9.14 (s, 1H), 8.39 (d, J = 5.8 Hz, 1H), 8.28 (d, J = 1.7 Hz, 1H), 8.02 (d, J = 9.0 Hz, 1H), 7.72-7.67 (m, 2H), 6.96-6.82 (m, 3H), 6.56 (s, 1H), 6.00 (s, 1H), 4.28-4.17 (m, 2H), 2.26 (s, 3H), 1.25 (t, J = 7.1 Hz, 3H). | Rt = 2.62 min, m/z 488.2 [M + H]+ (Method 1) |

| Ex. | Structure | Intermediate 1X/aldehyde/ amino heterocycle | 1H NMR | LC-MS |
|---|---|---|---|---|
| 11 | ethyl 6-((1H-indazol-5-yl)carbamoyl)-5-methyl-7-(tetrahydro-2H-pyran-4-yl)-4,7-dihydropyrazolo[1,5-a]pyrimidine-2-carboxylate | Intermediate 1B/ tetrahydropyran-4-carbaldehyde/ethyl 5-amino-1H-pyrazole-3-carboxylate | $^1$H NMR (400 MHz, d6-DMSO) δ 12.96 (s, 1H), 9.77 (s, 1H), 9.37 (s, 1H), 8.13 (s, 1H), 8.02 (s, 1H), 7.49-7.48 (m, 2H), 5.94 (s, 1H), 5.45 (d, J = 2.8 Hz, 1H), 4.32-4.20 (m, 2H), 3.83-3.73 (m, 2H), 3.22-3.12 (m, 2H), 2.18 (s, 3H), 2.08-2.00 (m, 1H), 1.69-1.57 (m, 1H), 1.47 (d, J = 12.1 Hz, 1H), 1.29 (t, J = 7.1 Hz, 3H), 1.19 (d, J = 12.4 Hz, 1H), 1.00-0.88 (m, 1H). | Rt = 2.98 min, m/z 451.2 [M + H]+ (Method 2) |
| 12 | ethyl 6-((1H-indazol-5-yl)carbamoyl)-5-methyl-7-(1-methylpiperidin-4-yl)-4,7-dihydropyrazolo[1,5-a]pyrimidine-2-carboxylate | Intermediate 1B/1-methyl-piperidine-4-carbaldehyde/ ethyl 5-amino-1H-pyrazole-3-carboxylate | $^1$H NMR (400 MHz, d6-DMSO) δ 12.96 (s, 1H), 9.75 (s, 1H), 9.33 (s, 1H), 8.12 (s, 1H), 8.02 (s, 1H), 7.49-7.47 (m, 2H), 5.92 (s, 1H), 5.45 (d, J = 2.1 Hz, 1H), 4.32-4.20 (m, 2H), 2.71-2.66 (m, 2H), 2.17 (s, 3H), 2.04 (s, 3H), 1.71-1.62 (m, 4H), 1.51 (d, J = 12.2 Hz, 1H), 1.31-1.23 (m, 4H), 0.97-0.85 (m, 1H). | Rt = 2.26 min, m/z 464.2 [M + H]+ (Method 2) |
| 13 | ethyl 6-((1H-indazol-5-yl)carbamoyl)-7-isobutyl-5-methyl-4,7-dihydropyrazolo[1,5-a]pyrimidine-2-carboxylate | Intermediate 1B/3-methylbutyr-aldehyde/ethyl 5-amino-1H-pyrazole-3-carboxylate | $^1$H NMR (400 MHz, d6-DMSO) δ 12.96 (s, 1H), 9.77 (s, 1H), 9.35 (s, 1H), 8.11 (s, 1H), 8.02 (s, 1H), 7.48-7.47 (m, 2H), 5.92 (s, 1H), 5.52 (t, J = 5.3 Hz, 1H), 4.32-4.20 (m, 2H), 2.14 (s, 3H), 1.80-1.57 (m, 3H), 1.29 (t, J = 7.1 Hz, 3H), 0.82 (d, J = 6.5 Hz, 3H), 0.73 (d, J = 6.4 H, 3H). | Rt = 3.63 min, m/z 423.2 [M + H]+ (Method 2) |
| 14 | ethyl 6-((1H-indazol-5-yl)carbamoyl)-7-cyclohexyl-5-methyl-4,7-dihydropyrazolo[1,5-a]pyrimidine-2-carboxylate | Intermediate 1B/ cyclohexane-carbaldehyde/ ethyl 5-amino-1H-pyrazole-3-carboxylate | $^1$H NMR (400 MHz, d6-DMSO) δ 12.95 (s, 1H), 9.73 (s, 1H), 9.28 (s, 1H), 8.11 (s, 1H), 8.01 (s, 1H), 7.49-7.47 (m, 2H), 5.91 (s, 1H), 5.41 (d, J = 2.4 Hz, 1H), 4.32-4.20 (m, 2H), 2.16 (s, 3H), 1.81-1.74 (m, 1H), 1.65-1.54 (m, 4H), 1.37-1.28 (m, 4H), 1.15-0.93 (m, 4H), 0.71-0.62 (m, 1H). | Rt = 3.92 min, m/z 449.2 [M + H]+ (Method 2) |

| Ex. | Structure | Intermediate 1X/aldehyde/ amino heterocycle | 1H NMR | LC-MS |
|---|---|---|---|---|
| 15 | ethyl 6-([1,2,4]triazolo[4,3-a]pyridin-7-ylcarbamoyl)-7-(3-fluoro-4-(trifluoromethyl)phenyl)-5-methyl-4,7-dihydropyrazolo[1,5-a]pyrimidine-2-carboxylate | Intermediate 1C/3-fluoro-4-(trifluoro-methyl)benz-aldehyde/ethyl 5-amino-1H-pyrazole-3-carboxylate | $^1$H NMR (400 MHz, d6-DMSO) δ 10.09-10.05 (m, 2H), 9.10 (d, J = 0.8 Hz, 1H), 8.46-8.44 (m, 1H), 8.00-7.98 (m, 1H), 7.77 (t, J = 7.9 Hz, 1H), 7.29-7.21 (m, 2H), 7.02 (dd, J = 1.9, 7.4 Hz, 1H), 6.70 (s, 1H), 6.07 (s, 1H), 4.28-4.16 (m, 2H), 2.27 (s, 3H), 1.25 (dd, J = 7.1, 7.1 Hz, 3H). | Rt = 3.56 min, m/z 530.2 [M + H]+ (Method 1) |
| 16 | ethyl 6-((1H-indazol-5-yl)carbamoyl)-3-cyano-5-methyl-7-(4-(trifluoromethyl)phenyl)-4,7-dihydropyrazolo[1,5-a]pyrimidine-2-carboxylate | Intermediate 1B/4-(trifluoro-methyl)benz-aldehyde/ethyl 5-amino-4-cyano-1H-pyrazole-3-carboxylate | $^1$H NMR (400 MHz, d6-DMSO) δ 12.97 (s, 1H), 10.68 (s, 1H), 9.86 (s, 1H), 7.99-7.97 (m, 2H), 7.72 (d, J = 8.3 Hz, 2H), 7.47-7.42 (m, 3H), 7.34 (dd, J = 1.7, 8.9 Hz, 1H), 6.67 (s, 1H), 4.33-4.22 (m, 2H), 2.23 (s, 3H), 1.26 (t, J = 7.1 Hz, 3H). | Rt = 4.20 min, m/z 536.2 [M + H]+ (Method 1) |
| 17 | ethyl 6-((1H-indazol-5-yl)carbamoyl)-7-(4-fluorophenyl)-5-methyl-4,7-dihydropyrazolo[1,5-a]pyrimidine-3-carboxylate | Intermediate 1B/4-fluorobenz-aldehyde/ethyl 5-amino-1H-pyrazole-4-carboxylate | $^1$H NMR (400 MHz, d6-DMSO) δ 12.94 (s, 1H), 9.83 (s, 1H), 8.90 (s, 1H), 7.99 (d, J = 2.4 Hz, 2H), 7.68 (s, 1H), 7.44 (d, J = 8.8 Hz, 1H), 7.37 (dd, J = 1.8, 8.9 Hz, 1H), 7.27-7.23 (m, 2H), 7.13 (dd, J = 8.9, 8.9 Hz, 2H), 6.51 (s, 1H), 4.25 (q, J = 7.0 Hz, 2H), 2.29 (s, 3H), 1.29 (dd, J = 7.1, 7.1 Hz, 3H). | Rt = 3.82 min, m/z 461.2 [M + H]+ (Method 1) |
| 18 | 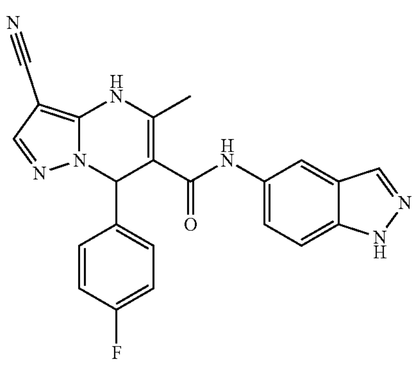 [SMILES: CC1=C(C(=O)Nc2ccc3[nH]ncc3c2)C(c2ccc(F)cc2)n2ncc(C#N)c2N1] | Intermediate 1B/4-fluorobenz-aldehyde/5-amino-1H-pyrazole-4-carbonitrile | $^1$H NMR (400 MHz, d6-DMSO) δ 12.94 (s, 1H), 10.38 (s, 1H), 9.80 (s, 1H), 7.98 (s, 2H), 7.84 (s, 1H), 7.44 (d, J = 8.9 Hz, 1H), 7.35 (dd, J = 1.8, 8.9 Hz, 1H), 7.29-7.25 (m, 2H), 7.14 (dd, J = 8.8, 8.8 Hz, 2H), 6.53 (s, 1H), 2.22 (s, 3H). | Rt = 3.31 min, m/z 414.2 [M + H]+ (Method 2) |

-continued

| Ex. | Structure | Intermediate 1X/aldehyde/ amino heterocycle | 1H NMR | LC-MS |
|---|---|---|---|---|
| | 3-cyano-7-(4-fluorophenyl)-N-(1H-indazol-5-yl)-5-methyl-4,7-dihydropyrazolo[1,5-a]pyrimidine-6-carboxamide | | | |
| 19 | 7-(4-fluorophenyl)-N6-(1H-indazol-5-yl)-5-methyl-4,7-dihydropyrazolo[1,5-a]pyrimidine-3,6-dicarboxamide | Intermediate 1B/4-fluorobenz-aldehyde/5-amino-1H-pyrazole-4-carboxamide | $^1$H NMR (400 MHz, d6-DMSO) δ 12.94 (s, 1H), 9.77 (s, 1H), 8.66 (s, 1H), 8.00-7.97 (m, 2H), 7.81 (s, 1H), 7.51 (s, 1H), 7.46-7.34 (m, 2H), 7.27-7.22 (m, 2H), 7.15-7.09 (m, 2H), 7.01 (s, 1H), 6.51 (s, 1H), 2.28 (s, 3H). | Rt = 2.79 min, m/z 432.3 [M + H]+ (Method 1) |
| 20 | 7-(4-fluorophenyl)-N-(1H-indazol-5-yl)-2-(4-methoxyphenyl)-5-methyl-4,7-dihydropyrazolo[1,5-a]pyrimidine-6-carboxamide | Intermediate 1B/4-fluorobenz-aldehyde/3-(4-methoxyphenyl)-1H-pyrazol-5-amine | $^1$H NMR (400 MHz, d6-DMSO) δ 12.92 (s, 1H), 9.64 (s, 1H), 9.56 (s, 1H), 8.00 (d, J = 15.6 Hz, 2H), 7.63 (d, J = 8.6 Hz, 2H), 7.45-7.38 (m, 2H), 7.27-7.22 (m, 2H), 7.14-7.08 (m, 2H), 6.91 (d, J = 8.8 Hz, 2H), 6.59 (s, 1H), 5.94 (s, 1H), 3.76 (s, 3H), 2.23 (s, 3H). | Rt = 4.02 min, m/z 495.3 [M + H]+ (Method 1) |
| 21 | 7-(4-fluorophenyl)-N-(1H-indazol-5-yl)-2-(2-methoxyphenyl)-5-methyl-4,7-dihydropyrazolo[1,5-a]pyrimidine-6-carboxamide | Intermediate 1B/4-fluorobenz-aldehyde/3-(2-methoxyphenyl)-1H-pyrazol-5-amine | $^1$H NMR (400 MHz, d6-DMSO) δ 12.93 (s, 1H), 9.65 (s, 1H), 9.50 (s, 1H), 8.00 (d, J = 16.1 Hz, 2H), 7.76-7.73 (m, 1H), 7.45-7.40 (m, 2H), 7.29-7.23 (m, 3H), 7.14-7.05 (m, 3H), 6.95-6.90 (m, 1H), 6.63 (s, 1H), 6.11 (s, 1H), 3.85 (s, 3H), 2.24 (s, 3H). | Rt = 4.08 min, m/z 495.3 [M + H]+ (Method 1) |
| 22 | 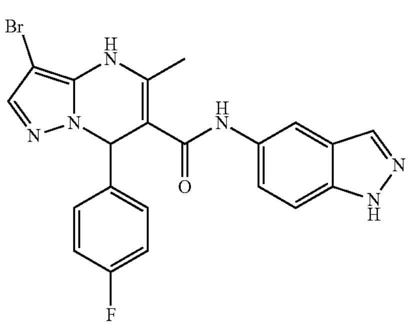 [SMILES: CC1=C(C(=O)Nc2ccc3[nH]ncc3c2)C(c2ccc(F)cc2)n2ncc(Br)c2N1] | Intermediate 1B/4-fluorobenz-aldehyde/4-bromo-1H-pyrazol-5-amine | $^1$H NMR (400 MHz, d6-DMSO) δ 12.94 (s, 1H), 9.70 (s, 1H), 9.45 (s, 1H), 7.98-7.96 (m, 2H), 7.45-7.35 (m, 3H), 7.25-7.20 (m, 2H), 7.14-7.08 (m, 2H), 6.51 (s, 1H), 2.25 (s, 3H). | Rt = 3.59 min, m/z 467.1/469.1 [M + H]+ (Method 1) |

-continued

| Ex. | Structure | Intermediate 1X/aldehyde/ amino heterocycle | 1H NMR | LC-MS |
|---|---|---|---|---|
| | 3-bromo-7-(4-fluorophenyl)-N-(1H-indazol-5-yl)-5-methyl-4,7-\ dihydropyrazolo[1,5-a]pyrimidine-6-carboxamide | | | |
| 23 | 7-(4-fluorophenyl)-N-(1H-indazol-5-yl)-5-methyl-4,7-dihydrotetrazolo[1,5-a]pyrimidine-6-carboxamide | Intermediate 1B/4-fluorobenz-aldehyde/1H-tetrazol-5-amine | $^1$H NMR (400 MHz, d6-DMSO) δ 12.95 (s, 1H), 10.78-10.69 (m, 1H), 9.80 (s, 1H), 7.98-7.93 (m, 2H), 7.46-7.29 (m, 4H), 7.21-7.15 (m, 2H), 6.88 (s, 1H), 2.22 (s, 3H). | Rt = 3.04 min, m/z 391.2 [M + H]+ (Method 1) |
| 24 | 7-(4-chlorophenyl)-N-(1H-indazol-5-yl)-5-methyl-4,7-dihydrotetrazolo[1,5-a]pyrimdine-6-carboxamide | Intermediate 1B/4-chlorobenz-aldehyde/1H-tetrazol-5-amine | $^1$H NMR (400 MHz, d6-DMSO) δ 12.96 (s, 1H), 10.76 (s, 1H), 9.85 (s, 1H), 7.99-7.95 (m, 2H), 7.46-7.33 (m, 6H), 6.89 (s, 1H), 2.24 (s, 3H). | Rt = 3.27 min, m/z 407.1 [M + H]+ (Method 2) |
| 25 | 7-(3-fluoro-4-(trifluoromethyl)phenyl)-N-(1H-indazol-5-yl)-5-methyl-4,7-dihydrotetrazolo[1,5-a]pyrimidine-6-carboxamide | Intermediate 1B/3-fluoro-4-(trifluoromethyl)-benzaldehyde/1H-tetrazol-5-amine | $^1$H NMR (400 MHz, d6-DMSO) δ 12.97 (s, 1H), 10.88 (s, 1H), 9.89 (s, 1H), 8.00-7.95 (m, 2H), 7.82 (dd, J = 7.8, 7.8 Hz, 1H), 7.53 (d, J = 11.4 Hz, 1H), 7.44 (dd, J = 9.0, 9.0 Hz, 2H), 7.33 (dd, J = 1.8, 8.9 Hz, 1H), 6.98 (s, 1H), 2.25 (s, 3H). | Rt = 3.62 min, m/z 459.1 [M + H]+ (Method 1) |

| Ex. | Structure | Intermediate 1X/aldehyde/ amino heterocycle | 1H NMR | LC-MS |
|---|---|---|---|---|
| 26 | 7-(2-fluoro-4-(trifluoromethyl)phenyl)-N-(1H-indazol-5-yl)-5-methyl-4,7-dihydrotetrazolo[1,5-a]pyrimidine-6-carboxamide | Intermediate 1B/2-fluoro-4-(trifluoromethyl)-benzaldehyde/1H-tetrazol-5-amine | $^1$H NMR (400 MHz, d6-DMSO) δ 12.96 (s, 1H), 10.91 (s, 1H), 9.94 (s, 1H), 7.99-7.95 (m, 2H), 7.74 (d, J = 10.2 Hz, 1H), 7.69-7.60 (m, 2H), 7.44 (d, J = 8.9 Hz, 1H), 7.33 (dd, J = 1.9, 9.0 Hz, 1H), 7.16 (s, 1H), 2.24 (s, 3H). | Rt = 3.57 min, m/z 459.1 [M + H]+ (Method 1) |
| 27 | N-(1H-indazol-5-yl)-5-methyl-7-(4-(trifluoromethyl)phenyl)-4,7-dihydrotetrazolo[1,5-a]pyrimidine-6-carboxamide | Intermediate 1B/4-(trifluoromethyl)-benzaldehyde/1H-tetrazol-5-amine | $^1$H NMR (400 MHz, d6-DMSO) δ 12.97 (s, 1H), 10.80 (s, 1H), 9.89 (s, 1H), 7.99-7.95 (m, 2H), 7.75 (d, J = 8.1 Hz, 2H), 7.56 (d, J = 8.1 Hz, 2H), 7.44 (d, J = 8.9 Hz, 1H), 7.35-7.31 (m, 1H), 6.99 (s, 1H), 2.25 (s, 3H). | Rt = 3.49 min, m/z 441.2 [M + H]+ (Method 2) |
| 28 | 7-(4-fluorophenyl)-N-(1H-indazol-5-yl)-2,5-dimethyl-4,7-dihydropyrazolo[1,5-a]pyrimidine-6-carboxamide | Intermediate 1B/4-fluorobenz-aldehyde/3-methyl-1H-pyrazol-5-amine | $^1$H NMR (400 MHz, d6-DMSO) δ 12.96-12.89 (m, 1H), 9.56 (s, 1H), 9.38 (s, 1H), 7.99-7.96 (m, 2H), 7.44-7.35 (m, 2H), 7.21-7.16 (m, 2H), 7.12-7.06 (m, 2H), 6.43 (s, 1H), 5.38 (s, 1H), 2.19 (s, 3H), 2.02 (s, 3H). | Rt = 3.04 min, m/z 403.1 [M + H]+ (Method 1) |

-continued

| Ex. | Structure | Intermediate 1X/aldehyde/ amino heterocycle | 1H NMR | LC-MS |
|---|---|---|---|---|
| 29 | 2-(tert-butyl)-7-(4-fluorophenyl)-N-(1H-indazol-5-yl)-5-methyl-4,7-dihydropyrazolo[1,5-a]pyrimidine-6-carboxamide | Intermediate 1B/4-fluorobenz-aldehyde/3-(tert-butyl)-1H-pyrazol-5-amine | $^1$H NMR (400 MHz, d6-DMSO) δ 12.92 (s, 1H), 9.61 (s, 1H), 9.35 (s, 1H), 8.03 (s, 1H), 7.97 (s, 1H), 7.42 (s, 2H), 7.14-7.06 (m, 4H), 6.55 (s, 1H), 5.44 (s, 1H), 2.19 (s, 3H), 1.17 (s, 9H). | Rt = 3.96 min m/z 445.3 [M + H]+ (Method 1) |
| 30 | 2-bromo-7-(4-fluorophenyl)-N-(1H-indazol-5-yl)-5-methyl-4,7-dihydropyrazolo[1,5-a]pyrimidine-6-carboxamide | Intermediate 1B/4-fluorobenz-aldehyde/3-bromo-1H-pyrazol-5-amine | $^1$H NMR (400 MHz, d6-DMSO) δ 12.94 (s, 1H), 9.68-9.65 (m, 2H), 7.98-7.96 (m, 2H), 7.45-7.33 (m, 2H), 7.27-7.22 (m, 2H), 7.16-7.10 (m, 2H), 6.47 (s, 1H), 5.70 (s, 1H), 2.20 (s, 3H). | Rt = 3.53 min, m/z 465.1/467.0 [M + H]+ (Method 1) |
| 31 | 2-cyano-7-(4-fluorophenyl)-N-(1H-indazol-5-yl)-5-methyl-4,7-dihydropyrazolo[1,5-a]pyrimidine-6-carboxamide | Intermediate 1B/4-fluorobenz-aldehyde/3-cyano-1H-pyrazol-5-amine | $^1$H NMR (400 MHz, d6-DMSO) δ 12.94 (s, 1H), 9.88 (s, 1H), 9.72 (s, 1H), 7.98-7.96 (m, 2H), 7.44-7.34 (m, 2H), 7.31-7.27 (m, 2H), 7.18-7.12 (m, 2H), 6.62 (s, 1H), 6.25 (s, 1H), 2.23 (s, 3H). | Rt = 3.52 min, m/z 414.1 [M + H]+ (Method 2) |
| 32 | 7-(6-chloropyridin-3-yl)-N-(1H-indazol-5-yl)-5-methyl-2-(trifluoromethyl)-4,7-dihydropyrazolo[1,5-a]pyrimidine-6-carboxamide | Intermediate 1B/6-chloronicotinaldehyde/3-(trifluoromethyl)-1H-pyrazol-5-amine | $^1$H NMR (400 MHz, d6-DMSO) δ 12.96 (s, 1H), 9.94 (s, 1H), 9.75 (s, 1H), 8.34 (d, J = 2.3 Hz, 1H), 7.99-7.97 (m, 2H), 7.71-7.67 (m, 1H), 7.52-7.43 (m, 2H), 7.38-7.33 (m, 1H), 6.64 (s, 1H), 6.02 (s, 1H), 2.24 (s, 3H). | Rt = 3.77 min, m/z 474.1 [M + H]+ (Method 2) |

-continued

| Ex. | Structure | Intermediate 1X/aldehyde/ amino heterocycle | 1H NMR | LC-MS |
|---|---|---|---|---|
| 33 | N-(1H-indazol-5-yl)-5-methyl-7-(1-methylpiperidin-4-yl)-2-(trifluoromethyl)-4,7-dihydropyrazolo[1,5-a]pyrimidine-6-carboxamide | Intermediate 1B/1-methyl-piperidine-4-carbaldehyde/3-(trifluoromethyl)-1H-pyrazol-5-amine | $^1$H NMR (400 MHz, d6-DMSO) δ 12.96 (s, 1H), 9.79 (s, 1H), 9.45 (s, 1H), 8.12 (s, 1H), 8.02 (s, 1H), 7.48-7.47 (m, 2H), 5.90 (s, 1H), 5.45 (s, 1H), 2.75-2.67 (m, 2H), 2.17 (s, 3H), 2.05 (s, 3H), 1.73-1.48 (m, 5H), 1.32-1.25 (m, 1H), 0.94-0.82 (m, 1H). | Rt = 2.52 min, m/z 460.2 [M + H]+ (Method 2) |
| 34 | 2-cyano-N-(1H-indazol-5-yl)-5-methyl-7-(4-(trifluoromethyl)phenyl)-4,7-dihydropyrazolo[1,5-a]pyrimidine-6-carboxamide | Intermediate 1B/4-(trifluoro-methyl)benz-aldehyde/3-cyano-1H-pyrazol-5-amine | $^1$H NMR (400 MHz, d6-DMSO) δ 12.95 (s, 1H), 9.97 (s, 1H), 9.76 (s, 1H), 7.98-7.97 (m, 2H), 7.71 (d, J = 8.2 Hz, 2H), 7.46-7.42 (m, 3H), 7.36 (dd, J = 1.7, 8.7 Hz, 1H), 6.70 (s, 1H), 6.30 (s, 1H), 2.22 (s, 3H). | Rt = 3.99 min, m/z 464.1 [M + H]+ (Method 1) |
| 35 | 7-(3-fluoro-4-(trifluoromethyl)phenyl)-N-(isoquinolin-6-yl)-2-(methoxymethyl)-5-methyl-4,7-dihydropyrazolo[1,5-a]pyrimidine-6-carboxamide | Intermediate 1B/4-(trifluoro-methyl)benz-aldehyde/3-(methoxymethyl)-1H-pyrazol-5-amine | $^1$H NMR (400 MHz, d6-DMSO) δ 12.93 (s, 1H), 9.67 (s, 1H), 9.57 (s, 1H), 7.98 (d, J = 9.0 Hz, 2H), 7.66 (d, J = 8.2 Hz, 2H), 7.45-7.31 (m, 4H), 6.58 (s, 1H), 5.59 (s, 1H), 4.19 (d, J = 3.8 Hz, 2H), 3.19 (s, 3H), 2.21 (s, 3H). | Rt = 3.64 min, m/z 483.3 [M + H]+ (Method 1) |
| 36 | 7-(3-fluoro-4-(trifluoromethyl)phenyl)-N-(isoquinolin-6-yl)-2-(methoxymethyl)-5-methyl-4,7-dihydropyrazolo[1,5-a]pyrimidine-6-carboxamide | Intermediate 1A/ 3-fluoro-4-(trifluoromethyl)-benzaldehyde/3-(methoxymethyl)-1H-pyrazol-5-amine | $^1$H NMR (400 MHz, d6-DMSO) δ 10.06 (s, 1H), 9.85 (s, 1H), 9.14 (s, 1H), 8.40-8.38 (m, 1H), 8.27 (d, J = 1.5 Hz, 1H), 8.02 (d, J = 9.0 Hz, 1H), 7.76-7.67 (m, 3H), 7.22-7.16 (m, 2H), 6.60 (s, 1H), 5.65 (s, 1H), 4.22-4.20 (m, 2H), 3.20 (s, 3H), 2.26 (s, 3H). | Rt = 3.21 min, m/z 512.2 [M + H]+ (Method 1) |

-continued

| Ex. | Structure | Intermediate 1X/aldehyde/ amino heterocycle | 1H NMR | LC-MS |
|---|---|---|---|---|
| 37 | 2-(2-(dimethylamino)ethyl)-7-(3-fluoro-4-(trifluoromethyl)phenyl)-N-(isoquinolin-6-yl)-5-methyl-4,7-dihydropyrazolo[1,5-a]pyrimidine-6-carboxamide | Intermediate 1A/ 3-fluoro-4-trifluoromethyl-benzaldehyde/3-(2-(dimethyl-amino)ethyl)-1H-pyrazol-5-amine | $^1$H NMR (400 MHz, d6-DMSO) δ 10.04 (s, 1H), 9.76 (s, 1H), 9.14 (s, 1H), 8.39 (d, J = 5.8 Hz, 2H), 8.29-8.26 (m, 1H), 8.02 (d, J = 9.0 Hz, 1H), 7.75-7.66 (m, 4H), 7.19-7.10 (m, 2H), 6.57 (s, 1H), 5.54 (s, 1H), 2.57-2.52 (m, 2H), 2.45-2.37 (m, 2H), 2.13 (s, 6H). | Rt = 2.42 min, m/z 539.1 [M + H]+ (Method 1) |
| 38 | 7-(1H-indol-6-yl)-N-(isoquinolin-6-yl)-2-(methoxymethyl)-5-methyl-4,7-dihydropyrazolo[1,5-a]pyrimidine-6-carboxamide | Intermediate 1A/1H-indole-6-carb-aldehyde/3-(methoxymethyl)-1H-pyrazol-5-amine | $^1$H NMR (400 MHz, d6-DMSO) δ 10.99 (s, 1H), 9.99 (s, 1H), 9.59 (s, 1H), 9.11 (s, 1H), 8.36 (d, J = 5.8 Hz, 1H), 8.28 (d, J = 1.6 Hz, 1H), 7.98 (d, J = 8.9 Hz, 1H), 7.73-7.62 (m, 2H), 7.38 (d, J = 8.2 Hz, 1H), 7.28-7.26 (m, 1H), 7.20 (s, 1H), 6.84 (dd, J = 1.5, 8.3 Hz, 1H), 6.67 (s, 1H), 6.32-6.30 (m, 1H), 5.57 (s, 1H), 4.17 (d, J = 5.1 Hz, 2H), 3.18 (s, 3H), 2.26 (s, 3H). | Rt = 2.68 min, m/z 465.3 [M + H]+ (Method 1) |
| 39 | 7-(6-chloropyridin-3-yl)-N-(6-fluoro-1H-indazol-5-yl)-5-methyl-2-(trifluoromethyl)-4,7-dihydropyrazolo[1,5-a]pyrimidine-6-carboxamide | Intermediate 1D/6-chloronicotin-aldehyde/3-(trifluoromethyl)-1H-pyrazol-5-amine | $^1$H NMR (400 MHz, d6-DMSO) δ 13.09 (s, 1H), 9.99 (s, 1H), 9.50 (s, 1H), 8.37 (d, J = 2.3 Hz, 1H), 8.04 (s, 1H), 7.77-7.69 (m, 2H), 7.52 (d, J = 8.3 Hz, 1H), 7.37 (d, J = 10.4 Hz, 1H), 6.63 (s, 1H), 6.02 (s, 1H), 2.29 (s, 3H). | Rt = 3.93 min, m/z 492.2 [M + H]+ (Method 1) |
| 40 | N-(6-fluoro-1H-indazol-5-yl)-7-(3-fluoro-4-(trifluoromethyl)phenyl)-5-methyl-4,7-dihydrotetrazolo[1,5-a]pyrimidine-6-carboxamide | Intermediate 1D/3-fluoro-4-(tri-fluoromethyl)-benzaldehyde/1H-tetrazol-5-amine | $^1$H NMR (400 MHz, d6-DMSO) δ 13.11 (s, 1H), 10.92 (s, 1H), 9.67 (s, 1H), 8.04 (s, 1H), 7.87-7.81 (m, 1H), 7.74 (d, J = 7.3 Hz, 1H), 7.56 (d, J = 11.4 Hz, 1H), 7.46-7.36 (m, 2H), 6.96 (s, 1H), 2.30 (s, 3H). | Rt = 3.74 min, m/z 477.2 [M + H]+ (Method 1) |

-continued

| Ex. | Structure | Intermediate 1X/aldehyde/amino heterocycle | 1H NMR | LC-MS |
|---|---|---|---|---|
| 113 | ethyl 6-((1,6-naphthyridin-2-yl)carbamoyl)-7-(3-fluoro-4-(trifluoromethyl)phenyl)-5-methyl-4,7-dihydropyrazolo[1,5-a]pyrimidine-2-carboxylate | Intermediate 1G/3-fluoro-4-(trifluoro-methyl)benz-aldehyde/ethyl 5-amino-1H-pyrazole-3-carboxylate | $^1$H NMR (400 MHz, d6-DMSO) δ 10.82 (s, 1H), 10.12 (s, 1H), 9.21 (s, 1H), 8.63 (d, J = 5.9 Hz, 1H), 8.44 (d, J = 9.0 Hz, 1H), 8.12 (d, J = 9.0 Hz, 1H), 7.75 (t, J = 7.8 Hz, 1H), 7.65 (d, J = 5.9 Hz, 1H), 7.38 (d, J = 11.6 Hz, 1H), 7.32 (d, J = 8.2 Hz, 1H), 6.68 (s, 1H), 6.06 (s, 1H), 4.28-4.16 (m, 2H), 2.32 (s, 3H), 1.25 (t, J = 7.1 Hz, 3H). | Rt = 3.65 mins, m/z 541.1 [M + H]$^+$ (Method 1) |
| 114 | ethyl 7-(3-fluoro-4-(trifluoromethyl)phenyl)-5-methyl-6-((4-methylisoquinolin-6-yl)carbamoyl)-4,7-dihydropyrazolo[1,5-a]pyrimidine-2-carboxylate | Intermediate 1H/3-fluoro-4-(trifluoro-methyl)benz-aldehyde/ethyl-3-amino-1H-pyrazole-5-carboxylate | $^1$H NMR (400 MHz, d6-DMSO) δ 10.14 (s, 1H), 10.01 (s, 1H), 9.01 (s, 1H), 8.28 (d, J = 5.5 Hz, 2H), 8.02 (d, J = 8.9 Hz, 1H), 7.80-7.74 (m, 2H), 7.32-7.24 (m, 2H), 6.72 (s, 1H), 6.07 (s, 1H), 4.29-4.17 (m, 2H), 2.48 (s, 3H), 2.29-2.28 (m, 3H), 1.25 (t, J = 7.1 Hz, 3H). | Rt = 3.43 mins, m/z 554.2 [M + H]$^+$ (Method 1) |
| 115 | ethyl 7-(4-(difluoromethyl)-3-fluorophenyl)-6-(isoquinolin-6-ylcarbamoyl)-5-methyl-4,7-dihydropyrazolo[1,5-a]pyrimidine-2-carboxylate | Intermediate 1A/4-(difluoromethyl)-3-fluorobenzaldehyde/ethyl 5-amino-1H-pyrazole-3-carboxylate | $^1$H NMR (400 MHz, d6-DMSO) δ 10.11 (s, 1H), 9.96 (s, 1H), 9.15 (s, 1H), 8.39 (d, J = 5.7 Hz, 1H), 8.28 (d, J = 1.7 Hz, 1H), 8.03 (d, J = 9.0 Hz, 1H), 7.72-7.68 (m, 2H), 7.60 (t, J = 7.6 Hz, 1H), 7.22-7.13 (m, 3H), 6.68 (s, 1H), 6.06 (s, 1H), 4.28-4.17 (m, 2H), 2.28 (s, 3H), 1.25 (t, J = 7.1 Hz, 3H). | Rt = 3.09 min, m/z 522.3 [M + H]$^+$ (Method 1) |

| Ex. | Structure | Intermediate 1X/aldehyde/ amino heterocycle | 1H NMR | LC-MS |
|---|---|---|---|---|
| 116 | 7-(3-fluoro-4-(trifluoromethyl)phenyl)-N-(isoquinolin-6-yl)-5-methyl-2-(oxetan-3-yl)-4,7-dihydropyrazolo[1,5-a]pyrimidine-6-carboxamide | Intermediate 1A/3-fluoro-4-(trifluoro-methyl)benzaldehyde/3-(oxetan-3-yl)-1H-pyrazol-5-amine | $^1$H NMR (400 MHz, d6-DMSO) δ 10.07 (s, 1H), 9.87 (s, 1H), 9.15 (s, 1H), 8.40 (d, J = 5.8 Hz, 1H), 8.28 (d, J = 2.0 Hz, 1H), 8.03 (d, J = 8.9 Hz, 1H), 7.77-7.68 (m, 3H), 7.22-7.16 (m, 2H), 6.61 (s, 1H), 5.76 (s, 1H), 4.80 (ddd, J = 8.4, 5.6, 2.7 Hz, 2H), 4.60 (ddd, J = 6.7, 5.6, 0.9 Hz, 2H), 4.11 (ddd, J = 15.4, 8.4, 7.0 Hz, 1H), 2.27 (s, 3H). | Rt = 0.63 min, m/z 523.7 [M + H]$^+$ (Method 7) |
| 117 | (7-(3-Fluoro-4-(trifluoromethyl)phenyl)-N-(isoquinolin-6-yl)-5-methyl-2-(methylthio)-4,7-dihydropyrazolo[1,5-a]pyrimidine-6-carboxamide | Intermediate 1A/3-fluoro-4-(trifluoro-methyl)benzaldehyde/3-(methylthio)-1H-pyrazol-5-amine | $^1$H NMR (400 MHz, d6-DMSO) δ 10.07 (s, 1H), 9.88 (s, 1H), 9.14 (s, 1H), 8.39 (d, J = 5.7 Hz, 1H), 8.27 (d, J = 1.7 Hz, 1H), 8.02 (d, J = 8.9 Hz, 1H), 7.78-7.67 (m, 3H), 7.21 (d, J = 9.7 Hz, 2H), 6.58 (s, 1H), 5.65 (s, 1H), 2.37 (s, 3H), 2.26 (s, 3H). | Rt = 3.38 min, m/z 514.2 [M + H]$^+$ (Method 1) |

Example 41

Step A

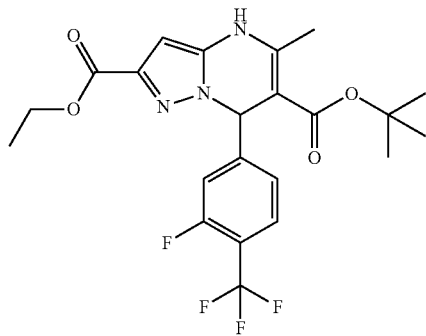 [SMILES: CCOC(=O)c1cc2n(n1)C(c1ccc(C(F)(F)F)c(F)c1)C(C(=O)OC(C)(C)C)=C(C)N2]

6-(tert-Butyl) 2-ethyl 7-(3-fluoro-4-(trifluoromethyl)phenyl)-5-methyl-4,7-dihydropyrazolo[1,5-a]pyrimidine-2,6-dicarboxylate (Intermediate 41A)

Ethyl 5-amino-1H-pyrazole-3-carboxylate (1.55 g, 10 mmol), tert-butyl acetoacetate (1.65 mL, 10 mmol), 3-fluoro-(4-trifluoromethyl)benzaldehyde (1.92 g, 10 mmol) and sodium bicarbonate (2.52 g, 30 mmol) were heated at 70° C. in DMF (3 mL) overnight. The reaction mixture was allowed to cool then partitioned between ethyl acetate (30 mL) and water (30 mL). The aqueous layer was further extracted with ethyl acetate (20 mL) and the combined organics were dried by passing through a hydrophobic fit, and evaporated to give an orange oil. The residue was dissolved in a minimum amount of DCM and loaded onto a 50 g Si cartridge. The product was eluted with 0-50% ethyl acetate in cyclohexane. The fractions containing the desired product were combined and evaporated to give a pale yellow solid. The solid was triturated with ethyl acetate/cyclohexane to give a white solid (1.25 g).

LCMS (Method 3): Rt=1.36 min, m/z 470.5 [M+H]+

Step B

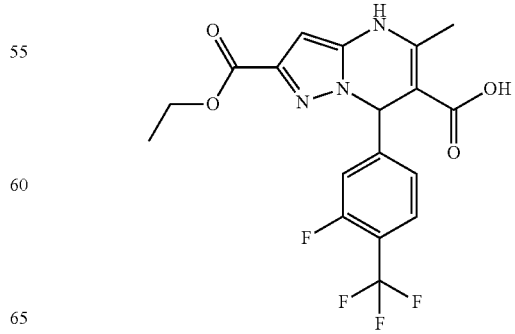

2-(Ethoxycarbonyl)-7-(3-fluoro-4-(trifluoromethyl)phenyl)-5-methyl-4,7-dihydropyrazolo[1,5-a]pyrimidine-6-carboxylic acid (Intermediate 41B)

Example 41A (1.25 g, 2.66 mmol) was dissolved in DCM (75 mL). Trimethylsilyl trifluoromethanesulfonate (0.96 ml, 5.33 mmol) was added slowly and the reaction mixture left to stir for 1 h. Triethylamine (0.74 ml, 5.33 mmol) was added and the reaction mixture was poured onto water. The organic layer was separated, dried by passing through a hydrophobic frit, and evaporated to give a white solid. The product was triturated with ethyl acetate/diethyl ether to give a white solid, (0.67 g)

LCMS (Method 3): Rt=1.06 min, m/z 414.3 [M+H]+ allowed to stand at RT overnight and then the mixture was partitioned between ethyl acetate (15 mL) and water (10 mL). The organic layer was separated and the aqueous was further extracted with ethyl acetate (2×15 mL). The combined organics were washed with brine (10 mL), dried ($Na_2SO_4$) and evaporated. The crude product was purified by chromatography on a 25 g Si cartridge eluting with 0-5% DCM in methanol. The desired product was obtained as a white solid (30 mg).

LCMS (Method 1): Rt=3.48 min, m/z 546.2 [M+H]+

$^1$H NMR (400 MHz, d6-DMSO) δ 11.26 (s, 1H), 10.17 (s, 1H), 8.92 (s, 1H), 8.26 (d, J=5.4 Hz, 1H), 7.86-7.74 (m, 2H), 7.30-7.22 (m, 2H), 7.08 (s, 1H), 6.80 (s, 1H), 6.09 (s, 1H), 4.29-4.17 (m, 2H), 2.31 (s, 3H), 1.25 (t, J=7.1 Hz, 3H).

Example 42

The following compound was prepared by analogous procedures to that used in Example 41 by varying the amine with that reported in the table below in step C.

| Ex | Structure | Amine | 1H NMR | LC-MS |
|---|---|---|---|---|
| 42 | ethyl 7-(3-fluoro-4-(trifluoromethyl)phenyl)-5-methyl-6-(thieno[2,3-c]pyridin-2-ylcarbamoyl)-4,7-dihydropyrazolo[1,5-a]pyrimidine-2-carboxylate | Thieno[2,3-c]pyridin-2-amine | $^1$H NMR (400 MHz, d6-DMSO) δ 11.37 (s, 1H), 10.22 (s, 1H), 8.97 (s, 1H), 8.34 (d, J = 4.8 Hz, 1H), 7.77 (t, J = 7.8 Hz, 1H), 7.61 (d, J = 5.3 Hz, 1H), 7.30-7.22 (m, 2H), 7.02 (s, 1H), 6.82 (s, 1H), 6.09 (s, 1H), 4.29-4.17 (m, 2H), 2.32 (s, 3H), 1.25 (t, J = 7.1 Hz, 3H). | Rt = 3.49 min, m/z 546.2 [M + H]+ (Method 1) |

Step C

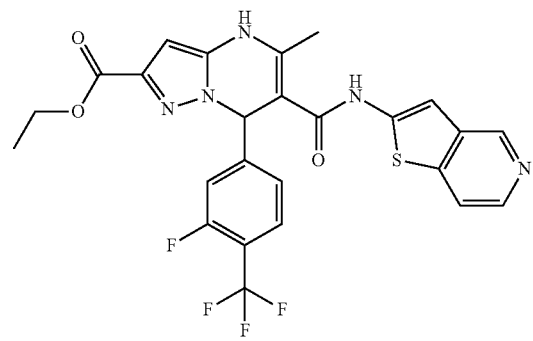 [SMILES: CCOC(=O)c1cc2n(n1)C(c1ccc(C(F)(F)F)c(F)c1)C(C(=O)Nc1cc3cnccc3s1)=C(C)N2]

Ethyl 7-(3-fluoro-4-(trifluoromethyl)phenyl)-5-methyl-6-(thieno[3,2-c]pyridin-2-ylcarbamoyl)-4,7-dihydropyrazolo[1,5-a]pyrimidine-2-carboxylate (Example 41)

Intermediate 41B (104 mg, 0.252 mmol) and thieno[3,2-c]pyridin-2-amine (69 mg, 0.460 mmol) were dissolved in DMF (2 mL) and DIPEA (88 μL, 0.504 mmol) and HATU (105 mg, 0.276 mmol) were added. The solution was

Example 43

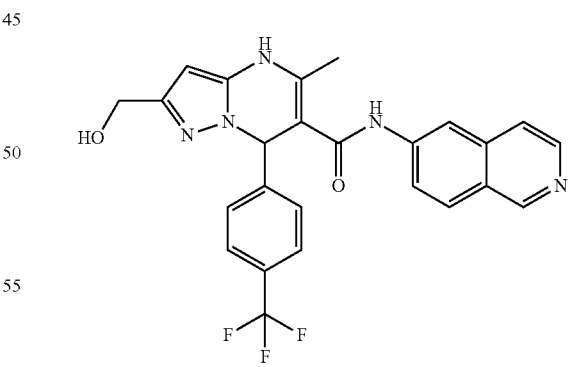

2-(hydroxymethyl)-N-(isoquinolin-6-yl)-5-methyl-7-(4-(trifluoromethyl)phenyl)-4,7-dihydropyrazolo[1,5-a]pyrimidine-6-carboxamide (Example 43)

A suspension of Example 1 (230 mg, 0.46 mmol) in THF (5 mL) was stirred under argon and cooled to 0° C. A solution of 2M lithium aluminium hydride in THF (0.7 mL, 1.35 mmol) was added dropwise and the reaction mixture was slowly allowed to warm to RT. After 3 h, the reaction was quenched by the addition of water (0.5 mL), 1N sodium hydroxide (0.5 mL) and then water (2 mL). The product was extracted into ethyl acetate (10 mL) and the organic extracts were dried by passing through a hydrophobic frit. After evaporation of the solvent, the crude product was chromatographed on a 25 g Si cartridge eluting with 0-10% methanol in DCM. The desired product was obtained as a yellow solid (89 mg).

LCMS (Method 1): Rt=2.80 min, m/z 480.2 [M+H]+

$^1$H NMR (400 MHz, d6-DMSO) δ 10.02 (s, 1H), 9.73 (s, 1H), 9.13 (s, 1H), 8.38 (d, J=5.7 Hz, 1H), 8.26 (d, J=1.8 Hz, 1H), 8.01 (d, J=8.9 Hz, 1H), 7.72-7.64 (m, 4H), 7.36 (d, J=8.1 Hz, 2H), 6.60 (s, 1H), 5.62 (s, 1H), 4.96 (dd, J=5.9, 5.9 Hz, 1H), 4.26 (d, J=5.8 Hz, 2H), 2.26 (s, 3H).

Example 44 to 71 and Examples 118 to 119

The following examples were prepared in analogy of Example 43 for reduction of corresponding ethyl ester to hydroxymethyl. Whereas the intermediate esters required are not described as examples, they were prepared according to a procedure similar to that used in Example 1 using the starting materials given in the table below.

| Ex. | Structure | Prepared from | 1H NMR | LC-MS |
|---|---|---|---|---|
| 44 | 2-(hydroxymethyl)-N-(isoquinolin-6-yl)-5-methyl-7-(1-methyl-1H-indol-4-yl)-4,7-dihydropyrazolo[1,5-a]pyrimidine-6-carboxamide | Intermediate 1A/ 1-methyl-1H-indole-4-carbaldehyde/ ethyl 5-amino-1H-pyrazole-3-carboxylate | $^1$H NMR (400 MHz, d6-DMSO) δ 9.95 (s, 1H), 9.63 (s, 1H), 9.10 (s, 1H), 8.35 (d, J = 5.7 Hz, 1H), 8.24-8.20 (m, 1H), 7.96 (d, J = 8.9 Hz, 1H), 7.66 (dd, J = 2.1, 8.8 Hz, 1H), 7.61 (d, J = 6.2 Hz, 1H), 7.25 (d, J = 8.1 Hz, 1H), 7.20 (d, J = 3.2 Hz, 1H), 7.00 (t, J = 7.7 Hz, 1H), 6.91-6.87 (m, 2H), 6.37 (d, J = 2.6 Hz, 1H), 5.56 (s, 1H), 4.90-4.85 (m, 1H), 4.20-4.17 (m, 2H), 3.70 (s, 3H), 2.23 (s, 3H). | Rt = 2.36 min, m/z 465.0 [M + H]+ (Method 1) |
| 45 | 2-(hydroxymethyl)-N-(isoquinolin-6-yl)-5-methyl-7-(1-methyl-1H-benzo[d]imidazol-6-yl)-4,7-dihydropyrazolo[1,5-a]pyrimidine-6-carboxamide | Intermediate 1A/ 1-methyl-1H-benzo[d]imidazole-6-carbaldehyde/ ethyl 5-amino-1H-pyrazole-3-carboxylate | $^1$H NMR (400 MHz, d6-DMSO) δ 10.04 (s, 1H), 9.63 (s, 1H), 9.17 (s, 1H), 8.37 (d, J = 5.9 Hz, 1H), 8.28 (d, J = 1.6 Hz, 1H), 8.20 (s, 1H), 8.03 (d, J = 9.0 Hz, 1H), 7.75-7.69 (m, 2H), 7.54 (d, J = 8.4 Hz, 1H), 7.40 (d, J = 1.1 Hz, 1H), 7.10 (dd, J = 1.6, 8.4 Hz, 1H), 6.64 (s, 1H), 5.58 (s, 1H), 4.92 (s, 1H), 4.23 (s, 2H), 3.74 (s, 3H), 2.28 (s, 3H). | Rt = 2.52 min, m/z 466.0 [M + H]+ (Method 1) |
| 46 | 7-(benzo[b]thiophen-6-yl)-2-(hydroxymethyl)-N-(isoquinolin-6-yl)-5-methyl-4,7-dihydropyrazolo[1,5-a]pyrimidine-6-carboxamide | Intermediate 1A/ benzo[b]thio-phene-6-carbaldehyde/ ethyl 5-amino-1H-pyrazole-3-carboxylate | $^1$H NMR (400 MHz, d6-DMSO) δ 10.01 (s, 1H), 9.65 (s, 1H), 9.13 (s, 1H), 8.36 (d, J = 5.8 Hz, 1H), 8.26 (d, J = 1.7 Hz, 1H), 8.00 (d, J = 8.9 Hz, 1H), 7.80-7.65 (m, 5H), 7.36 (dd, J = 0.7, 5.5 Hz, 1H), 7.24 (dd, J = 1.6, 8.3 Hz, 1H), 6.63 (s, 1H), 5.59 (s, 1H), 4.94 (s, 1H), 4.24 (s, 2H), 2.29-2.28 (m, 3H). | Rt = 2.51 min, m/z 468.0 [M + H]+ (Method 1) |

-continued

| Ex. | Structure | Prepared from | 1H NMR | LC-MS |
| --- | --- | --- | --- | --- |
| 47 | 7-(4-chloro-3-(trifluoromethyl)phenyl)-2-(hydroxymethyl)-N-(isoquinolin-6-yl)-5-methyl-4,7-dihydropyrazolo[1,5-a]pyrimidine-6-carboxamide | Intermediate 1A/ 4-chloro-3-(trifluoromethyl)-benzaldehyde/ethyl 5-amino-1H-pyrazole-3-carboxylate | $^1$H NMR (400 MHz, d6-DMSO) δ 10.00 (s, 1H), 9.79 (s, 1H), 9.14 (s, 1H), 8.38 (d, J = 5.7 Hz, 1H), 8.23 (m, 1H), 8.01 (d, J = 9.0 Hz, 1H), 7.69-7.60 (m, 4H), 7.46 (dd, J = 2.0, 8.3 Hz, 1H), 6.58 (s, 1H), 5.62 (s, 1H), 4.98 (t, J = 5.6 Hz, 1H), 4.26 (d, J = 5.0 Hz, 2H), 2.27 (s, 3H). | Rt = 2.95 min, m/z 514.0 [M + H]+ (Method 1) |
| 48 | 7-((3r,5r,7r)-adamantan-1-yl)-2-(hydroxymethyl)-N-(isoquinolin-6-yl)-5-methyl-4,7-dihydropyrazolo[1,5-a]pyrimidine-6-carboxamide | Intermediate 1A/ adamantane-1-carbaldehyde/ ethyl 5-amino-1H-pyrazole-3-carboxylate | $^1$H NMR (400 MHz, d6-DMSO) δ 10.04 (s, 1H), 9.27 (s, 1H), 9.14 (s, 1H), 8.39 (d, J = 5.8 Hz, 1H), 8.35 (d, J = 1.9 Hz, 1H), 8.02 (d, J = 9.0 Hz, 1H), 7.81 (dd, J = 2.0, 8.9 Hz, 1H), 7.70 (d, J = 5.9 Hz, 1H), 5.55-5.54 (m, 1H), 5.11 (s, 1H), 4.40-4.31 (m, 2H), 2.24 (s, 3H), 1.89-1.79 (m, 4H), 1.69-1.30 (m, 12H). | Rt = 3.12 min, m/z 470.1 [M + H]+ (Method 1) |
| 49 | 2-(hydroxymethyl)-N-(isoquinolin-6-yl)-5-methyl-7-(2-phenyloxazol-5-yl)-4,7-dihydropyrazolo[1,5-a]pyrimidine-6-carboxamide | Intermediate 1A/ 2-phenyloxazole-5-carbaldehyde/ ethyl 5-amino-1H-pyrazole-3-carboxylate | $^1$H NMR (400 MHz, d6-DMSO) δ 10.07 (s, 1H), 9.84 (s, 1H), 9.14 (s, 1H), 8.39 (d, J = 5.7 Hz, 1H), 8.32-8.31 (m, 1H), 8.03 (d, J = 9.0 Hz, 1H), 7.83-7.79 (m, 2H), 7.74 (dd, J = 2.0, 8.9 Hz, 1H), 7.68 (d, J = 5.9 Hz, 1H), 7.49-7.44 (m, 3H), 7.16 (s, 1H), 6.75 (s, 1H), 5.63 (s, 1H), 5.01 (s, 1H), 4.32 (s, 2H), 2.31 (s, 3H). | Rt = 2.50 min, m/z 479.0 [M + H]+ (Method 1) |
| 50 | 2-(hydroxymethyl)-N-(isoquinolin-6-yl)-5-methyl-7-(3-phenoxyphenyl)-4,7-dihydropyrazolo[1,5-a]pyrimidine-6-carboxamide | Intermediate 1A/ 3-phenoxybenz-aldehyde/ethyl 5-amino-1H-pyrazole-3-carboxylate | $^1$H NMR (400 MHz, d6-DMSO) δ 9.97 (s, 1H), 9.62 (s, 1H), 9.15 (m, 1H), 8.40 (d, J = 5.7 Hz, 1H), 8.26 (m, 1H), 8.01 (d J = 8.9 Hz, 1H), 7.68 (m, 2H), 7.26 (t, J = 7.9 Hz, 1H), 7.22-7.16 (m, 2H), 7.02 (m, 1H), 6.89-6.77 (m, 5H), 6.52 (s, 1H), 5.58 (s, 1H), 4.96 (br s, 1H), 4.28 (s, 2H), 2.23 (s, 3H). | Rt = 2.91 min, m/z 504.1 [M + H]+ (Method 1) |

| Ex. | Structure | Prepared from | 1H NMR | LC-MS |
|---|---|---|---|---|
| 51 | 2-(hydroxymethyl)-N-(isoquinolin-6-yl)-5-methyl-7-(3-(trifluoromethyl)phenyl)-4,7-dihydropyrazolo[1,5-a]pyrimidine-6-carboxamide | Intermediate 1A/ 3-(trifluoro-methyl)-benzaldehyde/ethyl 5-amino-1H-pyrazole-3-carboxylate | ¹H NMR (400 MHz, d6-DMSO) δ 10.00 (s, 1H), 9.73 (s, 1H), 9.13 (s, 1H), 8.38 (d, J = 5.7 Hz, 1H), 8.23-8.22 (m, 1H), 8.00 (d, J = 9.0 Hz, 1H), 7.69-7.65 (m, 2H), 7.60-7.44 (m, 4H), 6.61 (s, 1H), 5.62 (s, 1H), 4.97 (t, J = 5.9 Hz, 1H), 4.26 (d, J = 5.8 Hz, 2H), 2.27 (s, 3H). | Rt = 2.66 min, m/z 480.0 [M + H]+ (Method 1) |
| 52 | 2-(hydroxymethyl)-N-(isoquinolin-6-yl)-5-methyl-7-(2-phenylthiazol-5-yl)-4,7-dihydropyrazolo[1,5-a]pyrimidine-6-carboxamide | Intermediate 1A/ 2-phenylthiazole-5-carbaldehyde/ethyl 5-amino-1H-pyrazole-3-carboxylate | ¹H NMR (400 MHz, d6-DMSO) δ 10.04 (s, 1H), 9.88 (s, 1H), 9.14 (s, 1H), 8.40-8.37 (m, 1H), 8.32 (d, J = 1.7 Hz, 1H), 8.02 (d, J = 8.9 Hz, 1H), 7.85-7.82 (m, 2H), 7.77-7.67 (m, 3H), 7.46-7.43 (m, 3H), 6.91 (s, 1H), 5.61 (s, 1H), 5.01 (s, 1H), 4.32 (s, 2H), 2.31 (s, 3H). | Rt = 2.62 min, m/z 495.2 [M + H]+ (Method 1) |
| 53 | 2-(hydroxymethyl)-N-(isoquinolin-6-yl)-5-methyl-7-phenethyl-4,7-dihydropyrazolo[1,5-a]pyrimidine-6-carboxamide | Intermediate 1A/ 3-phenylpropanal/ ethyl 5-amino-1H-pyrazole-3-carboxylate | ¹H NMR (400 MHz, d6-DMSO) δ 10.07 (s, 1H), 9.35 (s, 1H), 9.16 (s, 1H), 8.42-8.38 (m, 2H), 8.05 (d, J = 8.9 Hz, 1H), 7.80-7.71 (m, 2H), 7.21-7.04 (m, 5H), 5.53 (s, 2H), 4.96 (s, 1H), 4.36 (d, J = 1.2 Hz, 2H), 2.76-2.65 (m, 1H), 2.31-2.13 (m, 5H), 1.93-1.83 (m, 1H). | Rt = 2.67 min, m/z 440.3 [M + H]+ (Method 1) |
| 54 | 7-(4-(tert-butyl)phenyl)-2-(hydroxymethyl)-N-(isoquinolin-6-yl)-5-methyl-4,7-dihydropyrazolo[1,5-a]pyrimidine-6-carboxamide | Intermediate 1A/ 4-(tert-butyl)-benzaldehyde/ethyl 5-amino-1H-pyrazole-3-carboxylate | ¹H NMR (400 MHz, d6-DMSO) δ 9.99 (s, 1H), 9.57 (s, 1H), 9.13 (s, 1H), 8.38 (d, J = 5.7 Hz, 1H), 8.31 (d, J = 1.5 Hz, 1H), 8.01 (d, J = 8.9 Hz, 1H), 7.75-7.65 (m, 2H), 7.27 (d, J = 8.4 Hz, 2H), 7.07 (d, J = 8.4 Hz, 2H), 6.52 (s, 1H), 5.58 (s, 1H), 4.95 (dd, J = 5.9, 5.9 Hz, 1H), 4.27-4.25 (m, 2H), 2.25 (s, 3H), 1.19 (s, 9H). | Rt = 3.02 min, m/z 468.3 [M + H]+ (Method 1) |

| Ex. | Structure | Prepared from | 1H NMR | LC-MS |
| --- | --- | --- | --- | --- |
| 55 | 7-(4-bromo-3-fluorophenyl)-2-(hydroxymethyl)-N-(isoquinolin-6-yl)-5-methyl-4,7-dihydropyrazolo[1,5-a]pyrimidine-6-carboxamide | Intermediate 1A/ 4-bromo-3-fluoro-benzaldehyde/ethyl 5-amino-1H-pyrazole-3-carboxylate | $^1$H NMR (400 MHz, d6-DMSO) δ 9.99 (s, 1H), 9.73 (s, 1H), 9.14 (s, 1H), 8.38 (d, J = 5.7 Hz, 1H), 8.26 (d, J = 1.7 Hz, 1H), 8.01 (d, J = 9.0 Hz, 1H), 7.71-7.60 (m, 3H), 7.09 (dd, J = 2.0, 9.5 Hz, 1H), 7.00 (dd, J = 1.9, 8.3 Hz, 1H), 6.49 (s, 1H), 5.60 (s, 1H), 4.95 (s, 1H), 4.26 (s, 2H), 2.26 (s, 3H). | Rt = 2.68 min, m/z 508.1/510.1 [M + H]+ (Method 1) |
| 56 | 7-(2,3-difluoro-4-(trifluoromethyl)phenyl)-2-(hydroxymethyl)-N-(isoquinolin-6-yl)-5-methyl-4,7-dihydropyrazolo[1,5-a]pyrimidine-6-carboxamide | Intermediate 1A/ 2,3-difluoro-4-(trifluoromethyl)-benzaldehyde/ethyl 5-amino-1H-pyrazole-3-carboxylate | $^1$H NMR (400 MHz, d6-DMSO) δ 10.10 (s, 1H), 9.89 (s, 1H), 9.14 (s, 1H), 8.38 (d, J = 5.8 Hz, 1H), 8.23 (d, J = 1.8 Hz, 1H), 8.01 (d, J = 8.9 Hz, 1H), 7.69-7.65 (m, 2H), 7.57 (t, J = 7.2 Hz, 1H), 7.21 (t, J = 7.2 Hz, 1H), 6.76 (s, 1H), 5.62 (s, 1H), 4.98 (t, J = 5.9 Hz, 1H), 4.25 (d, J = 5.6 Hz, 2H), 2.28 (s, 3H). | Rt = 2.89 min, m/z 516.2 [M + H]+ (Method 1) |
| 57 | 7-(4-chloro-3-fluorophenyl)-2-(hydroxymethyl)-N-(isoquinolin-6-yl)-5-methyl-4,7-dihydropyrazolo[1,5-a]pyrimidine-6-carboxamide | Intermediate 1A/ 4-chloro-3-fluorobenz-aldehyde/ethyl 5-amino-1H-pyrazole-3-carboxylate | $^1$H NMR (400 MHz, d6-DMSO) δ 9.99 (s, 1H), 9.72 (s, 1H), 9.13 (s, 1H), 8.38 (d, J = 5.7 Hz, 1H), 8.26 (d, J = 1.7 Hz, 1H), 8.01 (d, J = 9.0 Hz, 1H), 7.71-7.66 (m, 2H), 7.51 (t, J = 8.0 Hz, 1H), 7.15-7.04 (m, 2H), 6.50 (s, 1H), 5.60 (s, 1H), 4.97 (t, J = 5.9 Hz, 1H), 4.26 (d, J = 5.7 Hz, 2H), 2.26 (s, 3H). | Rt = 2.63 min, m/z 464.2 [M + H]+ (Method 1) |
| 58 | 7-(3-fluoro-4-methylphenyl)-2-(hydroxymethyl)-N-(isoquinolin-6-yl)-5-methyl-4,7-dihydropyrazolo[1,5-a]pyrimidine-6-carboxamide | Intermediate 1A/ 3-fluoro-4-methylbenz-aldehyde/ethyl 5-amino-1H-pyrazole-3-carboxylate | $^1$H NMR (400 MHz, d6-DMSO) δ 9.97 (s, 1H), 9.64 (s, 1H), 9.13 (s, 1H), 8.38 (d, J = 5.7 Hz, 1H), 8.28 (d, J = 1.7 Hz, 1H), 8.01 (d, J = 8.9 Hz, 1H), 7.72-7.66 (m, 2H), 7.19-7.13 (m, 1H), 6.94 (dd, J = 1.6, 7.7 Hz, 1H), 6.85 (dd, J = 1.5, 10.6 Hz, 1H), 6.49 (s, 1H), 5.58 (s, 1H), 4.97 (bs s, 1H), 4.26 (s, 2H), 2.25 (s, 3H), 2.12 (s, 3H). | Rt = 2.57 min, m/z 444.2 [M + H]+ (Method 1) |

-continued

| Ex. | Structure | Prepared from | 1H NMR | LC-MS |
|---|---|---|---|---|
| 59 | 7-(2-fluoro-4-methylphenyl)-2-(hydroxymethyl)-N-(isoquinolin-6-yl)-5-methyl-4,7-dihydropyrazolo[1,5-a]pyrimidine-6-carboxamide | Intermediate 1A/ 2-fluoro-4-methylbenz-aldehyde/ethyl 5-amino-1H-pyrazole-3-carboxylate | $^1$H NMR (400 MHz, d6-DMSO) δ 10.03 (s, 1H), 9.61 (s, 1H), 9.12 (s, 1H), 8.37 (d, J = 5.7 Hz, 1H), 8.26 (d, J = 1.7 Hz, 1H), 8.00 (d, J = 9.0 Hz, 1H), 7.69-7.64 (m, 2H), 7.07-7.02 (m, 1H), 6.91-6.85 (m, 2H), 6.73 (s, 1H), 5.55 (s, 1H), 4.94 (bs s, 1H), 4.24 (s, 2H), 2.23 (d, J = 0.4 Hz, 3H), 2.20 (s, 3H). | Rt = 2.46 min, m/z 444.2 [M + H]+ (Method 1) |
| 60 | 7-(2,3-dihydro-1H-inden-2-yl)-2-(hydroxymethyl)-N-(isoquinolin-6-yl)-5-methyl-4,7-dihydropyrazolo[1,5-a]pyrimidine-6-carboxamide | Intermediate 1A/ 2,3-dihydro-1H-indene-2-carbaldehyde/ethyl 5-amino-1H-pyrazole-3-carboxylate | $^1$H NMR (400 MHz, d6-DMSO) δ 10.09 (s, 1H), 9.40 (s, 1H), 9.15 (s, 1H), 8.41-8.36 (m, 2H), 8.03 (d, J = 9.0 Hz, 1H), 7.79 (dd, J = 2.0, 8.9 Hz, 1H), 7.70 (d, J = 5.9 Hz, 1H), 7.12-7.00 (m, 4H), 5.67 (d, J = 3.2 Hz, 1H), 5.54 (s, 1H), 4.93 (t, J = 5.9 Hz, 1H), 4.32 (d, J = 5.9 Hz, 2H), 3.13 (dd, J = 10.1, 14.9 Hz, 1H), 2.81-2.66 (m, 3H), 2.48-2.42 (m, 1H), 2.22 (s, 3H). | Rt = 2.78 min, m/z 452.3 [M + H]+ (Method 1) |
| 61 | 7-(4-bromophenyl)-2-(hydroxymethyl)-N-(isoquinolin-6-yl)-5-methyl-4,7-dihydropyrazolo[1,5-a]pyrimidine-6-carboxamide | Intermediate 1A/ 4-bromobenz-aldehyde/ethyl 5-amino-1H-pyrazole-3-carboxylate | $^1$H NMR (400 MHz, d6-DMSO) δ 9.98 (s, 1H), 9.66 (s, 1H), 9.13 (s, 1H), 8.38 (d, J = 5.7 Hz, 1H), 8.26 (d, J = 1.8 Hz, 1H), 8.00 (d, J = 9.0 Hz, 1H), 7.71-7.65 (m, 2H), 7.48-7.45 (m, 2H), 7.14-7.11 (m, 2H), 6.50 (s, 1H), 5.58 (s, 1H), 4.95 (t, J = 5.8 Hz, 1H), 4.25 (d, J = 5.3 Hz, 2H), 2.25 (s, 3H). | Rt = 2.63 min, m/z 490.2/492.1 [M + H]+ (Method 1) |
| 62 | 7-(4-chlorophenyl)-2-(hydroxymethyl)-N-(isoquinolin-6-yl)-5-methyl-4,7-dihydropyrazolo[1,5-a]pyrimidine-6-carboxamide | Intermediate 1A/ 4-chlorobenz-aldehyde/ethyl 5-amino-1H-pyrazole-3-carboxylate | $^1$H NMR (400 MHz, d6-DMSO) δ 9.98 (s, 1H), 9.66 (s, 1H), 9.13 (s, 1H), 8.38 (d, J = 5.7 Hz, 1H), 8.26 (d, J = 1.7 Hz, 1H), 8.00 (d, J = 8.9 Hz, 1H), 7.72-7.65 (m, 2H), 7.35-7.32 (m, 2H), 7.20-7.17 (m, 2H), 6.52 (s, 1H), 5.59 (s, 1H), 4.95 (t, J = 5.8 Hz, 1H), 4.25 (d, J = 5.6 Hz, 2H), 2.25 (s, 3H). | Rt = 2.56 min, m/z 446.2 [M + H]+ (Method 1) |

| Ex. | Structure | Prepared from | 1H NMR | LC-MS |
|---|---|---|---|---|
| 63 | 2-(hydroxymethyl)-7-(1H-indol-6-yl)-N-(isoquinolin-6-yl)-5-methyl-4,7-dihydropyrazolo[1,5-a]pyrimidine-6-carboxamide | Intermediate 1A/ 1H-indole-6-carbaldehyde/ethyl 5-amino-1H-pyrazole-3-carboxylate | $^1$H NMR (400 MHz, d6-DMSO) δ 10.98 (s, 1H), 9.95 (s, 1H), 9.54 (s, 1H), 9.10 (s, 1H), 8.36 (d, J = 5.7 Hz, 1H), 8.27 (d, J = 1.5 Hz, 1H), 7.97 (d, J = 9.0 Hz, 1H), 7.70 (dd, J = 2.0, 9.0 Hz, 1H), 7.63 (d, J = 6.1 Hz, 1H), 7.38 (d, J = 8.3 Hz, 1H), 7.27 (t, J = 2.9 Hz, 1H), 7.21 (s, 1H), 6.86 (dd, J = 1.4, 8.2 Hz, 1H), 6.63 (s, 1H), 6.31 (s, 1H), 5.57 (s, 1H), 4.91 (t, J = 5.9 Hz, 1H), 4.24 (d, J = 5.5 Hz, 2H), 2.26 (s, 3H). | Rt = 2.39 min, m/z 451.2 [M + H]+ (Method 1) |
| 64 | 7-(4-chloro-2-fluorophenyl)-2-(hydroxymethyl)-N-(isoquinolin-6-yl)-5-methyl-4,7-dihydropyrazolo[1,5-a]pyrimidine-6-carboxamide | Intermediate 1A/ 4-chloro-2-fluoro-benzaldehyde/ethyl 5-amino-1H-pyrazole-3-carboxylate | H NMR (400 MHz, d6-DMSO) δ 10.06 (s, 1H), 9.71 (s, 1H), 9.13 (s, 1H), 8.38 (d, J = 5.7 Hz, 1H), 8.24 (d, J = 1.7 Hz, 1H), 8.00 (d, J = 9.0 Hz, 1H), 7.69-7.65 (m, 2H), 7.34-7.30 (m, 1H), 7.21-7.18 (m, 2H), 6.72 (s, 1H), 5.57 (s, 1H), 4.96 (t, J = 5.9 Hz, 1H), 4.24 (d, J = 5.9 Hz, 2H), 2.24 (s, 3H). | Rt = 2.57 min, m/z 464.2 [M + H]+ (Method 1) |
| 65 | 7-(3-fluoro-4-(trifluoromethyl)phenyl)-2-(hydroxymethyl)-N-(isoquinolin-6-yl)-5-methyl-4,7-dihydropyrazolo[1,5-a]pyrimidine-6-carboxamide | Intermediate 1A/ 3-fluoro-4-(trifluoromethyl)-benzaldehyde/ethyl 5-amino-1H-pyrazole-3-carboxylate | H NMR (400 MHz, d6-DMSO) δ 10.03 (s, 1H), 9.80 (s, 1H), 9.14 (s, 1H), 8.39 (d, J = 5.7 Hz, 1H), 8.26 (d, J = 1.8 Hz, 1H), 8.02 (d, J = 9.0 Hz, 1H), 7.76-7.67 (m, 3H), 7.23-7.16 (m, 2H), 6.56 (s, 1H), 5.64 (s, 1H), 4.98 (t, J = 5.9 Hz, 1H), 4.27 (d, J = 5.9 Hz, 2H), 2.27 (s, 3H). | Rt = 2.89 min, m/z 498.2 [M + H]+ (Method 1) |
| 66 | 2-(hydroxymethyl)-N-(isoquinolin-6-yl)-5-methyl-7-(p-tolyl)-4,7-dihydropyrazolo[1,5-a]pyrimidine-6-carboxamide | Intermediate 1A/ 4-methylbenz-aldehyde/ethyl 5-amino-1H-pyrazole-3-carboxylate | $^1$H NMR (400 MHz, d6-DMSO) δ 9.94 (s, 1H), 9.55 (s, 1H), 9.12 (s, 1H), 8.37 (d, J = 5.7 Hz, 1H), 8.28 (d, J = 1.7 Hz, 1H), 7.99 (d, J = 9.0 Hz, 1H), 7.72-7.65 (m, 2H), 7.06-7.04 (m, 4H), 6.49 (s, 1H), 5.56 (s, 1H), 4.93 (t, J = 5.8 Hz, 1H), 4.25 (d, J = 5.6 Hz, 2H), 2.24 (s, 3H), 2.19 (s, 3H). | Rt = 2.49 min, m/z 426.3 [M + H]+ (Method 1) |

| Ex. | Structure | Prepared from | 1H NMR | LC-MS |
| --- | --- | --- | --- | --- |
| 67 | 2-(hydroxymethyl)-N-(1H-indazol-5-yl)-5-methyl-7-(p-tolyl)-4,7-dihydropyrazolo[1,5-a]pyrimidine-6-carboxamide | Example 3 | $^1$H NMR (400 MHz, d6-DMSO) δ 12.92 (s, 1H), 9.55 (s, 1H), 9.35 (s, 1H), 8.01-7.95 (m, 2H), 7.44-7.36 (m, 2H), 7.06-7.05 (m, 4H), 6.42 (s, 1H), 5.52 (s, 1H), 4.94-4.90 (m, 1H), 4.24 (d, J = 3.4 Hz, 2H), 2.21-2.19 (m, 6H). | Rt = 2.87 min, m/z 415.2 [M + H]+ (Method 1) |
| 68 | 7-(4-chloro-2-fluorophenyl)-2-(hydroxymethyl)-N-(1H-indazol-5-yl)-5-methyl-4,7-dihydropyrazolo[1,5-a]pyrimidine-6-carboxamide | Example 7 | $^1$H NMR (400 MHz, d6-DMSO) δ 12.92 (s, 1H), 9.66 (s, 1H), 9.51 (s, 1H), 7.96 (s, 2H), 7.44-7.30 (m, 3H), 7.21-7.18 (m, 2H), 6.66 (s, 1H), 5.53 (s, 1H), 4.94 (t, J = 5.7 Hz, 1H), 4.23 (d, J = 5.1 Hz, 2H), 2.19 (s, 3H). | Rt = 2.97 min, m/z 453.1 [M + H]+ (Method 1) |
| 69 | 2-(hydroxymethyl)-N-(1H-indazol-5-yl)-5-methyl-7-(4-(trifluoromethyl)phenyl)-4,7-dihydropyrazolo[1,5-a]pyrimidine-6-carboxamide | Example 2 | $^1$H NMR (400 MHz, d6-DMSO) δ 12.92 (s, 1H), 9.63 (s, 1H), 9.52 (s, 1H), 7.99-7.96 (m, 2H), 7.65 (d, J = 8.1 Hz, 2H), 7.44-7.33 (m, 4H), 6.54 (s, 1H), 5.58 (s, 1H), 4.94 (t, J = 5.9 Hz, 1H), 4.25 (d, J = 5.7 Hz, 2H), 2.21 (s, 3H). | Rt = 3.10 min, m/z 469.1 [M + H]+ (Method 2) |
| 70 | 7-(6-chloropyridin-3-yl)-2-(hydroxymethyl)-N-(1H-indazol-5-yl)-5-methyl-4,7-dihydropyrazolo[1,5-a]pyrimidine-6-carboxamide | Example 5 | $^1$H NMR (400 MHz, d6-DMSO) δ 12.93 (s, 1H), 9.63 (s, 1H), 9.58 (s, 1H), 8.26 (d, J = 2.3 Hz, 1H), 7.97-7.96 (m, 2H), 7.60 (dd, J = 2.5, 8.3 Hz, 1H), 7.48-7.34 (m, 3H), 6.47 (s, 1H), 5.57 (s, 1H), 4.95 (t, J = 5.9 Hz, 1H), 4.25 (d, J = 5.8 Hz, 2H), 2.23 (s, 3H). | Rt = 2.48 min, m/z 436.1 [M + H]+ (Method 2) |

| Ex. | Structure | Prepared from | 1H NMR | LC-MS |
|---|---|---|---|---|
| 71 | 7-(4-fluorophenyl)-2-(hydroxymethyl)-N-(1H-indazol-5-yl)-5-methyl-4,7-dihydropyrazolo[1,5-a]pyrimidine-6-carboxamide | Example 4 | $^1$H NMR (400 MHz, d6-DMSO) δ 12.96-12.88 (m, 1H), 9.57 (s, 1H), 9.43 (s, 1H), 7.99-7.96 (m, 2H), 7.44-7.34 (m, 2H), 7.23-7.18 (m, 2H), 7.12-7.06 (m, 2H), 6.46 (s, 1H), 5.54 (s, 1H), 4.91 (s, 1H), 4.25 (s, 2H), 2.21 (s, 3H). | Rt = 2.69 min, m/z 419.2 [M + H]+ (Method 1) |
| 118 | 5-cyclopropyl-7-(3-fluoro-4-(trifluoromethyl)phenyl)-2-(hydroxymethyl)-N-(isoquinolin-6-yl)-4,7-dihydropyrazolo[1,5-a]pyrimidine-6-carboxamide | Intermediate 1E/3-fluoro-4-trifluoro-methylbenz-aldehyde/ethyl 5-amino-1H-pyrazole-3-carboxylate | $^1$H NMR (400 MHz, d6-DMSO) δ 10.16 (s, 1H), 9.27 (s, 1H), 9.14 (s, 1H), 8.39 (d, J = 5.8 Hz, 1H), 8.30 (d, J = 1.8 Hz, 1H), 8.02 (d, J = 9.0 Hz, 1H), 7.76-7.67 (m, 3H), 7.21-7.17 (m, 2H), 6.41 (s, 1H), 5.64 (s, 1H), 4.98 (s, 1H), 4.25 (s, 2H), 2.38-2.30 (m, 1H), 0.89-0.73 (m, 4H). | Rt = 2.87 mins, m/z 524.2 [M + H]+ (Method 1) |
| 119 | 7-(3-fluoro-4-(trifluoromethyl)phenyl)-2-(hydroxymethyl)-N-(isoquinolin-6-yl)-5-(methoxymethyl)-4,7-dihydropyrazolo[1,5-a]pyrimidine-6-carboxamide | Intermediate 1F/3-fluoro-4-trifluoro-methylbenz-aldehyde/ethyl 5-amino-1H-pyrazole-3-carboxylate | $^1$H NMR (400 MHz, d6-DMSO) δ 10.10 (s, 1H), 9.88 (s, 1H), 9.15 (s, 1H), 8.39 (d, J = 5.7 Hz, 1H), 8.27 (d, J = 1.8 Hz, 1H), 8.03 (d, J = 9.0 Hz, 1H), 7.75 (t, J = 8.0 Hz, 1H), 7.71-7.64 (m, 2H), 7.24-7.17 (m, 2H), 6.72 (s, 1H), 5.76 (s, 1H), 5.01 (t, J = 5.7 Hz, 1H), 4.58-4.47 (m, 2H), 4.27 (d, J = 5.4 Hz, 2H), 3.35 (s, 3H). | Rt = 2.84 mins, m/z 528.2 [M + H]+ (Method 1) |

Examples 72A-D

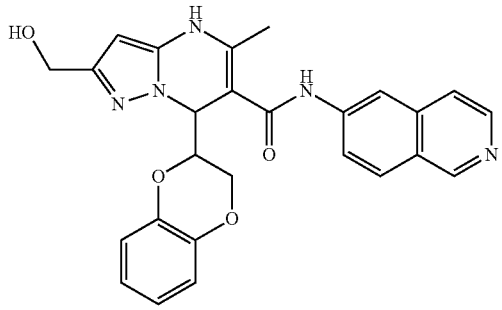 [SMILES: CC1=C(C(=O)Nc2ccc3cnccc3c2)C(C2COc3ccccc3O2)n2nc(CO)cc2N1]

7-(2,3-dihydrobenzo[b][1,4]dioxin-2-yl)-2-(hydroxymethyl)-N-(isoquinolin-6-yl)-5-methyl-4,7-dihydropyrazolo[1,5-a]pyrimidine-6-carboxamide A mixture of Intermediate 1A (291 mg, 1.27 mmol), ethyl 5-amino-1H-pyrazole-3-carboxylate (200 mg, 1.01 mmol) and 2,3-dihydrobenzo[1,4]dioxine-2-carbaldehyde (300 mg, 1.29 mmol) in DMF (1 mL) was heated at 120° C. for 2 h. The reaction mixture was allowed to cool to RT and then poured onto ice. The solid formed was filtered off, washed with water and dried in a desiccator at 50° C. overnight. The crude material was chromatographed on a Si cartridge eluting with 0-10% methanol in DCM. Evaporation gave a yellow oil (383 mg, 0.75 mmol) which was dissolved in THF (9 mL). The solution was cooled to 0° C. under argon and 2M lithium aluminium hydride (1.12 mL, 2.25 mmol) was added dropwise. The reaction was allowed to warm slowly to RT and, after 3 h, it was quenched by the addition of water (1 mL) and 1N sodium hydroxide (0.4 mL). The mixture was diluted with THF and filtered through Celite®. The solid cake was washed with 10% methanol in DCM and the filtrate was evaporated to give an orange oil. The crude material was chromatographed on a 25 g Si cartridge eluting with 0-10% methanol in ethyl acetate. The mixture of four stereoisomers was obtained as a yellow solid (136 mg). The isomers were separated by SFC using the conditions below.

Example 72A

LCMS (Method 1): Rt=2.63 min, m/z 470.2 [M+H]+
$^1$H NMR (400 MHz, d6-DMSO) δ 10.04 (s, 1H), 9.63 (s, 1H), 9.16 (s, 1H), 8.40 (d, J=5.8 Hz, 1H), 8.32 (d, J=1.6 Hz, 1H), 8.04 (d, J=8.9 Hz, 1H), 7.79-7.67 (m, 2H), 6.83-6.68 (m, 3H), 6.56 (dd, J=1.7, 7.9 Hz, 1H), 5.76 (d, J=2.4 Hz, 1H), 5.59 (s, 1H), 5.02-4.96 (m, 1H), 4.49-4.44 (m, 1H), 4.34 (d, J=5.3 Hz, 2H), 4.13 (dd, J=2.2, 11.5 Hz, 1H), 4.02 (dd, J=9.2, 11.5 Hz, 1H), 2.24 (s, 3H).

Example 72B

LCMS (Method 1): Rt=2.56 min, m/z 470.2 [M+H]+
$^1$H NMR (400 MHz, d6-DMSO) δ 10.07 (s, 1H), 9.63 (s, 1H), 9.14 (s, 1H), 8.39 (d, J=5.7 Hz, 1H), 8.31 (d, J=1.7 Hz, 1H), 8.01 (d, J=8.9 Hz, 1H), 7.75-7.68 (m, 2H), 6.79 (d, J=7.6 Hz, 1H), 6.73-6.63 (m, 1H), 6.62-6.60 (m, 2H), 5.74 (d, J=5.4 Hz, 1H), 5.60 (s, 1H), 5.00 (s, 1H), 4.36-4.23 (m, 4H), 3.81 (dd, J=7.1, 11.4 Hz, 1H), 2.23 (s, 3H).

Example 72C

LCMS (Method 1): Rt=2.63 min, m/z 470.2 [M+H]+
$^1$H NMR (400 MHz, d6-DMSO) δ 10.04 (s, 1H), 9.63 (s, 1H), 9.16 (s, 1H), 8.40 (d, J=5.8 Hz, 1H), 8.32 (d, J=1.6 Hz, 1H), 8.04 (d, J=8.9 Hz, 1H), 7.79-7.67 (m, 2H), 6.83-6.68 (m, 3H), 6.56 (dd, J=1.7, 7.9 Hz, 1H), 5.76 (d, J=2.4 Hz, 1H), 5.59 (s, 1H), 5.02-4.96 (m, 1H), 4.49-4.44 (m, 1H), 4.34 (d, J=5.3 Hz, 2H), 4.13 (dd, J=2.2, 11.5 Hz, 1H), 4.02 (dd, J=9.2, 11.5 Hz, 1H), 2.24 (s, 3H).

Example 72D

LCMS (Method 1): Rt=2.55 min, m/z 470.2 [M+H]+
$^1$H NMR (400 MHz, d6-DMSO) δ 10.07 (s, 1H), 9.63 (s, 1H), 9.14 (s, 1H), 8.39 (d, J=5.7 Hz, 1H), 8.31 (d, J=1.7 Hz, 1H), 8.01 (d, J=8.9 Hz, 1H), 7.75-7.68 (m, 2H), 6.79 (d, J=7.6 Hz, 1H), 6.73-6.63 (m, 1H), 6.62-6.60 (m, 2H), 5.74 (d, J=5.4 Hz, 1H), 5.60 (s, 1H), 5.00 (s, 1H), 4.36-4.23 (m, 4H), 3.81 (dd, J=7.1, 11.4 Hz, 1H), 2.23 (s, 3H).

| Separation | Separation | Analysis | $1^{st}$ eluting | $2^{nd}$ eluting | $3^{rd}$ eluting |
|---|---|---|---|---|---|
| 1 | MD SFC<br>YMC Cellulose-SC<br>50/50 IPA(0.1% DEA)/CO$_2$<br>100 mL/min<br>40° C.<br>320 nM; column size: 250 × 20 mm id 5 μm | MD SFC<br>YMC Cellulose-SC<br>40/60 IPA(0.1% DEA)/CO$_2$<br>5 mL/min<br>40° C.<br>320 nM; column size: 250 × 4.6 mm id 5 μm | Rt = 2.8 min<br>(mixture of two isomers) | Example 72A<br>Rt = 4.3 min | Example 72B<br>Rt = 5.3 min |
| 2<br>($1^{st}$ eluting peak from Separation 1) | MD SFC<br>YMC Amylose-C<br>40/60 MeOH/CO$_2$<br>15 mL/min<br>40° C.<br>320 nM; column size: 250 × 10 mm id 5 μm | MD SFC<br>YMC Amylose-C<br>40/60 MeOH/CO$_2$<br>5 mL/min<br>40° C.<br>320 nM; column size: 250 × 4.6 mm id 5 μm | Example 72C<br>Rt = 2.2 min | Example 72D<br>Rt = 3.9 min | |

Example 73

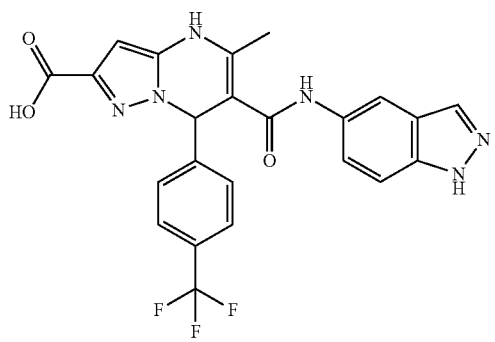 [SMILES: CC1=C(C(=O)Nc2ccc3[nH]ncc3c2)C(c2ccc(C(F)(F)F)cc2)n2nc(C(=O)O)cc2N1]

6-((1H-indazol-5-yl)carbamoyl)-5-methyl-7-(4-(trifluoromethyl)phenyl)-4,7-dihydropyrazolo[1,5-a]pyrimidine-2-carboxylic acid (Example 73)

Example 2 (153 mg, 0.30 mmol) in MeOH (1.3 mL) was stirred at RT for 5 min. 2N sodium hydroxide solution (1.2 mL) was added and the reaction mixture was stirred at 45° C. for 20 min. After cooling to RT the mixture was filtered and acidified by the addition of 1N HCl. The product was extracted into ethyl acetate (2×15 mL) and the combined extracts were dried ($Na_2SO_4$) and evaporated. The crude product was purified by MDAP (acidic) to give a white solid (75 mg).

LCMS (Method 1): Rt=3.31 min, m/z 483.2 [M+H]+

$^1$H NMR (400 MHz, d6-DMSO) δ 12.94 (br s, 2H), 9.74-9.71 (m, 2H), 7.99 (dd, J=1.0, 6.4 Hz, 2H), 7.69 (d, J=8.2 Hz, 2H), 7.46-7.36 (m, 4H), 6.68 (s, 1H), 5.99 (s, 1H), 2.22 (s, 3H).

Examples 74 and 75

The following compounds were prepared by analogous procedures to that used in Example 73.

| Ex | Structure | Starting material | 1H NMR | LC-MS |
|---|---|---|---|---|
| 74 | 6-((1H-indazol-5-yl)carbamoyl)-5-methyl-7-(p-tolyl)-4,7-dihydropyrazolo[1,5-a]pyrimidine-2-carboxylic acid | Example 3 | $^1$H NMR (400 MHz, d6-DMSO) δ 12.92 (br s, 2H), 9.65 (s, 1H), 9.55 (s, 1H), 8.02-7.97 (m, 2H), 7.45-7.37 (m, 2H), 7.08 (s, 4H), 6.55 (s, 1H), 5.93 (s, 1H), 2.22 (s, 6H). | Rt = 3.01 min, m/z 429.2 [M + H]+ (Method 1) |
| 75 | 6-((1H-indazol-5-yl)carbamoyl)-7-(4-fluorophenyl)-5-methyl-4,7-dihydropyrazolo[1,5-a]pyrimidine-2-carboxylic acid | Example 4 | $^1$H NMR (400 MHz, d6-DMSO) δ 12.93 (s, 1H), 9.66 (s, 1H), 9.63 (s, 1H), 7.99-7.98 (m, 2H), 7.45-7.35 (m, 2H), 7.27-7.22 (m, 2H), 7.16-7.10 (m, 2H), 6.59 (s, 1H), 5.95 (s, 1H), 2.22 (s, 3H). | Rt = 2.87 min, m/z 433.2 [M + H]+ (Method 1) |

Example 76

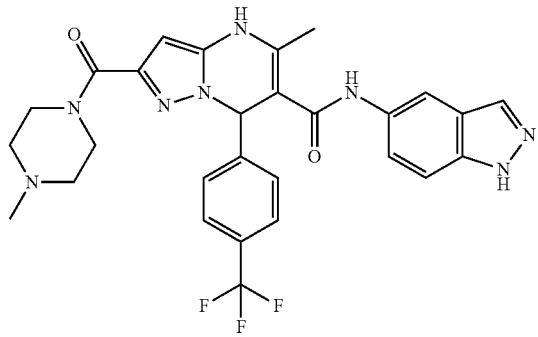 [SMILES: CC1=C(C(=O)Nc2ccc3[nH]ncc3c2)C(c2ccc(C(F)(F)F)cc2)n2nc(C(=O)N3CCN(C)CC3)cc2N1]

N-(1H-indazol-5-yl)-5-methyl-2-(4-methylpiperazine-1-carbonyl)-7-(4-(trifluoromethyl)phenyl)-4,7-dihydropyrazolo[1,5-a]pyrimidine-6-carboxamide (Example 76)

A solution of 1-methylpiperazine (111 mg, 1.1 mmol) in toluene (665 µL) was flushed with argon for 5 min. 2M trimethylaluminium in toluene (665 µL, 1.33 mmol) was added and the reaction mixture was stirred at RT for 2 h. A further volume of toluene (1 mL) was added followed by Example 2 (115 mg, 0.225 mmol) and the reaction was stirred at RT under argon for 2 h at 60° C. and then at 80° C. overnight. Water (5 mL) was added carefully and the solid which precipitated was filtered off. The filtrate was extracted with ethyl acetate (3×10 mL) and the combined extracts were dried (Na$_2$SO$_4$) and evaporated. The residue was combined with the solid which had been obtained by filtration. The crude product was dissolved in a small amount of methanol and loaded onto a 5 g SCX-2 cartridge which had been conditioned with methanol. After flushing with more methanol, the product was eluted with 2M methanolic ammonia. The solid which was obtained was further purified on a 25 g Si cartridge eluting with 5-10% 2M methanol ammonia in methanol/DCM and then by MDAP (acidic) to give a white solid (15 mg).

LCMS (Method 1): Rt=2.70 min, m/z 565.3 [M+H]+

$^1$H NMR (400 MHz, d6-DMSO) δ 12.94 (s, 1H), 9.72 (s, 2H), 8.02-7.97 (m, 2H), 7.68 (d, J=8.2 Hz, 2H), 7.46-7.34 (m, 4H), 6.67 (s, 1H), 5.85 (s, 1H), 3.79-3.74 (m, 1H), 3.68-3.59 (m, 2H), 3.47-3.43 (m, 1H), 2.36-2.30 (m, 1H), 2.22 (m, 5H), 2.16 (m, 4H).

Example 77

Step A

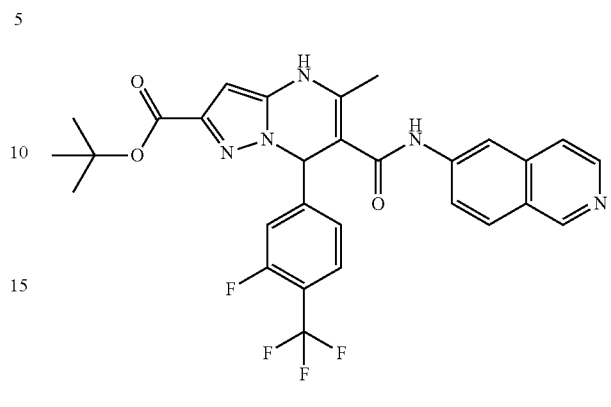

tert-Butyl 7-(3-fluoro-4-(trifluoromethyl)phenyl)-6-(isoquinolin-6-ylcarbamoyl)-5-methyl-4,7-dihydropyrazolo[1,5-a]pyrimidine-2-carboxylate (Intermediate 77A)

Intermediate 77A was prepared from Intermediate 1A, 3-fluoro-4-(trifluoromethyl)benzaldehyde and tert-butyl 5-amino-1H-pyrazole-3-carboxylate using a similar procedure to Example 1.

LCMS (Method 3): Rt=0.99 min, m/z 568.5 [M+H]+

Step B

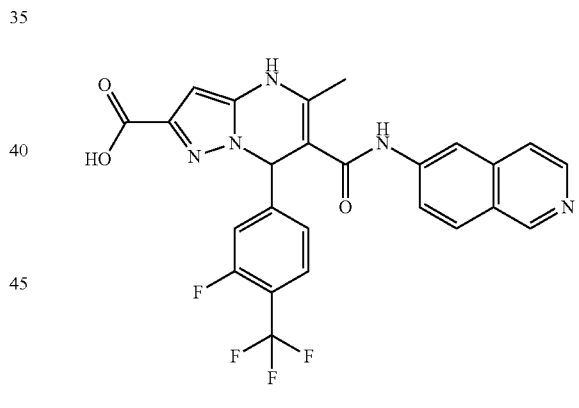

7-(3-Fluoro-4-(trifluoromethyl)phenyl)-6-(isoquinolin-6-ylcarbamoyl)-5-methyl-4,7-dihydropyrazolo[1,5-a]pyrimidine-2-carboxylic acid (Intermediate 77B)

Intermediate 77A (1.18 g, 2.08 mmol) was dissolved in 20% TFA in DCM (10 mL). After stirring at RT for 18 h the volatiles were evaporated. The residue was dissolved in methanol and evaporated several times then triturated with diethyl ether. The yellow solid was collected by filtration and dried (1.31 g).

LCMS (Method 3): Rt=0.78 min, m/z 512.4 [M+H]+

Step C

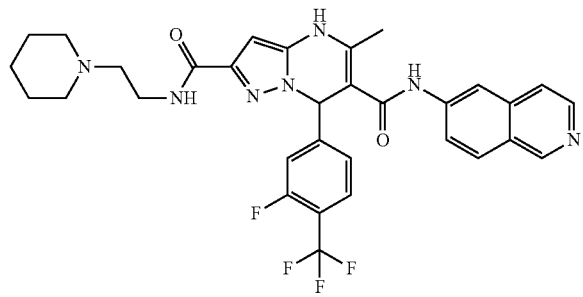 [SMILES: CC1=C(C(=O)Nc2ccc3cnccc3c2)C(c2ccc(C(F)(F)F)c(F)c2)n2nc(C(=O)NCCN3CCCCC3)cc2N1]

7-(3-fluoro-4-(trifluoromethyl)phenyl)-N6-(isoquinolin-6-yl)-5-methyl-N2-(2-(piperidin-1-yl)ethyl)-4,7-dihydropyrazolo[1,5-a]pyrimidine-2,6-dicarboxamide (Example 77)

Intermediate 77B (175 mg, 0.28 mmol), 2-(piperidin-1-yl)ethan-1-amine (43 mg, 0.336 mmol), DIPEA (0.25 mL, 1.4 mmol) and HATU (160 mg, 0.42 mmol) were dissolved in DMF (0.5 mL) and the solution was stirred at RT overnight. The mixture was partitioned between ethyl acetate (10 mL) and sat. aqueous sodium bicarbonate (10 mL). The organic phase was separated and dried by passing through a hydrophobic frit. Evaporation gave a crude product which was chromatographed on a 10 g Si cartridge eluting with 0-10% methanol in DCM and then 0-20% 2M methanolic ammonia in DCM. The resulting gum was triturated with diethyl ether to give the desired product as a yellow solid. This was further purified by MDAP (acidic) to give the formic acid salt as an off-white solid (38 mg).

LCMS (Method 1): Rt=2.52 min, m/z 622.3 $[M+H]^+$ $^1$H NMR (400 MHz, d6-DMSO) δ 10.13 (s, 1H), 9.99 (s, 1H), 9.15 (s, 1H), 8.41-8.38 (m, 1H), 8.28 (d, J=1.7 Hz, 1H), 8.18 (s, 1H), 8.03 (d, J=9.0 Hz, 1H), 7.84-7.67 (m, 4H), 7.29-7.20 (m, 2H), 6.67 (s, 1H), 6.00 (s, 1H), 3.34-3.23 (m, 2H), 2.44-2.34 (m, 6H), 2.27 (s, 3H), 1.49-1.43 (m, 4H), 1.37 (dd, J=4.9, 10.2 Hz, 2H).

Examples 78 to 90

The following compounds were prepared by analogous procedures to that used in Example 77. In some cases the compounds were obtained as the formic acid salt as identified by $^1$H NMR.

| Ex | Structure | Staring materials | 1H NMR | LC-MS |
|---|---|---|---|---|
| 78 | Formic acid salt. 7-(3-fluoro-4-(trifluoromethyl)phenyl)-N6-(isoquinolin-6-yl)-N2,5-dimethyl-N2-(2-(piperidin-1-yl)ethyl)-4,7-dihydropyrazolo[1,5-a]pyrimidine-2,6-dicarboxamide | Intermediate 77B/N-methyl-2-(piperidin-1-yl)ethan-1-amine | $^1$H NMR (400 MHz, d6-DMSO) δ 10.11 (s, 1H), 9.96 (s, 1H), 9.15 (s, 1H), 8.39 (d, J = 5.7 Hz, 1H), 8.29-8.25 (m, 1H), 8.17 (s, 1H), 8.03 (d, J = 9.0 Hz, 1H), 7.78-7.67 (m, 3H), 7.28-7.21 (m, 2H), 6.69-6.63 (m, 1H), 5.90 (s, 1H), 3.90-3.82 (m, 1H), 3.50-3.42 (m, 1H), 3.13 and 2.89 (two s, 3H), 2.46-2.22 (m, 7H), 2.08-1.96 (m, 2H), 1.45 (d, J = 5.0 Hz, 1H), 1.30-1.30 (m, 5H). | Rt = 2.58 min, m/z 636.3 [M + H]+ (Method 1) |

| Ex | Structure | Staring materials | 1H NMR | LC-MS |
|---|---|---|---|---|
| 79 | 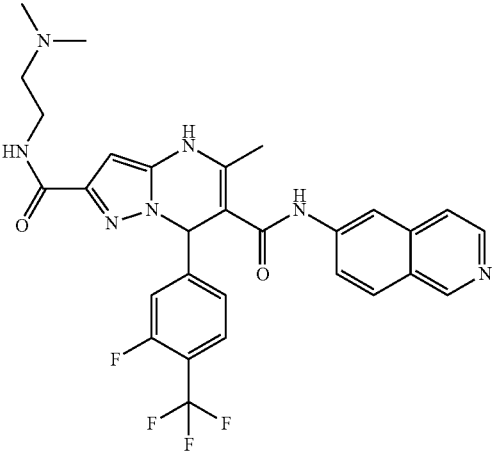 [SMILES: CC1=C(C(=O)Nc2ccc3cnccc3c2)C(c2ccc(C(F)(F)F)c(F)c2)n2nc(C(=O)NCCN(C)C)cc2N1]<br>N2-(2-(dimethylamino)ethyl)-7-(3-fluoro-4-(trifluoromethyl)phenyl)-N6-(isoquinolin-6-yl)-5-methyl-4,7-dihydropyrazolo[1,5-a]pyrimidine-2,6-dicarboxamide | Intermediate 77B/N,N-dimethyl-ethane-1,2-diamine | $^1$H NMR (400 MHz, d6-DMSO) δ 10.14 (s, 1H), 9.98 (s, 1H), 9.15 (s, 1H), 8.40 (d, J = 5.7 Hz, 1H), 8.28 (d, J = 1.7 Hz, 1H), 8.03 (d, J = 8.9 Hz, 1H), 7.79-7.69 (m, 4H), 7.25-7.17 (m, 2H), 6.67 (s, 1H), 6.02 (s, 1H), 3.29-3.17 (m, 2H), 2.35-2.30 (m, 2H), 2.26 (s, 3H), 2.13 (s, 6H). | Rt = 2.44 min, m/z 582.3 [M + H]+ (Method 1) |
| 80 | 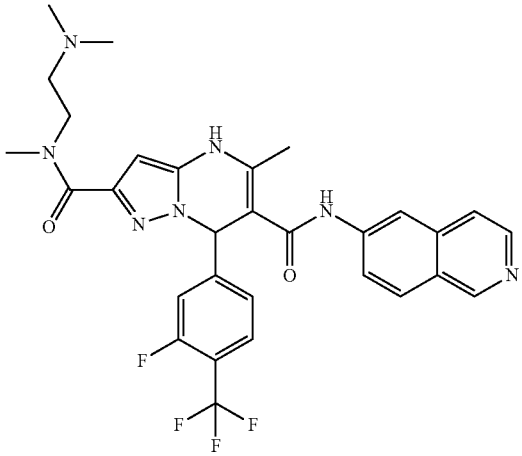 [SMILES: CC1=C(C(=O)Nc2ccc3cnccc3c2)C(c2ccc(C(F)(F)F)c(F)c2)n2nc(C(=O)N(C)CCN(C)C)cc2N1]<br>N2-(2-(dimethylamino)ethyl)-7-(3-fluoro-4-(trifluoromethyl)phenyl)-N6-(isoquinolin-6-yl)-N2,5-dimethyl-4,7-dihydropyrazolo[1,5-a]pyrimidine-2,6-dicarboxamide | Intermediate 77B/N,N,N'-trimethylethane-1,2-diamine | $^1$H NMR (400 MHz, d6-DMSO) δ 10.11 (s, 1H), 9.98 (s, 1H), 9.15 (s, 1H), 8.40 (d, J = 5.8 Hz, 1H), 8.27 (d, J = 2.2 Hz, 1H), 8.03 (d, J = 8.9 Hz, 1H), 7.77-7.67 (m, 3H), 7.31-7.23 (m, 2H), 6.67 (d, J = 10.1 Hz, 1H), 5.94 (s, 1H), 3.67-3.57 (m, 2H), 3.17 & 2.91 (s, 3H), 2.66-2.58 (m, 2H), 2.30 (s, 6H), 2.28 (d, J = 2.6 Hz, 3H). | Rt = 2.45 min, m/z 596.1 [M + H]+ (Method 1) |

| Ex | Structure | Staring materials | 1H NMR | LC-MS |
|---|---|---|---|---|
| 81 | 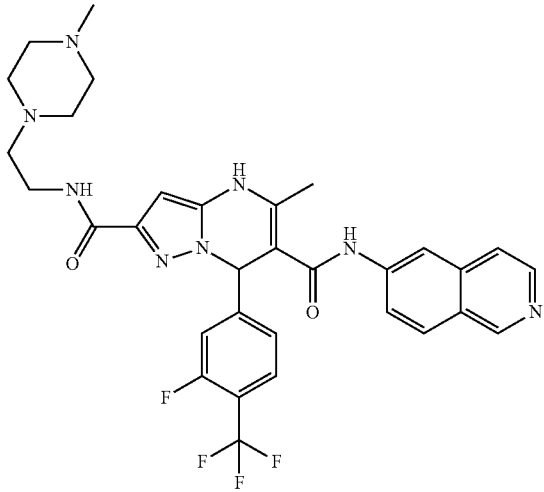 [SMILES: CC1=C(C(=O)Nc2ccc3cnccc3c2)C(c2ccc(C(F)(F)F)c(F)c2)n2nc(C(=O)NCCN3CCN(C)CC3)cc2N1]<br>7-(3-fluoro-4-(trifluoromethyl)phenyl)-N6-(isoquinolin-6-yl)-5-methyl-N2-(2-(4-methylpiperazin-1-yl)ethyl)-4,7-dihydropyrazolo[1,5-a]pyrimidine-2,6-dicarboxamide | Intermediate 77B/2-(4-methylpiperazin-1-yl)ethan-1-amine | $^1$H NMR (400 MHz, d6-DMSO) δ 10.13 (s, 1H), 9.97 (s, 1H), 9.15 (s, 1H), 8.41-8.38 (m, 1H), 8.28 (d, J = 1.7 Hz, 1H), 8.03 (d, J = 9.0 Hz, 1H), 7.81-7.67 (m, 4H), 7.28-7.19 (m, 2H), 6.67 (s, 1H), 6.00 (s, 1H), 3.29-3.20 (m, 2H), 2.40-2.32 (m, 6H), 2.30-2.23 (m, 7H), 2.14 (s, 3H). | Rt = 2.39 min, m/z 637.4 [M + H]+ (Method 1) |
| 82 | 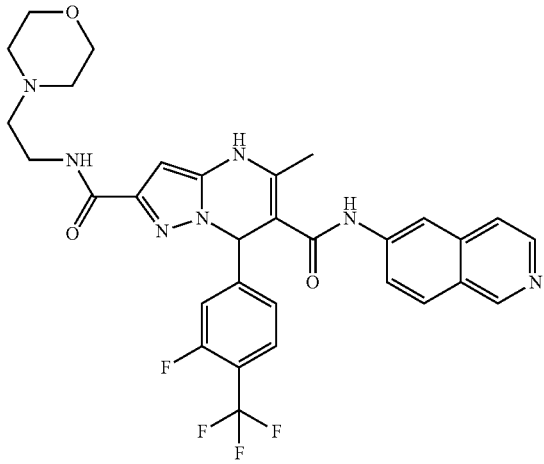 [SMILES: CC1=C(C(=O)Nc2ccc3cnccc3c2)C(c2ccc(C(F)(F)F)c(F)c2)n2nc(C(=O)NCCN3CCOCC3)cc2N1]<br>7-(3-fluoro-4-(trifluoromethyl)phenyl)-N6-(isoquinolin-6-yl)-5-methyl-N2-(2-morpholinoethyl)-4,7-dihydropyrazolo[1,5-a]pyrimidine-2,6-dicarboxamide | Intermediate 77B/2-morpholino-ethan-1-amine | $^1$H NMR (400 MHz, d6-DMSO) δ 10.14 (s, 1H), 9.98 (s, 1H), 9.15 (s, 1H), 8.40 (d, J = 5.7 Hz, 1H), 8.28 (s, 1H), 8.03 (d, J = 8.9 Hz, 1H), 7.88-7.67 (m, 4H), 7.28-7.19 (m, 2H), 6.67 (s, 1H), 6.01 (s, 1H), 3.56-3.49 (m, 4H), 3.41-3.20 (m, 2H), 2.42-2.32 (m, 6H), 2.27 (s, 3H). | Rt = 2.46 min, m/z 624.2 [M + H]+ (Method 1) |

| Ex | Structure | Staring materials | 1H NMR | LC-MS |
|---|---|---|---|---|
| 83 | 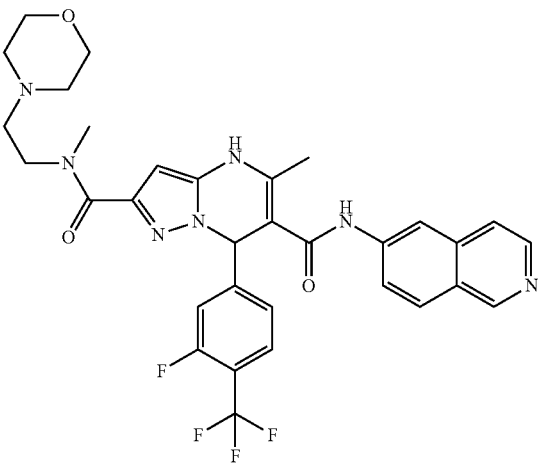 [SMILES: CC1=C(C(=O)Nc2ccc3cnccc3c2)C(c2ccc(C(F)(F)F)c(F)c2)n2nc(C(=O)N(C)CCN3CCOCC3)cc2N1]<br>7-(3-fluoro-4-(trifluoromethyl)phenyl)-N6-(isoquinolin-6-yl)-N2,5-dimethyl-N2-(2-morpholinoethyl)-4,7-dihydropyrazolo[1,5-a]pyrimidine-2,6-dicarboxamide | Intermediate 77B/N-methyl-2-morpholinoethan-1-amine | $^1$H NMR (400 MHz, d6-DMSO) δ 10.10 (s, 1H), 9.95 (s, 1H), 9.15 (s, 1H), 8.39 (d, J = 5.7 Hz, 1H), 8.27-8.26 (m, 1H), 8.03 (d, J = 8.9 Hz, 1H), 7.78-7.67 (m, 3H), 7.28-7.23 (m, 2H), 6.68-6.63 (m, 1H), 5.91 (s, 1H), 3.54-3.47 (m, 2H), 3.42-3.35 (m, 4H), 3.14 & 2.90 (s, 3H), 2.47-2.31 (m, 3H), 2.28 (s, 3H), 2.11-2.01 (m, 3H). | Rt = 2.47 min, m/z 638.2 [M + H]+ (Method 1) |
| 84 | 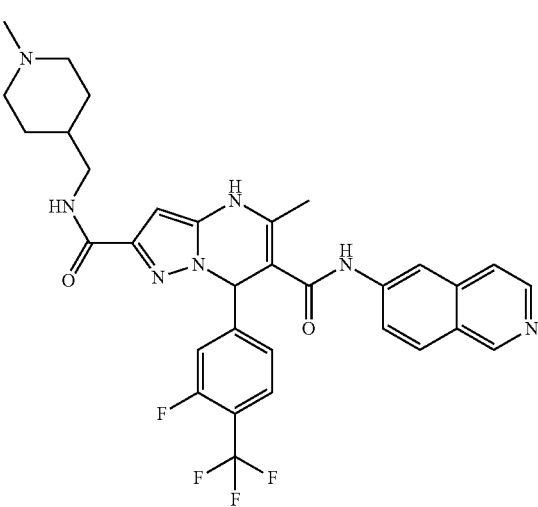<br>7-(3-fluoro-4-(trifluoromethyl)phenyl)-N6-(isoquinolin-6-yl)-5-methyl-N2-((1-methylpiperidin-4-yl)methyl)-4,7-dihydropyrazolo[1,5-a]pyrimidine-2,6-dicarboxamide | Intermediate 77B/(1-methyl-piperidin-4-yl)-methanamine | $^1$H NMR (400 MHz, d6-DMSO) δ 10.15 (s, 1H), 9.99 (s, 1H), 9.15 (s, 1H), 8.40 (d, J = 5.7 Hz, 1H), 8.28 (d, J = 1.7 Hz, 1H), 8.21 (s, 1H), 8.05-7.97 (m, 2H), 7.78-7.68 (m, 3H), 7.25-7.17 (m, 2H), 6.66 (s, 1H), 6.03 (s, 1H), 3.18-3.09 (m, 1H), 3.01-2.93 (m, 1H), 2.80 (d, J = 11.3 Hz, 2H), 2.26 (s, 3H), 2.20 (s, 3H), 1.97-1.90 (m, 2H), 1.56 (d, J = 12.1 Hz, 2H), 1.52-1.45 (m, 1H), 1.24-1.09 (m, 2H). | Rt = 2.48 min, m/z 622.4 [M + H]+ (Method 1) |

-continued

| Ex | Structure | Staring materials | 1H NMR | LC-MS |
|---|---|---|---|---|
| 85 | 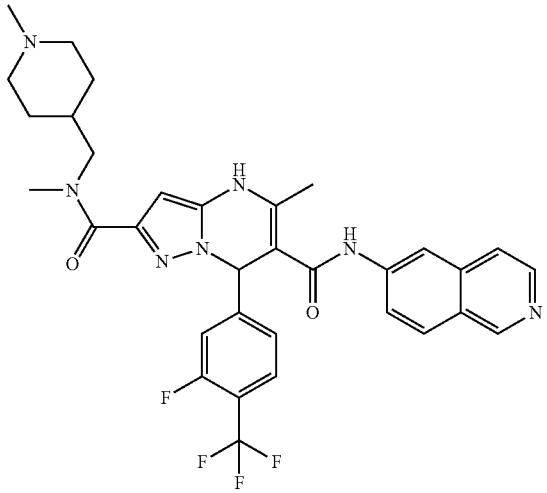 [SMILES: CC1=C(C(=O)Nc2ccc3cnccc3c2)C(c2ccc(C(F)(F)F)c(F)c2)n2nc(C(=O)N(C)CC3CCN(C)CC3)cc2N1]<br>7-(3-fluoro-4-(trifluoromethyl)phenyl)-N6-(isoquinolin-6-yl)-N2,5-dimethyl-N2-((1-methylpiperidin-4-yl)methyl)-4,7-dihydropyrazolo[1,5-a]pyrimidine-2,6-dicarboxamide | Intermediate 77B/N-methyl-1-(1-methyl-piperidin-4-yl)-methenamine | $^1$H NMR (400 MHz, d6-DMSO) δ 10.11 (s, 1H), 9.96 (s, 1H), 9.15 (s, 1H), 8.39 (d, J = 5.7 Hz, 1H), 8.29-8.25 (m, 1H), 8.20 (s, 1H), 8.02 (d, J = 8.9 Hz, 1H), 7.77-7.67 (m, 3H), 7.32-7.20 (m, 2H), 6.69-6.64 (m, 1H), 5.91-5.88 (m, 1H), 3.75-3.65 (m, 1H), 3.40-3.21 (m, 2H), 3.09 and 2.89 (two s, 3H), 2.84 (d, J = 11.1 Hz, 1H), 2.67-2.61 (m, 2H), 2.28 (s, 3H), 2.24 and 2.12 (two s, 3H), 2.03-1.97 (m, 1H), 1.75-1.17 (m, 3H), 0.95-0.79 (m, 1H). | Rt = 2.50 min, m/z 636.4 [M + H]+ (Method 1) |
| 86 | 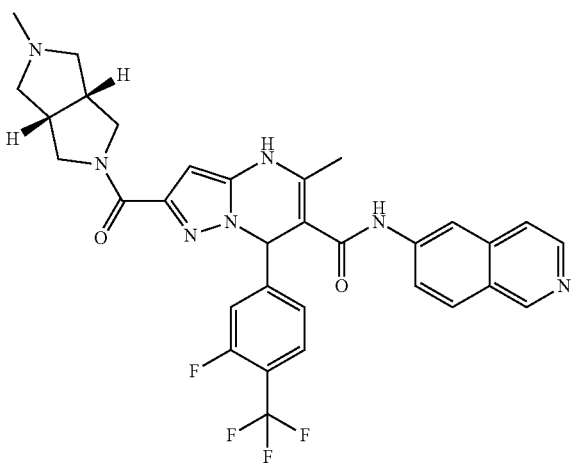 [SMILES: CC1=C(C(=O)Nc2ccc3cnccc3c2)C(c2ccc(C(F)(F)F)c(F)c2)n2nc(C(=O)N3C[C@H]4CN(C)C[C@H]4C3)cc2N1]<br>7-(3-fluoro-4-(trifluoromethyl)phenyl)-N-(isoquinolin-6-yl)-5-methyl-2-(5-methyloctahydropyrrolo[3,4-c]pyrrole-2-carbonyl)-4,7-dihydropyrazolo[1,5-a]pyrimidine-6-carboxamide | Intermediate 77B/(3aR,6aS)-2-methyl-octahydropyrrolo[3,4-C]pyrrole | $^1$H NMR (400 MHz, d6-DMSO) δ 10.12 (s, 1H), 9.97 (s, 1H), 9.15 (s, 1H), 8.40 (d, J = 5.7 Hz, 1H), 8.28 (d, J = 1.8 Hz, 1H), 8.17 (s, 1H), 8.03 (d, J = 8.9 Hz, 1H), 7.77-7.68 (m, 3H), 7.30-7.21 (m, 2H), 6.71-6.68 (m, 1H), 5.96-5.94 (m, 1H), 3.91-3.79 (m, 2H), 3.74-3.59 (m, 2H), 3.47-3.32 (m, 2H), 2.81-2.73 (m, 2H), 2.46-2.38 (m, 1H), 2.37-2.28 (m, 4H), 2.21 and 2.19 (two s, 3H). | Rt = 2.40 min, m/z 620.3 [M + H]+ (Method 1) |

-continued

| Ex | Structure | Staring materials | 1H NMR | LC-MS |
|---|---|---|---|---|
| 87 | 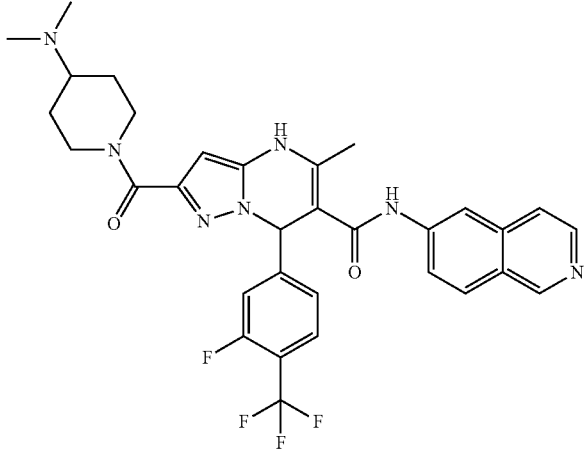  2-(4-(dimethylamino)piperidine-1-carbonyl)-7-(3-fluoro-4-(trifluoromethyl)phenyl)-N-(isoquinolin-6-yl)-5-methyl-4,7-dihydropyrazolo[1,5-a]pyrimidine-6-carboxamide | Intermediate 77B/N,N-dimethyl-piperidin-4-amine | $^1$H NMR (400 MHz, d6-DMSO) δ 10.13-10.09 (m, 1H), 9.97 (s, 1H), 9.15 (s, 1H), 8.39 (d, J = 5.8 Hz, 1H), 8.28 (d, J = 1.7 Hz, 1H), 8.03 (d, J = 8.9 Hz, 1H), 7.79-7.68 (m, 3H), 7.29-7.22 (m, 2H), 6.68 (s, 1H), 5.87 (s, 1H), 4.41-4.39 (m, 2H), 2.98 (d, J = 11.9 Hz, 1H), 2.69-2.66 (m, 1H), 2.30-2.18 (m, 9H), 1.86-1.76 (m, 1H), 1.72-1.63 (m, 2H), 1.30-1.17 (m, 2H). | Rt = 2.40 min, m/z 622.4 [M + H]+ (Method 1) |
| 88 | 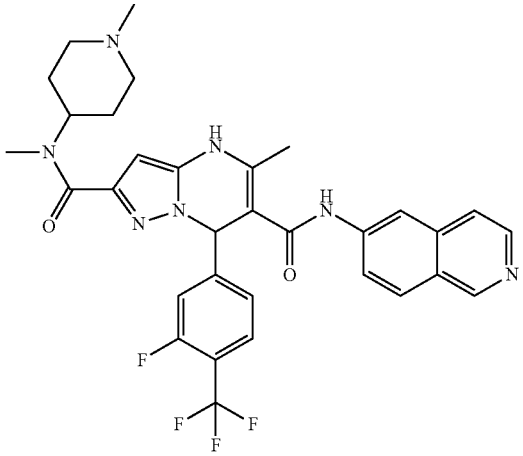 [SMILES: CC1=C(C(=O)Nc2ccc3cnccc3c2)C(c2ccc(C(F)(F)F)c(F)c2)n2nc(C(=O)N(C)C3CCN(C)CC3)cc2N1]  7-(3-fluoro-4-(trifluoromethyl)phenyl)-N6-(isoquinolin-6-yl)-N2,5-dimethyl-N2-(1-methylpiperidin-4-yl)-4,7-dihydropyrazolo[1,5-a]pyrimidine-2,6-dicarboxamide | Intermediate 77B/N,1-dimethylpiperidin-4-amine | $^1$H NMR (400 MHz, d6-DMSO) δ 10.10-10.07 (m, 1H), 9.96 (s, 1H), 9.15 (s, 1H), 8.39 (d, J = 5.7 Hz, 1H), 8.27 (s, 1H), 8.02 (d, J = 8.9 Hz, 1H), 7.80-7.67 (m, 3H), 7.30-7.22 (m, 2H), 6.66 (s, 1H), 5.86 (s, 1H), 3.86 (m, 1H), 2.76 (s, 3H), 2.69-2.53 (m, 2H), 2.28 (s, 3H), 1.99 (s, 3H), 1.75-1.62 (m, 2H), 1.49 (m, 1H), 1.41-1.13 (m, 3H). | Rt = 2.38 min, m/z 622.4 [M + H]+ (Method 1) |

| Ex | Structure | Staring materials | 1H NMR | LC-MS |
|---|---|---|---|---|
| 89 | N2-(3-(dimethylamino)propyl)-7-(3-fluoro-4-(trifluoromethyl)phenyl)-N6-(isoquinolin-6-yl)-N2,5-dimethyl-4,7-dihydropyrazolo[1,5-a]pyrimidine-2,6-dicarboxamide | Intermediate 77B/ N,N,N'-trimethyl-propane-1,3-diamine | ¹H NMR (400 MHz, d6-DMSO) δ 10.12 (s, 1H), 9.97 (s, 1H), 9.21-9.15 (m, 1H), 8.46-8.39 (m, 1H), 8.28 (s, 1H), 8.19 (s, 1H), 8.03 (d, J = 8.9 Hz, 1H), 7.78-7.68 (m, 3H), 7.28-7.22 (m, 2H), 6.66 (d, J = 11.9 Hz, 1H), 5.90 (d, J = 5.9 Hz, 1H), 3.65-3.56 (m, 1H), 3.39-3.30 (m, 1H), 3.11 and 2.89 (two s, 3H), 2.33-2.26 (m, 4H), 2.21 and 2.02 (two s, 6H), 1.98-1.91 (m, 1H), 1.71-1.63 (m, 1H), 1.60-1.54 (m, 1H). | Rt = 2.46 min, m/z 610.4 [M + H]+ (Method 1) |
| 90 | 7-(4-fluorophenyl)-N-(1H-indazol-5-yl)-5-methyl-2-(morpholine-4-carbonyl)-4,7-dihydropyrazolo[1,5-a]pyrimidine-6-carboxamide | Example 75/ morpholine | ¹H NMR (400 MHz, d6-DMSO) δ 12.93 (s, 1H), 9.66 (s, 1H), 9.63 (s, 1H), 8.00 (s, 1H), 7.97 (s, 1H), 7.45-7.35 (m, 2H), 7.26-7.09 (m, 4H), 6.59 (s, 1H), 5.84 (s, 1H), 3.87-3.74 (m, 2H), 3.68-3.45 (m, 6H), 2.23 (s, 3H). | Rt = 3.00 min, m/z 502.2 [M + H]+ (Method 1) |

Example 91

Step A

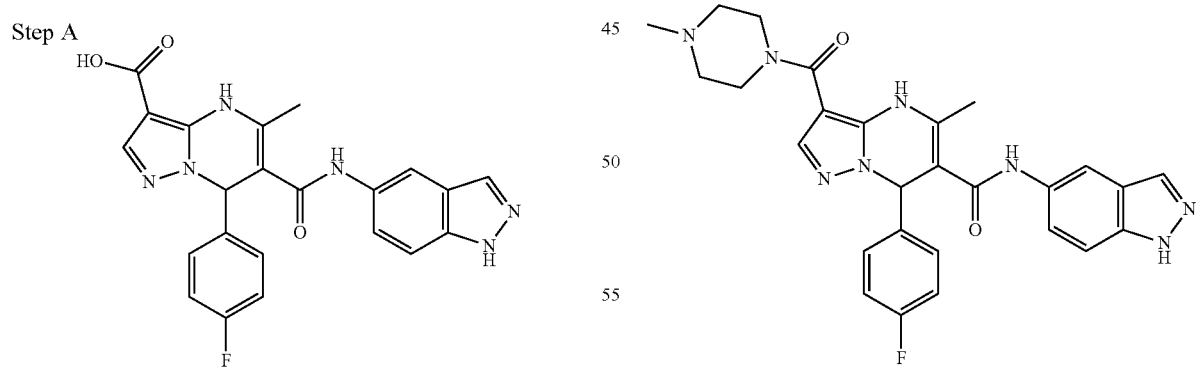

6-((1H-Indazol-5-yl)carbamoyl)-7-(4-fluorophenyl)-5-methyl-4,7-dihydropyrazolo[1,5-a]pyrimidine-3-carboxylic acid (Intermediate 91A)

Intermediate 91A was prepared from Example 17 using a method analogous to that used for the preparation of Example 73.
LCMS (Method 2): Rt=2.94 min, m/z 433.2 [M+H]+

Step B 7-(4-fluorophenyl)-N-(1H-indazol-5-yl)-5-methyl-3-(4-methylpiperazine-1-carbonyl)-4,7-dihydropyrazolo[1,5-a]pyrimidine-6-carboxamide (Example 91)

Example 91 was prepared from Intermediate 91A and 1-methylpiperazine using a method similar to that used in the synthesis of Example 77.

LCMS (Method 1): Rt=2.29 min, m/z 515.2 [M+H]+ (Method 1)

¹H NMR (400 MHz, d6-DMSO) δ 12.90 (s, 1H), 9.72 (s, 1H), 8.92 (s, 1H), 7.97-7.93 (m, 2H), 7.57 (s, 1H), 7.42-7.38 (m, 1H), 7.36-7.31 (m, 1H), 7.25-7.20 (m, 2H), 7.13-7.06 (m, 2H), 6.49 (s, 1H), 3.58 (m, 4H), 2.29 (m, 4H), 2.23 (s, 3H), 2.17 (s, 3H).

Example 92

The following example was also prepared from Intermediate 91A and the amine shown using a method similar to that used in step B for the synthesis of Example 77.

Evaporation gave a crude product which was chromatographed on a 25 g Si cartridge eluting with 0-8% 2M methanolic ammonia in DCM. The resulting white solid was dissolved in 10% TFA in DCM (10 mL) and the solution was allowed to stand at RT overnight. The volatiles were evaporated and the residue was dissolved in a small amount of methanol. The solution was loaded onto a 5 g SCX-2 cartridge which had been conditioned with methanol. After flushing with methanol, the product was eluted with 2M methanolic ammonia. Evaporation gave a yellow gum which was dissolved in water/acetonitrile and freeze-dried to give a pale yellow solid (19 mg).

LCMS (Method 1): Rt=2.22 min, m/z 501.2 [M+H]+

| Ex | Structure | Amine | 1H NMR | LC-MS |
|---|---|---|---|---|
| 92 | 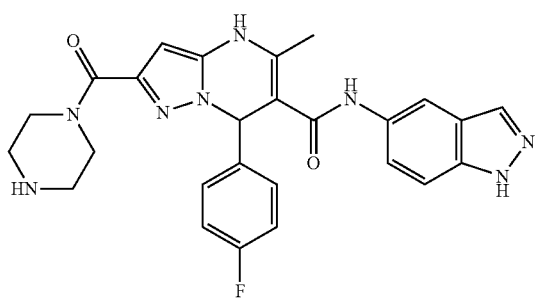 [SMILES: CC1=C(C(=O)Nc2ccc3[nH]ncc3c2)C(c2ccc(F)cc2)n2nc(C(=O)N3CCNCC3)cc2N1]<br>Formic acid salt.<br>N3-(2-(dimethylamino)ethyl)-7-(4-fluorophenyl)-N6-(1H-indazol-5-yl)-5-methyl-4,7-dihydropyrazolo[1,5-a]pyrimidine-3,6-dicarboxamide | N,N-dimethyl-ethane-1,2-diamine | ¹H NMR (400 MHz, d6-DMSO) δ 12.94-12.93 (m, 1H), 9.77 (s, 1H), 8.72 (s, 1H), 8.20 (s, 1H), 8.01-7.97 (m, 3H), 7.82 (s, 1H), 7.43 (d, J = 8.9 Hz, 1H), 7.37 (dd, J = 1.9, 9.0 Hz, 1H), 7.25-7.21 (m, 2H), 7.15-7.09 (m, 2H), 6.51 (s, 1H), 3.37-3.21 (m, 2H), 2.39 (dd, J = 6.9, 6.9 Hz, 2H), 2.28 (s, 3H), 2.20 (s, 6H). | Rt = 2.35 min, m/z 503.3 [M + H]+ (Method 1) |

Example 93

7-(4-fluorophenyl)-N-(1H-indazol-5-yl)-5-methyl-2-(piperazine-1-carbonyl)-4,7-dihydropyrazolo[1,5-a]pyrimidine-6-carboxamide (Example 93)

Example 75 (100 mg, 0.23 mmol), 1-Boc-piperazine (47 mg, 0.255 mmol), DIPEA (81 mg, 0.46 mmol) and HATU (97 mg, 0.255 mmol) were dissolved in DMF (2 mL) and the solution was stirred at RT overnight. The mixture was partitioned between ethyl acetate (10 mL) and water (10 mL). The organic phase was separated and dried (Na₂SO₄).

¹H NMR (400 MHz, d6-DMSO) δ 12.93 (s, 1H), 9.66 (s, 1H), 9.62 (s, 1H), 7.99 (m, 2H), 7.46-7.36 (m, 2H), 7.26-7.20 (m, 2H), 7.15-7.09 (m, 2H), 6.58 (s, 1H), 5.79 (s, 1H), 3.75-3.63 (m, 1H), 3.60-3.49 (m, 2H), 3.44-3.36 (m, 2H), 2.71-2.56 (m, 4H), 2.23 (s, 3H).

Example 94

Step A

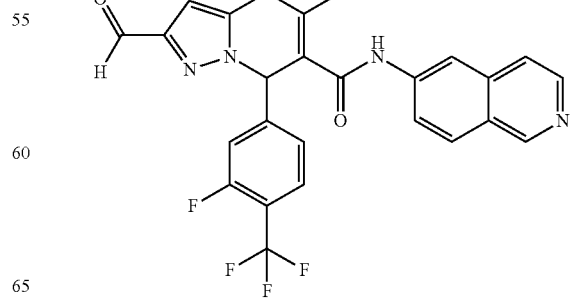

7-(3-Fluoro-4-(trifluoromethyl)phenyl)-2-formyl-N-(isoquinolin-6-yl)-5-methyl-4,7-dihydropyrazolo[1,5-a]pyrimidine-6-carboxamide (Intermediate 94A)

Example 65 (2.49 g, 5.0 mmol) was dissolved in a mixture of DCM (170 mL) and DMF (17 mL). The solution was cooled to 0° C. and Dess-Martin periodinane (2.55 g, 6.0 mmol) was added portion wise. The solution was stirred whilst being allowed to warm to RT over 3 h. 1N sodium hydroxide (10 mL) was added and the mixture was stirred for 10 min. The solvent was reduced in vacuo and then water (20 mL) and ethyl acetate (20 mL) were added. The organic layer was separated and the aqueous was further extracted with ethyl acetate (2×15 mL). The combined organic extracts were washed with brine (20 mL), dried ($Na_2SO_4$) and evaporated to give a yellow solid (2.48 g). Although the desired product was contaminated with unreacted starting material, it was used without further purification.

LCMS (Method 3): Rt=0.87 min, m/z 496.5 [M+H]$^+$
Step B 2-((dimethylamino)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide (Example 94)

Intermediate 94A (450 mg, 909 mmol) was dissolved in THF (10 mL) and 2M dimethylamine in THF (909 µL, 1.82 mmol) was added. The mixture was stirred at RT for 1 h before the addition of sodium triacetoxyborohydride (384 mg, 1.82 mmol). The reaction was stirred at RT for 90 min and then sat. sodium bicarbonate (10 mL) was added. The product was extracted into ethyl acetate (2×20 mL) and the combined extracts were dried ($Na_2SO_4$) and evaporated. The crude product was purified on a 25 g Si cartridge eluting with 0-10% 2M methanolic ammonia in DCM. The product was obtained as a yellow solid (60 mg).

LCMS (Method 1): Rt=2.41 min, m/z 525.3 [M+H]$^+$ $^1$H NMR (400 MHz, d6-DMSO) δ 10.06 (s, 1H), 9.80 (s, 1H), 9.14 (s, 1H), 8.39 (d, J=5.7 Hz, 1H), 8.28 (d, J=1.7 Hz, 1H), 8.02 (d, J=9.0 Hz, 1H), 7.76-7.67 (m, 3H), 7.18-7.10 (m, 2H), 6.60 (s, 1H), 5.58 (s, 1H), 3.30-3.17 (m, 2H), 2.25 (s, 3H), 2.10 (s, 6H).

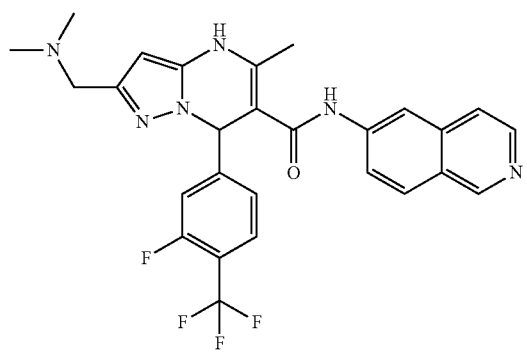 [SMILES: CC1=C(C(=O)Nc2ccc3cnccc3c2)C(c2ccc(C(F)(F)F)c(F)c2)n2nc(CN(C)C)cc2N1]

Examples 95 to 106

The following compounds were prepared by analogous procedures of Example 94 starting from the aldehyde intermediate and amine combination given in the table below.

| Ex. | Structure | Aldehyde Intermediate/ amine | 1H NMR | LC-MS |
|---|---|---|---|---|
| 95 | 7-(3-fluoro-4-(trifluoromethyl)phenyl)-N-(isoquinolin-6-yl)-5-methyl-2-(morpholinomethyl)-4,7-dihydropyrazolo[1,5-a]pyrimidine-6-carboxamide | Intermediate 94A/ morpholine | $^1$H NMR (400 MHz, d6-DMSO) δ 10.06 (s, 1H), 9.79 (s, 1H), 9.14 (s, 1H), 8.39 (d, J = 5.7 Hz, 1H), 8.28 (d, J = 1.7 Hz, 1H), 8.02 (d, J = 9.0 Hz, 1H), 7.76-7.67 (m, 3H), 7.19-7.11 (m, 2H), 6.61 (s, 1H), 5.59 (s, 1H), 3.57-3.51 (m, 4H), 3.37-3.23 (m, 2H), 2.35-2.28 (m, 4H), 2.25 (s, 3H). | Rt = 2.44 min, m/z 567.3 [M + H]+ (Method 1) |

| Ex. | Structure | Aldehyde Intermediate/ amine | 1H NMR | LC-MS |
|---|---|---|---|---|
| 96 | 7-(3-fluoro-4-(trifluoromethyl)phenyl)-N-(isoquinolin-6-yl)-5-methyl-2-((4-methylpiperazin-1-yl)methyl)-4,7-dihydropyrazolo[1,5-a]pyrimidine-6-carboxamide | Intermediate 94A/1-methyl-piperazine | $^1$H NMR (400 MHz, d6-DMSO) δ 10.06 (s, 1H), 9.78 (s, 1H), 9.14 (s, 1H), 8.40-8.38 (m, 1H), 8.28 (d, J = 1.8 Hz, 1H), 8.02 (d, J = 9.0 Hz, 1H), 7.75-7.67 (m, 3H), 7.19-7.11 (m, 2H), 6.61 (s, 1H), 5.57 (s, 1H), 3.31-3.21 (m, 2H), 2.33-2.22 (m, 11H), 2.13 (s, 3H). | Rt = 2.37 min, m/z 580.4 [M + H]+ (Method 1) |
| 97 | 7-(3-fluoro-4-(trifluoromethyl)phenyl)-N-(isoquinolin-6-yl)-5-methyl-2-(piperidin-1-ylmethyl)-4,7-dihydropyrazolo[1,5-a]pyrimidine-6-carboxamide | Intermediate 94A/piperidine | $^1$H NMR (400 MHz, d6-DMSO) δ 10.06 (s, 1H), 9.78 (s, 1H), 9.14 (s, 1H), 8.39 (d, J = 5.7 Hz, 1H), 8.28 (d, J = 1.8 Hz, 1H), 8.02 (d, J = 8.9 Hz, 1H), 7.75-7.67 (m, 3H), 7.19-7.09 (m, 2H), 6.61 (s, 1H), 5.60-5.55 (m, 1H), 3.24 (s, 2H), 2.31-2.26 (m, 7H), 1.51-1.35 (m, 6H). | Rt = 2.59 min, m/z 565.3 [M + H]+ (Method 1) |
| 98 | 7-(3-fluoro-4-(trifluoromethyl)phenyl)-N-(isoquinolin-6-yl)-2-(((2-methoxyethyl)(methyl)amino)methyl-5-methyl-4,7-dihydropyrazolo[1,5-a]pyrimidine-6-carboxamide | Intermediate 94A/2-methoxy-N-methylethan-1-amine | $^1$H NMR (400 MHz, d6-DMSO) δ 10.06 (s, 1H), 9.79 (s, 1H), 9.14 (s, 1H), 8.40-8.38 (m, 1H), 8.28 (d, J = 1.7 Hz, 1H), 8.02 (d, J = 8.9 Hz, 1H), 7.75-7.67 (m, 3H), 7.18-7.09 (m, 2H), 6.60 (s, 1H), 5.57 (s, 1H), 3.40-3.35 (m, 4H), 3.19 (s, 3H), 2.48-2.41 (m, 2H), 2.25 (s, 3H), 2.13 (s, 3H). | Rt = 2.53 min, m/z 569.3 [M + H]+ (Method 1) |

-continued

| Ex. | Structure | Aldehyde Intermediate/amine | 1H NMR | LC-MS |
|---|---|---|---|---|
| 99 | 7-(3-fluoro-4-(trifluoromethyl)phenyl)-N-(isoquinolin-6-yl)-2-((4-methoxypiperidin-1-yl)methyl)-5-methyl-4,7-dihydropyrazolo[1,5-a]pyrimidine-6-carboxamide | Intermediate 94A/4-methoxy-piperidine | $^1$H NMR (400 MHz, d6-DMSO) δ 10.06 (s, 1H), 9.78 (s, 1H), 9.14 (s, 1H), 8.39 (d, J = 5.7 Hz, 1H), 8.28 (d, J = 1.7 Hz, 1H), 8.02 (d, J = 9.0 Hz, 1H), 7.75-7.67 (m, 3H), 7.18-7.10 (m, 2H), 6.61 (s, 1H), 5.57 (s, 1H), 3.27-3.19 (m, 5H), 3.15-3.07 (m, 1H), 2.60-2.60 (m, 2H), 2.25 (s, 3H), 2.07-1.97 (m, 2H), 1.83-1.77 (m, 2H), 1.41-1.32 (m, 2H). | Rt = 2.56 min, m/z 595.3 [M + H]+ (Method 1) |
| 100 | 7-(3-fluoro-4-(trifluoromethyl)phenyl)-N-(isoquinolin-6-yl)-2-((3-methoxyazetidin-1-yl)methyl)-5-methyl-4,7-dihydropyrazolo[1,5-a]pyrimidine-6-carboxamide | Intermediate 94A/3-methoxy-azetidine | $^1$H NMR (400 MHz, d6-DMSO) δ 10.06 (s, 1H), 9.79 (s, 1H), 9.14 (s, 1H), 8.39 (d, J = 5.7 Hz, 1H), 8.28 (d, J = 1.7 Hz, 1H), 8.02 (d, J = 9.0 Hz, 1H), 7.75-7.67 (m, 3H), 7.18-7.10 (m, 2H), 6.59 (s, 1H), 5.55 (s, 1H), 3.94-3.87 (m, 1H), 3.41-3.29 (m, 4H), 3.11 (s, 3H), 2.79 (m, 2H), 2.25 (s, 3H). | Rt = 2.50 min, m/z 567.3 [M + H]+ (Method 1) |
| 101 | 7-(3-fluoro-4-(trifluoromethyl)phenyl)-N-(isoquinolin-6-yl)-2-((3-(methoxymethyl)azetidin-1-yl)methyl)-5-methyl-4,7-dihydropyrazolo[1,5-a]pyrimidine-6-carboxamide | Intermediate 94A/3-methoxymethyl-azetidine | $^1$H NMR (400 MHz, d6-DMSO) δ 10.05 (s, 1H), 9.78 (s, 1H), 9.14 (s, 1H), 8.39 (d, J = 5.7 Hz, 1H), 8.27 (d, J = 1.8 Hz, 1H), 8.02 (d, J = 8.9 Hz, 1H), 7.76-7.67 (m, 3H), 7.19-7.10 (m, 2H), 6.58 (s, 1H), 5.53 (s, 1H), 3.40-3.32 (m, 4H), 3.21 (s, 3H), 3.20-3.16 (m, 2H), 2.84-2.78 (m, 2H), 2.57-2.52 (m, 1H), 2.25 (s, 3H). | Rt = 2.58 min, m/z 581.3 [M + H]+ (Method 1) |

| Ex. | Structure | Aldehyde Intermediate/ amine | 1H NMR | LC-MS |
|---|---|---|---|---|
| 102 | 7-(3-fluoro-4-(trifluoromethyl)phenyl)-N-(isoquinolin-6-yl)-5-methyl-2-(pyrrolidin-1-ylmethyl)-4,7-dihydropyrazolo[1,5-a]pyrimidine-6-carboxamide | Intermediate 94A/ pyrrolidine | ¹H NMR (400 MHz, d6-DMSO) δ 10.06 (s, 1H), 9.80 (s, 1H), 9.14 (s, 1H), 8.39 (d, J = 5.8 Hz, 1H), 8.28 (d, J = 1.7 Hz, 1H), 8.02 (d, J = 9.0 Hz, 1H), 7.76-7.67 (m, 3H), 7.19-7.11 (m, 2H), 6.60 (s, 1H), 5.60 (s, 1H), 3.52-3.39 (m, 2H), 2.42 (s, 4H), 2.25 (s, 3H), 1.66 (s, 4H). | Rt = 2.50 min, m/z 551.3 [M + H]+ (Method 1) |
| 103 | 7-(3-fluoro-4-(trifluoromethyl)phenyl)-N-(isoquinolin-6-yl)-5-methyl-2-((8-methyl-2,8-diazaspiro[4.5]decan-2-yl)methyl)-4,7-dihydropyrazolo[1,5-a]pyrimidine-6-carboxamide | Intermediate 94A/8-methyl-2,8-diaza-spiro[4.5]decane | ¹H NMR (400 MHz, d6-DMSO) δ 10.06 (s, 1H), 9.78 (s, 1H), 9.14 (s, 1H), 8.39 (d, J = 5.7 Hz, 1H), 8.28 (d, J = 1.7 Hz, 1H), 8.02 (d, J = 9.0 Hz, 1H), 7.75-7.67 (m, 3H), 7.19-7.09 (m, 2H), 6.60 (s, 1H), 5.57 (s, 1H), 3.43-3.35 (m, 2H), 2.47-2.43 (m, 4H), 2.25 (m, 7H), 2.15 (s, 3H), 1.51-1.40 (m, 6H). | Rt = 2.04 min, m/z 634.4 [M + H]+ (Method 1) |
| 104 | 7-(3-fluoro-4-(trifluoromethyl)phenyl)-N-(isoquinolin-6-yl)-5-methyl-2-((methyl((1-methylpiperidin-4-yl)methyl)amino)methyl)-4,7-dihydropyrazolo[1,5-a]pyrimidine-6-carboxamide | Intermediate 94A/N-methyl-1-(1-methyl-piperidine-4-yl)methanamine | ¹H NMR (400 MHz, d6-DMSO) δ 10.06 (s, 1H), 9.78 (s, 1H), 9.14 (s, 1H), 8.39 (d, J = 5.7 Hz, 1H), 8.28 (d, J = 1.7 Hz, 1H), 8.02 (d, J = 9.0 Hz, 1H), 7.75-7.67 (m, 3H), 7.18-7.09 (m, 2H), 6.60 (s, 1H), 5.55 (s, 1H), 3.29-3.24 (m, 2H), 2.75 (s, 2H), 2.25 (s, 3H), 2.18 (s, 3H), 2.10 (s, 3H), 2.03 (d, J = 7.2 Hz, 2H), 1.88 (s, 2H), 1.59 (m, 2H), 1.41 (s, 1H), 1.06-0.93 (m, 2H). | Rt = 2.02 min, m/z 622.4 [M + H]+ (Method 1) |

-continued

| Ex. | Structure | Aldehyde Intermediate/ amine | 1H NMR | LC-MS |
|---|---|---|---|---|
| 105 | 7-(3-fluoro-4-(trifluoromethyl)phenyl)-N-(isoquinolin-6-yl)-5-methyl-2-((4-(pyrrolidin-1-yl)piperidin-1-yl)methyl)-4,7-dihydropyrazolo[1,5-a]pyrimidine-6-carboxamide | Intermediate 94A/4-(pyrrolidin-1-yl)piperidine | $^1$H NMR (400 MHz, d6-DMSO) δ 10.06 (s, 1H), 9.78 (s, 1H), 9.14 (s, 1H), 8.39 (d, J = 5.8 Hz, 1H), 8.28 (d, J = 1.6 Hz, 1H), 8.02 (d, J = 8.9 Hz, 1H), 7.75-7.67 (m, 3H), 7.19-7.09 (m, 2H), 6.61 (s, 1H), 5.57 (s, 1H), 3.29-3.20 (m, 2H), 2.73-2.64 (m, 2H), 2.47-2.39 (m, 4H), 2.25 (s, 3H), 1.95-1.82 (m, 3H), 1.79-1.71 (m, 2H), 1.67-1.62 (m, 4H), 1.38-1.28 (m, 2H). | Rt = 2.10 min, m/z 634.4 [M + H]+ (Method 2) |
| 106 | 2-((3-((dimethylamino)methyl)azetidin-1-yl)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide | Intermediate 94A/1-(azetidin-3-yl)-N,N-dimethyl-methanamine | $^1$H NMR (400 MHz, d6-DMSO) δ 10.05 (s, 1H), 9.78 (s, 1H), 9.14 (s, 1H), 8.39 (d, J = 5.7 Hz, 1H), 8.27 (d, J = 1.7 Hz, 1H), 8.02 (d, J = 9.0 Hz, 1H), 7.75-7.67 (m, 3H), 7.19-7.10 (m, 2H), 6.58 (s, 1H), 5.53 (s, 1H), 3.38-3.21 (m, 4H), 2.73-2.68 (m, 2H), 2.48-2.41 (m, 1H), 2.32-2.28 (m, 2H), 2.26 (s, 3H), 2.05 (s, 6H). | Rt = 2.03 min, m/z 594.4 [M + H]+ (Method 1) |

Example 107

Step A

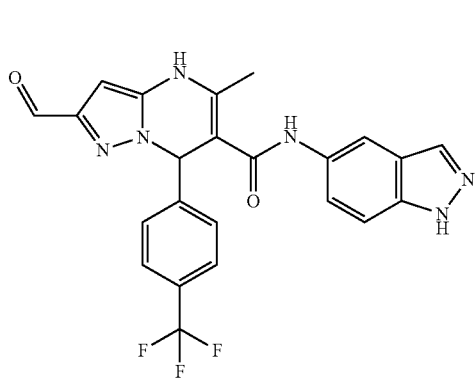 [SMILES: CC1=C(C(=O)Nc2ccc3[nH]ncc3c2)C(c2ccc(C(F)(F)F)cc2)n2nc(C=O)cc2N1]

2-Formyl-N-(1H-indazol-5-yl)-5-methyl-7-(4-(trifluoromethyl)phenyl)-4,7-dihydropyrazolo[1,5-a]pyrimidine-6-carboxamide (Intermediate 107A)

Intermediate 107A was prepared in similar way of Intermediate 94A starting from Example 69.

Step B

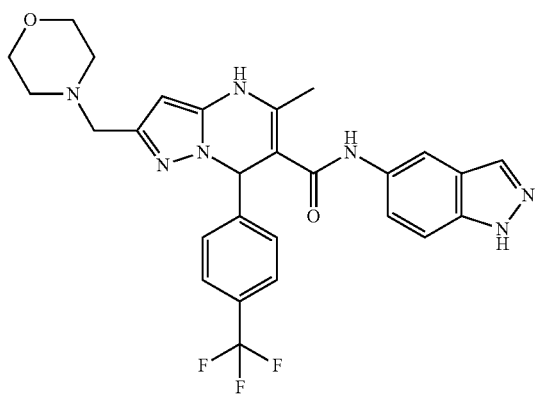 [SMILES: CC1=C(C(=O)Nc2ccc3[nH]ncc3c2)C(c2ccc(C(F)(F)F)cc2)n2nc(CN3CCOCC3)cc2N1]

N-(1H-indazol-5-yl)-5-methyl-2-(morpholinomethyl)-7-(4-(trifluoromethyl)phenyl)-4,7-dihydropyrazolo[1,5-a]pyrimidine-6-carboxamide (Example 107)

Example 107 was prepared in a similar way of step B of Example 94 by using analogues procedure starting from Intermediate 107A and morpholine.

LCMS (Method 1): Rt=2.76 min, m/z 538.3 [M+H]$^+$ $^1$H NMR (400 MHz, d6-DMSO) δ 12.93 (s, 1H), 9.67 (s, 1H), 9.52 (s, 1H), 7.99 (d, J=13.4 Hz, 2H), 7.65 (d, J=8.1 Hz, 2H), 7.45-7.37 (m, 2H), 7.30 (d, J=8.1 Hz, 2H), 6.59 (s, 1H), 5.54 (s, 1H), 3.56-3.51 (m, 4H), 3.35-3.22 (m, 2H), 2.31 (m, 4H), 2.20 (s, 3H).

Example 108

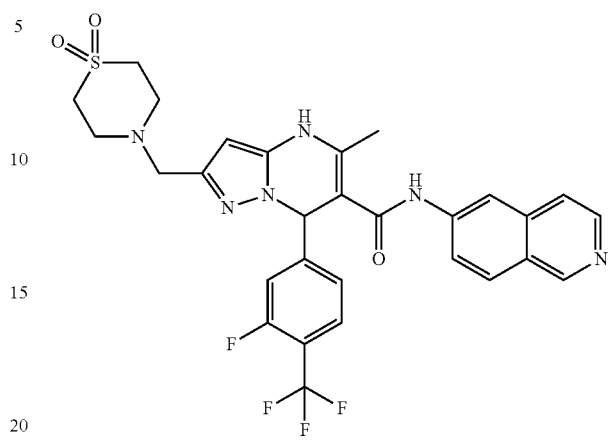

2-((1,1-Dioxidothiomorpholino)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide (Example 108)

A solution of Example 65 (250 mg, 0.502 mmol) and DIPEA (262 µL, 1.51 mmol) in DMF (4 mL) was cooled in ice and a solution of methanesulfonyl chloride (63 mg, 0.552 mmol) in DMF (2 mL) was added. The reaction was stirred at 0° C. for 30 min. A further quantity of methanesulfonyl chloride (31 mg, 0.275 mmol) was added and the reaction was stirred for another 30 min before the addition of another quantity of methanesulfonyl chloride (31 mg, 0.275 mmol). After stirring at 0° C. for 1 h the reaction was quenched by the addition of a solution of thiomorpholine 1,1-dioxide hydrochloride (207 mg, 1.21 mmol) and DIPEA (0.262 mL, 1.51 mmol) in DMF (2 mL). The reaction was stirred at RT for 30 min and then another portion of thiomorpholine 1,1-dioxide hydrochloride (103 mg, 0.603 mmol) was added. Stirring was continued for 90 min. The reaction mixture was concentrated in vacuo and the residue was dissolved in methanol. The solution was loaded onto a 5 g SCX-2 cartridge which had been conditioned with methanol. After flushing with methanol the product was eluted with 2M methanolic ammonia. Evaporation gave the crude product which was purified by MDAP (acidic) to give a yellow solid (109 mg).

LCMS (Method 1): Rt=2.91 min, m/z 615.2 [M+H]$^+$ $^1$H NMR (400 MHz, d6-DMSO) δ 10.08 (s, 1H), 9.84 (s, 1H), 9.14 (s, 1H), 8.39 (d, J=5.7 Hz, 1H), 8.28 (d, J=1.7 Hz, 1H), 8.04-8.01 (m, 1H), 7.76-7.67 (m, 3H), 7.15 (d, J=9.7 Hz, 2H), 6.62 (s, 1H), 5.63 (s, 1H), 3.56 (d, J=13.7, 1H), 3.49 (d, J=13.7 Hz, 1H), 3.10-3.03 (m, 4H), 2.87-2.81 (m, 4H), 2.25 (s, 3H).

Preparation of Intermediates 120A, 121A and 123A

The following intermediates were prepared using the same procedure of Example 43 by reduction of the corresponding ethyl ester to hydroxymethyl. The intermediate esters required were prepared according to a procedure similar to that used in Example 1 using the starting materials given in the table below.

| Int. | Structure | Starting materials for intermediate ester (Intermediate 1X/aldehyde/amino heterocycle) | LC-MS |
|---|---|---|---|
| 120A | 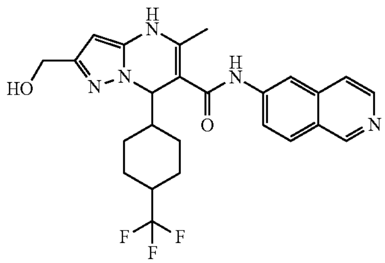 [SMILES: CC1=C(C(=O)Nc2ccc3cnccc3c2)C(C2CCC(C(F)(F)F)CC2)n2nc(CO)cc2N1] | Intermediate 1A/4-(trifluoro-methyl)cyclohexane-1-carbaldehyde/ethyl-3-amino-1H-pyrazole-5-carboxylate and | Rt = 0.95 min, m/z 486.3 [M + H]+ (Method 6) |
| 121A | 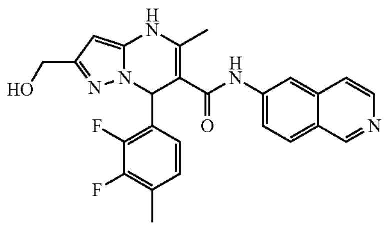 [SMILES: CC1=C(C(=O)Nc2ccc3cnccc3c2)C(c2ccc(C)c(F)c2F)n2nc(CO)cc2N1] | Intermediate 1A/2,3-difluoro-4-methylbenzaldehyde/ethyl-3-amino-1H-pyrazole-5-carboxylate | Rt = 0.86 min, m/z 462.3 [M + H]+ (Method 6) |
| 123A | 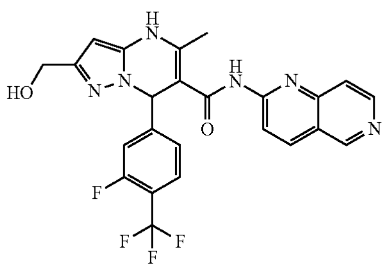 [SMILES: CC1=C(C(=O)Nc2ccc3cnccc3n2)C(c2ccc(C(F)(F)F)c(F)c2)n2nc(CO)cc2N1] | Intermediate 1G/3-fluoro-4-(trifluoromethyl)benzaldehyde/ethyl-3-amino-1H-pyrazole-5-carboxylate | Rt = 0.94 min, m/z 499.2 [M + H]+ (Method 6) |

Examples 109 to 110 and Examples 120 to 124

The following compounds were prepared by analogous procedures of Example 108 by replacing the alcohol and the amine with those reported in the table below.

| Ex | Structure | Alcohol/amine | 1H NMR | LC-MS |
|---|---|---|---|---|
| 109 | 2-((4-acetylpiperazin-1-yl)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide | Example 65/1-(piperazin-1-yl)ethan-1-one | $^1$H NMR (400 MHz, d6-DMSO) δ 10.06 (s, 1H), 9.80 (s, 1H), 9.15 (s, 1H), 8.40 (d, J = 5.8 Hz, 1H), 8.30-8.26 (m, 1H), 8.03 (d, J = 9.0 Hz, 1H), 7.76-7.68 (m, 3H), 7.19-7.11 (m, 2H), 6.62 (s, 1H), 5.60 (s, 1H), 3.44-3.27 (m, 6H), 2.36-2.31 (m, 2H), 2.30-2.24 (m, 2H), 2.27 (s, 3H), 1.96 (s, 3H). | Rt = 2.40 min, m/z 608.2 [M + H]+ (Method 1) |

| Ex | Structure | Alcohol/amine | 1H NMR | LC-MS |
|---|---|---|---|---|
| 110 | 2-((dimethylamino)methyl)-7-(3-fluoro-4-methylphenyl)-N-(isoquinolin-6-yl)-5-methyl-4,7-dihydropyrazolo[1,5-a]pyrimidine-6-carboxamide | Example 58/ dimethylamine | $^1$H NMR (400 MHz, d6-DMSO) δ 10.00 (s, 1H), 9.63 (s, 1H), 9.13 (s, 1H), 8.38 (d, J = 5.7 Hz, 1H), 8.30 (d, J = 1.8 Hz, 1H), 8.01 (d, J = 8.9 Hz, 1H), 7.72 (dd, J = 2.0, 8.9 Hz, 1H), 7.68 (d, J = 5.9 Hz, 1H), 7.16 (t, J = 8.0 Hz, 1H), 6.88 (dd, J = 1.7, 7.8 Hz, 1H), 6.78 (dd, J = 1.6, 10.6 Hz, 1H), 6.53 (s, 1H), 5.52 (s, 1H), 3.22 (dd, J = 13.1, 37.6 Hz, 2H), 2.24 (s, 3H), 2.12 (d, J = 1.2 Hz, 3H), 2.10 (s, 6H). | Rt = 2.07 min, m/z 471.0 [M + H]+ (Method 1) |
| 120 | 2-((dimethylamino)methyl)-N-(isoquinolin-6-yl)-5-methyl-7-(4-(trifluoromethyl)cyclohexyl)-4,7-dihydropyrazolo[1,5-a]pyrimidine-6-carboxamide | Intermediate 120A/ dimethylamine | $^1$H NMR (400 MHz, d6-DMSO) δ 10.05 (s, 1H), 9.33 (s, 1H), 9.15 (s, 1H), 8.41-8.37 (m, 2H), 8.03 (d, J = 8.9 Hz, 1H), 7.79 (dd, J = 2.0, 8.9 Hz, 1H), 7.71 (d, J = 5.9 Hz, 1H), 5.46-5.41 (m, 2H), 3.34-3.22 (m, 2H), 2.37-2.24 (m, 1H), 2.20 (s, 3H), 2.13 (s, 6H), 1.79-1.72 (m, 4H), 1.55-1.34 (m, 4H), 0.93-0.93 (m, 1H). | Rt = 2.25 min, m/z 513.2 [M + H]+ (Method 2) |
| 121 | 7-(2,3-difluoro-4-methylphenyl)-2-((dimethylamino)methyl)-N-(isoquinolin-6-yl)-5-methyl-4,7-dihydropyrazolo[1,5-a]pyrimidine-6-carboxamide | Intermediate 121A/ dimethylamine | $^1$H NMR (400 MHz, d6-DMSO) δ 10.10 (s, 1H), 9.74 (s, 1H), 9.13 (s, 1H), 8.38 (d, J = 5.7 Hz, 1H), 8.27 (d, J = 1.5 Hz, 1H), 8.19 (s, 1.7H, formic acid), 8.01 (d, J = 8.9 Hz, 1H), 7.70-7.66 (m, 2H), 6.99 (dd, J = 7.3, 7.3 Hz, 1H), 6.88-6.82 (m, 1H), 6.77 (s, 1H), 5.55 (s, 1H), 3.33 (dd, J = 13.3, 42.4 Hz, 2H), 2.23 (s, 3H), 2.19-2.15 (m, 9H). | Rt = 2.09 min, m/z 489.3 [M + H]+ (Method 1) |
| 122 | 7-(2,3-difluoro-4-(trifluoromethyl)phenyl)-2-((dimethylamino)methyl-N-(isoquinolin-6-yl)-5-methyl-4,7-dihydropyrazolo[1,5-a]pyrimidine-6-carboxamide | Example 56/ dimethylamine | $^1$H NMR (400 MHz, d6-DMSO) δ 10.14 (s, 1H), 9.91 (s, 1H), 9.14 (s, 1H), 8.39 (d, J = 5.8 Hz, 1H), 8.25 (d, J = 1.7 Hz, 1H), 8.18 (s, 1.6H, formic acid), 8.02 (d, J = 8.9 Hz, 1H), 7.70-7.66 (m, 2H), 7.57 (dd, J = 7.1, 7.1 Hz, 1H), 7.17 (dd, J = 7.2, 7.2 Hz, 1H), 6.81 (s, 1H), 5.59 (s, 1H), 3.30 (dd, J = 13.4, 36.0 Hz, 2H), 2.26 (s, 3H), 2.13 (s, 6H). | Rt = 2.34 min, m/z 543.2 [M + H]+ (Method 1) |

-continued

| Ex | Structure | Alcohol/amine | 1H NMR | LC-MS |
|---|---|---|---|---|
| 123 | 2-((dimethylamino)methyl)-7-(3-fluoro-4-(trifluoromethyl)phenyl)-5-methyl-N-(1,6-naphthyridin-2-yl)-4,7-dihydropyrazolo[1,5-a]pyrimidine-6-carboxamide | Intermediate 123A/ dimethylamine | H NMR (400 MHz, d6-DMSO) δ 10.73 (s, 1H), 9.92 (s, 1H), 9.21 (s, 1H), 8.63 (d, J = 5.9 Hz, 1H), 8.43 (d, J = 9.2 Hz, 1H), 8.12 (d, J = 9.0 Hz, 1H), 7.72 (t, J = 7.8 Hz, 1H), 7.64 (d, J = 6.1 Hz, 1H), 7.26-7.21 (m, 2H), 6.54 (s, 1H), 5.56 (s, 1H), 3.26-3.15 (m, 2H), 2.30 (s, 3H), 2.08 (s, 6H). | Rt = 2.44 min, m/z 526.1 [M + H]⁺ (Method 1) |
| 124 | 7-(2,3-dihydro-1H-inden-2-yl)-2-((dimethylamino)methyl)-N-(isoquinolin-6-yl)-5-methyl-4,7-dihydropyrazolo[1,5-a]pyrimidine-6-carboxamide | Example 60/ dimethylamine | ¹H NMR (400 MHz, d6-DMSO) δ 10.11 (s, 1H), 9.42 (s, 1H), 9.15 (s, 1H), 8.41-8.37 (m, 2H), 8.21 (s, 1.2H, formic acid), 8.04 (d, J = 8.9 Hz, 1H), 7.79 (dd, J = 2.0, 8.9 Hz, 1H), 7.71 (d, J = 5.9 Hz, 1H), 7.10-6.99 (m, 4H), 5.69 (d, J = 3.3 Hz, 1H), 5.48 (s, 1H), 3.19-3.10 (m, 2H), 2.86-2.66 (m, 4H), 2.46 (t, J = 6.9 Hz, 1H), 2.22 (s, 3H), 2.11 (s, 6H). | Rt = 2.25 min, m/z 479.3 [M + H]⁺ (Method 1) |

Example 111

Step A

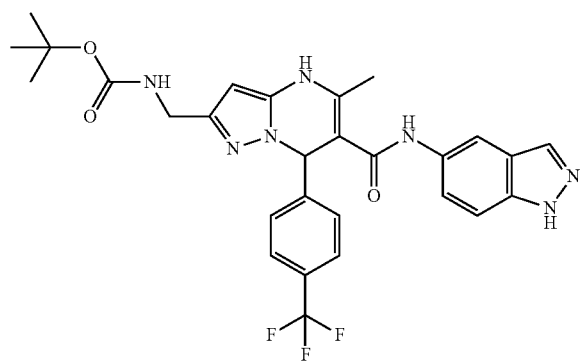 [SMILES: CC1=C(C(=O)Nc2ccc3[nH]ncc3c2)C(c2ccc(C(F)(F)F)cc2)n2nc(CNC(=O)OC(C)(C)C)cc2N1]

tert-Butyl ((6-((1H-indazol-5-yl)carbamoyl)-5-methyl-7-(4-(trifluoromethyl)-phenyl)-4,7-dihydropyrazolo[1,5-a]pyrimidin-2-yl)methyl)carbamate (Intermediate 111A)

Example 34 (92 mg, 0.2 mmol) was dissolved in methanol (1.5 mL) and the solution was cooled in an ice bath under argon. Di-tert-butylcarbonate (87 mg, 0.4 mmol) was added followed by nickel chloride hexahydrate (4.8 mg, 0.02 mmol). Sodium borohydride (53 mg, 1.4 mmol) was added portion wise and then the mixture was stirred whilst being allowed to warm to RT. After stirring overnight, diethylenetriamine (22 µL, 0.2 mmol) was added and stirring was continued for 30 min. A color change from black to lilac was noted. The solvent was evaporated and then the residue was partitioned between ethyl acetate (10 mL) and sat. sodium bicarbonate (10 mL). The organic layer was separated, dried (Na₂SO₄) and evaporated to give a white solid. The crude product was purified by chromatography on a 10 g Si cartridge eluting with 10-100% ethyl acetate in cyclohexane. The Boc-protected amine was obtained as a white solid (66 mg).

LCMS (Method 3): Rt=1.06 min, m/z 568.4 [M+H]⁺

Step B

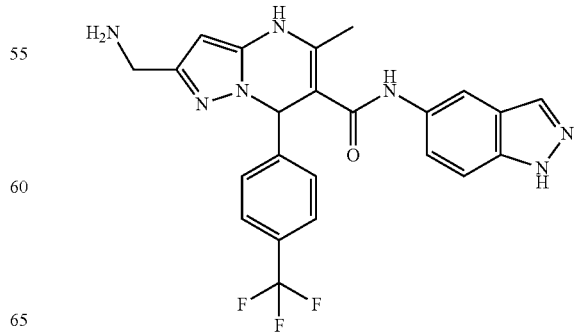

2-(aminomethyl)-N-(1H-indazol-5-yl)-5-methyl-7-(4-(trifluoromethyl)phenyl)-4,7-dihydropyrazolo[1,5-a]pyrimidine-6-carboxamide (Example 1H)

Intermediate 111A (66 mg, 0.12 mmol) was dissolved in 20% TFA in DCM (3 mL). After 1 h the volatiles were evaporated and the residue was dissolved in methanol. The solution was loaded onto a 2 g SCX-2 cartridge which had been conditioned with methanol. After flushing with methanol the product was eluted with 2M methanolic ammonia. Evaporation gave a white solid. The product was purified by chromatography on a 10 g Si cartridge eluting with 0-20% 2M methanolic ammonia in DCM, and obtained as a white solid (36 mg).

LCMS (Method 1): Rt=2.62 min, m/z 468.2 [M+H]$^+$ $^1$H NMR (400 MHz, d6-DMSO) δ 12.94 (s, 1H), 9.64 (s, 1H), 9.56 (s, 1H), 7.99-7.96 (m, 2H), 7.68-7.63 (m, 2H), 7.44-7.31 (m, 4H), 6.54 (s, 1H), 5.65 (s, 1H), 4.20-4.20 (m, 2H), 3.60 (s, 2H), 2.21 (s, 3H).

Example 112

Step A

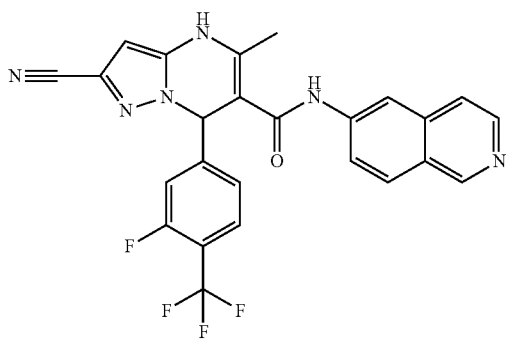 [SMILES: CC1=C(C(=O)Nc2ccc3cnccc3c2)C(c2ccc(C(F)(F)F)c(F)c2)n2nc(C#N)cc2N1]

2-Cyano-7-(3-fluoro-4-(trifluoromethyl)phenyl)-N-(isoquinolin-6-yl)-5-methyl-4,7-dihydropyrazolo[1,5-a]pyrimidine-6-carboxamide (Intermediate 112A)

Intermediate 112A was prepared in a similar manner to Example 1 starting with Intermediate 1A, 5-amino-1H-pyrazole-3-carbonitrile and 3-fluoro-4-(trifluoromethyl)-benzaldehyde.

LCMS (Method 3): Rt=0.95 min, m/z 493.5 [M+H]$^+$

Step B

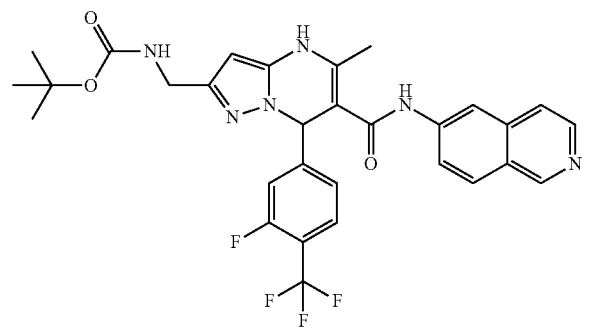 [SMILES: CC1=C(C(=O)Nc2ccc3cnccc3c2)C(c2ccc(C(F)(F)F)c(F)c2)n2nc(CNC(=O)OC(C)(C)C)cc2N1]

tert-Butyl ((7-(3-fluoro-4-(trifluoromethyl)phenyl)-6-(isoquinolin-6-ylcarbamoyl)-5-methyl-4,7-dihydropyrazolo[1,5-a]pyrimidin-2-yl)methyl)carbamate (Intermediate 112B)

Intermediate 112B was prepared from Intermediate 112A in a similar manner to Intermediate 111A.

LCMS (Method 3): Rt=1.05 min, m/z 597.5 [M+H]$^+$

Step C

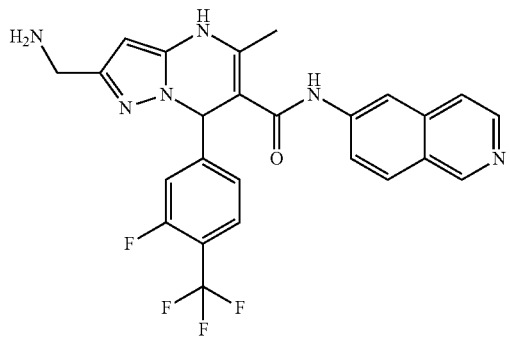 [SMILES: CC1=C(C(=O)Nc2ccc3cnccc3c2)C(c2ccc(C(F)(F)F)c(F)c2)n2nc(CN)cc2N1]

2-(aminomethyl)-7-(3-fluoro-4-(trifluoromethyl)phenyl)-N-(isoquinolin-6-yl)-5-methyl-4,7-dihydropyrazolo[1,5-a]pyrimidine-6-carboxamide (Example 112)

Example 112 was prepared from Intermediate 112B in a manner similar to that used for Example 111.

LCMS (Method 1): Rt=2.32 min, m/z 497.2 [M+H]+

$^1$H NMR (400 MHz, d6-DMSO) δ 10.02 (s, 1H), 9.79 (s, 1H), 9.14 (s, 1H), 8.39 (d, J=5.7 Hz, 1H), 8.27 (d, J=1.7 Hz, 1H), 8.02 (d, J=8.9 Hz, 1H), 7.75-7.66 (m, 3H), 7.22-7.15 (m, 2H), 6.55 (s, 1H), 5.65 (s, 1H), 3.51 (s, 2H), 2.26 (s, 3H), 1.39 (s, 2H).

Example 125

Step A

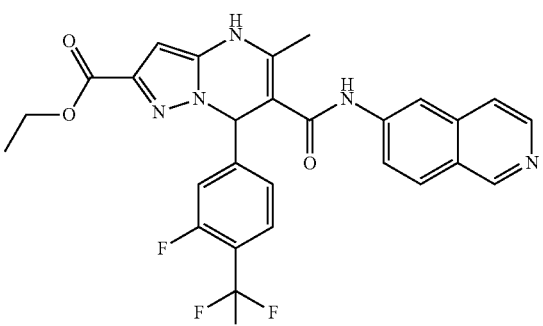

ethyl 7-(3-fluoro-4-(trifluoromethyl)phenyl)-6-(isoquinolin-6-ylcarbamoyl)-5-methyl-4,7-dihydropyrazolo[1,5-a]pyrimidine-2-carboxylate (Intermediate 125A)

Intermediate 125A was prepared according to a method analogous to that used for Example 1 starting from Intermediate 1A, 3-fluoro-4-(trifluoromethyl)benzaldehyde and ethyl-3-amino-1H-pyrazole-5-carboxylate.

LCMS (Method 2): Rt=3.38 min, m/z 540.3 [M+H]$^+$

Step B

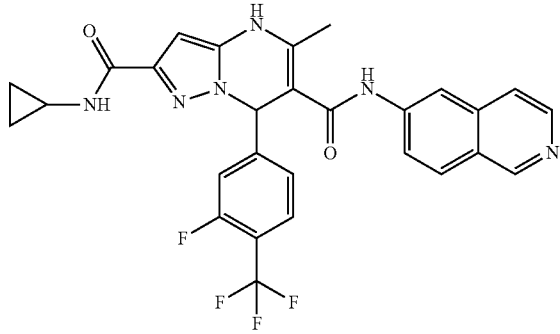 [SMILES: CC1=C(C(=O)Nc2ccc3cnccc3c2)C(c2ccc(C(F)(F)F)c(F)c2)n2nc(C(=O)NC3CC3)cc2N1]

N2-cyclopropyl-7-(3-fluoro-4-(trifluoromethyl)phenyl)-N6-(isoquinolin-6-yl)-5-methyl-4,7-dihydropyrazolo[1,5-a]pyrimidine-2,6-dicarboxamide (Example 125)

Intermediate 125A (200 mg, 0.37 mmol), cyclopropylamine (32 mg, 0.56 mmol) and DABAL adduct (143 mg, 0.56 mmol) in THF (5 mL) were heated in the microwave at 100° C. for 8 mins. The reaction mixture was carefully added in portions to a saturated aqueous solution of potassium sodium tartrate (Rochelle's salt) then DCM. The phases were separated. The organics were evaporated to give a yellow solid which was treated with methanol and diethyl ether. A small amount of undesolved solid was removed by filtration and the solution was allowed to stand at RT. The pure product was obtained as a white solid in two crops (48 and 47 mg).

LCMS (Method 1): Rt=3.12 min, m/z 551.4 [M+H]$^+$ $^1$H NMR (400 MHz, d6-DMSO) δ 10.15 (s, 1H), 9.98 (s, 1H), 9.15 (s, 1H), 8.40 (d, J=5.8 Hz, 1H), 8.29 (d, J=1.6 Hz, 1H), 8.05-8.01 (m, 2H), 7.75 (t, J=7.9 Hz, 1H), 7.72-7.67 (m, 2H), 7.23-7.15 (m, 2H), 6.62 (s, 1H), 6.03 (s, 1H), 2.77-2.70 (m, 1H), 2.26 (s, 3H), 0.64-0.52 (m, 4H).

Examples 126 to 128

The following examples were prepared from the indicated starting materials using a similar procedure to that used for Example 125 by replacing appropriate amine as shown in the table below.

| Ex. | Structure | Amine | 1H NMR | LC-MS |
|---|---|---|---|---|
| 126 | ![structure] 7-(3-fluoro-4-(trifluoromethyl)phenyl)-N6-isoquinolin-6-yl)-N2,N2,5-trimethyl-4,7-dihydropyrazolo[1,5-a]pyrimidine-2,6-dicarboxamide | dimethylamine | $^1$H NMR (400 MHz, d6-DMSO) δ 10.11 (s, 1H), 9.98 (s, 1H), 9.15 (s, 1H), 8.39 (d, J = 5.7 Hz, 1H), 8.28 (d, J = 1.6 Hz, 1H), 8.03 (d, J = 8.9 Hz, 1H), 7.76 (dd, J = 8.0, 8.0 Hz, 1H), 7.72-7.67 (m, 2H), 7.28-7.22 (m, 2H), 6.68 (s, 1H), 5.90 (s, 1H), 3.13 (s, 3H), 2.91 (s, 3H), 2.28 (s, 3H). | Rt = 3.01 min, m/z 539.3 [M + H]$^+$ (Method 1) |
| 127 | ![structure] 7-(3-fluoro-4-(trifluoromethyl)phenyl)-N6-(isoquinolin-6-yl)-5-methyl-N2-(3-oxo-3-(pyrrolidin-1-yl)propyl)-4,7-dihydropyrazolo[1,5-a]pyrimidine-2,6-dicarboxamide | 3-amino-1-(pyrrolidin-1-yl)propan-1-one | $^1$H NMR (400 MHz, d6-DMSO) δ 10.14 (s, 1H), 10.01 (s, 1H), 9.15 (s, 1H), 8.40 (d, J = 5.7 Hz, 1H), 8.28 (d, J = 1.6 Hz, 1H), 8.03 (d, J = 9.0 Hz, 1H), 7.91 (t, J = 6.0 Hz, 1H), 7.79-7.73 (m, 1H), 7.72-7.67 (m, 2H), 7.25-7.17 (m, 2H), 6.66 (s, 1H), 6.02 (s, 1H), 3.41-3.33 (m, 4H), 3.25 (t, J = 6.9 Hz, 2H), 2.44 (t, J = 7.0 Hz, 2H), 2.26 (s, 3H), 1.84-1.70 (m, 4H). | Rt = 3.02 min, m/z 636.2 [M + H]$^+$ (Method 1) |

| Ex. | Structure | Amine | 1H NMR | LC-MS |
|---|---|---|---|---|
| 128 | 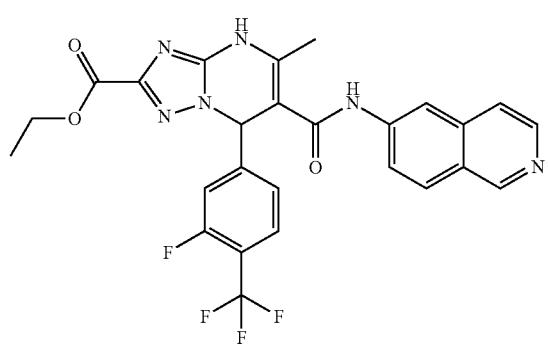<br>N2-(3,3-difluorocyclobutyl)-7-(3-fluoro-4-(trifluoromethyl)phenyl)-N6-(isoquinolin-6-yl)-5-methyl-4,7-dihydropyrazolo[1,5-a]pyrimidine-2,6-dicarboxamide | 3,3-difluorocyclobutan-1-amine | $^1$H NMR (400 MHz, d6-DMSO) δ 10.17 (s, 1H), 9.98 (s, 1H), 9.15 (s, 1H), 8.52 (d, J = 7.3 Hz, 1H), 8.40 (d, J = 5.7 Hz, 1H), 8.28 (d, J = 1.7 Hz, 1H), 8.04 (d, J = 9.0 Hz, 1H), 7.79-7.73 (m, 1H), 7.72-7.67 (m, 2H), 7.23-7.15 (m, 2H), 6.64 (s, 1H), 6.05 (s, 1H), 4.25-4.17 (m, 1H), 2.88-2.72 (m, 4H), 2.26 (s, 3H). | Rt = 3.40 min, m/z 601.3 [M + H]$^+$ (Method 1) |

Example 129

Step A

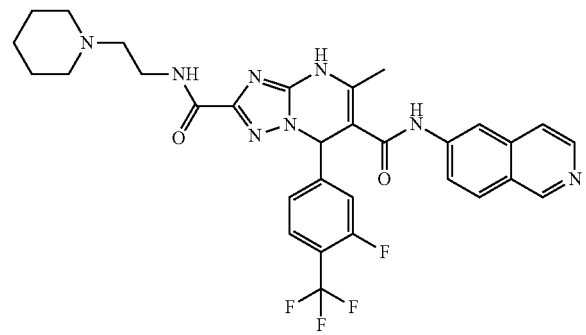 [SMILES: CC1=C(C(=O)Nc2ccc3cnccc3c2)C(c2ccc(C(F)(F)F)c(F)c2)n2nc(C(=O)NCCN3CCCCC3)nc2N1]

ethyl 7-(3-fluoro-4-(trifluoromethyl)phenyl)-6-(isoquinolin-6-ylcarbamoyl)-5-methyl-4,7-dihydro-[1,2,4]triazolo[1,5-a]pyrimidine-2-carboxylate (Intermediate 129A)

Intermediate 129A was prepared according to a method analogous to that used for Example 1 starting from Intermediate 1A, 3-fluoro-4-(trifluoromethyl)benz-aldehyde and ethyl 5-amino-1H-1,2,4-triazole-3-carboxylate.

LCMS (Method 6): Rt=0.93 min, m/z 541.3 [M+H]$^+$

Step B 7-(3-fluoro-4-(trifluoromethyl)phenyl)-N6-(isoquinolin-6-yl)-5-methyl-N2-(2-(piperidin-1-yl)ethyl)-4,7-dihydro-[1,2,4]triazolo[1,5-a]pyrimidine-2,6-dicarboxamide (Example 129)

Example 129 was prepared in a similar way of Example 121 starting from Intermediate 129A and 2-(piperidin-1-yl)ethan-1-amine.

LCMS (Method 1): Rt=2.38 min, m/z 623.4 [M+H]$^+$ $^1$H NMR (400 MHz, d6-DMSO) δ 10.62 (s, 1H), 10.27 (s, 1H), 9.16 (s, 1H), 8.40 (d, J=5.7 Hz, 1H), 8.25 (d, J=1.7 Hz, 1H), 8.09 (s, 1H), 8.04 (d, J=9.0 Hz, 1H), 7.79 (dd, J=7.8, 7.8 Hz, 1H), 7.70 (d, J=5.9 Hz, 1H), 7.66 (dd, J=2.0, 8.9 Hz, 1H), 7.45 (d, J=11.4 Hz, 1H), 7.36 (d, J=8.2 Hz, 1H), 6.71 (s, 1H), 3.41-3.33 (m, 4H), 2.48-2.32 (m, 4H), 2.26 (s, 3H), 1.61-1.45 (m, 4H), 1.45-1.34 (m, 2H).

Example 130

Step A

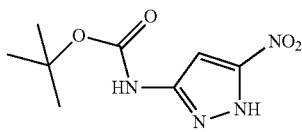 [SMILES: CC(C)(C)OC(=O)Nc1cc([N+](=O)[O-])[nH]n1]

tert-Butyl (5-nitro-1H-pyrazol-3-yl) carbamate (Intermediate 130A)

A stirred suspension of 5-nitro-1H-pyrazole-3-carboxylic acid (1.2 g, 7.64 mmol) in t-butanol (20 ml) was treated with TEA (4.3 mL, 30.60 mmol) then diphenylphosphorylazide (4.9 mL, 22.90 mmol) before heating at 90° C. overnight. The cooled mixture was concentrated in vacuo and the crude product was purified on a 80 g Si cartridge eluting with 5-55% ethyl acetate in iso-hexane. Fractions containing product were combined and evaporated under reduced pressure to give the title compound as a white solid (1.36 g).

LCMS (Method 6): Rt=1.12 min, m/z 227.0 [M−H]$^-$

Step B

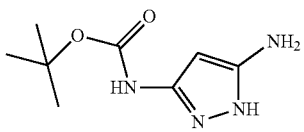

tert-Butyl (5-amino-1H-pyrazol-3-yl) carbamate
(Intermediate 130B)

A stirred mixture of intermediate 130A (4.00 g, 17.50 mmol) and 10% Pd/C (500 mg) in ethanol (denatured, 100 mL) was placed under a balloon atmosphere of hydrogen gas at RT overnight. The mixture was filtered via Celite® and the filtrate evaporated under reduced pressure to give the title compound as a pale yellow foam (3.50 g).

LCMS (Method 6): Rt=0.74 min, m/z 197.0 [M−H]⁻

Step C

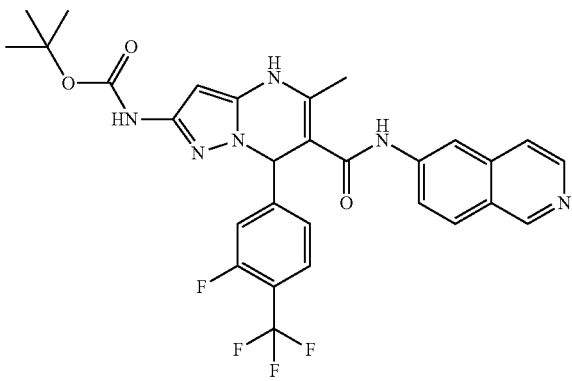 [SMILES: CC1=C(C(=O)Nc2ccc3cnccc3c2)C(c2ccc(C(F)(F)F)c(F)c2)n2nc(NC(=O)OC(C)(C)C)cc2N1]

tert-Butyl (7-(3-fluoro-4-(trifluoromethyl)phenyl)-6-(isoquinolin-6-yl) carbamoyl)-5-methyl-4,7-dihydro-pyrazolo[1,5-a]pyrimidin-2-yl) carbamate (Intermediate 130C)

A stirred mixture of intermediate 130B (260 mg, 1.31 mmol), Intermediate 1A (299 mg, 1.31 mmol) and 3-fluoro-4-(trifluoromethyl)benzaldehyde (252 mg, 1.31 mmol) in 1,2-dimethoxyethane (3 mL) was heated at 80° C. for 2 h. The cooled solution was poured into water (75 mL) to form a solid. This was filtered off, washed with water and dried. The crude product was purified on a 40 g Si cartridge eluting with 0-10% 2M methanolic ammonia in DCM. The appropriate fractions were combined and evaporated under reduced pressure to give the title compound as a pale yellow solid (0.42 g).

LCMS (Method 6): Rt=1.11 min, m/z 583.3 [M+H]⁺

Step D

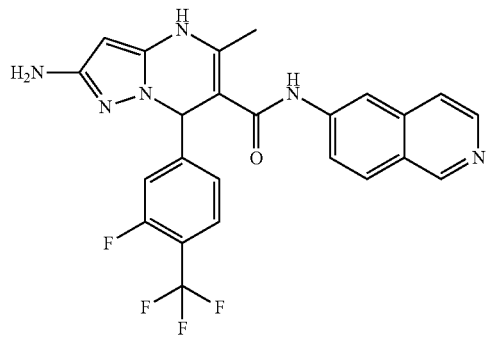 [SMILES: CC1=C(C(=O)Nc2ccc3cnccc3c2)C(c2ccc(C(F)(F)F)c(F)c2)n2nc(N)cc2N1]

2-Amino-7-(3-fluoro-4-(trifluoromethyl)phenyl)-N-(isoquinolin-6-yl)-5-methyl-4,7-dihydropyrazolo[1,5-a]pyrimidine-6-carboxamide (Example 130)

A mixture of intermediate 130C (0.42 g, 0.72 mmol) in DCM (10 mL) was treated with a solution of TFA (3.0 mL, 38.9 mmol) in DCM (10 ml) and the mixture was stirred at RT for 3 h. The reaction mixture was loaded onto a 10 g SCX-2 cartridge which had been conditioned with DCM. The cartridge was flushed with methanol and product was then eluted using 2M methanolic ammonia. The crude product was purified on a 40 g Si cartridge eluting with 0-10% 2M methanolic ammonia in DCM. The fractions containing the product were combined and evaporated under reduced pressure to give the title compound as a pale yellow solid (0.26 g).

LCMS (Method 1): Rt=2.56 min, m/z 483.1 [M+H]⁺

¹H NMR (400 MHz, d6-DMSO) δ 9.98 (s, 1H), 9.59 (s, 1H), 9.13 (s, 1H), 8.38 (d, J=5.7 Hz, 1H), 8.26 (d, J=1.5 Hz, 1H), 8.01 (d, J=8.9 Hz, 1H), 7.73-7.66 (m, 3H), 7.16 (d, J=7.9 Hz, 1H), 7.11 (d, J=11.2 Hz, 1H), 6.29 (s, 1H), 4.93 (s, 1H), 4.67 (s, 2H), 2.23 (s, 3H).

Example 131

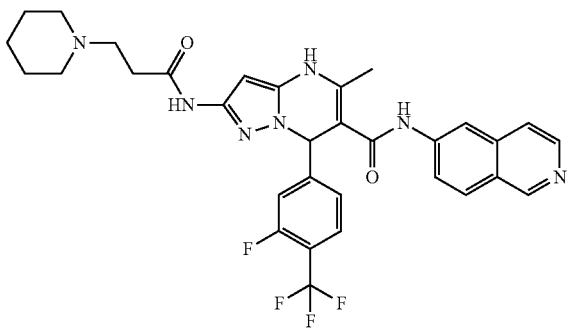 [SMILES: CC1=C(C(=O)Nc2ccc3cnccc3c2)C(c2ccc(C(F)(F)F)c(F)c2)n2nc(NC(=O)CCN3CCCCC3)cc2N1]

7-(3-Fluoro-4-(trifluoromethyl)phenyl)-N-(isoquinolin-6-yl)-5-methyl-2-(3-(piperidin-1-yl)propanamido)-4,7-dihydropyrazolo[1,5-a]pyrimidine-6-carboxamide (Example 131)

A mixture of Example 130 (0.26 g, 0.54 mmol), 3-piperidin-1-yl propionic acid (89 mg, 0.57 mmol) and DIPEA (0.19 mL, 1.08 mmol) in DCM (20 ml) at RT was treated with HATU (225 mg, 0.59 mmol) and stirred for 2 h. The reaction mixture was concentrated in vacuo and the residue partitioned between water and 2-methyl THF. The organic extracts were separated, combined, washed with water and saturated brine, dried (Na$_2$SO$_4$) and evaporated. The crude product was purified by MDAP (basic) to give the title compound as a white solid (115 mg).

LCMS (Method 1): Rt=2.44 min, m/z 622.1 [M+H]$^+$ $^1$H NMR (400 MHz, d6-DMSO) δ 10.49 (s, 1H), 10.04 (s, 1H), 9.85-9.85 (m, 1H), 9.14 (s, 1H), 8.38 (d, J=5.7 Hz, 1H), 8.25 (d, J=1.7 Hz, 1H), 8.01 (d, J=9.0 Hz, 1H), 7.73 (t, J=8.0 Hz, 1H), 7.71-7.66 (m, 2H), 7.25-7.19 (m, 2H), 6.47 (s, 1H), 6.01 (s, 1H), 2.51-2.44 (m, 2H), 2.39-2.30 (m, 6H), 2.27 (s, 3H), 1.48-1.41 (m, 4I), 1.35 (d, J=5.3 Hz, 2H).

Example 132 and 133

The following examples were prepared from Example 130 using a similar procedure to that used in Example 131 by substituting the acid with that specified in the table.

Example 134

Step A

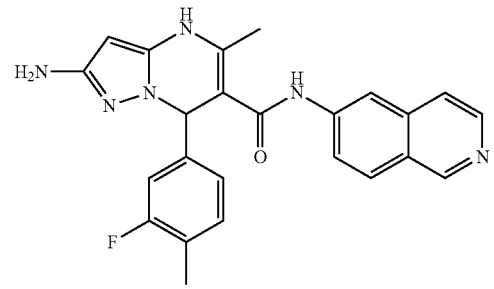 [SMILES: CC1=C(C(=O)Nc2ccc3cnccc3c2)C(c2ccc(C)c(F)c2)n2nc(N)cc2N1]

2-Amino-7-(3-fluoro-4-methylphenyl)-N-(isoquinolin-6-yl)-5-methyl-4,7-dihydropyrazolo[1,5-a]pyrimidine-6-carboxamide (Intermediate 134A)

Intermediate 134A was prepared using a similar method to step C of Example 130 by replacing 3-fluoro-4-(trifluoromethyl)benzaldehyde with 3-fluoro-4-methylbenzaldehyde.

LCMS (Method 6): Rt=1.12 min, m/z 428.8 [M+H]$^+$

| Ex. | Structure | Starting materials | 1H NMR | LC-MS |
|---|---|---|---|---|
| 132 | 7-(3-fluoro-4-(trifluoromethyl)phenyl)-N-(isoquinolin-6-yl)-5-methyl-2-(2-(pyrrolidin-1-yl)acetamido)-4,7-dihydropyrazolo[1,5-a]pyrimidine-6-carboxamide | 2-(pyrrolidin-1-yl)acetic acid | $^1$H NMR (400 MHz, d6-DMSO) δ 10.06 (s, 1H), 9.94 (s, 1H), 9.85 (br s, 1H), 9.14 (s, 1H), 8.39 (d, J = 5.8 Hz, 1H), 8.25 (d, J = 1.9 Hz, 1H), 8.02 (d, J = 8.9 Hz, 1H), 7.73 (t, J = 7.8 Hz, 1H), 7.71-7.66 (m, 2H), 7.25-7.19 (m, 2H), 6.46 (s, 1H), 6.03 (s, 1H), 3.22-3.11 (m, 2H), 2.56-2.51 (m, 4H), 2.26 (s, 3H), 1.72-1.66 (m, 4H). | Rt = 2.37 min, m/z 594.2 [M + H]$^+$ (Method 1) |
| 133 | 7-(3-fluoro-4-(trifluoromethyl)phenyl)-N-(isoquinolin-6-yl)-5-methyl-2-(2-((1-methylpiperidin-4-yl)oxy)acetamido)-4,7-dihydropyrazolo[1,5-a]pyrimidine-6-carboxamide | 2-((1-methylpiperidin-4-yl)oxy)acetic acid | $^1$H NMR (400 MHz, d6-DMSO) δ 10.06 (s, 1H), 9.95 (s, 1H), 9.86 (s, 1H), 9.14 (s, 1H), 8.39 (d, J = 5.7 Hz, 1H), 8.25 (d, J = 1.7 Hz, 1H), 8.02 (d, J = 9.0 Hz, 1H), 7.76-7.67 (m, 3H), 7.24-7.19 (m, 2H), 6.48 (s, 1H), 6.03 (s, 1H), 3.98 (s, 2H), 3.38-3.34 (m, 1H), 2.62-2.52 (m, 2H), 2.27 (s, 3H), 2.11 (s, 3H), 1.97 (t, J = 10.0 Hz, 2H), 1.85-1.78 (m, 2H), 1.50-1.41 (m, 2H). | Rt = 2.35 min, m/z 638.3 [M + H]$^+$ (Method 1) |

Step B

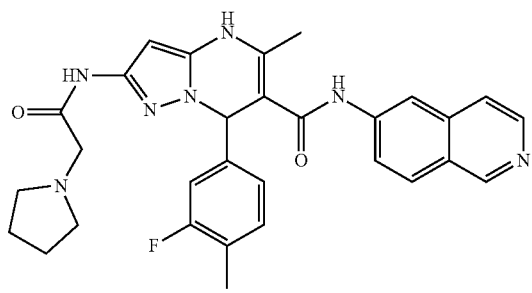 [SMILES: CC1=C(C(=O)Nc2ccc3cnccc3c2)C(c2ccc(C)c(F)c2)n2nc(NC(=O)CN3CCCC3)cc2N1]

7-(3-fluoro-4-methylphenyl)-N-(isoquinolin-6-yl)-5-methyl-2-(2-(pyrrolidin-1-yl)acetamido)-4,7-dihydropyrazolo[1,5-a]pyrimidine-6-carboxamide (Example 134)

The following example was prepared from intermediate 134A and 2-(pyrrolidin-1-yl)acetic acid using a similar procedure to that used in Example 131.

LCMS (Method 1): Rt=2.10 min, m/z 540.4 [M+H]+

$^1$H NMR (400 MHz, d6-DMSO) δ 10.00 (s, 1H), 9.90 (s, 1H), 9.67 (s, 1H), 9.13 (s, 1H), 8.38 (d, J=5.7 Hz, 1H), 8.27 (d, J=1.7 Hz, 1H), 8.01 (d, J=9.0 Hz, 1H), 7.71-7.66 (m, 2H), 7.17 (dd, J=8.0, 8.0 Hz, 1H), 6.93 (dd, J=1.6, 7.8 Hz, 1H), 6.86 (dd, J=1.5, 10.5 Hz, 1H), 6.38 (s, 1H), 5.98 (s, 1H), 3.16 (d, J=3.2 Hz, 2H), 2.56-2.52 (m, 4H), 2.24 (s, 3H), 2.13 (d, J=1.1 Hz, 3H), 1.69 (dd, J=6.5, 6.5 Hz, 4H).

Example 135

Step A

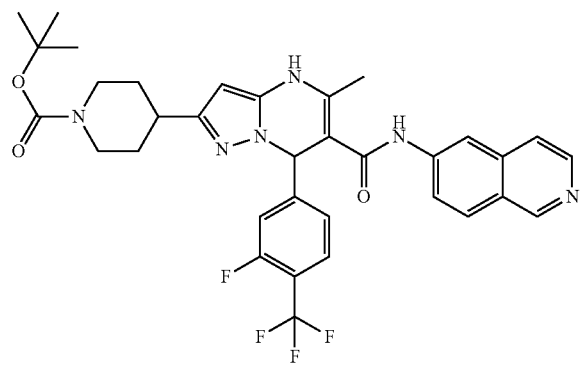 [SMILES: CC1=C(C(=O)Nc2ccc3cnccc3c2)C(c2ccc(C(F)(F)F)c(F)c2)n2nc(C3CCN(C(=O)OC(C)(C)C)CC3)cc2N1]

tert-Butyl 4-(7-(3-fluoro-4-(trifluoromethyl)phenyl)-6-(isoquinolin-6-ylcarbamoyl)-5-methyl-4,7-dihydropyrazolo[1,5-a]pyrimidin-2-yl)piperidine-1-carboxylate (Intermediate 135A)

Intermediate 135A was prepared in a similar manner to Example 1 using intermediate 1A, tert-butyl 4-(5-amino-1H-pyrazol-3-yl)piperidine-1-carboxylate, and 3-fluoro-4-(trifluoro-methyl)benzaldehyde as starting materials.

LCMS (Method 6): Rt=1.12 min, m/z 651.5 [M+H]+

Step B

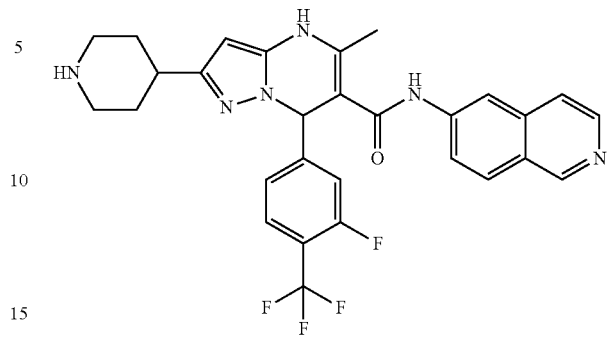

7-(3-Fluoro-4-(trifluoromethyl)phenyl)-N-(isoquinolin-6-yl)-5-methyl-2-(piperidin-4-yl)-4,7-dihydropyrazolo[1,5-a]pyrimidine-6-carboxamide (Intermediate 135B)

Intermediate 135A (1.46 g, 2.24 mmol) was dissolved in a mixture of DCM (16 mL) and TFA (4 mL) and the reaction was stirred at RT for 2 h. The mixture was loaded onto a 20 g SCX-2 cartridge which was eluted with DCM, methanol and then 2M methanolic ammonia. Relevant fractions were evaporated to dryness to give a yellow gum (1.16 g).

LCMS (Method 6): Rt=0.7 min, m/z 551.4 [M+H]+

Step C

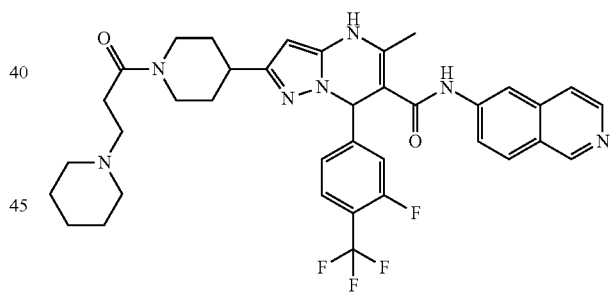

7-(3-fluoro-4-(trifluoromethyl)phenyl)-N-(isoquinolin-6-yl)-5-methyl-2-(1-(3-(piperidin-1-yl)propanoyl)piperidin-4-yl)-4,7-dihydropyrazolo[1,5-a]pyrimidine-6-carboxamide (Example 135)

Intermediate 135B (0.25 g, 0.454 mmol), 3-(piperidin-1-yl)propanoic acid (79 mg, 0.5 mmol), DIPEA (0.16 mL, 0.91 mmol) and HATU (207 mg, 0.55 mmol) were dissolved in DMF (10 mL) and the solution was stirred at RT for 16 h. DMF was evaporated and the mixture was partitioned between ethyl acetate (3×30 mL) and water (25 mL). The organic phase was separated and washed with brine. Dried over (Na$_2$SO$_4$) and filtered. Evaporation gave a crude prod uct which was purified by MDAP (basic) to afford an off-white solid (147 mg).

LCMS (Method 1): Rt=2.59 min, m/z 690.4 [M+H]+

$^1$H NMR (400 MHz, d6-DMSO) δ 10.06 (s, 1H), 9.78 (s, 1H), 9.14 (s, 1H), 8.39 (d, J=5.7 Hz, 1H), 8.28 (d, J=1.6 Hz, 1H), 8.02 (d, J=8.9 Hz, 1H), 7.75-7.67 (m, 3H), 7.17-7.09 (m, 2H), 6.61 (s, 1H), 5.53 (s, 1H), 4.35 (d, J=10.7 Hz, 1H), 3.88 (d, J=13.1 Hz, 1H), 3.05 (t, J=12.0 Hz, 1H), 2.71 (tdd, J=3.7, 11.2, 11.2 Hz, 1H), 2.62 (t, J=12.4 Hz, 1H), 2.48-2.43 (m, 4H), 2.29 (s, 4H), 2.25 (s, 3H), 1.84-1.76 (m, 2H), 1.46 (m, 5H), 1.40-1.27 (m, 3H).

Example 136

Step A

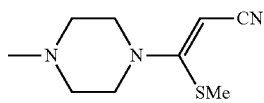

(Z)-3-(4-Methylpiperazin-1-yl)-3-(methylthio)acrylonitrile (Intermediate 136A)

A solution of 2-cyano-3,3-bis(methylthio)acrylic acid (4.5 g, 23.8 mmol) in methanol (30 mL) at RT was treated with 1-methylpiperazine (4.48 mL, 40.4 mmol) and TEA (3.32 mL, 23.8 mmol). The reaction was stirred at RT overnight. The reaction mixture was concentrated and the crude material was purified by chromatography on an 80 g Si cartridge eluting with 0-10% methanol in DCM. The title compound was obtained as a yellow liquid (1.3 g).

LCMS (Method 6): Rt=0.21 min, m/z 198.2 [M+H]+

Step B

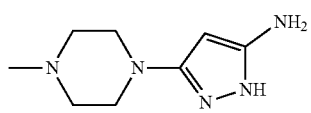

3-(4-Methylpiperazin-1-yl)-1H-pyrazol-5-amine (Intermediate 136B)

Intermediate 136A (1.30 g, 6.59 mmol) was dissolved in IMS (30 mL) and treated with 1M hydrazine in THF (22 mL, 22 mmol). The reaction mixture was stirred at 85° C. overnight. The ethanol was evaporated and a further amount of 1M hydrazine in THF (30 mL, 30 mmol) was added. Heating was continued at 85° C. for a further 6 h. The reaction mixture was allowed to cool and evaporated in vacuo. The crude product was purified on a 25 g Si cartridge eluting with 0-10% methanol in DCM then 10% 2M methanolic ammonia in DCM. The product was obtained as a gum (0.68 g).

LCMS (Method 6): Rt=0.15 min, m/z 182.3 [M+H]+

Step C

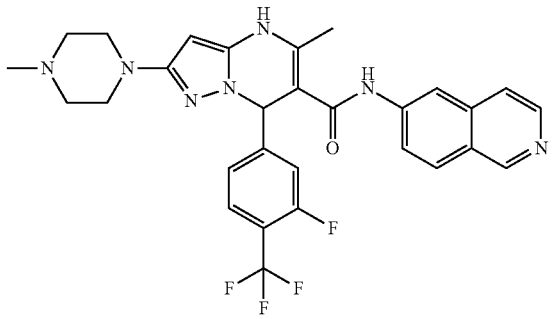 [SMILES: CC1=C(C(=O)Nc2ccc3cnccc3c2)C(c2ccc(C(F)(F)F)c(F)c2)n2nc(N3CCN(C)CC3)cc2N1]

7-(3-Fluoro-4-(trifluoromethyl)phenyl)-N-(isoquinolin-6-yl)-5-methyl-2-(4-methylpiperazin-1-yl)-4,7-dihydropyrazolo[1,5-a]pyrimidine-6-carboxamide (Example 136)

Example 136 was prepared from intermediates 1A and 136B, and 3-fluoro-4-(trifluoromethyl)benzaldehyde using a method analogous to that used for Example 1.

LCMS (Method 1): Rt=2.38 min, m/z 566.1 [M+H]+

$^1$H NMR (400 MHz, d6-DMSO) δ 10.01 (s, 1H), 9.72 (s, 1H), 9.14 (s, 1H), 8.39 (d, J=5.8 Hz, 1H), 8.30-8.27 (m, 1H), 8.02 (d, J=9.0 Hz, 1H), 7.74-7.67 (m, 3H), 7.16-7.07 (m, 2H), 6.43 (s, 1H), 5.20 (s, 1H), 3.03-2.99 (m, 4H), 2.33 (t, J=4.7 Hz, 4H), 2.23 (s, 3H), 2.17 (s, 3H).

Example 137A and 137B

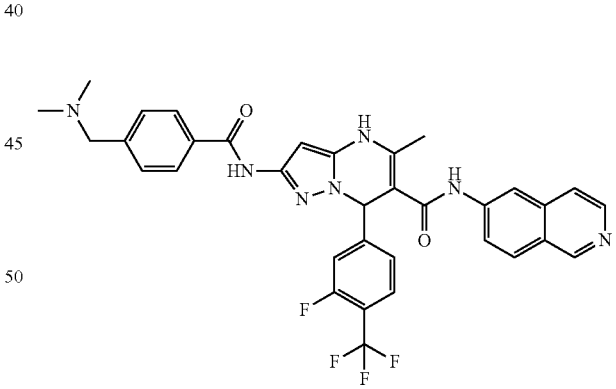

2-(4-((Dimethylamino)methyl)benzamido)-7-(3-fluoro-4-(trifluoromethyl)-phenyl)-N-(isoquinolin-6-yl)-5-methyl-4,7-dihydropyrazolo[1,5-a]pyrimidine-6-carboxamide Examples 137A and 137B were prepared in a similar manner to Example 131 by using Example 130 and 4-((dimethylamino)methyl)benzoic acid as starting materials. The racemic product was separated immediately by SFC according to the table.

| Separation | Analysis | 1st eluting | 2nd eluting |
|---|---|---|---|
| MD SFC<br>YMC Amylose-SA<br>40/60 IPA (0.1% DEA)/CO$_2$<br>100 mL/min<br>40° C. 240 nM; column dimensions 250 × 20 mm, 5 µm | MD SFC<br>YMC Amylose-C<br>40/60 IPA (0.1% DEA)/CO$_2$<br>0.95 mL/min<br>40° C. 240 nM; column dimensions 150 × 2.0 mm, 5 µm | Example 137A<br>Rt = 2.0 min | Example 137B<br>Rt = 2.7 min |

Example 137A

LCMS (Method 1): Rt=2.50 min, m/z 644.4 [M+H]$^+$
$^1$H NMR (400 MHz, d6-DMSO) δ 10.76 (s, 1H), 10.09 (s, 1H), 9.91 (s, 1H), 9.14 (s, 1H), 8.39 (d, J=5.7 Hz, 1H), 8.26 (d, J=1.7 Hz, 1H), 8.02 (d, J=9.0 Hz, 1H), 7.93 (d, J=8.3 Hz, 2H), 7.77-7.67 (m, 3H), 7.36 (d, J=8.4 Hz, 2H), 7.27-7.22 (m, 2H), 6.53 (s, 1H), 6.21 (s, 1H), 3.42 (s, 2H), 2.28 (s, 3H), 2.14 (s, 6H).

Example 137B

LCMS (Method 1): Rt=2.49 min, m/z 644.4 [M+H]$^+$
$^1$H NMR (400 MHz, d6-DMSO) δ 10.76 (s, 1H), 10.09 (s, 1H), 9.92 (s, 1H), 9.14 (s, 1H), 8.39 (d, J=5.7 Hz, 1H), 8.26 (d, J=1.7 Hz, 1H), 8.02 (d, J=8.9 Hz, 1H), 7.93 (d, J=8.3 Hz, 2H), 7.78-7.67 (m, 3H), 7.36 (d, J=8.4 Hz, 2H), 7.27-7.22 (m, 2H), 6.53 (s, 1H), 6.21 (s, 1H), 3.42 (s, 2H), 2.28 (s, 1H), 2.14 (s, 6H).

Examples 138A and 138B 7-(3-Fluoro-4-(trifluoromethyl)phenyl)-N-(isoquinolin-6-yl)-5-methyl-2-((3-(piperidin-1-yl)propanamido)methyl)-4,7-dihydropyrazolo[1,5-a]pyrimidine-6-carboxamide A mixture of Example 112 (0.45 g, 0.91 mmol), 3-piperidin-1-yl propionic acid (157 mg, 0.99 mmol) and DIPEA (0.32 mL, 1.81 mmol) in DMF (10 ml) at RT was treated with HATU (414 mg, 1.09 mmol) and stirred for 16 h. The reaction mixture was concentrated in vacuo and purified on a 40 g Si cartridge eluting with 0-50% methanol in DCM to give a racemic product (0.383 g). The racemate was immediately separated by SFC using the conditions given in the table.

| Separation | Analysis | 1st eluting | 2nd eluting |
|---|---|---|---|
| MD SFC<br>YMC Cellulose-C<br>25/75 MeOH (0.1% DEA)/CO$_2$<br>100 mL/min<br>40° C. 240 nM; column dimensions 250 × 20 mm, 5 µm | MD SFC<br>YMC Cellulose-C<br>25/75 MeOH (0.1% DEA)/CO$_2$<br>0.95 mL/min<br>40° C. 240 nM; column dimensions 150 × 2.0 mm, 5 µm | Example 138A<br>Rt = 2.2 min | Example 138B<br>Rt = 2.9 min |

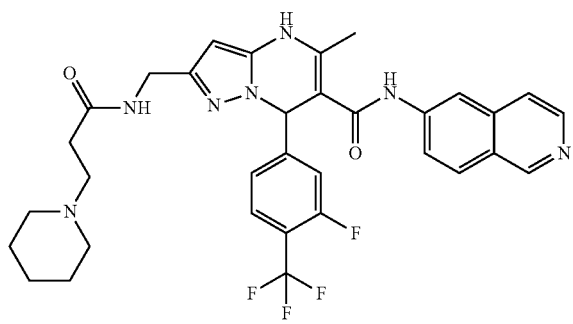 [SMILES: CC1=C(C(=O)Nc2ccc3cnccc3c2)C(c2ccc(C(F)(F)F)c(F)c2)n2nc(CNC(=O)CCN3CCCCC3)cc2N1]

Example 138A

LCMS (Method 1): Rt=2.39 min, m/z 636.4 [M+H]$^+$
$^1$H NMR (400 MHz, d6-DMSO) δ 10.04 (s, 1H), 9.78 (s, 1H), 9.14 (s, 1H), 8.42-8.37 (m, 2H), 8.26 (d, J=1.7 Hz, 1H), 8.02 (d, J=9.0 Hz, 1H), 7.76-7.67 (m, 3H), 7.23-7.14 (m, 2H), 6.56 (s, 1H), 5.55 (s, 1H), 4.16-4.01 (m, 2H), 2.60-2.52 (m, 2H), 2.38-2.29 (m, 3H), 2.28-2.25 (m, 6H), 1.48-1.43 (m, 4H), 1.40-1.29 (m, 2H).

Example 138B

LCMS (Method 1): Rt=2.39 min, m/z 636.4 [M+H]$^+$
$^1$H NMR (400 MHz, d6-DMSO) δ 10.04 (s, 1H), 9.79 (s, 1H), 9.14 (s, 1H), 8.41-8.36 (m, 2H), 8.27 (d, J=1.7 Hz, 1H), 8.02 (d, J=8.9 Hz, 1H), 7.76-7.68 (m, 3H), 7.23-7.14 (m, 2H), 6.56 (s, 1H), 5.55 (s, 1H), 4.16-4.00 (m, 2H), 2.46 (t, J=7.1 Hz, 2H), 2.29-2.22 (m, 9H), 1.48-1.38 (m, 4H), 1.38-1.29 (m, 2H).

The following examples were resolved from corresponding racemate example, using the conditions given below, to give the pure enantiomers.

| Racemate | Separation | Analysis | 1st eluting | 2nd eluting |
| --- | --- | --- | --- | --- |
| Example 4 | MD SFC<br>YMC Cellulose-C<br>30/70 MeOH/$CO_2$<br>15 mL/min<br>40° C.<br>240 nM; column dimensions<br>250 × 10 mm id 5 μm | MD SFC<br>YMC Cellulose-C<br>30/70 MeOH/$CO_2$<br>5 mL/min<br>40° C.<br>240 nM; column dimensions<br>250 × 4.6 mm id 5 μm | Example 4A<br>Rt = 2.4 min | Example 4B<br>Rt = 3.7 min |
| Example 7 | MD HPLC<br>YMC Cellulose-C<br>50/50 IPA/heptane<br>20 mL/min<br>40° C.<br>210 nM; 250 × 20 mm id 5 μm | MD HPLC<br>YMC Cellulose-C<br>40/60 IPA/heptane<br>1 mL/min<br>RT<br>210 nM; column dimensions<br>250 × 4.6 mm id 5 μm | Example 7A<br>Rt = 4.3 min | Example 7B<br>Rt = 10.8 min |
| Example 23 | MD SFC<br>Lux Cellulose-4<br>40/60 MeOH/CO2<br>100 mL/min<br>40° C.<br>240 nM; column dimensions<br>250 × 20 mm id 5 μm | MD SFC<br>Lux Cellulose-4<br>55/45 MeOH/$CO_2$<br>100 mL/min<br>40° C.<br>240 nM; column dimensions<br>250 × 4.6 mm id 5 μm | Example 23A<br>Rt = 1.9 min | Example 23B<br>Rt = 2.7 min |
| Example 24 | MD SFC<br>Lux Cellulose-4<br>40/60 MeOH/CO2<br>100 mL/min<br>40° C.<br>245 nM; column dimensions<br>250 × 20 mm id 5 μm | MD SFC<br>Lux Cellulose-4<br>40/60 MeOH/$CO_2$<br>5 mL/min<br>40° C.<br>245 nM; column dimensions<br>250 × 4.6 mm id 5 μm | Example 24A<br>Rt = 2.4 min | Example 24B<br>Rt = 3.6 min |
| Example 25 | MD SFC<br>Lux Cellulose-4<br>30/70 MeOH/CO2<br>100 mL/min<br>40° C.<br>240 nM; column dimensions<br>250 × 20 mm id 5 μm | MD SFC<br>Lux Cellulose-4<br>30/70 MeOH/$CO_2$<br>5 mL/min<br>40° C.<br>240 nM; column dimensions<br>250 × 4.6 mm id 5 μm | Example 25A<br>Rt = 2.0 min | Example 25B<br>Rt = 3.0 min |
| Example 26 | MD SFC<br>Lux Cellulose-4<br>30/70 MeOH/$CO_2$<br>100 mL/min<br>40° C.<br>240 nM; column dimensions<br>250 × 20 mm id 5 μm | MD SFC<br>Lux Cellulose-4<br>30/70 MeOH/$CO_2$<br>5 mL/min<br>40° C.<br>240 nM; column dimensions<br>250 × 4.6 mm id 5 μm | Example 26A<br>Rt = 2.1 min | Example 26B<br>Rt = 3.0 min |
| Example 27 | MD SFC<br>Lux Cellulose-4<br>30/70 MeOH/$CO_2$<br>100 mL/min<br>40° C.<br>240 nM; column dimensions<br>250 × 20 mm id 5 μm | MD SFC<br>Lux Cellulose-4<br>30/70 MeOH/$CO_2$<br>5 mL/min<br>40° C.<br>240 nM; column dimensions<br>250 × 4.6 mm id 5 μm | Example 27A<br>Rt = 2.3 min | Example 27B<br>Rt = 3.5 min |
| Example 32 | MD SFC<br>YMC Cellulose-C<br>30/70 MeOH/$CO_2$<br>15 mL/min<br>40° C.<br>245 nM; column dimensions<br>250 × 10 mm id 5 μm | MD SFC<br>YMC Cellulose-C<br>30/70 MeOH/$CO_2$<br>5 mL/min<br>40° C.<br>245 nM; column dimensions<br>250 × 4.6 mm id 5 μm | Example 32A<br>Rt = 1.4 min | Example 32B<br>Rt = 3.5 min |
| Example 40 | MD SFC<br>Lux Cellulose-4<br>30/70 MeOH/$CO_2$<br>15 mL/min<br>40° C.<br>240 nM; column dimensions<br>250 × 10 mm id 5 μm | MD SFC<br>Lux Cellulose-4<br>30/70 MeOH/$CO_2$<br>5 mL/min<br>40° C.<br>240 nM; column dimensions<br>250 × 4.6 mm id 5 μm | Example 40A<br>Rt = 2.1 min | Example 40B<br>Rt = 3.7 min |
| Example 43 | MD SFC<br>Lux Cellulose-4<br>30/70 MeOH(0.1% DEA)/$CO_2$<br>100 mL/min<br>40° C.<br>245 nM; column dimensions<br>250 × 20 mm id 5 μm | MD SFC<br>Lux Cellulose-4<br>30/70 MeOH(0.1% DEA)/$CO_2$<br>5 mL/min<br>40° C.<br>245 nM; column dimensions<br>250 × 4.6 mm id 5 μm | Example 43A<br>Rt = 2.1 | Example 43B<br>Rt = 3.7 |
| Example 60 | MD SFC<br>Lux Cellulose-4<br>40/60 MeOH/$CO_2$<br>100 mL/min<br>40° C.<br>240 nM; column dimensions<br>250 × 10 mm id 5 μm | MD SFC<br>Lux Cellulose-4<br>40/60 MeOH/$CO_2$<br>5 mL/min<br>40° C.<br>240 nM; column dimensions<br>250 × 4.6 mm id 5 μm | Example 60A<br>Rt = 2.2 min | Example 60B<br>Rt = 4.2 min |
| Example 61 | MD SFC<br>Lux Cellulose-4 | MD SFC<br>Lux Cellulose-4 | Example 61A<br>Rt = 2.3 min | Example 61B<br>Rt = 4.0 min |

-continued

| Racemate | Separation | Analysis | 1st eluting | 2nd eluting |
| --- | --- | --- | --- | --- |
| | 40/60 MeOH/CO$_2$<br>100 mL/min<br>40° C.<br>240 nM; column dimensions<br>250 × 20 mm id 5 μm | 40/60 MeOH/CO$_2$<br>5 mL/min<br>40° C.<br>240 nM; column dimensions<br>250 × 4.6 mm id 5 μm | | |
| Example 62 | MD SFC<br>Lux Cellulose-4<br>40/60 MeOH/CO2<br>100 mL/min<br>40° C.<br>240 nM; column dimensions<br>250 × 10 mm id 5 μm | MD SFC<br>Lux Cellulose-4<br>40/60 MeOH/CO2<br>5 mL/min<br>40° C.<br>240 nM; column dimensions<br>250 × 4.6 mm id 5 μm | Example 62A<br>Rt = 2.0 min | Example 62B<br>Rt = 3.4 min |
| Example 65 | MD SFC<br>YMC Amylose-C<br>30/70 IPA/CO$_2$<br>15 mL/min<br>40° C.<br>240 nM; column dimensions<br>250 × 10 mm id 5 μm | MD SFC<br>YMC Amylose-C<br>30/70 IPA/CO$_2$<br>5 mL/min<br>40° C.<br>240 nM; column dimensions<br>250 × 4.6 mm id 5 μm | Example 65A<br>Rt = 2.4 min | Example 65B<br>Rt = 4.6 min |
| Example 69 | MD SFC<br>YMC Amylose-C<br>35/65 IPA/CO$_2$<br>90 mL/min<br>40° C.<br>245 nM; column dimensions<br>250 × 20 mm id 5 μm | MD SFC<br>YMC Amylose-C<br>35/65 IPA/CO$_2$<br>5 mL/min<br>40° C.<br>245 nM; column dimensions<br>250 × 4.6 mm id 5 μm | Example 69A<br>Rt = 2.4 min | Example 69B<br>Rt = 4.6 min |
| Example 71 | MD SFC<br>YMC Cellulose-SC<br>30/70 MeOH/CO$_2$<br>100 mL/min<br>40° C.<br>240 nM; column dimensions<br>250 × 20 mm id 5 μm | MD SFC<br>YMC Cellulose-SC<br>30/70 MeOH/CO$_2$<br>5 mL/min<br>40° C.<br>240 nM; column dimensions<br>250 × 4.6 mm id 5 μm | Example 71A<br>Rt = 2.4 min | Example 71B<br>Rt = 3.2 min |
| Example 77 | MD SFC<br>YMC Cellulose-C<br>55/45 MeOH (0.1% DEA)/CO2<br>70 mL/min<br>40° C. 240 nM; column<br>dimensions 250 × 20 mm, 5<br>μm | MD SFC<br>YMC Cellulose-C<br>55/45 IPA (0.1% DEA)/CO2<br>0.95 mL/min<br>40° C. 240 nM; column<br>dimensions 150 × 2.0 mm, 5<br>μm | Example 77A<br>Rt = 0.9 min | Example 77B<br>Rt = 1.3 min |
| Example 78 | MD SFC<br>YMC Cellulose-SC<br>50/50 IPA(0.1% DEA)/CO$_2$<br>15 mL/min<br>40° C.<br>240 nM; column dimensions<br>250 × 10 mm id 5 μm | MCSFC<br>YMC Cellulose-C 35/65 IPA<br>(0.1% DEA)/CO2,<br>0.95 ml/min<br>40° C.<br>240 nM; column dimensions<br>150 × 2.0 mm id 5 μm | Example 78A<br>Rt = 1.3 min | Example 78B<br>Rt = 2.0 min |
| Example 94 | MD SFC<br>YMC Amylose-C<br>25/75 IPA/CO2<br>100 mL/min<br>40° C.<br>240 nM; column dimensions<br>250 × 20 mm id 5 μm | MD SFC<br>YMC Amylose-C<br>25/75 IPA/CO2<br>5 mL/min<br>40° C.<br>240 nM; column dimensions<br>250 × 4.6 mm id 5 μm | Example 94 A<br>Rt = 2.2 min | Example 94 B<br>Rt = 3.7 min |
| Example 96 | MD SFC<br>YMC Amylose-C<br>30/70 IPA/CO$_2$<br>15 mL/min<br>40° C.<br>240 nM; column dimensions<br>250 × 10 mm id 5 μm | MD SFC<br>YMC Amylose-C<br>30/70 IPA/CO$_2$<br>5 mL/min<br>40° C.<br>240 nM; column dimensions<br>250 × 4.6 mm id 5 μm | Example 96A<br>Rt = 1.8 min | Example 96B<br>Rt = 3.5 min |
| Example 97 | MD SFC<br>YMC Amylose-C<br>30/70 IPA(0.1% DEA)/CO$_2$<br>15 mL/min<br>40° C.<br>240 nM; column dimensions<br>250 × 10 mm id 5 μm | MD SFC<br>YMC Amylose-C<br>30/70 IPA(0.1% DEA)/CO$_2$<br>5 mL/min<br>40° C.<br>240 nM; column dimensions<br>250 × 4.6 mm id 5 μm | Example 97A<br>Rt = 3.0 min | Example 97B<br>Rt = 4.7 min |
| Example 104<br>Separation 1 | MD SFC<br>YMC Cellulose-SC<br>35/65 MeOH(0.1% DEA)/CO$_2$<br>15 mL/min<br>40° C.<br>240 nM; column dimensions<br>250 × 10 mm id 5 μm | MD SFC<br>YMC Cellulose-SC<br>35/65 MeOH(0.1% DEA)/CO$_2$<br>5 mL/min<br>40° C.<br>240 nM; column dimensions<br>250 × 4.6 mm id 5 μm | Example 104A<br>Rt = 3.6 min | Rt = 4.5 mins, (further<br>purification required) |
| Example 104<br>Separation 2 | MD SFC<br>YMC Cellulose-SC | MD SFC<br>YMC Cellulose-SC | | Example 104B<br>Rt = 3.3 min |

-continued

| Racemate | Separation | Analysis | 1st eluting | 2nd eluting |
|---|---|---|---|---|
| | 35/65 MeOH(0.5% DEA)/CO$_2$<br>15 mL/min<br>40° C.<br>240 nM; column dimensions<br>250 × 10 mm id 5 μm | 35/65 MeOH(0.5% DEA)/CO$_2$<br>5 mL/min<br>40° C.<br>240 nM; column dimensions<br>250 × 4.6 mm id 5 μm | | |
| Example 110 | MD SFC<br>YMC Amylose-C<br>30/70 IPA(0.1% DEA)/CO$_2$<br>15 mL/min<br>40° C.<br>240 nM; column dimensions<br>250 × 10 mm id 5 μm | MD SFC<br>YMC Cellulose-SC<br>35/65 MeOH(0.1% DEA)/CO$_2$<br>5 mL/min<br>40° C.<br>240 nM; column dimensions<br>150 × 2.0 mm id 5 μm | Example 110A<br>Rt = 2.6 min | Example 110B<br>Rt-3.8 min |
| Example 121 | MD SFC<br>YMC Amylose-C<br>20/80 MeOH (0.1%<br>DEA)/CO2<br>100 mL/min<br>40° C. 240 nM; column<br>dimensions 250 × 10 mm, 5<br>μm | MD SFC<br>YMC Amylose-C<br>20/80 MeOH (0.1%<br>DEA)/CO2<br>0.95 mL/min<br>40° C. 240 nM; column<br>dimensions 150 × 2.0 mm, 5<br>μm | Example 121A<br>Rt = 3.4 min | Example 121B<br>Rt = 4.8 min<br>Not isolated |
| Example 122 | MD SFC<br>YMC Amylose-C<br>20/80 EtOH (0.1% DEA)/CO2<br>15 mL/min<br>40° C. 240 nM; column<br>dimensions 250 × 10 mm, 5<br>μm | MD SFC<br>YMC Amylose-C<br>20/80 EtOH (0.1% DEA)/CO2<br>0.95 mL/min<br>40° C. 240 nM; column<br>dimensions 150 × 2.0 mm, 5<br>μm | Example 122A<br>Rt = 2.4 min | Example 122B<br>Rt = 3.4 min |
| Example 124 | MD SFC<br>YMC Amylose-C<br>30/70 IPA (0.1% DEA)/CO2<br>15 mL/min<br>40° C. 230 nM; column<br>dimensions 250 × 10 mm, 5<br>μm | MD SFC<br>YMC Amylose-C<br>30/70 IPA (0.1% DEA)/CO2<br>0.95 mL/min<br>40° C. 240 nM; column<br>dimensions 150 × 2.0 mm, 5<br>μm | Example 124A<br>Rt = min | Example 124B<br>Rt = min |
| Example 129 | MD SFC<br>YMC Cellulose-C<br>40/60 IPA (0.1% DEA)/CO2<br>90 mL/min<br>40° C. 245 nM; column<br>dimensions 250 × 20 mm, 5<br>μm | MD SFC<br>YMC Cellulose-C<br>40/60 IPA (0.1% DEA)/CO2<br>0.95 mL/min<br>40° C. 245 nM; column<br>dimensions 150 × 2.0 mm, 5<br>μm | Example 129A<br>Rt = 1.5 min | Example 129B<br>Rt = 2.3 min |
| Example 130 | MD SFC<br>YMC Amylose-C<br>35/65 EtOH/ACN(0.1%<br>DEA)/CO2<br>15 mL/min<br>40° C. 240 nM; column<br>dimensions 250 × 10 mm, 5<br>μm | MD SFC<br>YMC Amylose-C<br>35/65 EtOH (0.1% DEA)/CO2<br>5 mL/min<br>40° C. 240 nM; column<br>dimensions 250 × 4.6 mm, 5<br>μm | Example 130A<br>Rt = 2.2 min | Example 130B<br>Rt = 4.1 min |
| Example 131 | MD SFC<br>YMC Cellulose-SC<br>50/50 (80/20/0.1%<br>MeOH/DCM/DEA)/CO2<br>70 mL/min<br>40° C. 245 nM; column<br>dimensions 250 × 20 mm, 5<br>μm | MD SFC<br>YMC Cellulose-SC<br>50/50 MeOH (0.1%<br>DEA)/CO2<br>0.95 mL/min<br>40° C. 245 nM; column<br>dimensions 150 × 2.0 mm, 5<br>μm | Example 131A<br>Rt = 1.3 min | Example 131B<br>Rt = 2.1 min |
| Example 132 | MD SFC<br>YMC Cellulose-SC<br>40/60 MeOH (0.1%<br>DEA)/CO2<br>15 mL/min<br>40° C. 240 nM; column<br>dimensions 250 × 10 mm, 5<br>μm | MD SFC<br>YMC Cellulose-SC<br>40/60 MeOH (0.1%<br>DEA)/CO2<br>0.95 mL/min<br>40° C. 240 nM; column<br>dimensions 150 × 2.0 mm, 5<br>μm | Example 132A<br>Rt = 1.3 min | Example 132B<br>Rt = 2.6 min |
| Example 135 | MD SFC<br>YMC Amylose-C<br>40/60 IPA (0.1% DEA)/CO2<br>15 mL/min<br>40° C. 240 nM; column<br>dimensions 250 × 10 mm, 5<br>μm | MD SFC<br>YMC Amylose-C<br>40/60 IPA (0.1% DEA)/CO2<br>0.95 mL/min<br>40° C. 240 nM; column<br>dimensions 150 × 2.0 mm, 5<br>μm | Example 135A<br>Rt = 1.2 min | Example 135B<br>Rt = 3.2 min |

PHARMACOLOGICAL ACTIVITY OF THE COMPOUNDS OF THE INVENTION

In Vitro Inhibitory Activity Assay Description

The effectiveness of compounds of the present invention to inhibit Rho kinase activity can be determined in a 10 µl assay containing 40 mM Tris pH7.5, 20 mM $MgCl_2$ 0.1 mg/ml BSA, 50 µM DTT and 2.5 µM peptide substrate (Myelin Basic Protein) using an ADP-Glo kit (Promega). Compounds were dissolved in DMSO such that the final concentration of DMSO was 1% in the assay. All reactions/incubations are performed at 25° C. Compound (2 ul) and either Rho kinase 1 or 2 (4 µl) were mixed and incubated for 30 mins. Reactions were initiated by addition of ATP (4 µl) such that the final concentration of ATP in the assay was 10 µM. After a 1 hour incubation 10 µl of ADP-Glo Reagent was added and after a further 45 minute incubation 20 ul of Kinase Detection Buffer was added and the mixture incubated for a further 30 minutes. The luminescent signal was measured on a luminometer. Controls consisted of assay wells that did not contain compound with background determined using assay wells with no enzyme added. Compounds were tested in dose-response format and the inhibition of kinase activity was calculated at each concentration of compound. To determine the $IC_{50}$ (concentration of compound required to inhibit 50% of the enzyme activity) data were fit to a plot of % inhibition vs $Log_{10}$ compound concentration using a sigmoidal fit with a variable slope and fixing the maximum to 100% and the minimum to 0%. To determine the Ki values the Cheng-Prusoff equation was utilized ($Ki=IC_{50}/(1+[S]/Km)$).

Compounds according to the invention showed Ki values lower than 5 µM and for most of the compounds of the invention Ki is even lower that 500 nM.

The results for individual compounds are provided below in Table 1 and are expressed as range of activity.

TABLE 1

| Example No | ROCK1 | ROCK2 |
| --- | --- | --- |
| 1 | +++ | +++ |
| 2 | +++ | +++ |
| 3 | +++ | +++ |
| 5 | +++ | +++ |
| 6 | ++ | ++ |
| 8 | +++ | +++ |
| 9 | +++ | +++ |
| 10 | +++ | +++ |
| 11 | ++ | ++ |
| 12 | + | + |
| 13 | ++ | ++ |
| 14 | ++ | +++ |
| 15 | + | + |
| 16 | +++ | +++ |
| 17 | + | + |
| 18 | +++ | +++ |
| 19 | ++ | ++ |
| 20 | +++ | +++ |
| 21 | ++ | ++ |
| 22 | +++ | +++ |
| 28 | +++ | +++ |
| 29 | +++ | +++ |
| 30 | +++ | +++ |
| 31 | +++ | +++ |
| 33 | + | + |
| 34 | +++ | +++ |
| 35 | +++ | +++ |
| 36 | +++ | +++ |
| 37 | +++ | +++ |
| 38 | +++ | +++ |
| 39 | +++ | +++ |
| 41 | + | ++ |
| 42 | +++ | +++ |
| 44 | ++ | ++ |
| 45 | + | + |
| 46 | +++ | +++ |
| 47 | +++ | +++ |
| 48 | ++ | ++ |
| 49 | ++ | +++ |
| 50 | ++ | +++ |
| 51 | +++ | +++ |
| 52 | +++ | +++ |
| 53 | +++ | +++ |
| 54 | ++ | +++ |
| 55 | +++ | +++ |
| 56 | +++ | +++ |
| 57 | +++ | +++ |
| 58 | +++ | +++ |
| 59 | +++ | +++ |
| 63 | +++ | +++ |
| 64 | +++ | +++ |
| 66 | +++ | +++ |
| 67 | +++ | +++ |
| 68 | +++ | +++ |
| 70 | +++ | +++ |
| 72A | +++ | +++ |
| 72B | +++ | +++ |
| 72C | ++ | ++ |
| 72D | ++ | ++ |
| 73 | +++ | +++ |
| 74 | +++ | +++ |
| 75 | +++ | +++ |
| 76 | +++ | +++ |
| 77 | +++ | +++ |
| 79 | +++ | +++ |
| 80 | +++ | +++ |
| 81 | +++ | +++ |
| 82 | +++ | +++ |
| 83 | +++ | +++ |
| 84 | +++ | +++ |
| 85 | +++ | +++ |
| 86 | +++ | +++ |
| 87 | +++ | +++ |
| 88 | +++ | +++ |
| 89 | +++ | +++ |
| 90 | +++ | +++ |
| 91 | + | + |
| 92 | + | + |
| 93 | +++ | +++ |
| 95 | +++ | +++ |
| 98 | +++ | +++ |
| 99 | +++ | +++ |
| 100 | +++ | +++ |
| 101 | +++ | +++ |
| 102 | +++ | +++ |
| 103 | +++ | +++ |
| 105 | +++ | +++ |
| 106 | +++ | +++ |
| 107 | +++ | +++ |
| 108 | +++ | +++ |
| 109 | +++ | +++ |
| 111 | +++ | +++ |
| 112 | +++ | +++ |
| 113 | +++ | +++ |
| 114 | +++ | +++ |
| 115 | +++ | +++ |
| 116 | +++ | +++ |
| 117 | +++ | +++ |
| 118 | +++ | +++ |
| 119 | +++ | +++ |
| 120 | +++ | +++ |
| 121 | +++ | +++ |
| 122 | +++ | +++ |
| 123 | +++ | +++ |
| 124 | +++ | +++ |
| 125 | +++ | +++ |
| 126 | +++ | +++ |
| 127 | +++ | +++ |
| 128 | +++ | +++ |
| 129 | +++ | +++ |

TABLE 1-continued

| Example No | ROCK1 | ROCK2 |
|---|---|---|
| 130 | +++ | +++ |
| 131 | +++ | +++ |
| 132 | +++ | +++ |
| 133 | +++ | +++ |
| 134 | +++ | +++ |
| 135 | +++ | +++ |
| 136 | +++ | +++ |
| 137A | + | + |
| 137B | +++ | +++ |
| 138A | +++ | +++ |
| 138B | + | + |
| 4A | + | + |
| 4B | +++ | +++ |
| 7A | +++ | +++ |
| 7B | +++ | +++ |
| 23A | +++ | +++ |
| 23B | ++ | ++ |
| 24A | +++ | +++ |
| 24B | ++ | ++ |
| 25A | +++ | +++ |
| 25B | ++ | ++ |
| 26A | +++ | +++ |
| 26B | ++ | ++ |
| 27A | +++ | +++ |
| 27B | ++ | ++ |
| 32A | + | + |
| 32B | +++ | +++ |
| 40A | +++ | +++ |
| 40B | ++ | ++ |
| 43A | + | ++ |
| 43B | +++ | +++ |
| 60A | +++ | +++ |
| 60B | ++ | ++ |
| 61A | +++ | +++ |
| 61B | ++ | ++ |
| 62A | +++ | +++ |
| 62B | ++ | ++ |
| 65A | +++ | +++ |
| 65B | +++ | +++ |
| 69A | ++ | ++ |
| 69B | +++ | +++ |
| 71A | +++ | +++ |
| 71B | + | + |
| 77A | + | + |
| 77B | +++ | +++ |
| 78A | ++ | +++ |
| 78B | +++ | +++ |
| 94A | ++ | ++ |
| 94B | +++ | +++ |
| 96A | ++ | ++ |
| 96B | +++ | +++ |
| 97A | ++ | ++ |
| 97B | +++ | +++ |
| 104A | +++ | +++ |
| 104B | ++ | +++ |
| 110A | ++ | ++ |
| 110B | +++ | +++ |
| 121B | +++ | +++ |
| 122A | + | + |
| 122B | +++ | +++ |
| 124A | + | + |
| 124B | +++ | +++ |
| 129A | +++ | +++ |
| 129B | +++ | +++ |
| 130A | + | + |
| 130B | +++ | +++ |
| 131A | +++ | +++ |
| 131B | +++ | +++ |
| 132A | +++ | +++ |
| 132B | + | + |
| 135A | + | + |
| 135B | +++ | +++ | wherein the compounds are classified in term of potency with respect to their inhibitory activity on rock1 rock 2 isoforms according to the following classification criterion:

+++: Ki<50 nM
++: Ki in the range 50-500 nM
+: Ki>500 nM

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

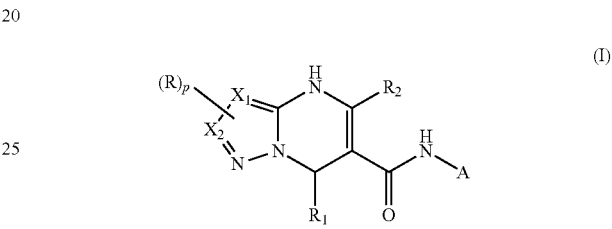

wherein
X$_1$ and X$_2$ are in each occurrence independently a carbon atom or a nitrogen atom;
each R, when present, is:
—H
—CN,
halogen,
—NR$_5$R$_6$,
(C$_1$-C$_6$) alkyl,
(C$_1$-C$_6$) haloalkyl,
(C$_1$-C$_6$) hydroxyalkyl,
(C$_1$-C$_6$) aminoalkyl,
(C$_3$-C$_{10}$) cycloalkyl,
(C$_2$-C$_6$) alkenyl,
(C$_5$-C$_7$) cycloalkenyl,
(C$_2$-C$_6$) alkynyl,
(C$_2$-C$_6$) hydroxyalkynyl,
hydroxycarbonyl,
—OR$_7$
(C$_1$-C$_6$) alkylthio,
(C$_1$-C$_6$) alkoxy-(C$_1$-C$_6$) alkyl,
(C$_1$-C$_6$) alkoxycarbonyl,
(C$_1$-C$_6$) aminoalkylcarbonyl,
carbamoyl,
(C$_3$-C$_6$) cycloalkyl-(C$_1$-C$_6$) alkyl,
(C$_3$-C$_6$) heterocycloalkyl-(C$_1$-C$_6$) alkyl,
aryl,
heteroaryl, or
(C$_3$-C$_6$) heterocycloalkyl;
wherein any of said (C$_3$-C$_6$) cycloalkyl, aryl, heteroaryl, and (C$_3$-C$_6$) heterocycloalkyl is optionally and independently substituted with one or more groups selected from the group consisting of
halogen,
—OH,
(C$_1$-C$_6$) alkyl,
(C$_1$-C$_6$) haloalkyl,
(C$_1$-C$_6$) hydroxyalkyl, ($C_1$-$C_6$) aminoalkyl,
($C_3$-$C_{10}$) cycloalkyl,
($C_2$-$C_6$) alkenyl,
($C_5$-$C_7$) cycloalkenyl,
($C_2$-$C_6$) alkynyl,
($C_2$-$C_6$) hydroxyalkynyl,
($C_1$-$C_6$) alkoxyl, and
($C_1$-$C_6$) aminoalkylcarbonyl;

$R_5$ and $R_6$ are in each occurrence independently selected from the group consisting of
H,
($C_1$-$C_6$) alkyl,
($C_1$-$C_6$) haloalkyl,
($C_1$-$C_6$) hydroxyalkyl,
($C_1$-$C_6$) aminoalkyl,
($C_1$-$C_6$) alkoxyl,
($C_1$-$C_6$) alkoxy-($C_1$-$C_6$) alkyl,
($C_3$-$C_6$) heterocycloalkyl-($C_1$-$C_6$) alkyl,
($C_3$-$C_6$) heterocycloalkyloxyl alkanoyl,
aryl,
heteroaryl, and
($C_3$-$C_6$) heterocycloalkyl;

wherein any of said aryl, heteroaryl, and ($C_3$-$C_6$) heterocycloalkyl is optionally and independently substituted with one or more groups selected from the group consisting of
halogen,
—OH, and
($C_1$-$C_6$) alkyl; or $R_5$ and $R_6$ taken together with the nitrogen atom they are linked to form a 4 to 6 membered heterocyclic radical, wherein at least one further ring carbon atom in the said heterocyclic radical may be replaced by at least one heteroatom selected from the group consisting of N, S, or O; and said heterocyclic radical can be further optionally substituted by a group selected from the group consisting of
H,
—CN,
halogen,
-oxo,
—NR$_5$R$_6$
($C_1$-$C_6$) alkyl,
($C_1$-$C_6$) haloalkyl,
($C_1$-$C_6$) hydroxyalkyl,
($C_1$-$C_6$) aminoalkyl,
($C_1$-$C_6$) alkoxyl,
($C_1$-$C_6$) alkoxy-($C_1$-$C_6$) alkyl, and
alkanoyl;

$R_7$ is in each occurrence independently selected from the group the group consisting of
H,
($C_1$-$C_6$) alkyl,
($C_1$-$C_6$) haloalkyl,
($C_1$-$C_6$) hydroxyalkyl,
($C_1$-$C_6$) aminoalkyl,
($C_1$-$C_6$) alkoxy-($C_1$-$C_6$) alkyl,
($C_3$-$C_6$) heterocycloalkyl-($C_1$-$C_6$) alkyl,
aryl,
heteroaryl, and
($C_3$-$C_6$) heterocycloalkyl;

wherein any of said aryl, heteroaryl, and ($C_3$-$C_6$) heterocycloalkyl is optionally and independently substituted with one or more groups selected from the group consisting of
halogen,
—OH, and
($C_1$-$C_6$) alkyl;

p is zero or 1 or 2;

$R_1$ is selected from the group consisting of
($C_1$-$C_6$) alkyl,
($C_1$-$C_6$) haloalkyl,
($C_1$-$C_6$) hydroxyalkyl,
($C_1$-$C_6$) aminoalkyl,
($C_3$-$C_{10}$) cycloalkyl,
($C_2$-$C_6$) alkenyl,
($C_5$-$C_7$) cycloalkenyl,
($C_2$-$C_6$) alkynyl,
($C_2$-$C_6$) hydroxyalkynyl,
($C_3$-$C_6$) cycloalkyl-($C_1$-$C_6$) alkyl,
($C_3$-$C_6$) heterocycloalkyl-($C_1$-$C_6$) alkyl,
aryl ($C_1$-$C_6$) alkyl,
aryl,
heteroaryl, and
($C_3$-$C_6$) heterocycloalkyl;

each of which cycloalkyl, cycloalkenyl, aryl, heteroaryl, and ($C_3$-$C_6$) heterocycloalkyl is optionally and independently substituted with one or more groups selected from the group consisting of
nitro,
halogen,
—NR$_5$R$_6$,
—CN,
—OH,
—S(O)$_2$—($C_1$-$C_6$) alkyl,
($C_1$-$C_6$) alkyl,
($C_1$-$C_6$) haloalkyl,
($C_1$-$C_6$) alkoxyl,
($C_1$-$C_6$) haloalkoxyl,
($C_1$-$C_6$) aminoalkoxyl,
($C_1$-$C_6$) hydroxyalkoxyl,
($C_3$-$C_6$) heterocycloalkyloxyl,
($C_3$-$C_6$) heterocycloalkyl ($C_1$-$C_6$) alkoxyl,
carbamoyl,
alkanoyl,
aryloxyl,
aryl ($C_1$-$C_6$) alkoxyl,
aryloxy-($C_1$-$C_6$) alkyl
($C_1$-$C_6$) alkoxycarbonyl,
($C_1$-$C_6$) alkoxy-($C_1$-$C_6$) alkyl,
($C_1$-$C_6$) alkoxycarbonyl-amino-,
($C_1$-$C_6$) hydroxyalkyl,
($C_2$-$C_6$) alkenyl,
($C_2$-$C_6$) alkynyl,
($C_2$-$C_6$) hydroxyalkynyl,
aryl,
heteroaryl, and
($C_3$-$C_6$) heterocycloalkyl;

$R_2$ is
($C_1$-$C_6$) alkyl,
($C_1$-$C_6$) haloalkyl,
($C_1$-$C_6$) hydroxyalkyl,
($C_1$-$C_6$) aminoalkyl,
($C_3$-$C_{10}$) cycloalkyl,
($C_1$-$C_6$) alkoxyl, or
($C_1$-$C_6$) alkoxy-($C_1$-$C_6$) alkyl;

A is 1H-indazol-5yl, 6-fluoro-1H-indazole-5yl, isoquinoline-6yl, thieno[2,3-c]pyridine-2yl, thieno[3,2-c]pyridine-2yl, [1,2,4]triazolo[4,3-a]pyridine-7yl, or 1,6-naphthyridin-2-yl each of which is optionally substituted by one or more groups selected from the group consisting of
halogen,
—OH, ($C_1$-$C_6$) alkyl,
($C_1$-$C_6$) alkoxyl,
($C_2$-$C_6$) alkenyl,
($C_2$-$C_6$) alkynyl,
aryl,
heteroaryl, and
($C_3$-$C_6$) heterocycloalkyl;
each of which aryl, heteroaryl, and ($C_3$-$C_6$) heterocycloalkyl being further optionally substituted,
or a pharmaceutically acceptable salt thereof.

2. A compound or salt according to claim 1, wherein each of $X_1$ and $X_2$ is a carbon atom, represented by the formula Ia:

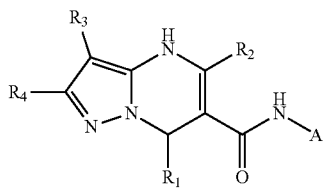

Ia wherein $R_3$ and $R_4$ are in each occurrence independently selected from the group consisting of
—H
—CN,
halogen,
—$NR_5R_6$,
($C_3$-$C_6$) alkyl,
($C_1$-$C_6$) haloalkyl,
($C_1$-$C_6$) hydroxyalkyl,
($C_1$-$C_6$) aminoalkyl,
($C_3$-$C_{10}$) cycloalkyl,
($C_2$-$C_6$) alkenyl,
($C_5$-$C_7$) cycloalkenyl,
($C_2$-$C_6$) alkynyl,
($C_2$-$C_6$) hydroxyalkynyl,
hydroxycarbonyl,
—$OR_7$,
($C_1$-$C_6$) alkylthio,
($C_1$-$C_6$) alkoxy-($C_1$-$C_6$) alkyl,
($C_1$-$C_6$) alkoxycarbonyl,
($C_1$-$C_6$) aminoalkylcarbonyl,
carbamoyl,
aryl,
heteroaryl, and
($C_3$-$C_6$) heterocycloalkyl;
wherein any of said aryl, heteroaryl, and ($C_3$-$C_6$) heterocycloalkyl optionally and independently substituted with one or more groups selected from the group consisting of
halogen,
—OH,
($C_1$-$C_6$) alkyl,
($C_1$-$C_6$) haloalkyl,
($C_1$-$C_6$) hydroxyalkyl,
($C_1$-$C_6$) aminoalkyl,
($C_3$-$C_{10}$) cycloalkyl,
($C_2$-$C_6$) alkenyl,
($C_5$-$C_7$) cycloalkenyl,
($C_2$-$C_6$) alkynyl,
($C_2$-$C_6$) hydroxyalkynyl,
($C_1$-$C_6$) alkoxyl, and
($C_1$-$C_6$) aminoalkylcarbonyl.

3. A compound or salt according to claim 1, wherein p is 0 and each of $X_1$ and $X_2$ is nitrogen, represented by the formula Ib:

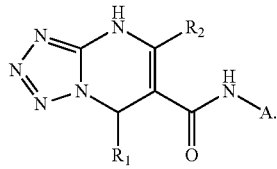

Ib

4. A compound or salt according to claim 2, wherein:
A is isoquinoline-6yl, 4-methylisoquinolin-6-yl, or 1H-indazole-5yl
$R_3$ is in each occurrence independently H or selected from the group consisting of
—CN,
halogen,
ethoxycarbonyl,
aminocarbonyl, N-(2-(dimethylamino)ethyl)aminocarbonyl, and
4-methylpiperazine-1-carbonyl; and
$R_4$ is in each occurrence independently selected from the group consisting of
—H
amino,
4-methylpiperazin-1-yl,
3-(piperidin-1-yl)propanamido,
2-(pyrrolidin-1-yl)acetamido,
((1-methylpiperidin-4-yl)oxy)acetamido;
—CN,
halogen,
methyl,
ethyl,
propyl,
isopropyl,
trifluoromethyl,
hydroxymethyl,
aminomethyl,
dimethylaminomethyl,
2-(N,N-dimethylamino)ethyl,
N-methyl-N-(2 methoxyethyl)-2-aminoethyl,
2-(N-methyl-N-((1-methylpiperidin-4-yl)methyl)amino)ethyl,
3-methoxyazetidinyl-ethyl,
3-(N,N-dimethyl amino methyl)azetidinyl-ethyl,
3-(methoxymethyl)azetidinyl-ethyl,
N-pyrrolidinyl-ethyl,
N-piperidinyl-ethyl,
4-methoxypiperidinyl-ethyl,
4-(pyrrolidin-1-yl)piperidinyl-ethyl,
4-methylpiperazin-N-yl-ethyl,
(1-acetylpiperazin-4-yl)-ethyl,
morpholin-N-yl-ethyl,
(thiomorpholine 1,1-dioxide)4yl-ethyl,
(8-methyl-2,8-diazaspiro[4.5]decan-2-yl)ethyl,
(3-(piperidin-1-yl)propanamido)methyl,
hydroxycarbonyl,
methylthio,
methoxymethyl,
ethoxycarbonyl,
aminocarbonyl,
N,N dimethyl-aminocarbonyl,
(3,3-difluorocyclobutyl)-aminocarbonyl, piperazine-1-carbonyl,
morpholine-N-carbonyl,
morpholine-N-carbonyl,
N-(2-(dimethylamino)ethyl)aminocarbonyl,
N-(2-(dimethylamino)ethyl)-N-methylaminocarbonyl,
N-(3-(dimethylamino)propyl)-N-methylaminocarbonyl,
4-methylpiperazine-1-carbonyl,
4-(dimethylamino)piperidin-1-carbonyl,
N-(2-(4-methylpiperazin-1-yl)ethyl)aminocarbonyl,
(2 morpholino-ethyl) aminocarbonyl,
N-methyl-N-(2 morpholino-ethyl) aminocarbonyl,
N-(2-(piperidin-1-yl)ethyl) aminocarbonyl,
N-methyl-N-(2-(piperidin-1-yl)ethyl)aminocarbonyl,
N-(1-methylpiperidin-4-yl-methyl) aminocarbonyl,
N-methyl-N-(1-methylpiperidin-4-yl)aminocarbonyl,
N-methyl-N-(1-methylpiperidin-4-yl)aminocarbonyl,
5-methyloctahydropyrrolo[3,4-c]pyrrole-2 carbonyl,
N-cyclopropyl-aminocarbonyl,
(piperidin-1-yl)ethyl aminocarbonyl,
p-methoxy-phenyl,
m-methoxy-phenyl,
o-methoxy-phenyl,
oxetan-3-yl, and
(2-(piperidin-1-yl)ethylcarbonyl)piperidin-4-yl;
$R_1$ is selected from the group consisting of
isopentanyl
cyclohexanyl,
4-(trifluoromethyl)cyclohexyl,
adamantan-yl
phenylethyl,
p-methylphenyl,
4-(tert-butyl)phenyl,
4-(hydroxy)phenyl,
p-fluorophenyl,
p-chlorophenyl,
p-bromophenyl,
4-chloro-2-fluoro-phenyl,
4-chloro-3-fluoro-phenyl,
3-fluoro-4-hydroxyphenyl,
4-(trifluoromethyl)phenyl,
3-fluoro-4-(trifluoromethyl)phenyl,
2,3-difluoro-4-(trifluoromethyl)phenyl,
4-chloro-3-(trifluoromethyl)phenyl,
3-methoxy-phenyl,
2,3-dihydro-1H-inden-2yl,
3-phenoxyphenyl,
2,3-difluoro-4-methylphenyl,
3-fluoro-4-methylphenyl,
4-(difluoromethyl)-3-fluorophenyl,
piperidinyl,
2,3-dihydrobenzo[b][1,4]dioxine-2yl,
benzo[d]thiazol-2yl,
2-chloro-5-pyridinyl,
1H-indole-6yl,
2-phenylthiazol-5yl,
2-phenyloxazole-5yl,
benzo[b]thiophene-6yl,
1-methyl-1H-benzo[d]imidazole-6yl,
1-methylpiperidin-4-yl, and
morpholin-N-yl;
$R_2$ is methyl, cyclopropyl, or methoxymethyl.

5. A compound according to claim 3, wherein:
A is 1H-indazole-5yl;
$R_1$ is p-fluorophenyl, p-chlorophenyl, 4-(trifluoromethyl) phenyl, or 3-fluoro-4-(trifluoromethyl)phenyl; and
$R_2$ is methyl.

6. A compound or salt according to claim 1, which is a compound selected from the group consisting of:
ethyl 6-(isoquinolin-6-ylcarbamoyl)-5-methyl-7-(4-(trifluoromethyl)phenyl)-4,7-dihydropyrazolo[1,5-a]pyrimidine-2-carboxylate;
ethyl 6-((1H-indazol-5-yl)carbamoyl)-5-methyl-7-(4-(trifluoromethyl)phenyl)-4,7-dihydropyrazolo[1,5-a]pyrimidine-2-carboxylate;
ethyl 6-((1H-indazol-5-yl)carbamoyl)-5-methyl-7-(p-tolyl)-4,7-dihydropyrazolo[1,5-a]pyrimidine-2-carboxylate;
ethyl 6-((1H-indazol-5-yl)carbamoyl)-7-(4-fluorophenyl)-5-methyl-4,7-dihydropyrazolo[1,5-a]pyrimidine-2-carboxylate;
ethyl 6-((1H-indazol-5-yl)carbamoyl)-7-(6-chloropyridin-3-yl)-5-methyl-4,7-dihydropyrazolo[1,5-a]pyrimidine-2-carboxylate;
ethyl 6-((1H-indazol-5-yl)carbamoyl)-7-(3-methoxyphenyl)-5-methyl-4,7-dihydropyrazolo[1,5-a]pyrimidine-2-carboxylate;
ethyl 6-((1H-indazol-5-yl)carbamoyl)-7-(4-chloro-2-fluorophenyl)-5-methyl-4,7-dihydropyrazolo[1,5-a]pyrimidine-2-carboxylate;
ethyl 7-(benzo[d]thiazol-2-yl)-6-(isoquinolin-6-ylcarbamoyl)-5-methyl-4,7-dihydropyrazolo[1,5-a]pyrimidine-2-carboxylate;
ethyl 7-(4-hydroxyphenyl)-6-(isoquinolin-6-ylcarbamoyl)-5-methyl-4,7-dihydropyrazolo[1,5-a]pyrimidine-2-carboxylate;
ethyl 7-(3-fluoro-4-hydroxyphenyl)-6-(isoquinolin-6-ylcarbamoyl)-5-methyl-4,7-dihydropyrazolo[1,5-a]pyrimidine-2-carboxylate;
ethyl 6-((1H-indazol-5-yl)carbamoyl)-5-methyl-7-(tetrahydro-2H-pyran-4-yl)-4,7-dihydropyrazolo[1,5-a]pyrimidine-2-carboxylate;
ethyl 6-((1H-indazol-5-yl)carbamoyl)-5-methyl-7-(1-methylpiperidin-4-yl)-4,7-dihydropyrazolo[1,5-a]pyrimidine-2-carboxylate;
ethyl 6-((1H-indazol-5-yl)carbamoyl)-7-isobutyl-5-methyl-4,7-dihydropyrazolo[1,5-a]pyrimidine-2-carboxylate;
ethyl 6-((1H-indazol-5-yl)carbamoyl)-7-cyclohexyl-5-methyl-4,7-dihydropyrazolo[1,5-a]pyrimidine-2-carboxylate;
ethyl 6-([1,2,4]triazolo[4,3-a]pyridin-7-ylcarbamoyl)-7-(3-fluoro-4-(trifluoromethyl)phenyl)-5-methyl-4,7-dihydropyrazolo[1,5-a]pyrimidine-2-carboxylate;
ethyl 6-((1H-indazol-5-yl)carbamoyl)-3-cyano-5-methyl-7-(4-(trifluoromethyl)phenyl)-4,7-dihydropyrazolo[1,5-a]pyrimidine-2-carboxylate;
ethyl 6-((1H-indazol-5-yl)carbamoyl)-7-(4-fluorophenyl)-5-methyl-4,7-dihydropyrazolo[1,5-a]pyrimidine-3-carboxylate;
3-cyano-7-(4-fluorophenyl)-N-(1H-indazol-5-yl)-5-methyl-4,7-dihydropyrazolo[1,5-a]pyrimidine-6-carboxamide;
7-(4-fluorophenyl)-N6-(1H-indazol-5-yl)-5-methyl-4,7-dihydropyrazolo[1,5-a]pyrimidine-3,6-dicarboxamide;
7-(4-fluorophenyl)-N-(1H-indazol-5-yl)-2-(4-methoxyphenyl)-5-methyl-4,7-dihydropyrazolo[1,5-a]pyrimidine-6-carboxamide;
7-(4-fluorophenyl)-N-(1H-indazol-5-yl)-2-(2-methoxyphenyl)-5-methyl-4,7-dihydropyrazolo[1,5-a]pyrimidine-6-carboxamide;
3-bromo-7-(4-fluorophenyl)-N-(1H-indazol-5-yl)-5-methyl-4,7-dihydropyrazolo[1,5-a]pyrimidine-6-carboxamide;

7-(4-fluorophenyl)-N-(1H-indazol-5-yl)-5-methyl-4,7-dihydrotetrazolo[1,5-a]pyrimidine-6-carboxamide;

7-(4-chlorophenyl)-N-(1H-indazol-5-yl)-5-methyl-4,7-dihydrotetrazolo[1,5-a]pyrimidine-6-carboxamide;

7-(3-fluoro-4-(trifluoromethyl)phenyl)-N-(1H-indazol-5-yl)-5-methyl-4,7-dihydrotetrazolo[1,5-a]pyrimidine-6-carboxamide;

7-(2-fluoro-4-(trifluoromethyl)phenyl)-N-(1H-indazol-5-yl)-5-methyl-4,7-dihydrotetrazolo[1,5-a]pyrimidine-6-carboxamide;

N-(1H-indazol-5-yl)-5-methyl-7-(4-(trifluoromethyl)phenyl)-4,7-dihydrotetrazolo[1,5-a]pyrimidine-6-carboxamide;

7-(4-fluorophenyl)-N-(1H-indazol-5-yl)-2,5-dimethyl-4,7-dihydropyrazolo[1,5-a]pyrimidine-6-carboxamide;

2-(tert-butyl)-7-(4-fluorophenyl)-N-(1H-indazol-5-yl)-5-methyl-4,7-dihydropyrazolo[1,5-a]pyrimidine-6-carboxamide;

2-bromo-7-(4-fluorophenyl)-N-(1H-indazol-5-yl)-5-methyl-4,7-dihydropyrazolo[1,5-a]pyrimidine-6-carboxamide;

2-cyano-7-(4-fluorophenyl)-N-(1H-indazol-5-yl)-5-methyl-4,7-dihydropyrazolo[1,5-a]pyrimidine-6-carboxamide;

7-(6-chloropyridin-3-yl)-N-(1H-indazol-5-yl)-5-methyl-2-(trifluoromethyl)-4,7-dihydropyrazolo[1,5-a]pyrimidine-6-carboxamide;

N-(1H-indazol-5-yl)-5-methyl-7-(1-methylpiperidin-4-yl)-2-(trifluoromethyl)-4,7-dihydropyrazolo[1,5-a]pyrimidine-6-carboxamide;

2-cyano-N-(1H-indazol-5-yl)-5-methyl-7-(4-(trifluoromethyl)phenyl)-4,7-dihydropyrazolo[1,5-a]pyrimidine-6-carboxamide;

N-(1H-indazol-5-yl)-2-(methoxymethyl)-5-methyl-7-(4-(trifluoromethyl)phenyl)-4,7-dihydropyrazolo[1,5-a]pyrimidine-6-carboxamide;

7-(3-fluoro-4-(trifluoromethyl)phenyl)-N-(isoquinolin-6-yl)-2-(methoxymethyl)-5-methyl-4,7-dihydropyrazolo[1,5-a]pyrimidine-6-carboxamide;

2-(2-(dimethylamino)ethyl)-7-(3-fluoro-4-(trifluoromethyl)phenyl)-N-(isoquinolin-6-yl)-5-methyl-4,7-dihydropyrazolo[1,5-a]pyrimidine-6-carboxamide;

7-(1H-indol-6-yl)-N-(isoquinolin-6-yl)-2-(methoxymethyl)-5-methyl-4,7-dihydropyrazolo[1,5-a]pyrimidine-6-carboxamide;

7-(6-chloropyridin-3-yl)-N-(6-fluoro-1H-indazol-5-yl)-5-methyl-2-(trifluoromethyl)-4,7-dihydropyrazolo[1,5-a]pyrimidine-6-carboxamide;

N-(6-fluoro-1H-indazol-5-yl)-7-(3-fluoro-4-(trifluoromethyl)phenyl)-5-methyl-4,7-dihydrotetrazolo[1,5-a]pyrimidine-6-carboxamide;

ethyl 7-(3-fluoro-4-(trifluoromethyl)phenyl)-5-methyl-6-(thieno[3,2-c]pyridin-2-ylcarbamoyl)-4,7-dihydropyrazolo[1,5-a]pyrimidine-2-carboxylate;

ethyl 7-(3-fluoro-4-(trifluoromethyl)phenyl)-5-methyl-6-(thieno[2,3-c]pyridin-2-ylcarbamoyl)-4,7-dihydropyrazolo[1,5-a]pyrimidine-2-carboxylate;

2-(hydroxymethyl)-N-(isoquinolin-6-yl)-5-methyl-7-(4-(trifluoromethyl)phenyl)-4,7-dihydropyrazolo[1,5-a]pyrimidine-6-carboxamide;

2-(hydroxymethyl)-N-(isoquinolin-6-yl)-5-methyl-7-(1-methyl-1H-indol-4-yl)-4,7-dihydropyrazolo[1,5-a]pyrimidine-6-carboxamide;

2-(hydroxymethyl)-N-(isoquinolin-6-yl)-5-methyl-7-(1-methyl-1H-benzo[d]imidazol-6-yl)-4,7-dihydropyrazolo[1,5-a]pyrimidine-6-carboxamide;

7-(benzo[b]thiophen-6-yl)-2-(hydroxymethyl)-N-(isoquinolin-6-yl)-5-methyl-4,7-dihydropyrazolo[1,5-a]pyrimidine-6-carboxamide;

7-(4-chloro-3-(trifluoromethyl)phenyl)-2-(hydroxymethyl)-N-(isoquinolin-6-yl)-5-methyl-4,7-dihydropyrazolo[1,5-a]pyrimidine-6-carboxamide;

7-((3r,5r,7r)-adamantan-1-yl)-2-(hydroxymethyl)-N-(isoquinolin-6-yl)-5-methyl-4,7-dihydropyrazolo[1,5-a]pyrimidine-6-carboxamide;

2-(hydroxymethyl)-N-(isoquinolin-6-yl)-5-methyl-7-(2-phenyloxazol-5-yl)-4,7-dihydropyrazolo[1,5-a]pyrimidine-6-carboxamide;

2-(hydroxymethyl)-N-(isoquinolin-6-yl)-5-methyl-7-(3-phenoxyphenyl)-4,7-dihydropyrazolo[1,5-a]pyrimidine-6-carboxamide;

2-(hydroxymethyl)-N-(isoquinolin-6-yl)-5-methyl-7-(3-(trifluoromethyl)phenyl)-4,7-dihydropyrazolo[1,5-a]pyrimidine-6-carboxamide;

2-(hydroxymethyl)-N-(isoquinolin-6-yl)-5-methyl-7-(2-phenylthiazol-5-yl)-4,7-dihydropyrazolo[1,5-a]pyrimidine-6-carboxamide;

2-(hydroxymethyl)-N-(isoquinolin-6-yl)-5-methyl-7-phenethyl-4,7-dihydropyrazolo[1,5-a]pyrimidine-6-carboxamide;

7-(4-(tert-butyl)phenyl)-2-(hydroxymethyl)-N-(isoquinolin-6-yl)-5-methyl-4,7-dihydropyrazolo[1,5-a]pyrimidine-6-carboxamide;

7-(4-bromo-3-fluorophenyl)-2-(hydroxymethyl)-N-(isoquinolin-6-yl)-5-methyl-4,7-dihydropyrazolo[1,5-a]pyrimidine-6-carboxamide;

7-(2,3-difluoro-4-(trifluoromethyl)phenyl)-2-(hydroxymethyl)-N-(isoquinolin-6-yl)-5-methyl-4,7-dihydropyrazolo[1,5-a]pyrimidine-6-carboxamide;

7-(4-chloro-3-fluorophenyl)-2-(hydroxymethyl)-N-(isoquinolin-6-yl)-5-methyl-4,7-dihydropyrazolo[1,5-a]pyrimidine-6-carboxamide;

7-(3-fluoro-4-methylphenyl)-2-(hydroxymethyl)-N-(isoquinolin-6-yl)-5-methyl-4,7-dihydropyrazolo[1,5-a]pyrimidine-6-carboxamide;

7-(2-fluoro-4-methylphenyl)-2-(hydroxymethyl)-N-(isoquinolin-6-yl)-5-methyl-4,7-dihydropyrazolo[1,5-a]pyrimidine-6-carboxamide;

7-(2,3-dihydro-1H-inden-2-yl)-2-(hydroxymethyl)-N-(isoquinolin-6-yl)-5-methyl-4,7-dihydropyrazolo[1,5-a]pyrimidine-6-carboxamide;

7-(4-bromophenyl)-2-(hydroxymethyl)-N-(isoquinolin-6-yl)-5-methyl-4,7-dihydropyrazolo[1,5-a]pyrimidine-6-carboxamide;

7-(4-chlorophenyl)-2-(hydroxymethyl)-N-(isoquinolin-6-yl)-5-methyl-4,7-dihydropyrazolo[1,5-a]pyrimidine-6-carboxamide;

2-(hydroxymethyl)-7-(1H-indol-6-yl)-N-(isoquinolin-6-yl)-5-methyl-4,7-dihydropyrazolo[1,5-a]pyrimidine-6-carboxamide;

7-(4-chloro-2-fluorophenyl)-2-(hydroxymethyl)-N-(isoquinolin-6-yl)-5-methyl-4,7-dihydropyrazolo[1,5-a]pyrimidine-6-carboxamide;

7-(3-fluoro-4-(trifluoromethyl)phenyl)-2-(hydroxymethyl)-N-(isoquinolin-6-yl)-5-methyl-4,7-dihydropyrazolo[1,5-a]pyrimidine-6-carboxamide;

2-(hydroxymethyl)-N-(isoquinolin-6-yl)-5-methyl-7-(p-tolyl)-4,7-dihydropyrazolo[1,5-a]pyrimidine-6-carboxamide;

2-(hydroxymethyl)-N-(1H-indazol-5-yl)-5-methyl-7-(p-tolyl)-4,7-dihydropyrazolo[1,5-a]pyrimidine-6-carboxamide;

7-(4-chloro-2-fluorophenyl)-2-(hydroxymethyl)-N-(1H-indazol-5-yl)-5-methyl-4,7-dihydropyrazolo[1,5-a]pyrimidine-6-carboxamide;

2-(hydroxymethyl)-N-(1H-indazol-5-yl)-5-methyl-7-(4-(trifluoromethyl)phenyl)-4,7-dihydropyrazolo[1,5-a]pyrimidine-6-carboxamide;

7-(6-chloropyridin-3-yl)-2-(hydroxymethyl)-N-(1H-indazol-5-yl)-5-methyl-4,7-dihydropyrazolo[1,5-a]pyrimidine-6-carboxamide;

7-(4-fluorophenyl)-2-(hydroxymethyl)-N-(1H-indazol-5-yl)-5-methyl-4,7-dihydropyrazolo[1,5-a]pyrimidine-6-carboxamide;

first stereoisomer of 7-(2,3-dihydrobenzo[b][1,4]dioxin-2-yl)-2-(hydroxymethyl)-N-(isoquinolin-6-yl)-5-methyl-4,7-dihydropyrazolo[1,5-a]pyrimidine-6-carboxamide;

second stereoisomer of 7-(2,3-dihydrobenzo[b][1,4]dioxin-2-yl)-2-(hydroxymethyl)-N-(isoquinolin-6-yl)-5-methyl-4,7-dihydropyrazolo[1,5-a]pyrimidine-6-carboxamide;

third stereoisomer of 7-(2,3-dihydrobenzo[b][1,4]dioxin-2-yl)-2-(hydroxymethyl)-N-(isoquinolin-6-yl)-5-methyl-4,7-dihydropyrazolo[1,5-a]pyrimidine-6-carboxamide;

fourth stereoisomer of 7-(2,3-dihydrobenzo[b][1,4]dioxin-2-yl)-2-(hydroxymethyl)-N-(isoquinolin-6-yl)-5-methyl-4,7-dihydropyrazolo[1,5-a]pyrimidine-6-carboxamide;

6-((1H-indazol-5-yl)carbamoyl)-5-methyl-7-(4-(trifluoromethyl)phenyl)-4,7-dihydropyrazolo[1,5-a]pyrimidine-2-carboxylic acid;

6-((1H-indazol-5-yl)carbamoyl)-5-methyl-7-(p-tolyl)-4,7-dihydropyrazolo[1,5-a]pyrimidine-2-carboxylic acid;

6-((1H-indazol-5-yl)carbamoyl)-7-(4-fluorophenyl)-5-methyl-4,7-dihydropyrazolo[1,5-a]pyrimidine-2-carboxylic acid;

N-(1H-indazol-5-yl)-5-methyl-2-(4-methylpiperazine-1-carbonyl)-7-(4-(trifluoromethyl)phenyl)-4,7-dihydropyrazolo[1,5-a]pyrimidine-6-carboxamide;

7-(3-fluoro-4-(trifluoromethyl)phenyl)-N6-(isoquinolin-6-yl)-5-methyl-N2-(2-(piperidin-1-yl)ethyl)-4,7-dihydropyrazolo[1,5-a]pyrimidine-2,6-dicarboxamide;

7-(3-fluoro-4-(trifluoromethyl)phenyl)-N6-(isoquinolin-6-yl)-N2,5-dimethyl-N2-(2-(piperidin-1-yl)ethyl)-4,7-dihydropyrazolo[1,5-a]pyrimidine-2,6-dicarboxamide;

N2-(2-(dimethylamino)ethyl)-7-(3-fluoro-4-(trifluoromethyl)phenyl)-N6-(isoquinolin-6-yl)-5-methyl-4,7-dihydropyrazolo[1,5-a]pyrimidine-2,6-dicarboxamide;

N2-(2-(dimethylamino)ethyl)-7-(3-fluoro-4-(trifluoromethyl)phenyl)-N6-(isoquinolin-6-yl)-N2,5-dimethyl-4,7-dihydropyrazolo[1,5-a]pyrimidine-2,6-dicarboxamide;

7-(3-fluoro-4-(trifluoromethyl)phenyl)-N6-(isoquinolin-6-yl)-5-methyl-N2-(2-(4-methylpiperazin-1-yl)ethyl)-4,7-dihydropyrazolo[1,5-a]pyrimidine-2,6-dicarboxamide;

7-(3-fluoro-4-(trifluoromethyl)phenyl)-N6-(isoquinolin-6-yl)-5-methyl-N2-(2-morpholinoethyl)-4,7-dihydropyrazolo[1,5-a]pyrimidine-2,6-dicarboxamide;

7-(3-fluoro-4-(trifluoromethyl)phenyl)-N6-(isoquinolin-6-yl)-N2,5-dimethyl-N2-(2-morpholinoethyl)-4,7-dihydropyrazolo[1,5-a]pyrimidine-2,6-dicarboxamide;

7-(3-fluoro-4-(trifluoromethyl)phenyl)-N6-(isoquinolin-6-yl)-5-methyl-N2-((1-methylpiperidin-4-yl)methyl)-4,7-dihydropyrazolo[1,5-a]pyrimidine-2,6-dicarboxamide;

7-(3-fluoro-4-(trifluoromethyl)phenyl)-N6-(isoquinolin-6-yl)-N2,5-dimethyl-N2-((1-methylpiperidin-4-yl)methyl)-4,7-dihydropyrazolo[1,5-a]pyrimidine-2,6-dicarboxamide;

7-(3-fluoro-4-(trifluoromethyl)phenyl)-N-(isoquinolin-6-yl)-5-methyl-2-(5-methyloctahydropyrrolo[3,4-c]pyrrole-2-carbonyl)-4,7-dihydropyrazolo[1,5-a]pyrimidine-6-carboxamide;

2-(4-(dimethylamino)piperidine-1-carbonyl)-7-(3-fluoro-4-(trifluoromethyl)phenyl)-N-(isoquinolin-6-yl)-5-methyl-4,7-dihydropyrazolo[1,5-a]pyrimidine-6-carboxamide;

7-(3-fluoro-4-(trifluoromethyl)phenyl)-N6-(isoquinolin-6-yl)-N2,5-dimethyl-N2-(1-methylpiperidin-4-yl)-4,7-dihydropyrazolo[1,5-a]pyrimidine-2,6-dicarboxamide;

N2-(3-(dimethylamino)propyl)-7-(3-fluoro-4-(trifluoromethyl)phenyl)-N6-(isoquinolin-6-yl)-N2,5-dimethyl-4,7-dihydropyrazolo[1,5-a]pyrimidine-2,6-dicarboxamide;

7-(4-fluorophenyl)-N-(1H-indazol-5-yl)-5-methyl-2-(morpholine-4-carbonyl)-4,7-dihydropyrazolo[1,5-a]pyrimidine-6-carboxamide;

7-(4-fluorophenyl)-N-(1H-indazol-5-methyl-3-(4-methylpiperazine-1-carbonyl)-4,7-dihydropyrazolo[1,5-a]pyrimidine-6-carboxamide;

N3-(2-(dimethylamino)ethyl)-7-(4-fluorophenyl)-N6-(1H-indazol-5-yl)-5-methyl-4,7-dihydropyrazolo[1,5-a]pyrimidine-6-carboxamide;

7-(4-fluorophenyl)-N-(1H-indazol-5-yl)-5-methyl-2-(piperazine-1-carbonyl)-4,7-dihydropyrazolo[1,5-a]pyrimidine-6-carboxamide;

2-((dimethylamino)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide;

7-(3-fluoro-4-(trifluoromethyl)phenyl)-N-(isoquinolin-6-yl)-5-methyl-2-(morpholinomethyl)-4,7-dihydropyrazolo[1,5-a]pyrimidine-6-carboxamide;

7-(3-fluoro-4-(trifluoromethyl)phenyl)-N-(isoquinolin-6-yl)-5-methyl-2-((4-methylpiperazin-1-yl)methyl)-4,7-dihydropyrazolo[1,5-a]pyrimidine-6-carboxamide;

7-(3-fluoro-4-(trifluoromethyl)phenyl)-N-(isoquinolin-6-yl)-5-methyl-2-(piperidin-1-ylmethyl)-4,7-dihydropyrazolo[1,5-a]pyrimidine-6-carboxamide;

7-(3-fluoro-4-(trifluoromethyl)phenyl)-N-(isoquinolin-6-yl)-2-(((2-methoxyethyl)(methyl)amino)methyl)-5-methyl-4,7-dihydropyrazolo[1,5-a]pyrimidine-6-carboxamide;

7-(3-fluoro-4-(trifluoromethyl)phenyl)-N-(isoquinolin-6-yl)-2-((4-methoxypiperidin-1-yl)methyl)-5-methyl-4,7-dihydropyrazolo[1,5-a]pyrimidine-6-carboxamide;

7-(3-fluoro-4-(trifluoromethyl)phenyl)-N-(isoquinolin-6-yl)-2-((3-methoxyazetidin-1-yl)methyl)-5-methyl-4,7-dihydropyrazolo[1,5-a]pyrimidine-6-carboxamide;

7-(3-fluoro-4-(trifluoromethyl)phenyl)-N-(isoquinolin-6-yl)-2-((3-(methoxymethyl)azetidin-1-yl)methyl)-5-methyl-4,7-dihydropyrazolo[1,5-a]pyrimidine-6-carboxamide;

7-(3-fluoro-4-(trifluoromethyl)phenyl)-N-(isoquinolin-6-yl)-5-methyl-2-(pyrrolidin-1-ylmethyl)-4,7-dihydropyrazolo[1,5-a]pyrimidine-6-carboxamide;

7-(3-fluoro-4-(trifluoromethyl)phenyl)-N-(isoquinolin-6-yl)-5-methyl-2-((8-methyl-2,8-diazaspiro[4.5]decan-2-yl)methyl)-4,7-dihydropyrazolo[1,5-a]pyrimidine-6-carboxamide;

7-(3-fluoro-4-(trifluoromethyl)phenyl)-N-(isoquinolin-6-yl)-5-methyl-2-((methyl((1-methylpiperidin-4-yl)methyl)amino)methyl)-4,7-dihydropyrazolo[1,5-a]pyrimidine-6-carboxamide;

7-(3-fluoro-4-(trifluoromethyl)phenyl)-N-(isoquinolin-6-yl)-5-methyl-2-((4-(pyrrolidin-1-yl)piperidin-1-yl)methyl)-4,7-dihydropyrazolo[1,5-a]pyrimidine-6-carboxamide;

2-((3-((dimethylamino)methyl)azetidin-1-yl)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide;

N-(1H-indazol-5-yl)-5-methyl-2-(morpholinomethyl)-7-(4-(trifluoromethyl)phenyl)-4,7-dihydropyrazolo[1,5-a]pyrimidine-6-carboxamide;

2-((1,1-dioxidothiomorpholino)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide;

2-((4-acetylpiperazin-1-yl)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide;

2-((dimethylamino)methyl)-7-(3-fluoro-4-methylphenyl)-N-(isoquinolin-6-yl)-5-methyl-4,7-dihydropyrazolo[1,5-a]pyrimidine-6-carboxamide;

2-(aminomethyl)-N-(1H-indazol-5-yl)-5-methyl-7-(4-(trifluoromethyl)phenyl)-4,7-dihydropyrazolo[1,5-a]pyrimidine-6-carboxamide;

2-(aminomethyl)-7-(3-fluoro-4-(trifluoromethyl)phenyl)-N-(isoquinolin-6-yl)-5-methyl-4,7-dihydropyrazolo[1,5-a]pyrimidine-6-carboxamide;

first eluting enantiomer of ethyl 6-((1H-indazol-5-yl)carbamoyl)-7-(4-fluorophenyl)-5-methyl-4,7-dihydropyrazolo[1,5-a]pyrimidine-2-carboxylate;

second eluting enantiomer of ethyl 6-(1H-indazol-5-yl)carbamoyl)-7-(4-fluorophenyl)-5-methyl-4,7-dihydropyrazolo[1,5-a]pyrimidine-2-carboxylate;

first eluting enantiomer of ethyl 6-((1H-indazol-5-yl)carbamoyl)-7-(4-chloro-2-fluorophenyl)-5-methyl-4,7-dihydropyrazolo[1,5-a]pyrimidine-2-carboxylate;

second eluting enantiomer of ethyl 6-((1H-indazol-5-yl)carbamoyl)-7-(4-chloro-2-fluorophenyl)-5-methyl-4,7-dihydropyrazolo[1,5-a]pyrimidine-2-carboxylate;

first eluting enantiomer of 7-(4-fluorophenyl)-N-(1H-indazol-5-yl)-5-methyl-4,7-dihydrotetrazolo[1,5-a]pyrimidine-6-carboxamide;

second eluting enantiomer of 7-(4-fluorophenyl)-N-(1H-indazol-5-yl)-5-methyl-4,7-dihydrotetrazolo[1,5-a]pyrimidine-6-carboxamide;

first eluting enantiomer of 7-(4-chlorophenyl)-N-(1H-indazol-5-yl)-5-methyl-4,7-dihydrotetrazolo[1,5-a]pyrimidine-6-carboxamide;

second eluting enantiomer of 7-(4-chlorophenyl)-N-(1H-indazol-5-yl)-5-methyl-4,7-dihydrotetrazolo[1,5-a]pyrimidine-6-carboxamide;

first eluting enantiomer of 7-(3-fluoro-4-(trifluoromethyl)phenyl)-N-(1H-indazol-5-yl)-5-methyl-4,7-dihydrotetrazolo[1,5-a]pyrimidine-6-carboxamide;

second eluting enantiomer of 7-(3-fluoro-4-(trifluoromethyl)phenyl)-N-(1H-indazol-5-yl)-5-methyl-4,7-dihydrotetrazolo[1,5-a]pyrimidine-6-carboxamide;

first eluting enantiomer of 7-(2-fluoro-4-(trifluoromethyl)phenyl)-N-(1H-indazol-5-yl)-5-methyl-4,7-dihydrotetrazolo[1,5-a]pyrimidine-6-carboxamide;

second eluting enantiomer of 7-(2-fluoro-4-(trifluoromethyl)phenyl)-N-(1H-indazol-5-yl)-5-methyl-4,7-dihydrotetrazolo[1,5-a]pyrimidine-6-carboxamide;

first eluting enantiomer of N-(1H-indazol-5-yl)-5-methyl-7-(4-(trifluoromethyl)phenyl)-4,7-dihydrotetrazolo[1,5-a]pyrimidine-6-carboxamide;

second eluting enantiomer of N-(1H-indazol-5-yl)-5-methyl-7-(4-(trifluoromethyl)phenyl)-4,7-dihydrotetrazolo[1,5-a]pyrimidine-6-carboxamide;

first eluting enantiomer of 7-(6-chloropyridin-3-yl)-N-(1H-indazol-5-yl)-5-methyl-2-(trifluoromethyl)-4,7-dihydropyrazolo[1,5-a]pyrimidine-6-carboxamide;

second eluting enantiomer of 7-(6-chloropyridin-3-yl)-N-(1H-indazol-5-yl)-5-methyl-2-(trifluoromethyl)-4,7-dihydropyrazolo[1,5-a]pyrimidine-6-carboxamide;

first eluting enantiomer of N-(6-fluoro-1H-indazol-5-yl)-7-(3-fluoro-4-(trifluoromethyl)phenyl)-5-methyl-4,7-dihydrotetrazolo[1,5-a]pyrimidine-6-carboxamide;

second eluting enantiomer of N-(6-fluoro-1H-indazol-5-yl)-7-(3-fluoro-4-(trifluoromethyl)phenyl)-5-methyl-4,7-dihydrotetrazolo[1,5-a]pyrimidine-6-carboxamide;

first eluting enantiomer of 2-(hydroxymethyl)-N-(isoquinolin-6-yl)-5-methyl-7-(4-(trifluoromethyl)phenyl)-4,7-dihydropyrazolo[1,5-a]pyrimidine-6-carboxamide;

second eluting enantiomer of 2-(hydroxymethyl)-N-(isoquinolin-6-yl)-5-methyl-7-(4-(trifluoromethyl)phenyl)-4,7-dihydropyrazolo[1,5-a]pyrimidine-6-carboxamide;

7-(2,3-dihydro-1H-inden-2-yl)-2-(hydroxymethyl)-N-(isoquinolin-6-yl)-5-methyl-4,7-dihydropyrazolo[1,5-a]pyrimidine-6-carboxamide;

7-(2,3-dihydro-1H-inden-2-yl)-2-(hydroxymethyl)-N-(isoquinolin-6-yl)-5-methyl-4,7-dihydropyrazolo[1,5-a]pyrimidine-6-carboxamide;

first eluting enantiomer of 7-(4-bromophenyl)-2-(hydroxymethyl)-N-(isoquinolin-6-yl)-5-methyl-4,7-dihydropyrazolo[1,5-a]pyrimidine-6-carboxamide;

second eluting enantiomer of 7-(4-bromophenyl)-2-(hydroxymethyl)-N-(isoquinolin-6-yl)-5-methyl-4,7-dihydropyrazolo[1,5-a]pyrimidine-6-carboxamide;

first eluting enantiomer of 7-(4-chlorophenyl)-2-(hydroxymethyl)-N-(isoquinolin-6-yl)-5-methyl-4,7-dihydropyrazolo[1,5-a]pyrimidine-6-carboxamide;

second eluting enantiomer of 7-(4-chlorophenyl)-2-(hydroxymethyl)-N-(isoquinolin-6-yl)-5-methyl-4,7-dihydropyrazolo[1,5-a]pyrimidine-6-carboxamide;

first eluting enantiomer of 7-(3-fluoro-4-(trifluoromethyl)phenyl)-2-(hydroxymethyl)-N-(isoquinolin-6-yl)-5-methyl-4,7-dihydropyrazolo[1,5-a]pyrimidine-6-carboxamide;

second eluting enantiomer of 7-(3-fluoro-4-(trifluoromethyl)phenyl)-2-(hydroxymethyl)-N-(isoquinolin-6-yl)-5-methyl-4,7-dihydropyrazolo[1,5-a]pyrimidine-6-carboxamide;

first eluting enantiomer of 2-(hydroxymethyl)-N-(1H-indazol-5-yl)-5-methyl-7-(4-(trifluoromethyl)phenyl)-4,7-dihydropyrazolo[1,5-a]pyrimidine-6-carboxamide;

second eluting enantiomer of (S)-2-(hydroxymethyl)-N-(1H-indazol-5-yl)-5-methyl-7-(4-(trifluoromethyl)phenyl)-4,7-dihydropyrazolo[1,5-a]pyrimidine-6-carboxamide;

first eluting enantiomer of 7-(4-fluorophenyl)-2-(hydroxymethyl)-N-(1H-indazol-5-yl)-5-methyl-4,7-dihydropyrazolo[1,5-a]pyrimidine-6-carboxamide;

second eluting enantiomer of 7-(4-fluorophenyl)-2-(hydroxymethyl)-N-(1H-indazol-5-yl)-5-methyl-4,7-dihydropyrazolo[1,5-a]pyrimidine-6-carboxamide;

first eluting enantiomer of 7-(3-fluoro-4-(trifluoromethyl)phenyl)-N6-(isoquinolin-6-yl)-N2,5-dimethyl-N2-(2-

(piperidin-1-yl)ethyl)-4,7-dihydropyrazolo[1,5-a]pyrimidine-2,6-dicarboxamide;

second eluting enantiomer of 7-(3-fluoro-4-(trifluoromethyl)phenyl)-N6-(isoquinolin-6-yl)-N2,5-dimethyl-N2-(2-(piperidin-1-yl)ethyl)-4,7-dihydropyrazolo[1,5-a]pyrimidine-2,6-dicarboxamide;

first eluting enantiomer of 2-((dimethylamino)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide;

second eluting enantiomer of 2-((dimethylamino)methyl)-7-(3-fluoro-4-(trifluoromethyl)phenyl)-N-(isoquinolin-6-yl)-5-methyl-4,7-dihydropyrazolo[1,5-a]pyrimidine-6-carboxamide;

first eluting enantiomer of 7-(3-fluoro-4-(trifluoromethyl)phenyl)-N-(isoquinolin-6-yl)-5-methyl-2-((4-methylpiperazin-1-yl)methyl)-4,7-dihydropyrazolo[1,5-a]pyrimidine-6-carboxamide;

second eluting enantiomer of 7-(3-fluoro-4-(trifluoromethyl)phenyl)-N-(isoquinolin-6-yl)-5-methyl-2-((4-methylpiperazin-1-yl)methyl)-4,7-dihydropyrazolo[1,5-a]pyrimidine-6-carboxamide;

first eluting enantiomer of 7-(3-fluoro-4-(trifluoromethyl)phenyl)-N-(isoquinolin-6-yl)-5-methyl-2-(piperidin-1-ylmethyl)-4,7-dihydropyrazolo[1,5-a]pyrimidine-6-carboxamide;

second eluting enantiomer of 7-(3-fluoro-4-(trifluoromethyl)phenyl)-N-(isoquinolin-6-yl)-5-methyl-2-(piperidin-1-ylmethyl)-4,7-dihydropyrazolo[1,5-a]pyrimidine-6-carboxamide;

first eluting enantiomer of 7-(3-fluoro-4-(trifluoromethyl)phenyl)-N-(isoquinolin-6-yl)-5-methyl-2-((methyl((1-methylpiperidin-4-yl)methyl)amino)methyl)-4,7-dihydropyrazolo[1,5-a]pyrimidine-6-carboxamide;

second eluting enantiomer of 7-(3-fluoro-4-(trifluoromethyl)phenyl)-N-(isoquinolin-6-yl)-5-methyl-2-((methyl((1-methylpiperidin-4-yl)methyl)amino)methyl)-4,7-dihydropyrazolo[1,5-a]pyrimidine-6-carboxamide;

first eluting enantiomer of 2-((dimethylamino)methyl)-7-(3-fluoro-4-methylphenyl)-N-(isoquinolin-6-yl)-5-methyl-4,7-dihydropyrazolo[1,5-a]pyrimidine-6-carboxamide;

second eluting enantiomer of 2-((dimethylamino)methyl)-7-(3-fluoro-4-methylphenyl)-N-(isoquinolin-6-yl)-5-methyl-4,7-dihydropyrazolo[1,5-a]pyrimidine-6-carboxamide;

ethyl 6-((1,6-naphthyridin-2-yl)carbamoyl)-7-(3-fluoro-4-(trifluoromethyl)phenyl)-5-methyl-4,7-dihydropyrazolo[1,5-a]pyrimidine-2-carboxylate;

ethyl 7-(3-fluoro-4-(trifluoromethyl)phenyl)-5-methyl-6-((4-methylisoquinolin-6-yl)carbamoyl)-4,7-dihydropyrazolo[1,5-a]pyrimidine-2-carboxylate;

ethyl 7-(4-(difluoromethyl)-3-fluorophenyl)-6-(isoquinolin-6-ylcarbamoyl)-5-methyl-4,7-dihydropyrazolo[1,5-a]pyrimidine-2-carboxylate;

7-(3-fluoro-4-(trifluoromethyl)phenyl)-N-(isoquinolin-6-yl)-5-methyl-2-(oxetan-3-yl)-4,7-dihydropyrazolo[1,5-a]pyrimidine-6-carboxamide;

7-(3-fluoro-4-(trifluoromethyl)phenyl)-N-(isoquinolin-6-yl)-5-methyl-2-(methylthio)-4,7-dihydropyrazolo[1,5-a]pyrimidine-6-carboxamide;

5-cyclopropyl-7-(3-fluoro-4-(trifluoromethyl)phenyl)-2-(hydroxymethyl)-N-(isoquinolin-6-yl)-4,7-dihydropyrazolo[1,5-a]pyrimidine-6-carboxamide;

7-(3-fluoro-4-(trifluoromethyl)phenyl)-2-(hydroxymethyl)-N-(isoquinolin-6-yl)-5-(methoxymethyl)-4,7-dihydropyrazolo[1,5-a]pyrimidine-6-carboxamide;

2-((dimethylamino)methyl)-N-(isoquinolin-6-yl)-5-methyl-7-(4-(trifluoromethyl)cyclohexyl)-4,7-dihydropyrazolo[1,5-a]pyrimidine-6-carboxamide;

7-(2,3-difluoro-4-methylphenyl)-2-((dimethylamino)methyl)-N-(isoquinolin-6-yl)-5-methyl-4,7-dihydropyrazolo[1,5-a]pyrimidine-6-carboxamide;

7-(2,3-difluoro-4-(trifluoromethyl)phenyl)-2-((dimethylamino)methyl)-N-(isoquinolin-6-yl)-5-methyl-4,7-dihydropyrazolo[1,5-a]pyrimidine-6-carboxamide;

2-((dimethylamino)methyl)-7-(3-fluoro-4-(trifluoromethyl)phenyl)-5-methyl-N-(1,6-naphthyridin-2-yl)-4,7-dihydropyrazolo[1,5-a]pyrimidine-6-carboxamide;

7-(2,3-dihydro-1H-inden-2-yl)-2-((dimethylamino)methyl)-N-(isoquinolin-6-yl)-5-methyl-4,7-dihydropyrazolo[1,5-a]pyrimidine-6-carboxamide;

N2-cyclopropyl-7-(3-fluoro-4-(trifluoromethyl)phenyl)-N6-(isoquinolin-6-yl)-5-methyl-4,7-dihydropyrazolo[1,5-a]pyrimidine-2,6-dicarboxamide;

7-(3-fluoro-4-(trifluoromethyl)phenyl)-N6-(isoquinolin-6-yl)-N2,N2,5-trimethyl-4,7-dihydropyrazolo[1,5-a]pyrimidine-2,6-dicarboxamide;

7-(3-fluoro-4-(trifluoromethyl)phenyl)-N6-(isoquinolin-6-yl)-5-methyl-N2-(3-oxo-3-(pyrrolidin-1-yl)propyl)-4,7-dihydropyrazolo[1,5-a]pyrimidine-2,6-dicarboxamide;

N2-(3,3-difluorocyclobutyl)-7-(3-fluoro-4-(trifluoromethyl)phenyl)-N6-(isoquinolin-6-yl)-5-methyl-4,7-dihydropyrazolo[1,5-a]pyrimidine-2,6-dicarboxamide;

7-(3-fluoro-4-(trifluoromethyl)phenyl)-N6-(isoquinolin-6-yl)-5-methyl-N2-(2-(piperidin-1-yl)ethyl)-4,7-dihydro-[1,2,4]triazolo[1,5-a]pyrimidine-2,6-dicarboxamide;

2-amino-7-(3-fluoro-4-(trifluoromethyl)phenyl)-N-(isoquinolin-6-yl)-5-methyl-4,7-dihydropyrazolo[1,5-a]pyrimidine-6-carboxamide;

7-(3-fluoro-4-(trifluoromethyl)phenyl)-N-(isoquinolin-6-yl)-5-methyl-2-(3-(piperidin-1-yl)propanamido)-4,7-dihydropyrazolo[1,5-a]pyrimidine-6-carboxamide;

7-(3-fluoro-4-(trifluoromethyl)phenyl)-N-(isoquinolin-6-yl)-5-methyl-2-(2-(pyrrolidin-1-yl)acetamido)-4,7-dihydropyrazolo[1,5-a]pyrimidine-6-carboxamide;

7-(3-fluoro-4-(trifluoromethyl)phenyl)-N-(isoquinolin-6-yl)-5-methyl-2-(2-((1-methylpiperidin-4-yl)oxy)acetamido)-4,7-dihydropyrazolo[1,5-a]pyrimidine-6-carboxamide;

7-(3-fluoro-4-methylphenyl)-N-(isoquinolin-6-yl)-5-methyl-2-(2-(pyrrolidin-1-yl)acetamido)-4,7-dihydropyrazolo[1,5-a]pyrimidine-6-carboxamide;

7-(3-fluoro-4-(trifluoromethyl)phenyl)-N-(isoquinolin-6-yl)-5-methyl-2-(1-(3-(piperidin-1-yl)propanoyl)piperidin-4-yl)-4,7-dihydropyrazolo[1,5-a]pyrimidine-6-carboxamide;

7-(3-fluoro-4-(trifluoromethyl)phenyl)-N-(isoquinolin-6-yl)-5-methyl-2-(4-methylpiperazin-1-yl)-4,7-dihydropyrazolo[1,5-a]pyrimidine-6-carboxamide;

first eluting enantiomer of 7-(2,3-difluoro-4-(trifluoromethyl)phenyl)-2-((dimethylamino)methyl)-N-(isoquinolin-6-yl)-5-methyl-4,7-dihydropyrazolo[1,5-a]pyrimidine-6-carboxamide;

second eluting enantiomer of 7-(2,3-difluoro-4-(trifluoromethyl)phenyl)-2-((dimethylamino)methyl)-N-(isoquinolin-6-yl)-5-methyl-4,7-dihydropyrazolo[1,5-a]pyrimidine-6-carboxamide;

second eluting enantiomer of 7-(2,3-difluoro-4-methylphenyl)-2-((dimethylamino)methyl)-N-(isoquinolin-6-yl)-5-methyl-4,7-dihydropyrazolo[1,5-a]pyrimidine-6-carboxamide;

first eluting enantiomer of 7-(2,3-dihydro-1H-inden-2-yl)-2-((dimethylamino)methyl)-N-(isoquinolin-6-yl)-5-methyl-4,7-dihydropyrazolo[1,5-a]pyrimidine-6-carboxamide;

second eluting enantiomer of 7-(2,3-dihydro-1H-inden-2-yl)-2-((dimethylamino)methyl)-N-(isoquinolin-6-yl)-5-methyl-4,7-dihydropyrazolo[1,5-a]pyrimidine-6-carboxamide;

first eluting enantiomer of 7-(3-fluoro-4-(trifluoromethyl)phenyl)-N6-(isoquinolin-6-yl)-5-methyl-N2-(2-(piperidin-1-yl)ethyl)-4,7-dihydro-[1,2,4]triazolo[1,5-a]pyrimidine-2,6-dicarboxamide; and second eluting enantiomer of 7-(3-fluoro-4-(trifluoromethyl)phenyl)-N6-(isoquinolin-6-yl)-5-methyl-N2-(2-(piperidin-1-yl)ethyl)-4,7-dihydro-[1,2,4]triazolo[1,5-a]pyrimidine-2,6-dicarboxamide;

or a pharmaceutically acceptable salt of said compound.

7. A pharmaceutical composition, comprising a compound or salt according to claim 1, either alone or in combination with another one or more other active ingredients, in admixture with one or more pharmaceutically acceptable carriers or excipients.

8. A method for the treatment of a pulmonary disease, said method comprising administering an effective amount of a compound or salt according to claim 1 to a subject in need thereof.

9. A method according to claim 8, wherein said pulmonary disease is asthma, chronic obstructive pulmonary disease, idiopathic pulmonary fibrosis, or pulmonary hypertension.

10. A method according to claim 8, wherein said pulmonary disease is pulmonary arterial hypertension.

11. A combination, comprising a compound or salt according to claim 1 and one or more active ingredients selected from the group consisting of an organic nitrate, a NO donor, inhaled NO; a stimulator of soluble guanylate cyclase (sGC), a prostaciclin analogue PGI2, an agonist of a prostacyclin receptor, a compound that inhibits the degradation of cyclic guanosine monophosphate (cGMP) and/or cyclic adenosine monophosphate (cAMP), a human neutrophilic elastase inhibitor, a compound which inhibits the signal transduction cascade, an active substance for lowering blood pressure, a neutral endopeptidase inhibitor, an osmotic agents, an ENaC blocker, an anti-inflammatory, a bronchodilatory, an antihistamine drug, an anti-tussive drug, an antibiotic, a DNase drug substance and selective cleavage agents, an agent that inhibits ALK5 and/or ALK4 phosphorylation of Smad2 and Smad3, a tryptophan hydroylase 1 (TPH1) inhibitor, and a multi-kinase inhibitor.

12. A pharmaceutical composition according to claim 7, which is in a form suitable to be administered by inhalation, such as inhalable powders, propellant-containing metering aerosols or propellant-free inhalable formulations.

13. A pharmaceutical composition according to claim 7, which is an inhalable powder, a propellant-containing metering aerosol, or a propellant-free inhalable formulation.

14. A device, comprising a pharmaceutical composition according to claim 7, which is a single-dose dry powder inhaler, a multi-dose dry powder inhaler, a metered dose inhaler, or a soft mist nebulizer.

* * * * *